(12) United States Patent
Hunt et al.

(10) Patent No.: US 10,189,863 B2
(45) Date of Patent: *Jan. 29, 2019

(54) 5,6-DIHYDRO-4H-BENZO[B]THIENO-[2,3-D]AZEPINE DERIVATIVES

(71) Applicant: PULMOCIDE LIMITED, London (GB)

(72) Inventors: Simon Fraser Hunt, Nottingham (GB); Stuart Thomas Onions, Nottingham (GB); Vladimir Sherbukhin, Nottingham (GB); Euan Alexander Fraser Fordyce, Nottingham (GB); Peter John Murray, London (GB); Matthew Stephen Coates, London (GB); Daniel William Brookes, London (GB); Kazuhiro Ito, London (GB); Peter Strong, London (GB)

(73) Assignee: PULMOCIDE LIMITED, London (GB)

( * ) Notice: Subject to any disclaimer, the term of this patent is extended or adjusted under 35 U.S.C. 154(b) by 0 days.

This patent is subject to a terminal disclaimer.

(21) Appl. No.: 15/516,809

(22) PCT Filed: Oct. 8, 2015

(86) PCT No.: PCT/GB2015/052945
§ 371 (c)(1),
(2) Date: Apr. 4, 2017

(87) PCT Pub. No.: WO2016/055792
PCT Pub. Date: Apr. 14, 2016

(65) Prior Publication Data
US 2017/0355717 A1    Dec. 14, 2017

(30) Foreign Application Priority Data
Oct. 10, 2014    (EP) .................................... 14188494

(51) Int. Cl.
| | | |
|---|---|---|
| *C07D 519/00* | (2006.01) | |
| *C07D 495/04* | (2006.01) | |
| *A61K 31/55* | (2006.01) | |
| *A61P 31/14* | (2006.01) | |
| *A61K 9/10* | (2006.01) | |
| *A61K 9/14* | (2006.01) | |
| *A61K 45/06* | (2006.01) | |

(52) U.S. Cl.
CPC .............. *C07D 519/00* (2013.01); *A61K 9/10* (2013.01); *A61K 9/14* (2013.01); *A61K 31/55* (2013.01); *A61K 45/06* (2013.01); *C07D 495/04* (2013.01)

(58) Field of Classification Search
CPC .......................... C07D 519/00; C07D 491/107; C07D 487/20; A61K 31/55
See application file for complete search history.

(56) References Cited

U.S. PATENT DOCUMENTS 8,999,969 B2    4/2015    Mackman et al.

FOREIGN PATENT DOCUMENTS

| WO | 97/47625 | 12/1997 |
|---|---|---|
| WO | 00/64876 | 11/2000 |
| WO | 2011/005842 A1 | 1/2011 |
| WO | 2011/046954 A1 | 4/2011 |
| WO | 2012/016217 A1 | 2/2012 |
| WO | 2012/129562 A2 | 9/2012 |
| WO | 2016/022464 A1 | 2/2016 |
| WO | 2017123884 | 7/2017 |
| WO | 2017134133 | 8/2017 |

OTHER PUBLICATIONS

Sudo, et al.—Antiviral Research (2005) vol. 65: 125-131—"YM-53403, a unique anti-respiratory syncytial virus agent with a novel mechanism of action".

Xiong, et al—Bioorganic & Medicinal Chemistry Letters (2013) vol. 23 No. 24: 6789-6793—"Discovery of a potent respiratory syncytial virus RNA polymerase inhibitor".

(Continued)

*Primary Examiner* — Susanna Moore

(74) *Attorney, Agent, or Firm* — Klauber & Jackson LLC

(57) ABSTRACT

There are provided 5,6-dihydro-4H-benzo[b]thieno-[2,3-d] azepine derivatives which are useful in the treatment of respiratory syncytial virus (RSV) infection and for the prevention of disease associated with RSV infection.

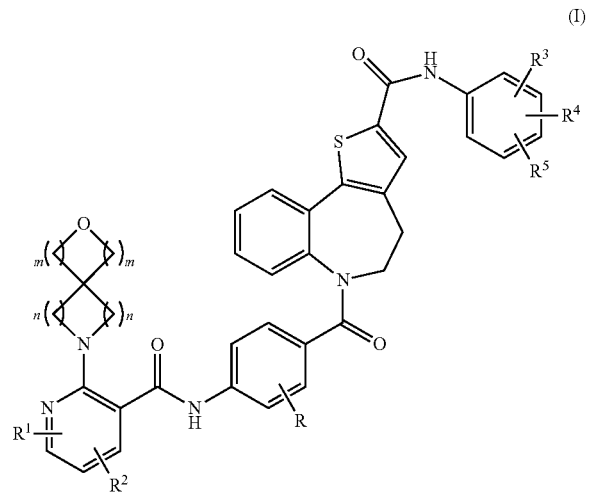

24 Claims, 2 Drawing Sheets

(56) References Cited

OTHER PUBLICATIONS

Yajun Zheng et al.—Bioorganic & Medicinal Chemistry Letters 24 (2014) 3673-3682—"The use of spirocyclic scaffolds in drug discovery".
Coates, M. et al; Antimicrob. Agents and Chem., (2017) 61 (9), 1-18—"Preclinical Characterization of PC786, an Inhaled Small-Molecule Respiratory Syncytial Virus L Protein Polymerase Inhibitor".

5,6-DIHYDRO-4H-BENZO[B]THIENO-[2,3-D]AZEPINE DERIVATIVES

CROSS REFERENCE TO RELATED APPLICATIONS

The present application is a National Stage Application claiming the priority of co-pending PCT Application No. PCT/GB2015/052945, filed Oct. 8, 2015, which in turn, claims priority from European Application No. 14188494.0, filed Oct. 10, 2014. Applicants claim the benefits of 35 U.S.C. § 120 as to the PCT application and priority under 35 U.S.C. § 119 as to the said European application, and the entire disclosures of both applications are incorporated herein by reference in their entireties.

FIELD OF THE INVENTION

The invention relates to novel compounds, compositions containing them, processes for making said compounds and their use in therapy. The compounds are intended to treat or prevent respiratory syncytial virus infections and associated disease particularly infections caused by the A and B strains thereof.

BACKGROUND OF THE INVENTION

Human respiratory syncytial virus (RSV) is a pneumovirus of the paramyxovirus family and the most common cause of bronchiolitis and pneumonia in infants under one year of age. Most children become infected with RSV prior to their second birthday resulting in 75-125,000 hospitalizations. The associated medical costs are thought to exceed $650 million annually in the United States alone. In addition, early-life, respiratory viral infections, notably with RSV, increase the risk of the subsequent development of childhood asthma (Holt and Sly, 2002.). RSV infection can produce severe, lower respiratory tract disease in patients of any age. The elderly, as well as those having compromised cardiac, pulmonary or immune systems are particularly vulnerable and it is estimated that some 14,000 deaths occur annually in the United States in subjects over 65 years old. In addition, RSV infection is increasingly regarded as an important precipitator of exacerbations in patients suffering from chronic obstructive pulmonary disease (COPD) (Mohan et al., 2010) as well as asthma (Newcomb and Peebles, 2009) and cystic fibrosis (Abman et al., 1988). In immunocompromised adults approximately 50% of upper respiratory tract infections with RSV progress to pneumonia.

The initial portal of entry by RSV is through the nose or eye rather than the mouth (Hall et al., 1981). Once established in the upper respiratory tract the virus is able to migrate readily into the lungs. The pathophysiology of RSV infection was investigated in a study of lung tissues obtained from deceased children (Johnson et al., 2007). Examination of tissues from four individuals revealed immunostaining of epithelial cells indicating the presence of RSV, without basal cells being affected. The epithelial localisation of the pathogenic organism provides a challenge to treatment since a supra-effective concentration of the drug substance has to be maintained at the discrete cellular site to enable the infection to be treated and subsequently cleared.

The RSV virus exists as two antigenic sub-groups: A and B. Viruses of the RSV A strain were formerly regarded as the sub-group pathogens responsible for the majority of clinical disease and were reported to produce a more symptomatic pathology (Walsh et al., 1997; Panayiotou et al., 2014). A common RSV A strain is RSV A2 (Olivier et al., 2009). However, during a recent outbreak in China virus strains from the RSV B sub-group were found to predominate in the afflicted population (Zhang et al., 2010).

Over the last two decades considerable progress has been made in the treatment of a number of viral diseases including human immunodeficiency virus (HIV) and both hepatitis B and hepatitis C. In all these cases gold standard therapies have evolved that consist of combination treatments that were brought about, at least to some extent, in response to the emergence of drug resistant disease.

FDA-approved drugs for the treatment of acute RSV infections comprise of (aerosolised) ribavirin and the humanised monoclonal antibody, palivizumab (Synagis). The latter agent targets the RSV fusion (F) protein and is limited to prophylactic use in high risk paediatric patients. Furthermore, clinical variants resistant to neutralisation by palivizumab were recently identified (Zhu et al., 2011) and therefore no truly effective vaccine is currently available. The use of ribavirin is limited by its low potency against the virus and by concerns over its side-effect profile. Consequently there is an urgent, unmet need for the discovery of novel, safe and effective therapies against RSV infection having an improved clinical profile. Moreover, in view of the emerging prominence of the RSV B strains in clinical disease it is highly desirable that these treatments be efficacious against infections arising from both RSV A and RSV B strains.

SUMMARY OF THE INVENTION

In a first aspect, the invention provides a compound of formula (I),

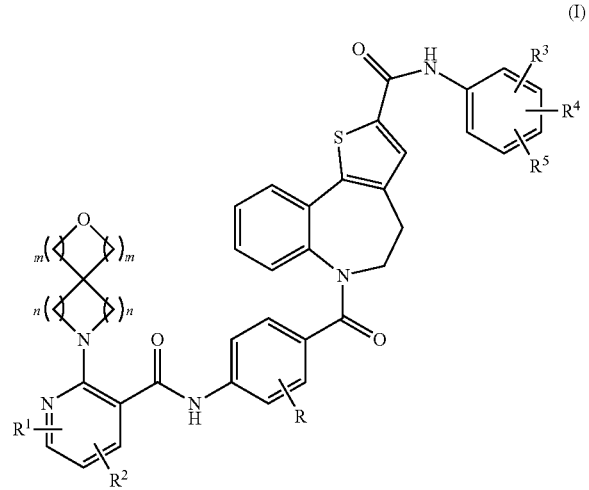

wherein:
R represents hydrogen or halo;
$R^3$ represents hydrogen, hydroxy, halo, cyano, $C_{1-4}$ alkyl, $C_{2-4}$ alkenyl, $C_{2-4}$ alkynyl, $C_{1-4}$ haloalkyl, $C_{3-6}$ cycloalkyl, $C_{1-4}$ alkoxy, $C_{1-4}$ hydroxyalkyl, $C_{1-4}$ haloalkoxy, —O(CH$_2$)$_2$OH or —O(CH$_2$)$_2$OC$_{1-2}$ alkyl;
$R^4$ represents hydrogen, halo, cyano, $C_{1-4}$ alkyl, $C_{2-4}$ alkenyl, $C_{2-4}$ alkynyl, $C_{1-4}$ haloalkyl, $C_{3-6}$ cycloalkyl, $C_{1-4}$ alkoxy or $C_{1-4}$ haloalkoxy;
$R^5$ represents hydrogen, halo, cyano, $C_{1-4}$ alkyl, $C_{2-4}$ alkenyl, $C_{2-4}$ alkynyl, $C_{1-4}$ haloalkyl, $C_{3-6}$ cycloalkyl, $C_{1-4}$ alkoxy or $C_{1-4}$ haloalkoxy;

m and n represent integers which may be independently selected from 1 and 2; and either (a) $R^1$ represents hydrogen, $C_{1-4}$ alkyl, $C_{2-4}$ alkenyl, $C_{2-4}$ alkynyl, $C_{1-4}$ haloalkyl, $C_{3-6}$ cycloalkyl, $C_{1-4}$ alkoxy, $C_{1-2}$ alkoxy$C_{1-2}$ alkyl or $C_{1-4}$ haloalkoxy; and $R^2$ represents hydrogen, halo, $C_{1-4}$ alkyl, $C_{2-4}$ alkenyl, $C_{2-4}$ alkynyl, $C_{1-4}$ haloalkyl, $C_{3-6}$ cycloalkyl, $C_{1-4}$ alkoxy, $C_{1-4}$ haloalkoxy, $C_{1-2}$ alkoxy$C_{1-2}$ alkyl, $C_{1-4}$ hydroxyalkyl, or cyano; or (b) $R^1$ and $R^2$ are in positions 6 and 5 respectively of the pyridine nucleus and are joined to form a bicyclic system comprising either a 5- or 6-membered carbocyclic ring or a 5- or 6-membered heterocyclic ring which contains heteroatoms selected only from O and S, which is fused to said pyridine nucleus;

or a pharmaceutically acceptable salt thereof ("compounds of the invention").

Biological data disclosed in the Examples reveals that compounds of the invention inhibit the cytopathic effect associated with infection by RSV A strains, and in preferred embodiments also inhibit the cytopathic effect associated with infection by RSV B strains.

DETAILED DESCRIPTION OF THE INVENTION

Figure 1:
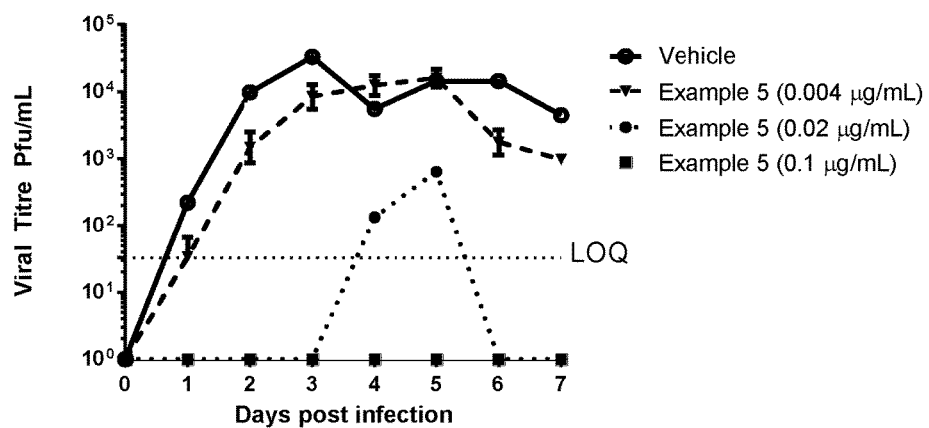
FIG. 1 shows the effect of Example 5 on virus titre in RSV A2 infected air-liquid interface (ALI) cultured epithelial cells following early intervention with test compound

Alkyl as used herein refers to straight chain or branched chain alkyl, such as, without limitation, methyl, ethyl, n-propyl, iso-propyl, butyl, n-butyl and tert-butyl. In one embodiment alkyl refers to straight chain alkyl.

Lower alkyl as used herein refers to $C_{1-4}$alkyl such as methyl or ethyl.

Alkoxy as used herein refers to straight or branched chain alkoxy, for example methoxy, ethoxy, propoxy, butoxy. Alkoxy as employed herein also extends to embodiments in which one or two oxygen atoms (e.g. a single oxygen atom) is located within the alkyl chain, for example —CH$_2$CH$_2$CH$_2$OCH$_3$, —CH$_2$CH$_2$OCH$_3$, —CH$_2$OCH$_2$CH$_2$OCH$_3$, or —CH$_2$OCH$_3$. Thus in one embodiment the alkoxy is linked through carbon to the remainder of the molecule, for example —C$_n$alkyl-O—C$_m$alkyl in which n=1 or 2 and m=1 or 2. In one embodiment the alkoxy group is linked through oxygen to the remainder of the molecule, for example —OC$_{1-4}$alkyl. In one embodiment the disclosure relates to straight chain alkoxy. In one embodiment the alkoxy is linked through oxygen to the remainder of the molecule but the alkoxy group contains a further oxygen atom, for example —OCH$_2$CH$_2$OCH$_3$.

Halo or halogen includes fluoro, chloro, bromo or iodo, in particular fluoro, chloro or bromo, especially fluoro or chloro.

Alkyl substituted by halo (haloalkyl) as employed herein refers to alkyl groups having 1 to 6 halogen atoms, for example 1 to 5 halogens, such as per haloalkyl, in particular perfluoroalkyl, more specifically —CF$_2$CF$_3$ or CF$_3$.

Alkoxy substituted by halo (haloalkoxy) as employed herein refers to alkoxy groups having 1 to 6 halogen atoms, for example 1 to 5 halogens, such as perhaloalkoxy, in particular perfluoroalkoxy, more specifically —OCF$_2$CF$_3$ or —OCF$_3$.

$C_{1-4}$ alkyl includes $C_1$, $C_2$, $C_3$ and $C_4$ alkyl. $C_{1-4}$ alkoxy includes $C_1$, $C_2$, $C_3$ and $C_4$ alkoxy. $C_{1-4}$ haloalkyl includes $C_1$, $C_2$, $C_3$ and $C_4$ haloalkyl. $C_{1-4}$ haloalkoxy includes $C_1$, $C_2$, $C_3$ and $C_4$ haloalkoxy.

$C_{3-6}$ cycloalkyl denotes a saturated, optionally branched carbocycle containing 3-6 carbon atoms. Unbranched examples include cyclopropyl, cyclobutyl, cyclopentyl and cyclohexyl. Branched examples include 2-methylcyclopropyl.

$C_{2-4}$ alkynyl means an unsaturated aliphatic, optionally branched moiety containing at least one triple bond. Examples include —C≡CH, —CH$_2$—C≡CH, —CH(CH$_3$)—C≡CH, —CH$_2$—C≡C—CH$_3$ and —C≡C—CH$_3$. Preferred alkynyl is $C_{2-3}$ alkynyl e.g. —C≡CH.

$C_{2-4}$ alkenyl signifies an unsaturated, aliphatic, optionally branched moiety containing at least one double bond and no triple bonds. Examples include —CH=CH$_2$, —CH$_2$—CH=CH$_2$, —CH(CH$_3$)—CH=CH$_2$, —CH$_2$—CH=CH(CH$_3$), —CH=CH—CH$_3$ and —CH=C(CH$_3$)$_2$. A preferred alkenyl is $C_{2-3}$ alkenyl, such as vinyl.

$C_{1-2}$ alkoxy$C_2$ alkyl includes a moiety such as CH$_3$OCH$_2$—.

When $R^1$ and $R^2$ are in positions 6 and 5 respectively of the pyridine nucleus and are joined to form a bicyclic system comprising either a 5- or 6-membered carbocyclic ring or a 5- or 6-membered heterocyclic ring which contains heteroatoms selected only from O and S, which is fused to said pyridine nucleus, said bicyclic system may be partially unsaturated or fully aromatic. Said heterocyclic ring may suitably contain 1 or 2 (preferably 1) heteroatom(s) selected from O and S. In one embodiment said heterocyclic ring contains 1 heteroatom which is O. In another embodiment said heterocyclic ring contains 1 heteroatom which is S.

When $R^1$ and $R^2$ are in positions 6 and 5 respectively of the pyridine nucleus and are joined to form a bicyclic system comprising either a 5- or 6-membered carbocyclic ring or a 5- or 6-membered heterocyclic ring which contains heteroatoms selected only from O and S, which is fused to said pyridine nucleus, examples include partially unsaturated bicyclic systems, for example, 6,7-dihydro-5H-cyclopenta[b]pyridine, and 5,6,7,8-tetrahydroquinoline and fully aromatic bicyclic systems such as quinoline.

When $R^1$ and $R^2$ are in positions 6 and 5 respectively of the pyridine nucleus and are joined to form a bicyclic system comprising either a 5- or 6-membered carbocyclic ring or a 5- or 6-membered heterocyclic ring which contains heteroatoms selected only from O and S, which is fused to said pyridine nucleus, examples include fully aromatic bicyclic systems such as thienopyridines (e.g. thieno[2,3-b]pyridine, thieno[3,4-b]pyridine or thieno[3,2-b]pyridine) and partially unsaturated bicyclic systems including dihydropyranopyridines (e.g. 3,4-dihydro-2H-pyrano[2,3-b]pyridine, 6,8-dihydro-5H-pyrano[3,4-b]pyridine, 7,8-dihydro-2H-pyrano[4,3-b]pyridine or 3,4-dihydro-2H-pyrano[3,2-b]pyridine).

Suitably n represents 1. Suitably m represents 2. Suitably n represents 1 and m represents 2. According to a less preferred alternative, n represents 2 and m represents 1. According to another less preferred alternative, n represents 1 and m represents 1. According to a still less preferred alternative, n represents 2 and m represents 2.

In one embodiment of the present invention there is provided a compound of formula (Ia):

(Ia)

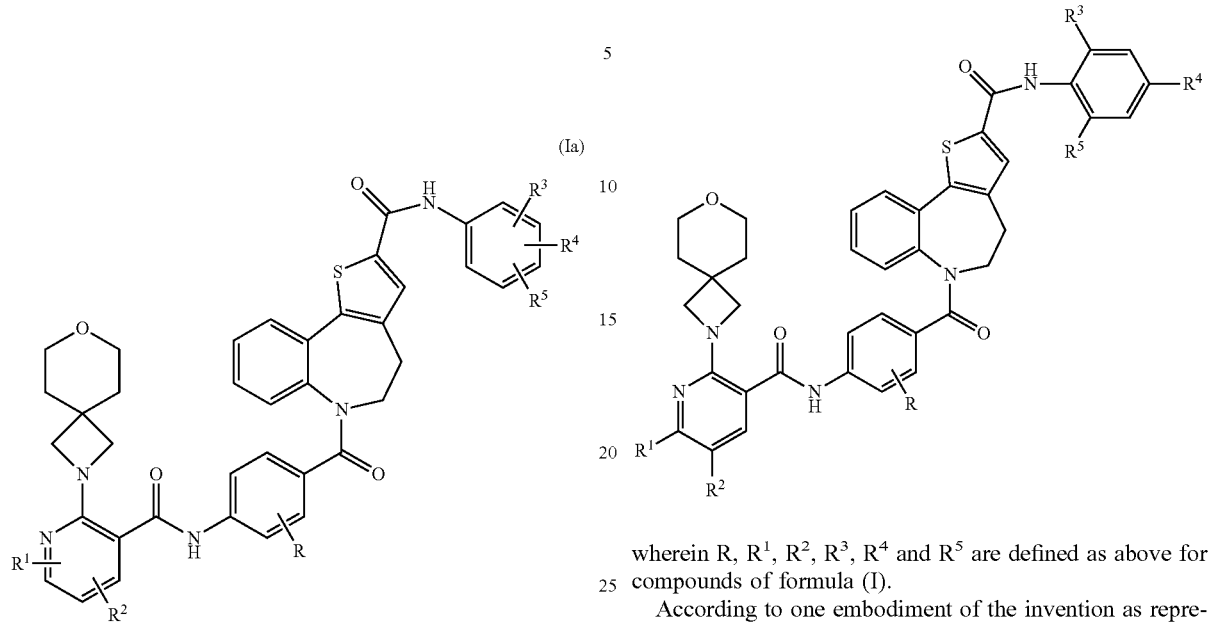

wherein R, R¹, R², R³, R⁴ and R⁵ are as defined above for compounds of formula (I).

In a second embodiment of the invention there is provided a compound of formula (Ib):

(Ib)

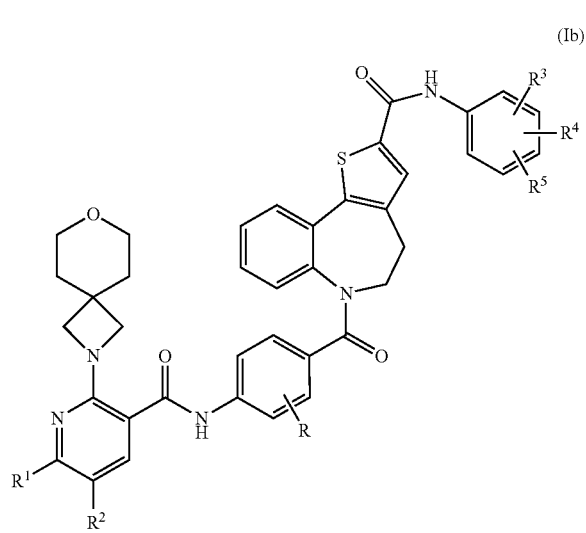

wherein R, R¹, R², R³, R⁴ and R⁵ are defined as above for compounds of formula (I).

In a third embodiment of the invention there is provided a compound of formula (Ic):

(Ic)

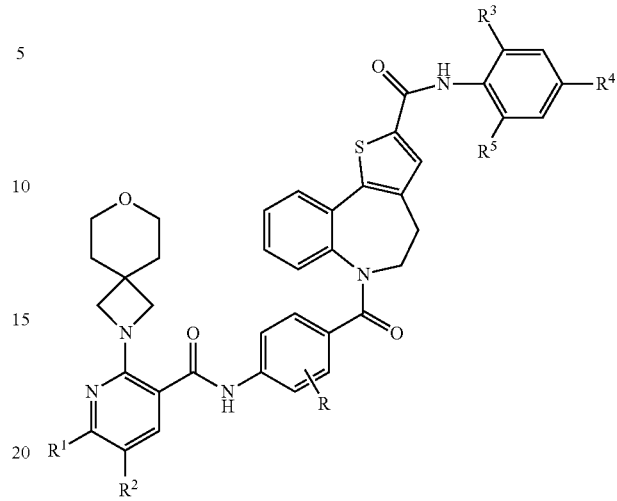

wherein R, R¹, R², R³, R⁴ and R⁵ are defined as above for compounds of formula (I).

According to one embodiment of the invention as represented by structures (I), (Ia), (Ib) or (Ic):

R represents hydrogen or halo;

$R^1$ represents hydrogen, $C_{1-4}$ alkyl, $C_{2-4}$ alkenyl, $C_{2-4}$ alkynyl, $C_{1-4}$ haloalkyl, $C_{3-6}$ cycloalkyl, $C_{1-4}$ alkoxy or $C_{1-4}$ haloalkoxy;

$R^2$ represents hydrogen, halo, $C_{1-4}$ alkyl, $C_{2-4}$ alkenyl, $C_{2-4}$ alkynyl, $C_{1-4}$ haloalkyl, $C_{3-6}$ cycloalkyl, $C_{1-4}$ alkoxy, $C_{1-4}$ haloalkoxy or cyano;

$R^3$ represents hydrogen, hydroxy, halo, cyano, $C_{1-4}$ alkyl, $C_{2-4}$ alkenyl, $C_{2-4}$ alkynyl, $C_{1-4}$ haloalkyl, $C_{3-6}$ cycloalkyl, $C_{1-4}$ alkoxy or $C_{1-4}$ haloalkoxy;

$R^4$ represents hydrogen, halo, cyano, $C_{1-4}$ alkyl, $C_{2-4}$ alkenyl, $C_{2-4}$ alkynyl, $C_{1-4}$ haloalkyl, $C_{3-6}$ cycloalkyl, $C_{1-4}$ alkoxy or $C_{1-4}$ haloalkoxy;

$R^5$ represents hydrogen, halo, cyano, $C_{1-4}$ alkyl, $C_{2-4}$ alkenyl, $C_{2-4}$ alkynyl, $C_{1-4}$ haloalkyl, $C_{3-6}$ cycloalkyl, $C_{1-4}$ alkoxy or $C_{1-4}$ haloalkoxy;

and m and n represent integers which may be independently selected from 1 and 2.

Particular embodiments of the invention, independently and in any combination, include the following:

R is preferably in the 3-position of the phenyl ring to which it is attached (i.e. the position adjacent to the carbonyl).

R is preferably hydrogen or fluoro, particularly hydrogen.

$R^1$ and $R^2$ are preferably, respectively, in the 6- and 5-positions of the pyridyl ring to which they are attached.

In an embodiment, $R^1$ represents hydrogen, $C_{1-4}$ alkyl, $C_{2-4}$ alkenyl, $C_{2-4}$ alkynyl, $C_{1-4}$ haloalkyl, $C_{3-6}$ cycloalkyl, $C_{1-4}$ alkoxy or $C_{1-4}$ haloalkoxy; and $R^2$ represents hydrogen, halo, $C_{1-4}$ alkyl, $C_{2-4}$ alkenyl, $C_{2-4}$ alkynyl, $C_{1-4}$ haloalkyl, $C_{3-6}$ cycloalkyl, $C_{1-4}$ alkoxy, $C_{1-4}$ haloalkoxy or cyano.

In an embodiment, $R^1$ and $R^2$ are, respectively, in the 6- and 5-positions of the pyridyl ring to which they are attached, and are defined as follows: $R^1$ and $R^2$ represent H; $R^1$ and $R^2$ represent Me; $R^1$ represents OMe and $R^2$ represents H; $R^1$ represents Me and $R^2$ represents H; $R^1$ represents H and $R^2$ represents cyclopropyl; $R^1$ represents H and $R^2$ represents Me; $R^1$ represents H and $R^2$ represents Et; $R^1$ represents H and $R^2$ represents ethynyl; $R^1$ represents H and $R^2$ represents —CH₂OMe; $R^1$ represents H and $R^2$ represents F; $R^1$ represents H and $R^2$ represents Cl; $R^1$ represents H and $R^2$ represents OMe; or $R^1$ represents H and $R^2$ represents C(=CH$_2$)Me.

Preferably one of $R^1$ and $R^2$ is C$_{1-4}$ alkyl, more preferably methyl, and the other is hydrogen (for example $R^1$ is hydrogen and $R^2$ is methyl). Alternatively, $R^1$ and $R^2$ are both hydrogen. In another embodiment, $R^1$ and $R^2$ are both methyl.

In an embodiment (i) $R^1$ is hydrogen in the 6-position of the pyridine ring and $R^2$ is methyl in the 5-position of the pyridine ring; or (ii) $R^1$ is methyl in the 6-position of the pyridine ring and $R^2$ is hydrogen in the 5-position of the pyridine ring; or (iii) $R^1$ is methyl in the 6-position of the pyridine ring and $R^2$ is methyl in the 5-position of the pyridine ring; or (iv) $R^1$ and $R^2$ both represent hydrogen; or (v) $R^1$ is methoxy in the 6-position of the pyridine ring and $R^2$ is hydrogen in the 5-position of the pyridine ring; or (vi) $R^1$ is hydrogen in the 6-position of the pyridine ring and $R^2$ is cyclopropyl in the 5-position of the pyridine ring. Preferably $R^1$ is hydrogen in the 6-position of the pyridine ring and $R^2$ is methyl in the 5-position of the pyridine ring.

In an alternative embodiment, $R^1$ and $R^2$ are in positions 6 and 5 respectively of the pyridine nucleus and are joined to form a bicyclic system in which a 5- or 6-membered carbocyclic or heterocyclic ring is fused to said pyridine nucleus.

Preferably $R^3$ represents hydrogen, hydroxy, halo, cyano, C$_{1-4}$ alkyl, C$_{2-4}$ alkenyl, C$_{2-4}$ alkynyl, C$_{1-4}$ haloalkyl, C$_{3-6}$ cycloalkyl, C$_{1-4}$ alkoxy or C$_{1-4}$ haloalkoxy.

Preferably $R^3$, $R^4$ and $R^5$ are selected from hydrogen, halo, C$_{1-4}$ alkyl, C$_{2-4}$ alkenyl, C$_{2-4}$ alkynyl, C$_{1-4}$ haloalkyl, C$_{1-4}$ haloalkoxy, C$_{1-4}$ alkoxy and cyano.

Preferably $R^5$ is selected from hydrogen, halo, C$_{1-4}$ alkyl, C$_{2-4}$ alkenyl, C$_{2-4}$ alkynyl, C$_{1-4}$ haloalkyl, C$_{1-4}$ haloalkoxy and C$_{1-4}$ alkoxy.

Preferably one of $R^3$, $R^4$ and $R^5$ is hydrogen and the remainder are substituent(s) other than hydrogen.

Alternatively, preferably, two of $R^3$, $R^4$ and $R^5$ is hydrogen and the remainder is a substituent other than hydrogen.

Preferably one of $R^3$, $R^4$ and $R^5$ is hydrogen and the remainder are selected from the group consisting of methyl, hydroxy, trifluormethyl, cyano and halo, more preferably methyl, trifluormethyl, cyano and halo, still more preferably methyl, fluoro, chloro and trifluoromethyl, and most preferably methyl, fluoro and chloro.

When one of $R^3$, $R^4$ and $R^5$ is other than hydrogen the said group is preferably located in the 2-position of the phenyl ring to which it is attached. When two of $R^3$, $R^4$ and $R^5$ are other than hydrogen the said groups are preferably located in the 2- and 6-positions of the phenyl ring to which they are attached.

When any of $R^3$, $R^4$ and $R^5$ are other than hydrogen, they are preferably halo, C$_{1-4}$ alkyl, C$_{2-4}$ alkenyl, C$_{2-4}$ alkynyl, C$_{1-4}$ haloalkyl, C$_{1-4}$ haloalkoxy, C$_{1-4}$ alkoxy or cyano and more preferably methyl, trifluormethyl, cyano or halo, and most preferably fluoro or chloro, particularly fluoro. Suitably n represents 1 and m represents 2.

For example $R^3$, $R^4$ and $R^5$ taken together with the phenyl ring to which they are attached may be selected from:
phenyl, 2-cyanophenyl, 2-fluorophenyl, 2-fluoro-6-iodopheny, 2-fluoro-6-cyclopropylphenyl, 2-fluoro-6-methylphenyl, 2,6-difluorophenyl, 2-methylphenyl, 2-chlorophenyl, 2-ethylphenyl, 4-ethynylphenyl, 2,4-difluorophenyl, 2-fluoro-4-chlorophenyl, 2-fluoro-4-methylphenyl, 2-fluoro-4-methoxyphenyl, 2,6-dimethylphenyl, 2-fluoro-6-chlorophenyl, 2-chloro-4-fluoro phenyl, 2,4,6-trifluorophenyl, 2-chlorophenyl, 2-methyl-6-cyanophenyl, 2-fluoro-6-vinyl, 2-fluoro-6-ethynyl, 2-fluoro-6-chloro, 2-fluoro-6-cyano, 2-fluoro-6-hydroxy, 2-fluoro-6-methoxy, 2-fluoro-6-OCH$_2$CH$_2$OH, 2-fluoro-6-OCH$_2$CH$_2$OMe, 2-fluoro-6-CH$_2$OH and 2-fluoro-6-trifluoro methyl.

Exemplary compounds of formula (I) are selected from the group consisting of:
6-(4-(2-(7-oxa-2-azaspiro[3.5]nonan-2-yl)nicotinamido) benzoyl)-N-phenyl-5,6-dihydro-4H-benzo[b]thieno[2,3-d]azepine-2-carboxamide;
6-(4-(2-(7-oxa-2-azaspiro[3.5]nonan-2-yl)nicotinamido) benzoyl)-N-(2-cyanophenyl)-5,6-dihydro-4H-benzo[b] thieno[2,3-d]azepine-2-carboxamide;
6-(4-(6-methoxy-2-(7-oxa-2-azaspiro[3.5]nonan-2-yl)nicotinamido)benzoyl)-N-(2-fluorophenyl)-5,6-dihydro-4H-benzo[b]thieno[2,3-d]azepine-2-carboxamide;
6-(4-(5-cyclopropyl-2-(7-oxa-2-azaspiro[3.5]nonan-2-yl) nicotinamido) benzoyl)-N-(2-fluorophenyl)-5,6-dihydro-4H-benzo[b]thieno[2,3-d]azepine-2-carboxamide;
6-(4-(2-(7-oxa-2-azaspiro[3.5]nonan-2-yl)nicotinamido) benzoyl)-N-(o-tolyl)-5,6-dihydro-4H-benzo[b]thieno[2, 3-d]azepine-2-carboxamide;
6-(4-(2-(7-oxa-2-azaspiro[3.5]nonan-2-yl)nicotinamido) benzoyl)-N-(2-fluorophenyl)-5,6-dihydro-4H-benzo[b] thieno[2,3-d]azepine-2-carboxamide;
6-(4-(2-(7-oxa-2-azaspiro[3.5]nonan-2-yl)nicotinamido) benzoyl)-N-(2-chlorophenyl)-5,6-dihydro-4H-benzo[b] thieno[2,3-d]azepine-2-carboxamide;
6-(4-(2-(7-oxa-2-azaspiro[3.5]nonan-2-yl)nicotinamido) benzoyl)-N-(2-ethylphenyl)-5,6-dihydro-4H-benzo[b] thieno[2,3-d]azepine-2-carboxamide;
6-(4-(2-(7-oxa-2-azaspiro[3.5]nonan-2-yl)nicotinamido) benzoyl)-N-(4-ethynylphenyl)-5,6-dihydro-4H-benzo[b] thieno[2,3-d]azepine-2-carboxamide;
6-(4-(2-(7-oxa-2-azaspiro[3.5]nonan-2-yl)nicotinamido) benzoyl)-N-(2,6-difluorophenyl)-5,6-dihydro-4H-benzo [b]thieno[2,3-d]azepine-2-carboxamide;
6-(4-(2-(7-oxa-2-azaspiro[3.5]nonan-2-yl)nicotinamido) benzoyl)-N-(2,4-difluorophenyl)-5,6-dihydro-4H-benzo [b]thieno[2,3-d]azepine-2-carboxamide;
6-(4-(2-(7-oxa-2-azaspiro[3.5]nonan-2-yl)nicotinamido) benzoyl)-N-(4-chloro-2-fluorophenyl)-5,6-dihydro-4H-benzo[b]thieno[2,3-d]azepine-2-carboxamide;
6-(4-(2-(7-oxa-2-azaspiro[3.5]nonan-2-yl)nicotinamido) benzoyl)-N-(2-fluoro-4-methylphenyl)-5,6-dihydro-4H-benzo[b]thieno[2,3-d]azepine-2-carboxamide;
6-(4-(2-(7-oxa-2-azaspiro[3.5]nonan-2-yl)nicotinamido) benzoyl)-N-(2-fluoro-4-methoxy phenyl)-5,6-dihydro-4H-benzo[b]thieno[2,3-d]azepine-2-carboxamide;
6-(4-(2-(7-oxa-2-azaspiro[3.5]nonan-2-yl)nicotinamido) benzoyl)-N-(2,6-dimethylphenyl)-5,6-dihydro-4H-benzo [b]thieno[2,3-d]azepine-2-carboxamide;
6-(4-(2-(7-oxa-2-azaspiro[3.5]nonan-2-yl)nicotinamido) benzoyl)-N-(2-fluoro-6-methylphenyl)-5,6-dihydro-4H-benzo[b]thieno[2,3-d]azepine-2-carboxamide;
6-(4-(2-(7-oxa-2-azaspiro[3.5]nonan-2-yl)nicotinamido) benzoyl)-N-(2-chloro-6-fluorophenyl)-5,6-dihydro-4H-benzo[b]thieno[2,3-d]azepine-2-carboxamide;
6-(4-(2-(7-oxa-2-azaspiro[3.5]nonan-2-yl)nicotinamido) benzoyl)-N-(2-chloro-4-fluorophenyl)-5,6-dihydro-4H-benzo[b]thieno[2,3-d]azepine-2-carboxamide;
6-(4-(2-(7-oxa-2-azaspiro[3.5]nonan-2-yl)nicotinamido) benzoyl)-N-(2,4,6-trifluorophenyl)-5,6-dihydro-4H-benzo[b]thieno[2,3-d]azepine-2-carboxamide;
6-(4-(2-(7-oxa-2-azaspiro[3.5]nonan-2-yl)nicotinamido)-2-fluorobenzoyl)-N-(2-fluorophenyl)-5,6-dihydro-4H-benzo[b]thieno[2,3-d]azepine-2-carboxamide;

6-(4-(2-(7-oxa-2-azaspiro[3.5]nonan-2-yl)nicotinamido)-2-fluorobenzoyl)-N-(2,6-difluorophenyl)-5,6-dihydro-4H-benzo[b]thieno[2,3-d]azepine-2-carboxamide;

6-(4-(2-(7-oxa-2-azaspiro[3.5]nonan-2-yl)nicotinamido)-2-fluorobenzoyl)-N-(2-chloro-6-fluorophenyl)-5,6-dihydro-4H-benzo[b]thieno[2,3-d]azepine-2-carboxamide;

6-(4-(5-methyl-2-(7-oxa-2-azaspiro[3.5]nonan-2-yl)nicotinamido) benzoyl)-N-phenyl-5,6-dihydro-4H-benzo[b]thieno[2,3-d]azepine-2-carboxamide;

N-(2-fluorophenyl)-6-(4-(5-methyl-2-(7-oxa-2-azaspiro[3.5]nonan-2-yl)nicotinamido)benzoyl)-5,6-dihydro-4H-benzo[b]thieno[2,3-d]azepine-2-carboxamide;

N-(2-chlorophenyl)-6-(4-(5-methyl-2-(7-oxa-2-azaspiro[3.5]nonan-2-yl)nicotinamido)benzoyl)-5,6-dihydro-4H-benzo[b]thieno[2,3-d]azepine-2-carboxamide;

6-(4-(5-methyl-2-(7-oxa-2-azaspiro[3.5]nonan-2-yl)nicotinamido) benzoyl)-N-(o-tolyl)-5,6-dihydro-4H-benzo[b]thieno[2,3-d]azepine-2-carboxamide;

N-(2-fluoro-6-methylphenyl)-6-(4-(5-methyl-2-(7-oxa-2-azaspiro[3.5]nonan-2-yl)nicotinamido) benzoyl)-5,6-dihydro-4H-benzo[b]thieno[2,3-d]azepine-2-carboxamide;

N-(2,4-difluorophenyl)-6-(4-(5-methyl-2-(7-oxa-2-azaspiro[3.5]nonan-2-yl)nicotinamido) benzoyl)-5,6-dihydro-4H-benzo[b]thieno[2,3-d]azepine-2-carboxamide;

N-(2-chloro-6-fluorophenyl)-6-(4-(5-methyl-2-(7-oxa-2-azaspiro[3.5]nonan-2-yl)nicotinamido) benzoyl)-5,6-dihydro-4H-benzo[b]thieno[2,3-d]azepine-2-carboxamide;

N-(2-fluoro-6-methylphenyl)-6-(4-(6-methyl-2-(7-oxa-2-azaspiro[3.5]nonan-2-yl)nicotinamido) benzoyl)-5,6-dihydro-4H-benzo[b]thieno[2,3-d]azepine-2-carboxamide;

N-(2-chloro-6-fluorophenyl)-6-(4-(6-methyl-2-(7-oxa-2-azaspiro[3.5]nonan-2-yl)nicotinamido) benzoyl)-5,6-dihydro-4H-benzo[b]thieno[2,3-d]azepine-2-carboxamide;

6-(4-(5,6-dimethyl-2-(7-oxa-2-azaspiro[3.5]nonan-2-yl) nicotinamido)benzoyl)-N-(o-tolyl)-5,6-dihydro-4H-benzo[b]thieno[2,3-d]azepine-2-carboxamide;

6-(4-(5,6-dimethyl-2-(7-oxa-2-azaspiro[3.5]nonan-2-yl) nicotinamido)benzoyl)-N-(2-fluorophenyl)-5,6-dihydro-4H-benzo[b]thieno[2,3-d]azepine-2-carboxamide;

6-(4-(5,6-dimethyl-2-(7-oxa-2-azaspiro[3.5]nonan-2-yl) nicotinamido)benzoyl)-N-(2-fluoro-6-methylphenyl)-5,6-dihydro-4H-benzo[b]thieno[2,3-d]azepine-2-carboxamide;

N-(2,4-difluorophenyl)-6-(4-(5,6-dimethyl-2-(7-oxa-2-azaspiro[3.5]nonan-2-yl)nicotinamido) benzoyl)-5,6-dihydro-4H-benzo[b]thieno[2,3-d]azepine-2-carboxamide;

N-(2-chloro-6-fluorophenyl)-6-(4-(5,6-dimethyl-2-(7-oxa-2-azaspiro[3.5]nonan-2-yl)nicotinamido) benzoyl)-5,6-dihydro-4H-benzo[b]thieno[2,3-d]azepine-2-carboxamide;

and pharmaceutically acceptable salts of any one thereof.

Further exemplary compounds of formula (I) are selected from the group consisting of:

N-(2-fluoro-6-iodophenyl)-6-(4-(5-methyl-2-(7-oxa-2-azaspiro[3.5]nonan-2-yl)nicotinamido) benzoyl)-5,6-dihydro-4H-benzo[b]thieno[2,3-d]azepine-2-carboxamide;

N-(2-cyclopropyl-6-fluorophenyl)-6-(4-(5-methyl-2-(7-oxa-2-azaspiro[3.5]nonan-2-yl)nicotinamido) benzoyl)-5,6-dihydro-4H-benzo[b]thieno[2,3-d]azepine-2-carboxamide;

6-(4-(2-(7-oxa-2-azaspiro[3.5]nonan-2-yl)-6,7-dihydro-5H-cyclopenta[b]pyridine-3-carboxamido)benzoyl)-N-(2-fluoro-6-methylphenyl)-5,6-dihydro-4H-benzo[b]thieno[2,3-d]azepine-2-carboxamide;

6-(4-(2-(7-oxa-2-azaspiro[3.5]nonan-2-yl)-5,6,7,8-tetrahydroquinoline-3-carboxamido) benzoyl)-N-(2-fluoro-6-methylphenyl)-5,6-dihydro-4H-benzo[b]thieno[2,3-d]azepine-2-carboxamide;

6-(4-(2-(7-oxa-2-azaspiro[3.5]nonan-2-yl)quinoline-3-carboxamido)benzoyl)-N-(2-fluoro-6-methylphenyl)-5,6-dihydro-4H-benzo[b]thieno[2,3-d]azepine-2-carboxamide;

6-(4-(5-cyclopropyl-2-(7-oxa-2-azaspiro[3.5]nonan-2-yl) nicotinamido) benzoyl)-N-(2-fluoro-6-methylphenyl)-5,6-dihydro-4H-benzo[b]thieno[2,3-d]azepine-2-carboxamide;

N-(4-(2-((2-fluoro-6-methylphenyl)carbamoyl)-5,6-dihydro-4H-benzo[b]thieno[2,3-d]azepine-6-carbonyl) phenyl)-2-(7-oxa-2-azaspiro[3.5]nonan-2-yl)-7,8-dihydro-5H-pyrano[4,3-b]pyridine-3-carboxamide;

6-(4-(5-(7-oxa-2-azaspiro[3.5]nonan-2-yl)thieno[3,2-b] pyridine-6-carboxamido)benzoyl)-N-(2,6-difluorophenyl)-5,6-dihydro-4H-benzo[b]thieno[2,3-d]azepine-2-carboxamide;

N-(2-fluoro-6-vinylphenyl)-6-(4-(5-methyl-2-(7-oxa-2-azaspiro[3.5]nonan-2-yl)nicotinamido) benzoyl)-5,6-dihydro-4H-benzo[b]thieno[2,3-d]azepine-2-carboxamide;

N-(2-ethynyl-6-fluorophenyl)-6-(4-(5-methyl-2-(7-oxa-2-azaspiro[3.5]nonan-2-yl)nicotinamido) benzoyl)-5,6-dihydro-4H-benzo[b]thieno[2,3-d]azepine-2-carboxamide;

N-(2,6-difluorophenyl)-6-(4-(5-methyl-2-(7-oxa-2-azaspiro[3.5]nonan-2-yl)nicotinamido) benzoyl)-5,6-dihydro-4H-benzo[b]thieno[2,3-d]azepine-2-carboxamide;

6-(4-(5-methyl-2-(7-oxa-2-azaspiro[3.5]nonan-2-yl)nicotinamido) benzoyl)-N-(2,4,6-trifluoro phenyl)-5,6-dihydro-4H-benzo[b]thieno[2,3-d]azepine-2-carboxamide;

N-(2,6-difluorophenyl)-6-(4-(6-methyl-2-(7-oxa-2-azaspiro[3.5]nonan-2-yl)nicotinamido) benzoyl)-5,6-dihydro-4H-benzo[b]thieno[2,3-d]azepine-2-carboxamide;

6-(4-(6-methyl-2-(7-oxa-2-azaspiro[3.5]nonan-2-yl)nicotinamido) benzoyl)-N-(2,4,6-trifluoro phenyl)-5,6-dihydro-4H-benzo[b]thieno[2,3-d]azepine-2-carboxamide;

N-(2-cyano-6-fluorophenyl)-6-(4-(5-methyl-2-(7-oxa-2-azaspiro[3.5]nonan-2-yl)nicotinamido) benzoyl)-5,6-dihydro-4H-benzo[b]thieno[2,3-d]azepine-2-carboxamide;

N-(2-fluoro-6-hydroxyphenyl)-6-(4-(5-methyl-2-(7-oxa-2-azaspiro[3.5]nonan-2-yl) nicotinamido) benzoyl)-5,6-dihydro-4H-benzo[b]thieno[2,3-d]azepine-2-carboxamide;

N-(2-fluoro-6-methoxyphenyl)-6-(4-(5-methyl-2-(7-oxa-2-azaspiro[3.5]nonan-2-yl) nicotinamido) benzoyl)-5,6-dihydro-4H-benzo[b]thieno[2,3-d]azepine-2-carboxamide;

N-(2-fluoro-6-(2-hydroxyethoxy) phenyl)-6-(4-(5-methyl-2-(7-oxa-2-azaspiro[3.5]nonan-2-yl) nicotinamido)benzoyl)-5,6-dihydro-4H-benzo[b]thieno[2,3-d]azepine-2-carboxamide;

N-(2-fluoro-6-(2-methoxyethoxy)phenyl)-6-(4-(5-methyl-2-(7-oxa-2-azaspiro[3.5]nonan-2-yl) nicotinamido)benzoyl)-5,6-dihydro-4H-benzo[b]thieno[2,3-d]azepine-2-carboxamide;

N-(2-chloro-6-methylphenyl)-6-(4-(5-methyl-2-(7-oxa-2-azaspiro[3.5]nonan-2-yl)nicotinamido) benzoyl)-5,6-dihydro-4H-benzo[b]thieno[2,3-d]azepine-2-carboxamide;

N-(2,6-dichlorophenyl)-6-(4-(5-methyl-2-(7-oxa-2-azaspiro[3.5]nonan-2-yl)nicotinamido) benzoyl)-5,6-dihydro-4H-benzo[b]thieno[2,3-d]azepine-2-carboxamide;

N-(2-(hydroxymethyl)-6-methylphenyl)-6-(4-(5-methyl-2-(7-oxa-2-azaspiro[3.5]nonan-2-yl) nicotinamido)benzoyl)-5,6-dihydro-4H-benzo[b]thieno[2,3-d]azepine-2-carboxamide;

6-(2-fluoro-4-(5-methyl-2-(7-oxa-2-azaspiro[3.5]nonan-2-yl)nicotinamido)benzoyl)-N-(2,4,6-trifluorophenyl)-5,6-dihydro-4H-benzo[b]thieno[2,3-d]azepine-2-carboxamide;

6-(4-(5-ethyl-2-(7-oxa-2-azaspiro[3.5]nonan-2-yl)nicotinamido)benzoyl)-N-(2-fluoro-6-methylphenyl)-5,6-dihydro-4H-benzo[b]thieno[2,3-d]azepine-2-carboxamide;

N-(2-chloro-6-fluorophenyl)-6-(4-(5-ethyl-2-(7-oxa-2-azaspiro[3.5]nonan-2-yl)nicotinamido) benzoyl)-5,6-dihydro-4H-benzo[b]thieno[2,3-d]azepine-2-carboxamide;

N-(2-cyano-6-methylphenyl)-6-(4-(5-methyl-2-(7-oxa-2-azaspiro[3.5]nonan-2-yl)nicotinamido) benzoyl)-5,6-dihydro-4H-benzo[b]thieno[2,3-d]azepine-2-carboxamide;

N-(2-fluoro-6-(trifluoromethyl)phenyl)-6-(4-(5-methyl-2-(7-oxa-2-azaspiro[3.5]nonan-2-yl) nicotinamido)benzoyl)-5,6-dihydro-4H-benzo[b]thieno[2,3-d]azepine-2-carboxamide;

N-(2,6-dimethylphenyl)-6-(4-(5-methyl-2-(7-oxa-2-azaspiro[3.5]nonan-2-yl)nicotinamido) benzoyl)-5,6-dihydro-4H-benzo[b]thieno[2,3-d]azepine-2-carboxamide;

N-(2-chloro-6-fluorophenyl)-6-(4-(5-cyclopropyl-2-(7-oxa-2-azaspiro[3.5]nonan-2-yl)nicotinamido) benzoyl)-5,6-dihydro-4H-benzo[b]thieno[2,3-d]azepine-2-carboxamide;

N-(2-chloro-6-fluorophenyl)-6-(4-(5-ethynyl-2-(7-oxa-2-azaspiro[3.5]nonan-2-yl)nicotinamido) benzoyl)-5,6-dihydro-4H-benzo[b]thieno[2,3-d]azepine-2-carboxamide;

N-(2-chloro-6-fluorophenyl)-6-(4-(5-(methoxymethyl)-2-(7-oxa-2-azaspiro[3.5]nonan-2-yl) nicotinamido)benzoyl)-5,6-dihydro-4H-benzo[b]thieno[2,3-d]azepine-2-carboxamide;

6-(4-(5-fluoro-2-(7-oxa-2-azaspiro[3.5]nonan-2-yl)nicotinamido)benzoyl)-N-(2-fluoro-6-methylphenyl)-5,6-dihydro-4H-benzo[b]thieno[2,3-d]azepine-2-carboxamide;

6-(4-(5-chloro-2-(7-oxa-2-azaspiro[3.5]nonan-2-yl)nicotinamido)benzoyl)-N-(2-fluoro-6-methylphenyl)-5,6-dihydro-4H-benzo[b]thieno[2,3-d]azepine-2-carboxamide;

N-(2-fluoro-6-methylphenyl)-6-(4-(5-methyl-2-(7-oxa-2-azaspiro[3.5]nonan-2-yl)nicotinamido) benzoyl-2,3,5,6-d4)-5,6-dihydro-4H-benzo[b]thieno[2,3-d]azepine-2-carboxamide;

N-(2-fluoro-6-methylphenyl)-6-(4-(5-methoxy-2-(7-oxa-2-azaspiro[3.5]nonan-2-yl) nicotinamido) benzoyl)-5,6-dihydro-4H-benzo[b]thieno[2,3-d]azepine-2-carboxamide;

6-(4-(5-cyclopropyl-2-(7-oxa-2-azaspiro[3.5]nonan-2-yl) nicotinamido) benzoyl)-N-(2,6-difluorophenyl)-5,6-dihydro-4H-benzo[b]thieno[2,3-d]azepine-2-carboxamide;

N-(2,6-difluorophenyl)-6-(4-(5-(prop-1-en-2-yl)-2-(7-oxa-2-azaspiro[3.5]nonan-2-yl)nicotinamido) benzoyl)-5,6-dihydro-4H-benzo[b]thieno[2,3-d]azepine-2-carboxamide;

6-(4-(2-(7-oxa-2-azaspiro[3.5]nonan-2-yl)-6, 7-dihydro-5H-cyclopenta[b]pyridine-3-carboxamido)benzoyl)-N-(2-cyano-6-methylphenyl)-5,6-dihydro-4H-benzo[b]thieno[2,3-d]azepine-2-carboxamide;

6-(4-(2-(7-oxa-2-azaspiro[3.5]nonan-2-yl)-6, 7-dihydro-5H-cyclopenta[b]pyridine-3-carboxamido)benzoyl)-N-(2,6-difluorophenyl)-5,6-dihydro-4H-benzo[b]thieno[2,3-d]azepine-2-carboxamide;

6-(4-(2-(7-oxa-2-azaspiro[3.5]nonan-2-yl)-6, 7-dihydro-5H-cyclopenta[b]pyridine-3-carboxamido)benzoyl)-N-(2-chloro-6-fluorophenyl)-5,6-dihydro-4H-benzo[b]thieno[2,3-d]azepine-2-carboxamide;

6-(4-(2-(7-oxa-2-azaspiro[3.5]nonan-2-yl)-6, 7-dihydro-5H-cyclopenta[b]pyridine-3-carboxamido)-2-fluorobenzoyl)-N-(2-cyano-6-methylphenyl)-5,6-dihydro-4H-benzo[b]thieno[2,3-d]azepine-2-carboxamide;

6-(4-(2-(7-oxa-2-azaspiro[3.5]nonan-2-yl)-6, 7-dihydro-5H-cyclopenta[b]pyridine-3-carboxamido)-2-fluorobenzoyl)-N-(2-fluoro-6-methylphenyl)-5,6-dihydro-4H-benzo[b]thieno[2,3-d]azepine-2-carboxamide;

6-(4-(2-(7-oxa-2-azaspiro[3.5]nonan-2-yl)-6,7-dihydro-5H-cyclopenta[b]pyridine-3-carboxamido)-2-fluorobenzoyl)-N-(2,6-difluorophenyl)-5,6-dihydro-4H-benzo[b]thieno[2,3-d]azepine-2-carboxamide;

6-(4-(2-(7-oxa-2-azaspiro[3.5]nonan-2-yl)-6, 7-dihydro-5H-cyclopenta[b]pyridine-3-carboxamido)-2-fluorobenzoyl)-N-(2-chloro-6-fluorophenyl)-5,6-dihydro-4H-benzo[b]thieno[2,3-d]azepine-2-carboxamide;

6-(4-(2-(7-oxa-2-azaspiro[3.5]nonan-2-yl)-5,6,7,8-tetrahydroquinoline-3-carboxamido) benzoyl)-N-(2-chloro-6-fluorophenyl)-5,6-dihydro-4H-benzo[b]thieno[2,3-d]azepine-2-carboxamide;

N-(4-(2-((2,6-difluorophenyl)carbamoyl)-5,6-dihydro-4H-benzo[b]thieno[2,3-d]azepine-6-carbonyl) phenyl)-2-(7-oxa-2-azaspiro[3.5]nonan-2-yl)-7,8-dihydro-5H-pyrano[4,3-b] pyridine-3-carboxamide;

N-(4-(2-((2-chloro-6-fluorophenyl)carbamoyl)-5,6-dihydro-4H-benzo[b]thieno[2,3-d]azepine-6-carbonyl) phenyl)-2-(7-oxa-2-azaspiro[3.5]nonan-2-yl)-7, 8-dihydro-5H-pyrano[4, 3-b]pyridine-3-carboxamide;

6-(4-(2-(7-oxa-2-azaspiro[3.5]nonan-2-yl)quinoline-3-carboxamido)benzoyl)-N-(2-fluorophenyl)-5,6-dihydro-4H-benzo[b]thieno[2,3-d]azepine-2-carboxamide;

6-(4-(2-(7-oxa-2-azaspiro[3.5]nonan-2-yl)quinoline-3-carboxamido)benzoyl)-N-(2,4-difluorophenyl)-5,6-dihydro-4H-benzo[b]thieno[2,3-d]azepine-2-carboxamide;

6-(4-(2-(7-oxa-2-azaspiro[3.5]nonan-2-yl)quinoline-3-carboxamido)benzoyl)-N-(2,6-difluorophenyl)-5,6-dihydro-4H-benzo[b]thieno[2,3-d]azepine-2-carboxamide;

6-(4-(2-(7-oxa-2-azaspiro[3.5]nonan-2-yl)quinoline-3-carboxamido)benzoyl)-N-(2-chloro-6-fluorophenyl)-5,6-dihydro-4H-benzo[b]thieno[2,3-d]azepine-2-carboxamide;

6-(4-(2-(7-oxa-2-azaspiro[3.5]nonan-2-yl)quinoline-3-carboxamido)benzoyl)-N-(2,4,6-trifluorophenyl)-5,6-dihydro-4H-benzo[b]thieno[2,3-d]azepine-2-carboxamide;

N-(2-fluoro-6-methyl-phenyl)-6-(4-((5-(7-oxa-2-azaspiro[3.5]nonan-2-yl)thieno[3,2-b]pyridine-6-carbonyl) amino)benzoyl)-4,5-dihydrothieno[3,2-d][1]benzazepine-2-carboxamide;

N-(2-fluoro-6-methylphenyl)-6-(4-(5-methyl-2-(2-oxa-6-azaspiro[3.3]heptan-6-yl)nicotinamido) benzoyl)-5,6-dihydro-4H-benzo[b]thieno[2,3-d]azepine-2-carboxamide;

N-(2-fluoro-6-methylphenyl)-6-(4-(5-methyl-2-(2-oxa-7-azaspiro[3.5]nonan-7-yl)nicotinamido) benzoyl)-5,6-dihydro-4H-benzo[b]thieno[2,3-d]azepine-2-carboxamide;

N-(2,6-difluorophenyl)-6-(4-(5-methyl-2-(2-oxa-7-azaspiro[3.5]nonan-7-yl)nicotinamido) benzoyl)-5,6-dihydro-4H-benzo[b]thieno[2,3-d]azepine-2-carboxamide;

N-(2-chloro-6-fluorophenyl)-6-(4-(5-methyl-2-(2-oxa-7-azaspiro[3.5]nonan-7-yl)nicotinamido) benzoyl)-5,6-dihydro-4H-benzo[b]thieno[2,3-d]azepine-2-carboxamide;

N-(2-fluoro-6-(trifluoromethyl)phenyl)-6-(4-(5-methyl-2-(2-oxa-7-azaspiro[3.5]nonan-7-yl) nicotinamido)benzoyl)-5,6-dihydro-4H-benzo[b]thieno[2,3-d]azepine-2-carboxamide;

N-(2-fluoro-6-methylphenyl)-6-(4-(5-methyl-2-(3-oxa-9-azaspiro[5.5]undecan-9-yl)nicotinamido) benzoyl)-5,6-dihydro-4H-benzo[b]thieno[2,3-d]azepine-2-carboxamide;

and pharmaceutically acceptable salts of any one thereof.

Pharmaceutically acceptable salts of compounds of formula (I) include in particular pharmaceutically acceptable acid addition salts of said compounds. The pharmaceutically acceptable acid addition salts of compounds of formula (I) are meant to comprise the therapeutically active non-toxic acid addition salts that the compounds of formula (I) are able to form. These pharmaceutically acceptable acid addition salts can conveniently be obtained by treating the free base form with such appropriate acids in a suitable solvent or mixture of solvents. Appropriate acids comprise, for example, inorganic acids such as hydrohalic acids, e.g. hydrochloric or hydrobromic acid, sulfuric, nitric, phosphoric acids and the like; or organic acids such as, for example, acetic, propanoic, hydroxyacetic, lactic, pyruvic, malonic, succinic, maleic, fumaric, malic, tartaric, citric, methanesulfonic, ethanesulfonic, benzenesulfonic, p-toluenesulfonic, cyclamic, salicylic, p-aminosalicylic, pamoic acid and the like.

Conversely said salt forms can be converted by treatment with an appropriate base into the free base form.

Salts as referred to herein, for example in relation to intermediate compounds, include pharmaceutically acceptable salts, such as those above mentioned, as well as other salts that may be disfavoured for pharmaceutical use. Salts of acidic compounds include salts formed with positive ions of Group 1 and Group 2 metals including, sodium, potassium, calcium and magnesium ions as well as with inorganic cations such as ammonium ion.

The definition of compounds of formula (I) is intended to include all stereoisomers of said compounds. Stereoisomers as employed herein refers to isomeric molecules that have the same molecular formula and sequence of bonded atoms (constitution), but that differ only in the three-dimensional orientations of their atoms in space. This contrasts with structural isomers, which share the same molecular formula, but the bond connections and/or their order differ(s) between different atoms/groups. In stereoisomers, the order and bond connections of the constituent atoms remain the same, but their orientation in space differs.

The definition of compounds of formula (I) is intended to include all tautomers of said compounds.

The definition of compounds of formula (I) is intended to include all solvates of said compounds (including solvates of salts of said compounds) unless the context specifically indicates otherwise. Examples of solvates include hydrates.

The compounds of the disclosure include those where the atom specified is a naturally occurring or non-naturally occurring isotope. In one embodiment the isotope is a stable isotope.

Thus the compounds of the disclosure include, for example deuterium containing compounds and the like.

The disclosure also extends to all polymorphic forms of the compounds herein defined.

Generic routes by which compound examples of the invention may be conveniently prepared are summarised below.

Thus compounds of formula (I) may be obtained by a general process (Scheme 1) whereby a thiophene carboxylic acid precursor (II), or a suitably protected derivative thereof, is reacted with an activating agent, to generate a reactive, electrophilic carboxylic acid derivative, followed by subsequent reaction with an amine of formula (III), or a suitably protected derivative thereof. It will be understood by persons skilled in the art that, in some instances, the activated carboxylic acid derivative, such as an acid chloride, may be isolated or in other cases may be a transient intermediate that is not isolated, but generated in situ and used directly. The compounds of formula (I) are revealed, in those instances wherein one or more protective groups have been employed by appropriate deprotection steps. An example of such a procedure is the removal of a tert-butoxycarbonyl (Boc) group from a secondary amine, by treatment with an appropriate strong acid, such as TFA.

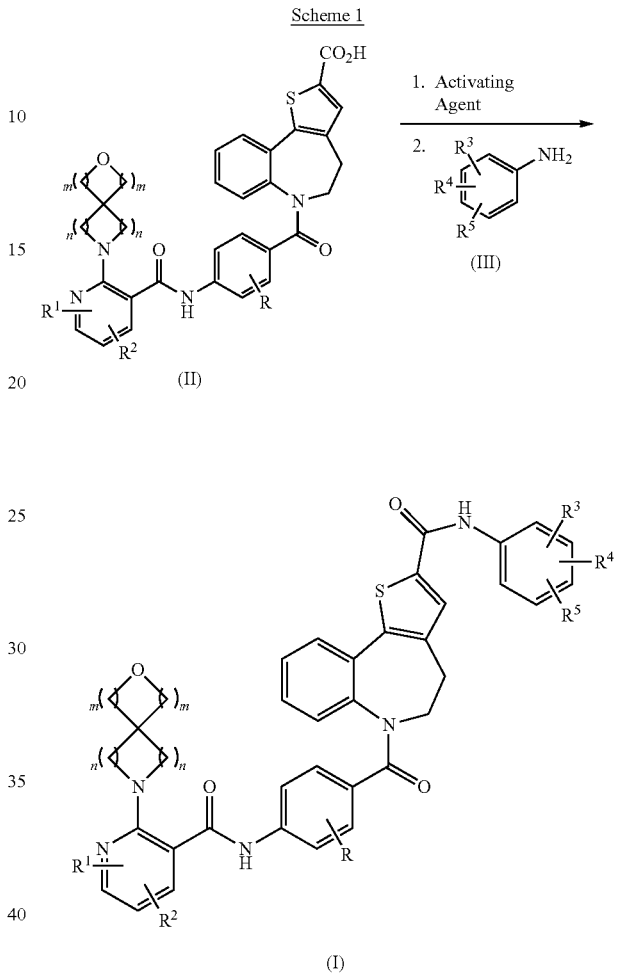

Reagents suitable for the activation of the carboxylate group include carbonyl diimidazole, chloro-N,N,2-trimethylprop-1-en-1-amine and a wide selection of peptide coupling agents such as benzotriazol-1-yloxytripyrrolidinophosphonium hexafluorophosphate (PyBOP®) and the like. Such reactions are conveniently carried out in a non-polar, aprotic solvent, such as DCM at or below ambient temperature, such as RT.

Compounds of formula (II) are readily prepared by $S_NAr$ displacement reactions between an activated pyridine, of formula (IV), and an amine of formula (V) or suitably protected derivatives thereof, wherein R, $R^1$ and $R^2$ are as defined above for compounds of formula (I), $R^a$ is a lower alkyl group, such as methyl or ethyl, and LG is a suitable leaving group such as a halogen atom, for example chlorine (Scheme 2). The compounds of formula (II) are obtained following subsequent hydrolysis of the ester —$CO_2R^a$ to the free acid. Conditions suitable for the displacement step are reaction in a polar, aprotic solvent such as DMF or NMP, optionally in the presence of a non-nucleophilic base, for example triethylamine and at elevated temperatures such as 100-150° C.

Scheme 2

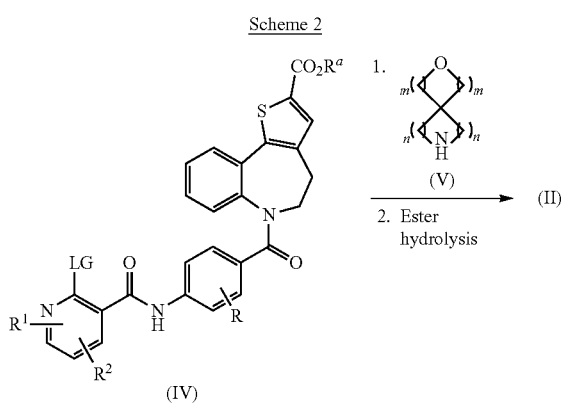

The alkyl ester may be conveniently hydrolysed by exposure to a suitable inorganic base, for example lithium hydroxide, in an aqueous mixture of aprotic and protic solvents, such THF:methanol:water. Such reactions may be subject to gentle heating to, for example, 30-50° C.

Intermediates represented by compounds of formula (IV) may be prepared by acylation of the anilines of formula (VI), with compounds of formula (VII), wherein R, $R^a$, $R^1$, and $R^2$ and LG are as defined herein above and $LG_1$ is a leaving group, such as a halogen atom, for example chlorine (Scheme 3). Conditions suitable for these transformations are reaction in a polar aprotic solvent such acetonitrile, in the presence of an organic base, as a 'proton sponge', for example pyridine at, or slightly above, RT for example at 40° C. Compounds of formula (VII) wherein, for example, $LG_1$ is chlorine are conveniently obtained from the corresponding acid by reaction with a chlorinating agent such as thionyl chloride, or oxalyl chloride optionally in the presence of a small, catalytic quantity of DMF.

Scheme 3

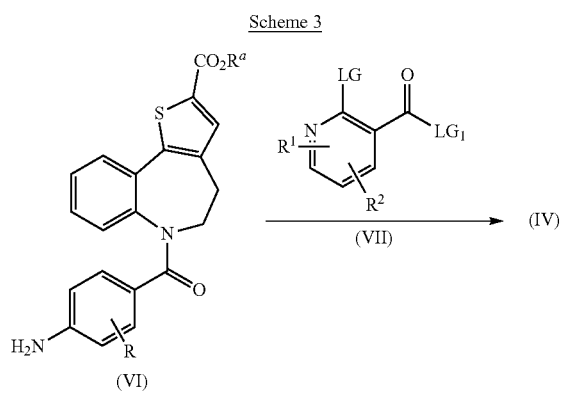

The compound intermediates of formula (VI), wherein R and $R^a$ are as defined above, are readily obtained by the chemoselective reduction of the corresponding nitroarenes of formula (VIII) (Scheme 4). A common method employed for such conversions is reduction of the nitro group with a suitable metal, by a process referred to in the art as 'a dissolving metal reduction.' A metal frequently employed for these transformations is iron, usually in the form of a powder. The reaction is conducted in the presence of a proton source such as an ammonium salt, for example ammonium chloride and in a mixture of protic solvents, for example an alcohol such as IPA containing water and at elevated temperatures such as 70-80° C.

Alternatively it is common practice to effect such transformations by hydrogenation over a suitable noble metal catalyst. An exemplary procedure is reduction with hydrogen at ambient temperature and pressure over palladium on carbon, or the like, in a solvent such as THF or ethanol or mixtures thereof. It may be advantageous to conduct the process in the presence of an acid, for example hydrochloric acid, to prevent the amine product from associating with the catalyst and thereby diminishing its activity.

Scheme 4

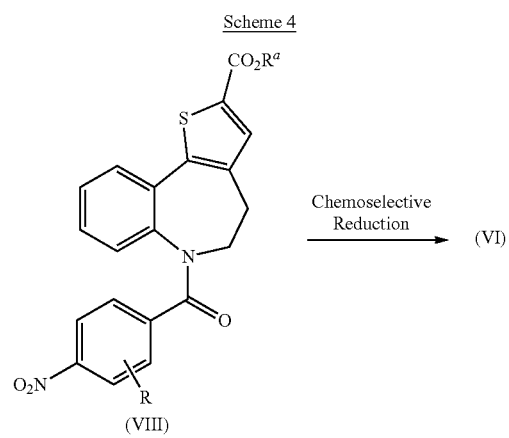

Compounds of the current invention may also be prepared by use of the same or similar procedures as those disclosed above, applied to the nitroarene intermediate of formula (VIII), in an alternative synthetic sequence. Thus compounds of formula (I) can be generated by the $S_NAr$ reaction between an electrophilic pyridine derivative of formula (IX), and an amine of formula (V), or suitably protected derivatives thereof, wherein R $R^1$, $R^2$, $R^3$, $R^4$ $R^5$, and m and n are as defined above for compounds of formula (I), and LG is a suitable leaving group such as a halogen atom, for example chlorine (Scheme 5). Typical conditions employed for such nucleophilic displacements are reaction in a polar, aprotic solvent, such as NMP, in the presence of a non-nucleophilic, organic base, for example triethylamine and usually at elevated temperatures, such as 100-120° C.

Scheme 5

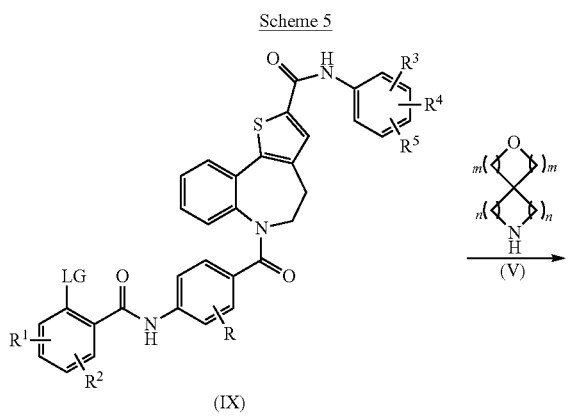

The reactive pyridine derivatives of formula (IX) result from the acylation of the anilines of formula (X) with the nicotinic acid derivatives of formula (VII) (Scheme 6) by a process analogous to that described herein above for intermediates of formula (IV). A suitable procedure for carrying out the N-acylation step is the generation of an acid chloride [(VII), LG$^1$=Cl], optionally performed in situ, for example with oxalyl chloride or the like, in DMF, followed by reaction with the amine substrate (X) in a basic solvent, such as pyridine, typically at ambient temperature.

Scheme 6

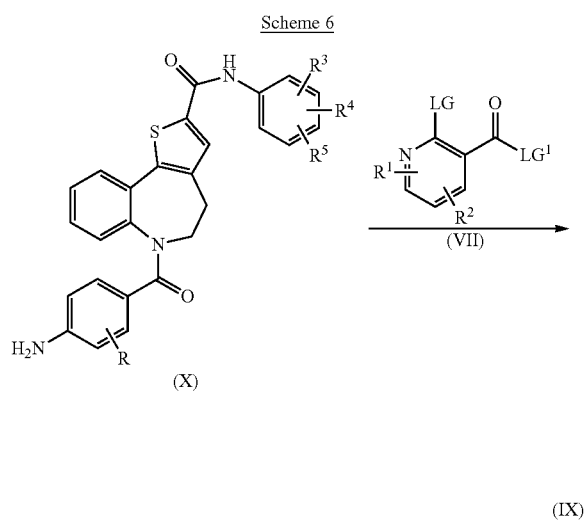

In some instances the intermediates of formula (IX), correspond to a sub genus (IXa), wherein R, R$^2$, R$^3$ R$^4$ and R$^5$ are as defined above for compounds of formula (I), or protected derivatives thereof, and R$^1$ is hydrogen. An alternative method of preparing such substrates is the use of a metal-catalysed, carbon-carbon bond forming reaction on a substrate of formula (IXb) wherein R, R$^3$ R$^4$ and R$^5$ are as defined above, R$^1$ is H and R$^2$ is a 5-bromo substituent (Scheme 7). Those skilled in the art will appreciate that an extensive methodology exists for conducting transformation of this type and wide range of suitable conditions may be used.

Scheme 7

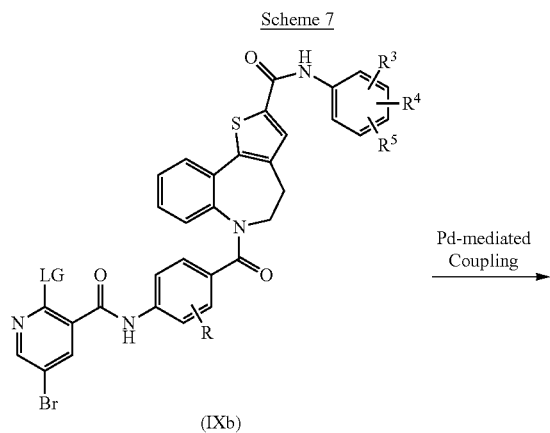

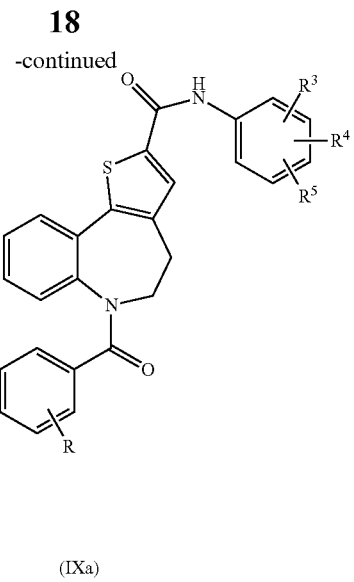

A pre-eminent process is a Suzuki cross-coupling reaction between the aryl bromide of formula (IXb), and a boronic acid of formula R$^2$B(OH)$_2$ or similar, using a palladium catalyst. A typical catalyst is palladium (II) acetate which in some cases may be used with a ligand to provide a soluble ligand complex. Ligands routinely employed for this purpose include phosphine ligands such as tricyclohexylphosphine. It is common for such reactions to be run under basic conditions, typically in the presence of bases such as potassium carbonate or tripotassium phosphate and for them to be heated, for example to 80-100° C. An extensive range of solvents such as THF, dioxane, ethanol and mixtures of toluene and water are applicable.

The compound intermediates of formula (IXb) are obtained by acylation of the anilines of formula (X) with a nicotinic acid derivative of formula (VIIa) (Scheme 8). An example of a suitable electrophile is the acid chloride [(VIIa); LG=LG$^1$=Cl], which may be readily generated from 5-bromo-2-chloronicotinic acid, and optionally reacted in situ according to the general procedures already described herein above.

Scheme 8

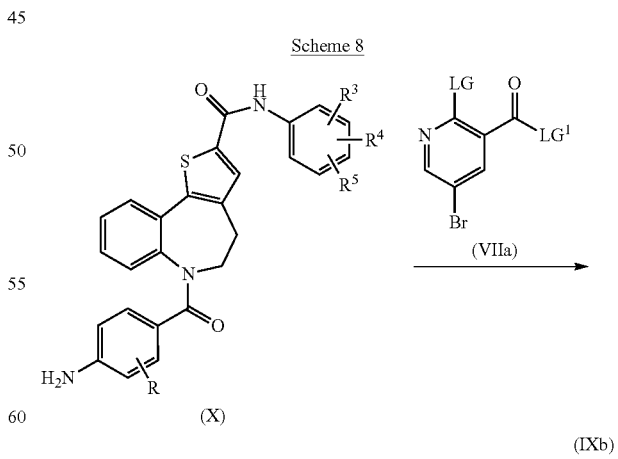

The compounds of formula (X) are readily accessible, in two synthetic steps, from the nitrobenzoyl-substituted thiophene carboxylic acids of formula (XI) by reaction with an aryl amine of formula (III), followed by chemoselective reduction of the nitro group using generic procedures similar to those recited above (Scheme 9). A typical electrophilic carboxylic acid derivative suitable for reaction with an amine, to generate an amide, is an acid halide for example an acid chloride. Such reagents may be formed in situ by exposure of the acid to a pre-formed mixture of oxalyl chloride or similar, in DMF, followed by addition of the amine component, in a basic solvent such as pyridine, at or below room temperature, for example between 0-20° C.

Scheme 9

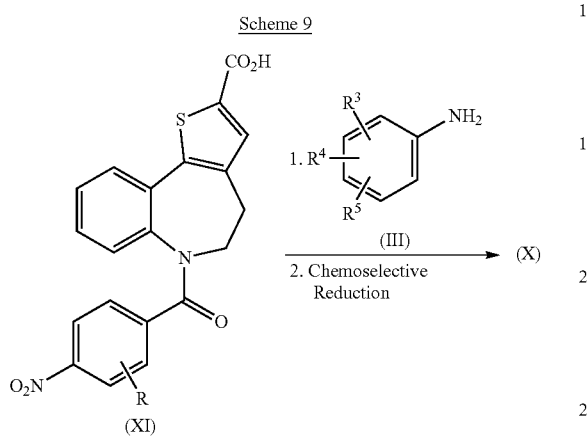

A commonly employed method for the selective reduction of a nitrobenzene into the corresponding aniline is a dissolving metal reduction as outlined herein above for the conversion of the intermediates of formula (VIII) into those of formula (VI). Such reductive transformations may be effected with alternative metals, such as zinc in the form of a powder and are typically conducted in an aqueous mixture of water miscible solvents, for example in methanol, THF and water, at ambient temperature. Alternatively, subsequent reduction of the nitroarene product may be conveniently achieved by catalytic hydrogenation as described above (Scheme 4).

The thiophene carboxylic acids of formula (XI) are readily derived from the corresponding esters of formula (VIII), which constitute intermediates common to both of the synthetic strategies, disclosed herein, for preparing compounds of the invention. (Scheme 10). The hydrolysis may be effected under either acidic or basic conditions. For example the esters of formula (VIII) may be saponified by exposure to a strong inorganic base, such a aqueous sodium hydroxide, in a mixture of water miscible solvents, for example THF and methanol at moderately elevated temperatures such as 30-50° C.

Scheme 10

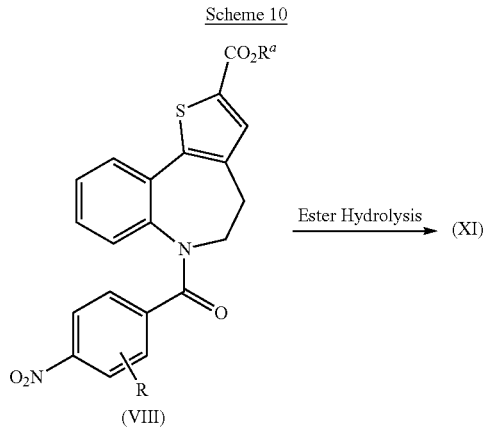

The nitroarenes of formula (VIII) are expediently prepared by reaction of an amino ester (XII) with a suitable 4-nitrobenzoic acid derivative (XIII), wherein R and $R^a$ are as defined above and $LG_2$ is a reactive leaving group such as a halogen, for example a chlorine atom (Scheme 11). For example the acylation may be carried out by treating the amine (XII), [either as its free base or as a salt] with an acid chloride derivative [(XIIIa); $LG_2$=Cl] in a polar, non-protic solvent, such as acetonitrile and in the presence of an organic base, typically pyridine at, or below, ambient temperatures such as 0-20° C.

Scheme 11

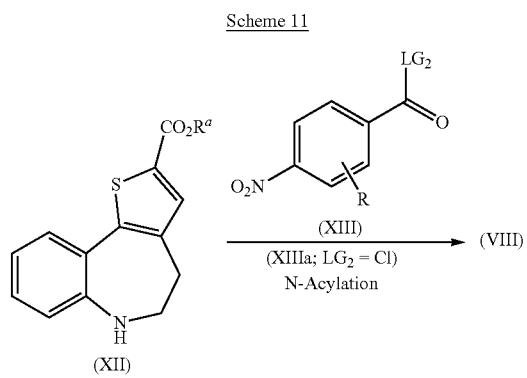

It will be evident to those skilled in the art that the N-acylation step may also be readily achieved on the free acids ($LG_2$=OH) corresponding to compounds of formula (XIII) under conditions commonly employed for the formation of amide bonds, for example with a peptide coupling reagent, such as a uronium coupling reagent, for example with O-(benzotriazol-1-yl)-N,N,N',N'-tetramethyluronium tetrafluoroborate (TBTU) and the like. Typically such reactions are conducted in the presence of a non nucleophilic base such as Hunig's base and in a non-protic, polar solvent, for example in DMF.

The ester derivatives of formula (XII) may be prepared from the previously disclosed acid (XIV) by any of the methods commonly employed in the art (Scheme 12). A small scale procedure for the preparation of this compound has been described (see: Peesapati, V. and Lingaiah N. *Org. Prep. & Proc. Int.*, 1993, 25(5), 602-606) starting from the N-tosyl azepinone (XV), via the protected thiophene ester (XVI). The methodology revealed by the authors provides the acid (XIV) in three steps and an overall yield of ~32%, following purification by thin-layer chromatography.

Scheme 12

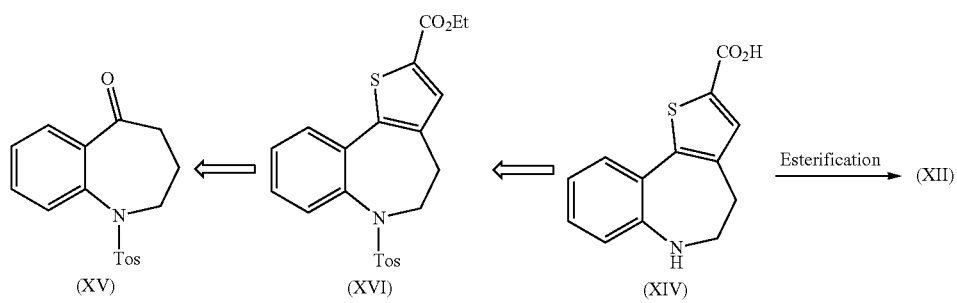

Advantageously, the azepine esters of formula (XII) are readily obtained by the acid-mediated, chemoselective removal of the carboxybenzyl (Cbz) protective group from an intermediate of formula (XVII), in which $R^a$ is as defined above (Scheme 13). Suitable conditions for the hydrolysis of the urethane group are exposure to an anhydrous acid HX wherein X is halo (such as HCl) in an alcoholic solvent ($R^aOH$), such as ethanolic HCl, at elevated temperatures, for example at reflux. In this instance the desired azepine esters may be isolated from the reaction medium as the corresponding acid salts (XIIa). The N-Cbz azepine esters (XVII) may be prepared starting from the N-Cbz azepinone (XVIII) using procedures which are analogous to those reported for the preparation of the tosyl derivative (XVI) (see Experimental Section).

Scheme 13

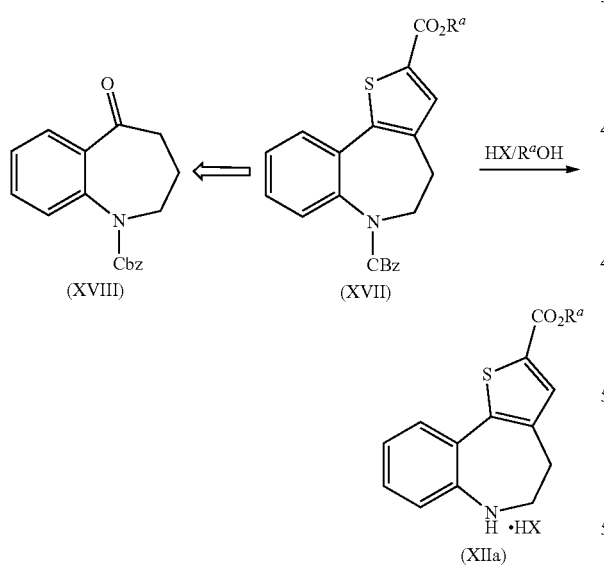

Alternatively the compounds of formula (VIII) may be obtained by condensation of a chloro-enal of formula (XX) with an alkyl 2-mercaptoacetate of formula (XIX), wherein R and $R^a$ are as defined above, in the presence of a non nucleophilic base (Scheme 14). Typical conditions which may be used to effect this transformation are reaction in non-protic, basic solvents such as a mixture pyridine and triethylamine, at elevated temperatures, for example at 70-110° C.

Scheme 14

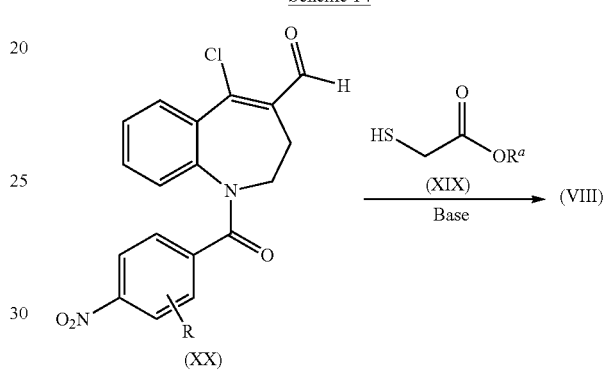

The chloro-enals of formula (XX) are accessible by the chloro formylation of the N-acyl azepinones of formula (XXI). Such conversions may be carried out with a Vilsmeier reagent formed in situ, for example by the reaction between DMF and phosphoryl trichloride (Scheme 15). The reaction is conveniently undertaken in DMF as the solvent and the Vilsmeier reagent is pre-formed before addition of the substrate, usually at reduced temperature, such as 0-5° C. If required the reaction may be then be heated, for example to 70-80° C.

Scheme 15

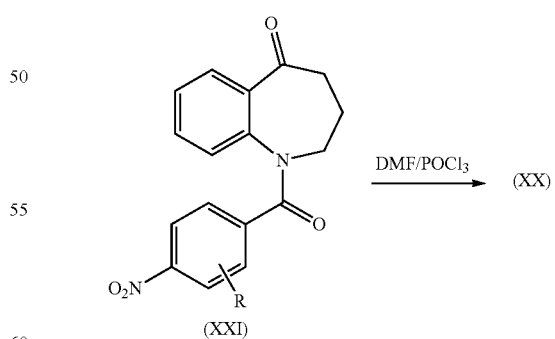

The amide intermediates of formula (XXI) are readily generated by acylation of the commercially available 3,4-dihydro-1H-benzo[b]azepin-5(2H)-one with a benzoic acid derivative, such as the benzoyl chloride [(XIIIa), $LG_2$=Cl] (Scheme 16). Exemplary conditions for this process are the same as those described herein above for the conversion of the azepine intermediates of formula (XII) into the N-benzoyl derivatives (VIII) (Scheme 11).

Scheme 16

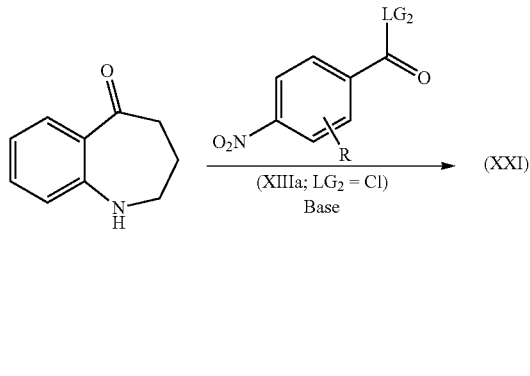

In some instances it may be advantageous to reorder the synthetic transformations described above in order to improve the overall efficiency of the process and/or the quality of the materials obtained therefrom. For example, the compounds of the invention may also be prepared from the aniline intermediate (X), defined herein, with an amino-nicotinic acid of formula (XXII) wherein $R^1$, $R^2$, m and n are as defined above for compounds of formula (I), under conditions suitable for such acylation reactions (Scheme 17), A typical procedure is the conversion of the carboxylic acid (XXII) into an activated derivative such as an acid halide, most commonly the corresponding acid chloride, followed by reaction with the amine under basic conditions as set out above [see Schemes 3, 6 and 8]. Alternatively the acylation may be accomplished under peptide coupling conditions for which a wide variety are available in the art.

Scheme 17

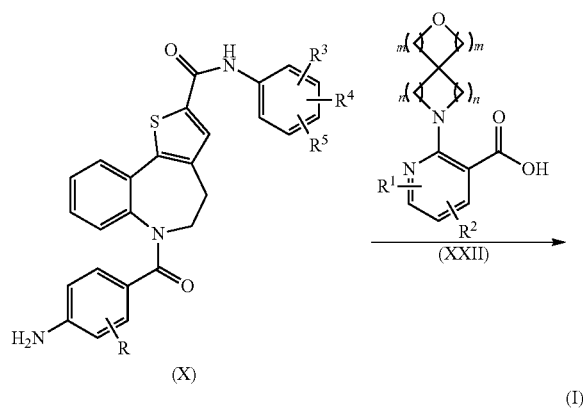

The acylation step described above may also be conveniently undertaken on the corresponding thienyl esters (VI) under essentially similar conditions (Scheme 18). Subsequent hydrolysis of the alkyl ester by saponification or by acidolysis provides the thienyl carboxylic acid Intermediates (II) which are transformed into the compounds of the present invention as described above (Scheme 1).

Scheme 18

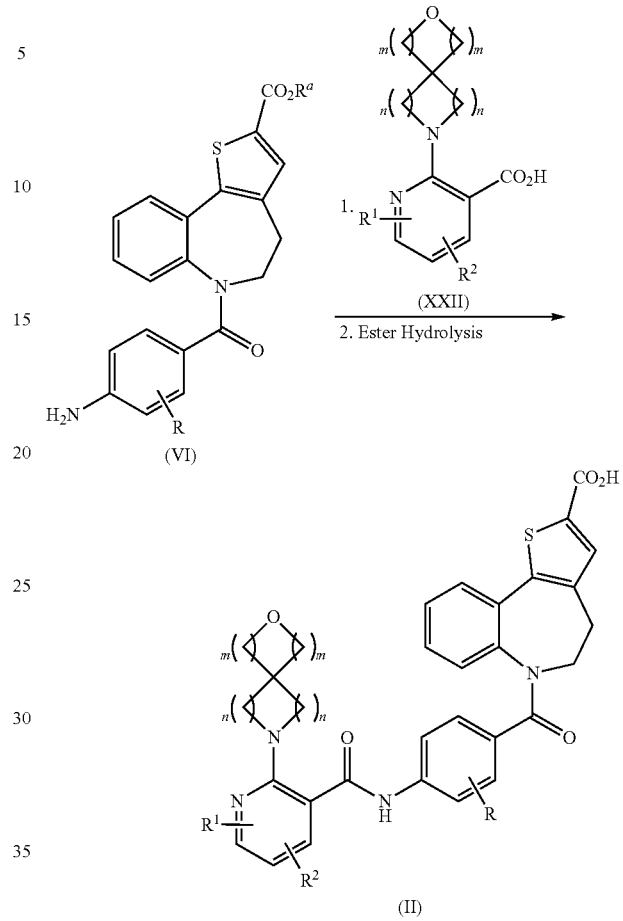

The amino-nicotinic acid components of formula (XXII) may be formed from nicotinate esters of formula (XXIII), wherein $R^1$ and $R^2$ are as defined above, $LG_3$ is a suitable leaving group, such as a chlorine atom, and $R^b$ is lower alkyl such as an ethyl radical, by reaction with a spirocyclic amine of formula (V), under conditions routinely employed for such $S_NAr$ displacements (Scheme 19). [See Schemes 2 and 5 for the preparation of compounds of formula (II) from those of formula (IV) and for the preparation of compounds of formula (I) from those of formula (IX), respectively]. The desired nicotinic acids are revealed by subsequent hydrolysis of the ester either under acidic or basic conditions.

Scheme 19

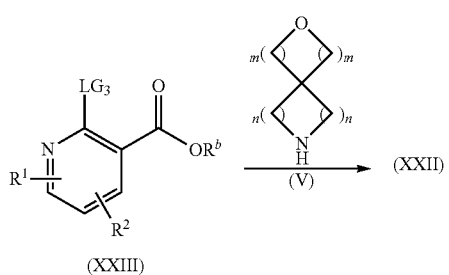

Protective groups and the means for their removal are described in "Protective Groups in Organic Synthesis", by Theodora W. Greene and Peter G. M. Wuts, published by John Wiley & Sons Inc; 4th Rev Ed., 2006, ISBN-10: 0471697540. A review of methodologies for the preparation of amides is covered in: '*Amide bond formation and peptide coupling*' Montalbetti, C.A.G.N. and Falque, V. *Tetrahedron*, 2005, 61, 10827-10852.

In various processes of the invention, carboxylic acid groups require conversion into activated derivatives for reaction with amines in order to form the corresponding amides. Reagents suitable for the activation of such carboxylic acid groups include carbonyl diimidazole, 1-chloro-N,N,2-trimethylprop-1-en-1-amine and a wide selection of peptide coupling agents such as benzotriazol-1-yloxytripyrrolidinophosphonium hexafluorophosphate (PyBOP®) and the like. Alternatively, such carboxylic acids may be activated by conversion into an acid halide most commonly the acid chloride. Such procedures may be performed as a separate transformation in which the acid halide is isolated and then used in the subsequent acylation step. Alternatively, in some instances. it is advantageous to generate said acid halide in situ and react it directly with an amine without prior isolation.

Novel intermediates as described herein include compounds of formula (II), (IV), (IX), (IXa), (IXb), (X) and (XXII) and form a further aspect of the invention, as do salts thereof (such as pharmaceutically acceptable salts).

Specific compounds of formula (XXII) which may be mentioned are compounds of formula (XXIIa-r)

(XXIIa)

(XXIIb)

(XXIIc)

(XXIId)

(XXIIe)

(XXIIf,g)

(XXIIh)

(XXIIj)

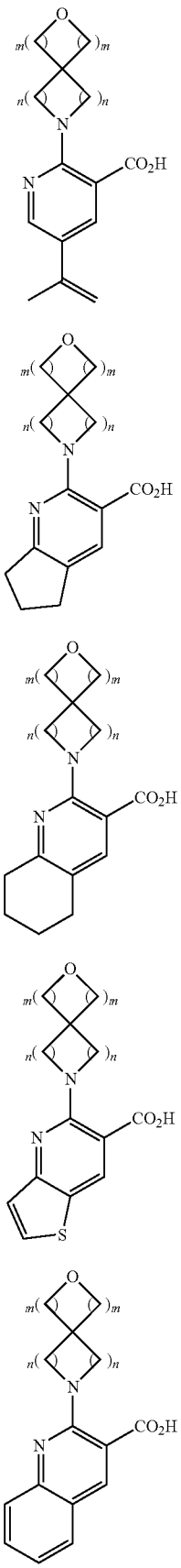

(XXIIk)

(XXIIm)

(XXIIn)

(XXIIp)

(XXIIq)

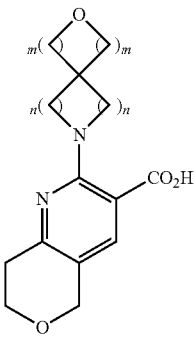

(XXIIr)

and salts thereof, and particularly said compounds wherein n is 1 and m is 2.

Compounds of the invention are useful as pharmaceuticals.

In an embodiment there is provided a pharmaceutical composition comprising a compound of the invention optionally in combination with one or more pharmaceutically acceptable diluents or carriers.

Suitably compounds of the invention are administered topically to the lung or nose, particularly, topically to the lung. Thus, in an embodiment there is provided a pharmaceutical composition comprising a compound of the invention optionally in combination with one or more topically acceptable diluents or carriers.

Suitably compositions for pulmonary or intranasal administration include powders, liquid solutions, liquid suspensions, nasal drops comprising solutions or suspensions or pressurised or non-pressurised aerosols.

The compositions may conveniently be administered in unit dosage form and may be prepared by any of the methods well-known in the pharmaceutical art, for example as described in Remington's Pharmaceutical Sciences, 17th ed., Mack Publishing Company, Easton, Pa., (1985). The compositions may also conveniently be administered in multiple unit dosage form.

Topical administration to the nose or lung may be achieved by use of a non-pressurised formulation such as an aqueous solution or suspension. Such formulations may be administered by means of a nebuliser e.g. one that can be hand-held and portable or for home or hospital use (i.e. non-portable). An example device is a RESPIMAT inhaler. The formulation may comprise excipients such as water, buffers, tonicity adjusting agents, pH adjusting agents, viscosity modifiers, surfactants and co-solvents (such as ethanol). Suspension liquid and aerosol formulations (whether pressurised or unpressurised) will typically contain the compound of the invention in finely divided form, for example with a $D_{50}$ of 0.5-10 μm e.g. around 1-5 μm. Particle size distributions may be represented using $D_{10}$, $D_{50}$ and $D_{90}$ values. The $D_{50}$ median value of particle size distributions is defined as the particle size in microns that divides the distribution in half. The measurement derived from laser diffraction is more accurately described as a volume distribution, and consequently the $D_{50}$ value obtained using this procedure is more meaningfully referred to as a $Dv_{50}$ value (median for a volume distribution). As used herein Dv values refer to particle size distributions measured using laser diffraction. Similarly, $D_{10}$ and D90 values, used in the context of laser diffraction, are taken to mean $Dv_{10}$ and $Dv_{90}$ values and refer to the particle size whereby 10% of the distribution lies below the $D_{10}$ value, and 90% of the distribution lies below the $D_{90}$ value, respectively.

According to one specific aspect of the invention there is provided a pharmaceutical composition comprising a compound of the invention in particulate form suspended in an aqueous medium. The aqueous medium typically comprises water and one or more excipients selected from buffers, tonicity adjusting agents, pH adjusting agents, viscosity modifiers and surfactants.

Topical administration to the nose or lung may also be achieved by use of an aerosol formulation. Aerosol formulations typically comprise the active ingredient suspended or dissolved in a suitable aerosol propellant, such as a chlorofluorocarbon (CFC) or a hydrofluorocarbon (HFC). Suitable CFC propellants include trichloromonofluoromethane (propellant 11), dichlorotetrafluoromethane (propellant 114), and dichlorodifluoromethane (propellant 12). Suitable HFC propellants include tetrafluoroethane (HFC-134a) and heptafluoropropane (HFC-227). The propellant typically comprises 40%-99.5% e.g. 40%-90% by weight of the total inhalation composition. The formulation may comprise excipients including co-solvents (e.g. ethanol) and surfactants (e.g. lecithin, sorbitan trioleate and the like). Other possible excipients include polyethylene glycol, polyvinylpyrrolidone, glycerine and the like. Aerosol formulations are packaged in canisters and a suitable dose is delivered by means of a metering valve (e.g. as supplied by Bespak, Valois or 3M or alternatively by Aptar, Coster or Vari).

Topical administration to the lung may also be achieved by use of a dry-powder formulation. A dry powder formulation will contain the compound of the disclosure in finely divided form, typically with an MMD of 1-10 μm or a $D_{50}$ of 0.5-10 μm e.g. around 1-5 μm. Powders of the compound of the invention in finely divided form may be prepared by a micronisation process or similar size reduction process. Micronisation may be performed using a jet mill such as those manufactured by Hosokawa Alpine. The resultant particle size distribution may be measured using laser diffraction (e.g. with a Malvern Mastersizer 2000S instrument). The formulation will typically contain a topically acceptable diluent such as lactose, glucose or mannitol (preferably lactose), usually of comparatively large particle size e.g. an MMD of 50 μm or more, e.g. 100 μm or more or a $D_{50}$ of 40-150 μm. As used herein, the term "lactose" refers to a lactose-containing component, including α-lactose monohydrate, β-lactose monohydrate, α-lactose anhydrous, β-lactose anhydrous and amorphous lactose. Lactose components may be processed by micronisation, sieving, milling, compression, agglomeration or spray drying. Commercially available forms of lactose in various forms are also encompassed, for example Lactohale® (inhalation grade lactose; DFE Pharma), InhaLac® 70 (sieved lactose for dry powder inhaler; Meggle), Pharmatose® (DFE Pharma) and Respitose® (sieved inhalation grade lactose; DFE Pharma) products. In one embodiment, the lactose component is selected from the group consisting of α-lactose monohydrate, α-lactose anhydrous and amorphous lactose. Preferably, the lactose is α-lactose monohydrate.

Dry powder formulations may also contain other excipients such as sodium stearate, calcium stearate or magnesium stearate.

A dry powder formulation is typically delivered using a dry powder inhaler (DPI) device. Example dry powder delivery systems include SPINHALER, DISKHALER, TURBOHALER, DISKUS, SKYEHALER, ACCUHALER and CLICKHALER. Further examples of dry powder delivery systems include ECLIPSE, NEXT, ROTAHALER, HANDIHALER, AEROLISER, CYCLOHALER, BREEZHALER/NEOHALER, MONODOSE, FLOWCAPS, TWINCAPS, X-CAPS, TURBOSPIN, ELPENHALER, MIATHALER, TWISTHALER, NOVOLIZER, PRESSAIR, ELLIPTA, ORIEL dry powder inhaler, MICRODOSE, PULVINAL, EASYHALER, ULTRAHALER, TAIFUN, PULMOJET, OMNIHALER, GYROHALER, TAPER, CONIX, XCELOVAIR and PROHALER.

Compounds of the invention are useful in the treatment of RSV infection and for the prevention or treatment of disease associated with RSV infection.

In an aspect of the invention there is provided use of a compound of the invention in the manufacture of a medicament for the treatment of RSV infection and for the prevention or treatment of disease associated with RSV infection.

In another aspect of the invention there is provided a method of treatment of a subject infected with RSV which comprises administering to said subject an effective amount of a compound of the invention.

In another aspect of the invention there is provided a method of prevention or treatment of disease associated with RSV infection in a subject which comprises administering to said subject an effective amount of a compound of the invention.

Compounds of the invention may be used in a prophylactic setting by administering them prior to infection.

In one embodiment the RSV infection is RSV A strain infection (e.g. with an RSV A2 strain). In another embodiment the RSV infection is RSV B strain infection (e.g. with RSV B Washington strain).

Subjects include human and animal subjects, especially human subjects.

Compounds of the invention are especially useful for the treatment of RSV infection and for the prevention or treatment of disease associated with RSV infection in at risk subjects. At risk subjects include premature infants, children with congenital defects of the lung or heart, immunocompromised subjects (e.g. those suffering from HIV infection), elderly subjects and subjects suffering from a chronic health condition affecting the heart or lung (e.g. congestive heart failure or chronic obstructive pulmonary disease).

Compounds of the invention may be administered in combination with a second or further active ingredient. Compounds of the invention may be co-formulated with a second or further active ingredient or the second or further active ingredient may be formulated to be administered separately by the same or a different route. According to an aspect of the invention there is provided a kit of parts comprising (a) a pharmaceutical composition comprising a compound of the invention optionally in combination with one or more diluents or carriers; (b) a pharmaceutical composition comprising a second active ingredient optionally in combination with one or more diluents or carriers; (c) optionally one or more further pharmaceutical compositions each comprising a third or further active ingredient optionally in combination with one or more diluents or carriers; and (d) instructions for the administration of the pharmaceutical compositions to a subject in need thereof. The subject in need thereof may suffer from or be susceptible to RSV infection.

Second or further active ingredients include active ingredients suitable for the treatment or prevention of RSV infection or disease associated with RSV infection or conditions co-morbid with RSV infection.

Second or further active ingredients may, for example, be selected from anti-viral agents (such as other anti-RSV agents) including F protein inhibitors (including anti-F-protein antibodies, such as palivizumab), RNA polymerase inhibitors and ribavirin and anti-inflammatory agents.

Compounds of the invention may be administered at a suitable interval, for example once per day, twice per day, three times per day or four times per day.

A suitable dose amount for a human of average weight (50-70 kg) is expected to be around 50 μg to 10 mg/day e.g. 500 μg to 5 mg/day although the precise dose to be administered may be determined by a skilled person.

Compounds of the invention are expected to have one or more of the following favourable attributes:

potent inhibition of cytopathic effect and/or virus replication and/or F-protein expression in humans (or an animal model, or an in vitro system) caused by RSV A strains, such as the A2 strain;

potent inhibition of cytopathic effect and/or virus replication and/or F-protein expression in humans (or an animal model, or an in vitro system) caused by RSV B strains;

long duration of action in lungs, preferably consistent with once daily dosing;

acceptable safety profile, especially following topical administration to the lung or nose.

Experimental Section

Abbreviations used herein are defined below (Table 1). Any abbreviations not defined are intended to convey their generally accepted meaning.

TABLE 1

| Abbreviations | |
|---|---|
| AcOH | glacial acetic acid |
| ALI | air liquid interface |
| aq | aqueous |
| BALF | bronchoalveolar lavage fluid |
| BEAS2B | SV40-immortalised human bronchial epithelial cell line |
| Boc | tert-butyloxycarbonyl |
| br | broad |
| BSA | bovine serum albumin |
| CatCart ® | catalytic cartridge |
| Cbz | carboxybenzyl |
| $CC_{50}$ | 50% cell cytotoxicity concentration |
| CDI | 1,1-carbonyl-diimidazole |
| conc | concentrated |
| CPE | cytopathic effect |
| d | doublet |
| DAB | 3,3'-diaminobenzidine |
| DCM | dichloromethane |
| DIPEA | N,N-diisopropylethylamine (aka Hunig's base) |
| DMEM | Dulbecco's Modified Eagle Medium |
| DMF | N,N-dimethylformamide |
| DMSO | dimethyl sulfoxide |
| DSS | dextran sodium sulphate |
| $(ES^+)$ | electrospray ionization, positive mode |
| Et | ethyl |
| EtOAc | ethyl acetate |
| FBS | foetal bovine serum |
| HATU | 1-[bis(dimethylamino)methylene]-1H-1,2,3-triazolo[4,5-b]pyridinium 3-oxid hexafluorophosphate |
| Hep2 | human laryngeal epithelioma cell line 2 |
| HPLC | high performance liquid chromatography (reverse phase) |
| hr | hour(s) |
| HRP | horse radish peroxidase |
| $IC_{50}$ | 50% inhibitory concentration |
| $IC_{75}$ | 75% inhibitory concentration |
| $IC_{90}$ | 90% inhibitory concentration |
| IgG | immunogloblin G |
| m | multiplet |
| $(M + H)^+$ | protonated molecular ion |
| Me | methyl |
| MeCN | acetonitrile |
| MeOH | methanol |
| MHz | megahertz |
| MMD | mass median diameter |

TABLE 1-continued

| Abbreviations | |
|---|---|
| MOI | multiplicity of infection |
| min | minute(s) |
| m/z | mass-to-charge ratio |
| NMP | N-methylpyrrolidine |
| NMR | nuclear magnetic resonance (spectroscopy) |
| nt | not tested |
| OD | optical density |
| PBS | phosphate buffered saline |
| PCR | polymerase chain reaction |
| $Pd(dppf)Cl_2$ | [1,1'-bis(diphenylphosphino)ferrocene]dichloropalladium(II) |
| Pen Srep | Penicillin-Streptomycin |
| PFU | plaque forming unit |
| Ph | phenyl |
| prep HPLC | preparative high performance liquid chromatography |
| PG | protective group |
| Ph | phenyl |
| q | quartet |
| RT | room temperature |
| RP HPLC | reverse phase high performance liquid chromatography |
| RPMI | Roswell Park Memorial Institute medium |
| RSV | respiratory syncytial virus |
| s | singlet |
| sat | saturated |
| SCX | solid supported cation exchange (resin) |
| SDS | sodium dodecyl sulphate |
| $S_NAr$ | nucleophilic aromatic substitution |
| t | triplet |
| THF | tetrahydrofuran |
| THP | tetrahydropyranyl |
| TLC | thin layer chromatography |
| TMB | 3,3',5,5'-tetramethylbenzidine |
| Tos | p-toluenesulfonyl |
| vol | volume(s) |
| WB | washing buffer |

General Procedures

All starting materials and solvents were obtained either from commercial sources or prepared according to the literature citation. Unless otherwise stated all reactions were stirred. Organic solutions were routinely dried over anhydrous magnesium sulfate. Hydrogenations were performed on a Thales H-cube flow reactor under the conditions stated or under pressure in a gas autoclave (bomb).

Column chromatography was performed on pre-packed silica (230-400 mesh, 40-63 μm) cartridges using the amount indicated. SCX was purchased from Supelco and treated with 1M hydrochloric acid prior to use. Unless stated otherwise the reaction mixture to be purified was first diluted with MeOH and made acidic with a few drops of AcOH. This solution was loaded directly onto the SCX and washed with MeOH. The desired material was then eluted by washing with 0.7 M $NH_3$ in MeOH.

Preparative Reverse Phase High Performance Liquid Chromatography

Method 1: Waters X-Select CSH column C18, 5 μm (19×50 mm), flow rate 28 mL min$^{-1}$ eluting with a $H_2O$-MeCN gradient containing 0.1% v/v formic acid over 6.5 min using UV detection at 254 nm. Gradient information: 0.0-0.2 min, 20% MeCN; 0.2-5.5 min, ramped from 20% MeCN to 40% MeCN; 5.5-5.6 min, ramped from 40% MeCN to 95% MeCN; 5.6-6.5 min, held at 95% MeCN.

Method 2: Waters X-Select CSH column C18, 5 μm (19×50 mm), flow rate 28 mL min$^{-1}$ eluting with a $H_2O$-MeCN gradient containing 0.1% v/v formic acid over 6.5 min using UV detection at 254 nm. Gradient information: 0.0-0.2 min, 20% MeCN; 0.2-5.5 min, ramped from 20% MeCN to 50% MeCN; 5.5-5.6 min, ramped from 50% MeCN to 95% MeCN; 5.6-6.5 min, held at 95% MeCN.

Method 3: Waters X-Select CSH column C18, 5 μm (19×50 mm), flow rate 28 mL min$^{-1}$ eluting with a $H_2O$-

MeCN gradient containing 0.1% v/v formic acid over 6.5 min using UV detection at 254 nm. Gradient information: 0.0-0.2 min, 35% MeCN; 0.2-5.5 min, ramped from 35% MeCN to 65% MeCN; 5.5-5.6 min, ramped from 65% MeCN to 95% MeCN; 5.6-6.5 min, held at 95% MeCN.

Method 4: Waters X-Select CSH column C18, 5 μm (19×50 mm), flow rate 28 mL min$^{-1}$ eluting with a H$_2$O-MeCN gradient containing 0.1% v/v formic acid over 10 min using UV detection at 254 nm. Gradient information: 0.0 min, 20% MeCN; 0.0-7.5 min, ramped from 20% MeCN to 50% MeCN; 7.5-8.0 min, ramped from 50% MeCN to 95% MeCN; 8.0-10.0 min, held at 95% MeCN.

Method 5: Waters X-Bridge BEH column C18, 5 μm (19×50 mm), flow rate 28 mL min$^{-1}$ eluting with a 10 mM NH$_4$HCO$_3$-MeCN gradient over 10 min using UV detection at 254 nm. Gradient information: 0.0-0.1 min, 35% MeCN; 0.1-7.5 min, ramped from 35% MeCN to 65% MeCN; 7.5-8.5 min, ramped from 65% MeCN to 95% MeCN; 8.5-8.6 min, ramped from 95% MeCN to 35% MeCN; 8.6-10.0 min, held at 35% MeCN.

Method 6: Waters X-Bridge Prep column C18, 5 μm (19×50 mm), flow rate 28 mL min$^{-1}$ eluting with a 10 mM NH$_4$HCO$_3$-MeCN gradient over 6.5 min using UV detection at 254 nm. Gradient information: 0.0-0.2 min, 35% MeCN; 0.2-5.5 min, ramped from 35% MeCN to 65% MeCN; 5.5-5.6 min, ramped from 65% MeCN to 95% MeCN; 5.6-6.5 min, held at 95% MeCN.

Method 7: Waters X-Select CSH column C18, 5 μm (19×50 mm), flow rate 28 mL min$^{-1}$ eluting with a H$_2$O-MeCN gradient containing 0.1% v/v formic acid over 10 min using UV detection at 254 nm. Gradient information: 0.0 min, 30% MeCN; 0.0-7.5 min, ramped from 30% MeCN to 45% MeCN; 7.5-8.0 min, ramped from 45% MeCN to 95% MeCN; 8.0-10.0 min, held at 95% MeCN.

Method 8: Waters X-Select CSH column C18, 5 μm (19×50 mm), flow rate 28 mL min$^{-1}$ eluting with a H$_2$O-MeCN gradient containing 0.1% v/v formic acid over 10 min using UV detection at 254 nm. Gradient information: 0.0 min, 30% MeCN; 0.0-7.5 min, ramped from 30% MeCN to 65% MeCN; 7.5-8.0 min, ramped from 65% MeCN to 95% MeCN; 8.0-10.0 min, held at 95% MeCN.

Method 9: Waters X-Select CSH column C18, 5 μm (19×50 mm), flow rate 28 mL min$^{-1}$ eluting with a H$_2$O-MeCN gradient containing 0.1% v/v formic acid over 6.5 min using UV detection at 254 nm. Gradient information: 0.0-0.2 min, 50% MeCN; 0.2-5.5 min, ramped from 50% MeCN to 80% MeCN; 5.5-5.6 min, ramped from 80% MeCN to 95% MeCN; 5.6-6.5 min, held at 95% MeCN.

Method 10: Waters X-Select CSH column C18, 5 μm (19×50 mm), flow rate 28 mL min$^{-1}$ eluting with a H$_2$O-MeCN gradient containing 0.1% v/v formic acid over 6.5 min using UV detection at 254 nm. Gradient information: 0.0-0.2 min, 20% MeCN; 0.2-5.5 min, ramped from 20% MeCN to 80% MeCN; 5.5-5.6 min, ramped from 80% MeCN to 95% MeCN; 5.6-6.5 min, held at 95% MeCN.

Method 11: Waters X-Select CSH column C18, 5 μm (19×50 mm), flow rate 28 mL min$^{-1}$ eluting with a H$_2$O-MeCN gradient containing 0.1% v/v formic acid over 10 min using UV detection at 254 nm. Gradient information: 0.0 min, 35% MeCN; 0.0-7.5 min, ramped from 35% MeCN to 65% MeCN; 7.5-8.0 min, ramped from 65% MeCN to 95% MeCN; 8.0-10.0 min, held at 95% MeCN.

Analytical Methods

Reverse Phase HPLC Conditions for the LCMS Analytical Methods

Methods 1a and 1b: Waters Xselect CSH C18 XP column, 2.5 μm (4.6×30 mm) at 40° C.; flow rate 2.5-4.5 mL min$^{-1}$ eluted with a H$_2$O-MeCN gradient containing either 0.1% v/v formic acid (Method 1a) or 10 mM NH$_4$HCO$_3$ in water (Method Ib) over 4 min employing UV detection at 254 nm. Gradient information: 0-3.00 min, ramped from 95% H$_2$O-5% MeCN to 5% H$_2$O-95% MeCN; 3.00-3.01 min, held at 5% H$_2$O-95% MeCN, flow rate increased to 4.5 mL min$^{-1}$; 3.01 3.50 min, held at 5% H$_2$O-95% MeCN; 3.50-3.60 min, returned to 95% H$_2$O-5% MeCN, flow rate reduced to 3.50 mL min$^{-1}$; 3.60-3.90 min, held at 95% H$_2$O-5% MeCN; 3.90-4.00 min, held at 95% H$_2$O-5% MeCN, flow rate reduced to 2.5 mL min$^{-1}$.

$^1$H NMR Spectroscopy $^1$H NMR spectra were acquired on a Bruker Avance III spectrometer at 400 MHz using residual undeuterated solvent as reference and unless specified otherwise were run in DMSO-d$_6$.

Preparation of Intermediates

Known synthetic intermediates were procured from commercial sources or were obtained using published literature procedures. Additional intermediates were prepared by the representative synthetic processes described herein.

2-Fluoro-6-vinylaniline

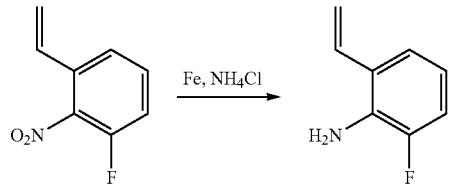

A mixture of 1-fluoro-2-nitro-3-vinylbenzene (0.90 g, 5.4 mmol), prepared as previously described[§], iron powder (3.0 g, 54 mmol) and ammonium chloride (2.9 g, 54 mmol) in EtOH:water (10:3, 65 mL) were heated at reflux for 1 hr. The reaction mixture was cooled to RT and was filtered through a celite pad. The filtrate was evaporated in vacuo and the residue was taken up into DCM (30 mL) and washed with water (20 mL). The organic layer was dried and evaporated in vacuo to afford the title compound as an orange oil (0.71 g, 96% yield); R$^t$1.80 min (Method 1a); m/z 138 (M+H)$^+$ (ES$^+$); $^1$H NMR δ: 5.15 (2H, s), 5.21 (1H, dd), 5.64 (1H, dd), 6.52 (1H, apparent td), 6.89-7.00 (2H, over-lapping m), 7.15 (1H, d). [$^§$Han X. et al., *Tetrahedron Lett.*, 2009, 50, 386-388.]

2-Ethynyl-6-fluoroaniline

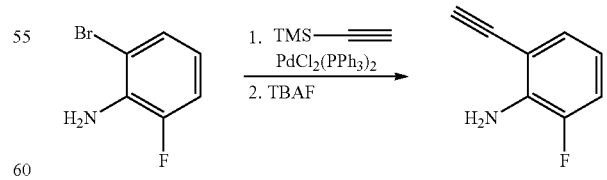

A mixture of 2-bromo-6-fluoroaniline (2.00 g, 10.5 mmol), ethynyltrimethylsilane (2.18 mL, 15.8 mmol), PdCl$_2$(PPh$_3$)$_2$ (111 mg, 0.158 mmol), CuI (30.0 mg, 0.158 mmol) and Et$_3$N (4.40 mL, 31.6 mmol) in DMF (2.0 mL) was heated at 50° C. for 8 hr and then cooled to RT. The volatiles were evaporated in vacuo and the resulting residue was dissolved in TBAF (1 M in THF, 10.5 mL) and allowed to stand at RT for 1 hr. The mixture was diluted with EtOAc (100 mL) and was washed with water (2×100 mL), and then dried and evaporated in vacuo. The residue was purified by flash column chromatography (SiO$_2$, 120 g, 0-10% DCM in isohexane, gradient elution) to afford the title compound as a clear orange oil (410 mg, 29%); $^1$H NMR δ: 4.45 (1H, s), 5.31 (2H, s), 6.51 (1H, apparent td), 7.02-7.10 (2H, over-lapping m).

2-(2-(3-Fluoro-2-nitrophenoxy)ethoxy)tetrahydro-2H-pyran

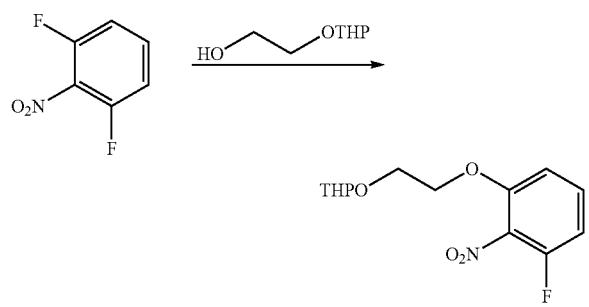

A mixture of 1,3-difluoro-2-nitrobenzene (1.00 g, 6.29 mmol), 2-((tetrahydro-2H-pyran-2-yl)oxy)ethanol (0.919 g, 6.29 mmol) and cesium carbonate (3.58 g, 11.0 mmol) in DMF (20 mL) was heated at 60° C. for 18 hr. After cooling to RT the reaction mixture was poured into water (100 mL) and was extracted with EtOAc (100 mL). The organic layer was separated, washed with water (2×50 mL) and evaporated in vacuo. The residue thus obtained was purified by flash column chromatography (SiO$_2$, 80 g, 0-50% EtOAc in isohexane, gradient elution) to afford the title compound as a yellow oil (1.36 g, 76% yield); $^1$H NMR (CDCl$_3$) δ: 1.48-1.65 (4H, over-lapping m), 1.68-1.86 (2H, over-lapping m), 3.50-3.56 (1H, m), 3.77-3.88 (2H, over-lapping m), 4.02-4.08 (1H, m), 4.27-4.30 (2H, over-lapping m), 4.67 (1H, apparent t), 6.84 (1H, td), 6.89 (1H, dt), 7.39 (1H, apparent td).

2-Fluoro-6-(2-((tetrahydro-2H-pyran-2-yl)oxy)ethoxy)aniline

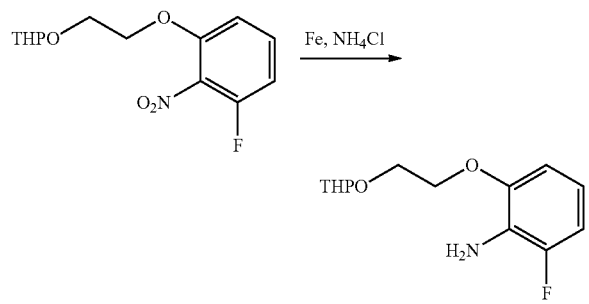

A mixture of 2-(2-(3-fluoro-2-nitrophenoxy)ethoxy)tetrahydro-2H-pyran (1.30 g, 4.56 mmol), iron powder (2.54 g, 45.6 mmol) and ammonium chloride (2.44 g, 45.6 mmol) in EtOH:water (10:3, 65 mL) was heated at reflux for 1 hr. The reaction mixture was cooled to RT and was then filtered through a celite pad. The filtrate was evaporated in vacuo and the residue was taken up into DCM (30 mL) and washed with water (20 mL). The organics were dried and evaporated in vacuo to afford the title compound as a colourless oil (1.00 g, 86% yield); $^1$H NMR (CDCl$_3$) δ: 1.50-1.67 (4H, over-lapping m), 1.71-1.89 (2H, over-lapping m), 3.51-3.58 (1H, m), 3.74 (2H, br), 3.80-3.94 (2H, over-lapping m), 4.08 (1H, dt), 4.19 (2H, apparent t), 4.72 (1H, br t), 6.59-6.72 (3H, over-lapping m).

Benzyl 5-oxo-2,3,4,5-tetrahydro-1H-benzo[b]azepine-1-carboxylate

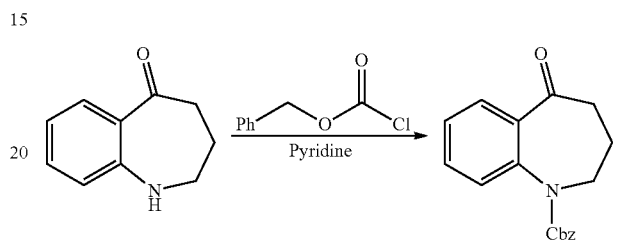

To a solution of 3,4-dihydro-1H-benzo[b]azepin-5(2H)-one (25.0 g, 155 mmol) in a mixture of DCM (258 mL) and pyridine (25.0 mL) at 0° C. was added dropwise benzyl chloroformate (38.0 mL, 264 mmol). The resulting mixture was warmed to RT for 18 hr and then water (150 mL) was added. After 15 min the biphasic mixture was separated and the organic layer was washed with 1 M hydrochloric acid (150 mL) and with brine (150 mL), and then dried and concentrated in vacuo to give the title compound as a yellow oil (54.3 g, 85% pure by HPLC, containing unreacted benzyl chloroformate); R$^t$2.21 min (Method 1a); m/z 296 (M+H)$^+$ (ES$^+$). This material was used in the subsequent step without additional purification.

Benzyl 5-chloro-4-formyl-2,3-dihydro-1H-benzo[b]azepine-1-carboxylate

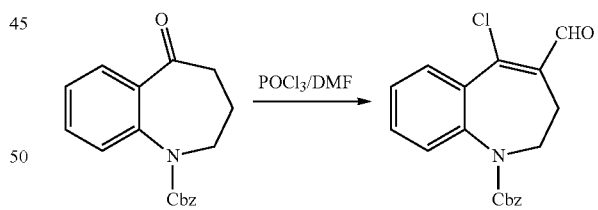

To neat DMF (330 mL) at 0° C. was added dropwise neat phosphoryl trichloride (20.5 mL, 221 mmol) and after 5 min at 0° C. the mixture was treated with a solution of benzyl 5-oxo-2,3,4,5-tetrahydro-1H-benzo[b]azepine-1-carboxylate (54.3 g, 184 mmol) in DMF (110 mL) via a cannula. The resulting yellow solution was stirred at 0° C. for 15 min, then allowed to attain RT for 30 min and afterwards was heated at 80° C. for 3 hr. The reaction mixture was cooled to RT for 16 hr and was then partitioned between EtOAc (700 mL) and sat aq NaOAc (800 mL). The aq layer was separated and was washed with EtOAc (400 mL). The combined organic extracts were washed with brine (2×800 mL), and then dried and concentrated in vacuo to give the title compound as a brown oil (69.9 g, 78% pure by HPLC); R$^t$2.47 min (Method 1a); m/z 342 (M+H)+ (ES+). This material was used in the subsequent step without additional purification.

6-Benzyl 2-ethyl 4,5-dihydro-6H-benzo[b]thieno[2,3-d]azepine-2,6-dicarboxylate

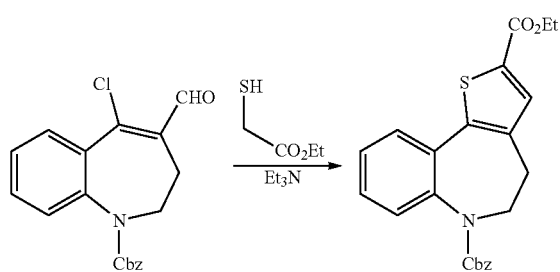 [SMILES: "Et3N" ; O=CC1=C(Cl)c2ccccc2N(C(=O)OCc2ccccc2)CC1 ; CCOC(=O)CS ; CCOC(=O)c1cc2c(s1)-c1ccccc1N(C(=O)OCc1ccccc1)CC2]

To a solution of benzyl 5-chloro-4-formyl-2,3-dihydro-1H-benzo[b]azepine-1-carboxylate (69.9 g, 205 mmol) in pyridine (432 mL) at RT was added ethyl 2-mercaptoacetate (45.0 mL, 409 mmol) followed by triethylamine (185 mL). The mixture was heated at 70° C. for 1 hr and at 115° C. for 3.5 hr and was allowed to cool to RT and left to stand at this temp for 60 hr. A white precipitate formed that was removed by filtration and was washed with acetonitrile (200 mL).

The combined filtrates were concentrated in vacuo, during which process excess pyridine was removed as an azeotrope by adding aliquots of acetonitrile (500 mL) and DCM (500 mL). The resulting residue was taken up in DCM (400 mL) and was washed with 1 M hydrochloric acid (300 mL). The aq layer was separated and was back extracted with DCM (100 mL). The combined organic extracts were washed with brine (400 mL) and then dried and evaporated in vacuo to give an oily residue. On standing for 16 hr a solid formed which was triturated with hexane (100 mL) and collected by filtration. The resulting cake was washed with acetonitrile (100 mL) and with MeOH (100 mL) and then air dried to afford the title compound as a cream coloured solid (24.5 g, 39% yield over 3 steps); R$^t$ 2.84 min (Method 1a); m/z 408 (M+H)+ (ES+).

Ethyl 5,6-dihydro-4H-benzo[b]thieno[2,3-d]azepine-2-carboxylate hydrochloride

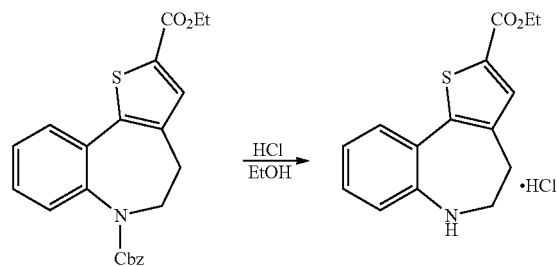 [SMILES: "EtOH" ; CCOC(=O)c1cc2c(s1)-c1ccccc1N(C(=O)OCc1ccccc1)CC2 ; Cl ; CCOC(=O)c1cc2c(s1)-c1ccccc1NCC2 ; Cl]

A mixture of 6-benzyl 2-ethyl 4,5-dihydro-6H-benzo[b]thieno[2,3-d]azepine-2,6-dicarboxylate (20.0 g, 49.1 mmol) in ethanolic HCl (393 mL, 1.25 M, 491 mmol) was heated at reflux for 15 hr and was then concentrated in vacuo. An additional aliquot of ethanolic HCl (393 mL, 1.25 M, 491 mmol) was added and the mixture was heated for a second time at reflux for 48 hr. The same process was repeated for a third time and after 18 hr at reflux the volatiles were removed in vacuo and the resulting solid was triturated with ether (300 mL). The product was collected by filtration and was dried to afford the title compound as a white solid (12.5 g, 79% yield); R$^t$2.47 min (Method 1a); m/z 274 (M+H)+ (ES+); $^1$H NMR δ: 1.29 (3H, t), 3.01 (2H, apparent t), 3.32 (2H, apparent t), 4.28 (2H, q), 6.73 (1H, apparent t), 6.86 (1H, d), 7.08 (1H, qd), 7.56 (1H, dd), 7.58 (1H, s).

Ethyl 6-(4-nitrobenzoyl)-5,6-dihydro-4H-benzo[b]thieno[2,3-d]azepine-2-carboxylate Method 1: Via Acylation of the Benzothienoazepine Precursor

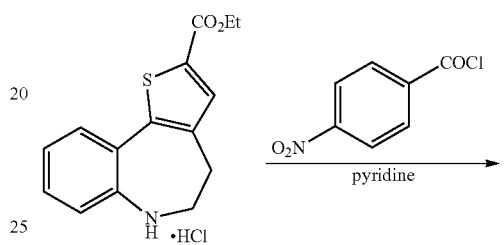

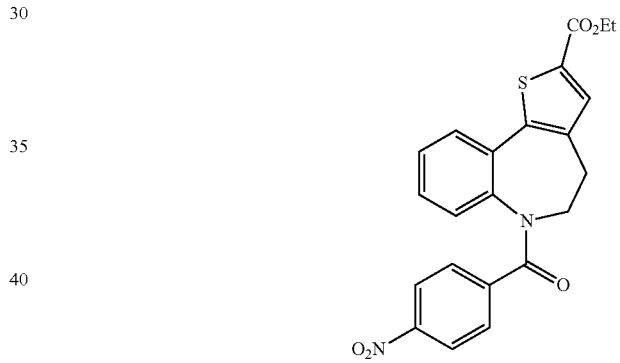

A solution of 4-nitrobenzoyl chloride (539 mg, 2.91 mmol) in acetonitrile (5.0 mL) was added dropwise to a solution of ethyl 5,6-dihydro-4H-benzo[b]thieno[2,3-d]azepine-2-carboxylate hydrochloride (750 mg, 2.42 mmol) in pyridine (5.0 mL) at RT. After 18 hr at RT the resulting mixture was poured carefully into 1 M hydrochloric acid (100 mL) and extracted with EtOAc (2×50 mL). The combined organic extracts were washed with sat aq NaHCO$_3$ (2×50 mL), and then dried and evaporated in vacuo. The crude solid thus obtained was purified by flash column chromatography (SiO$_2$, 12 g, 0-50% EtOAc in isohexane, gradient elution) to afford the title compound, as a colourless glass (987 mg, 95%); R$^t$2.58 min (Method 1a); m/z 423 (M+H)+ (ES+); $^1$H NMR (CDCl$_3$) δ: 1.42 (3H t), 3.13 (1H, dt), 3.31-3.38 (1H, m), 3.48-3.57 (1H, m), 4.41 (2H, q), 5.05-5.11 (1H, m), 6.70 (1H, d), 7.02 (1H, t), 7.24-7.27 (assume 3H, obscured by solvent), 7.71 (1H, s), 7.78 (1H, dd), 8.01 (2H, d).

Method 2 Via Acylation of the Benzoazepinone Precursor 1-(4-Nitrobenzoyl)-1,2,3,4-tetrahydro-5H-benzo[b]azepin-5-one

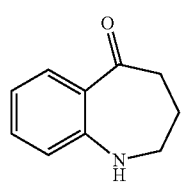 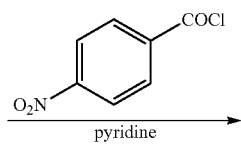

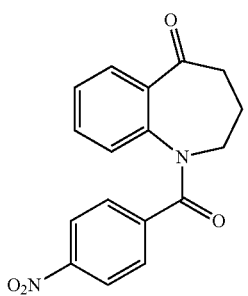

To a solution of 1,2,3,4-tetrahydro-benzo[b]azepin-5-one (25.0 g, 155 mmol) in pyridine (124 mL) at RT was added dropwise a solution of 4-nitrobenzoyl chloride (57.6 g, 310 mmol) in MeCN (124 mL). The resulting mixture was stirred at RT for 16 hr and was then quenched carefully with water (50 mL) and extracted with EtOAc (100 mL). The organic extracts were washed sequentially with sat aq NaHCO$_3$ (100 mL), sat aq NH$_4$Cl (2×100 mL), water (100 mL), brine (100 mL), and finally with 1 M hydrochloric acid (2×100 mL), dried and the volatiles evaporated in vacuo. The crude solid thus obtained was slurried with MeOH (300 mL) and was collected by filtration and dried to afford the title compound as a light yellow solid (44.8 g, 93% yield, 93% pure by HPLC); R$^t$ 1.92 min (Method 1a); m/z 311 (M+H)$^+$ (ES$^+$). This material was used in the subsequent step without additional purification.

5-Chloro-1-(4-nitrobenzoyl)-2,3-dihydro-1H-benzo[b]azepine-4-carbaldehyde

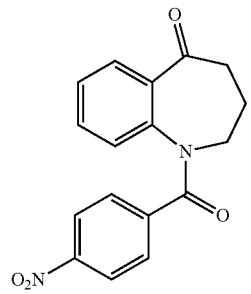 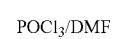

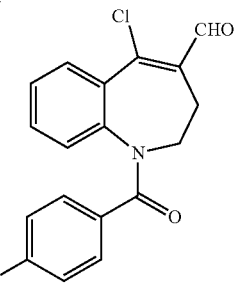

To neat DMF (236 mL) at 0° C. was added dropwise phosphoryl trichloride (15.8 mL, 170 mmol) and the resulting mixture treated with a solution of 1-(4-nitrobenzoyl)-1,2,3,4-tetrahydro-5H-benzo[b]azepin-5-one (44.8 g. 141 mmol) in DMF (141 mL) [the latter obtained by heating a suspension at 90° C. until full dissolution of the solid had occurred and the solution added whilst still hot] whilst maintaining the internal temp between 0-5° C. The reaction mixture was stirred at 0° C. for 15 min, then allowed to attain RT for 30 min and afterwards was heated at 80° C. for 72 hr. The resulting mixture was cooled to RT and was partitioned between EtOAc (500 mL) and sat aq NaOAc (500 mL). The aq layer was separated and was washed with EtOAc (2×500 mL). The combined organic extracts were washed with brine (8×300 mL), and then dried and evaporated in vacuo to give a brown solid. The crude product thus obtained was slurried with MeOH (300 mL) and was collected by filtration and dried to afford the title compound as a yellow solid (25.8 g, 51%, yield, 88% pure by HPLC); R$^t$2.28 min (Method 1a); m/z 357 (M+H)$^+$ (ES$^+$). This material was used in the subsequent step without additional purification.

Ethyl 6-(4-nitrobenzoyl)-5,6-dihydro-4H-benzo[b]thieno[2,3-d]azepine-2-carboxylate

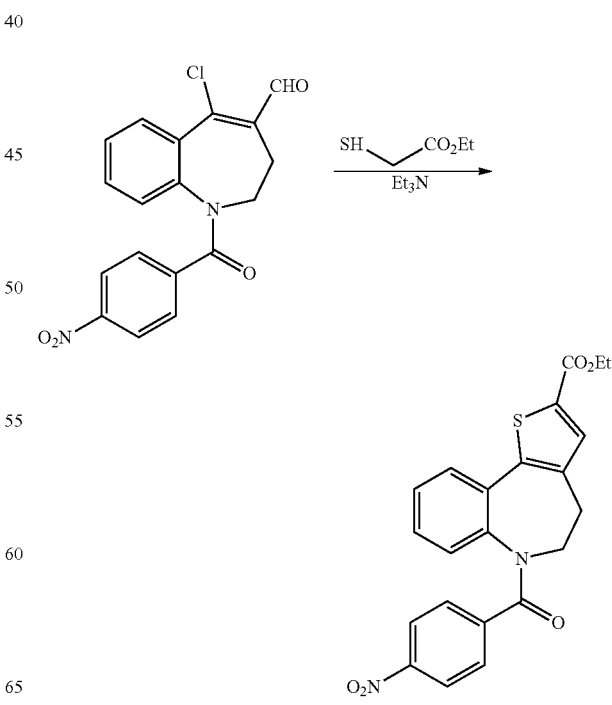

To a solution of 5-chloro-1-(4-nitrobenzoyl)-2,3-dihydro-1H-benzo[b]azepine-4-carbaldehyde (36.6 g, 89.0 mmol) in pyridine (260 mL) at RT was added ethyl 2-mercaptoacetate (18.6 mL, 170 mmol) followed by triethylamine (81.0 mL). The reaction mixture was heated at 70° C. for 1 hr, and at 118° C. for 2 hr and was then cooled to RT. The white precipitate that formed was removed by filtration and the filtrate concentrated in vacuo. The resulting residue was taken up in DCM (100 mL) and was washed with water (100 mL) and then with 1 M hydrochloric acid (70 mL). The organic extracts were dried and evaporated in vacuo. The crude solid thus obtained was slurried with MeOH (150 mL), collected by filtration and dried to afford the title compound as a yellow solid (34.2 g, 84% yield); R$^t$ 2.65 min (Method 1a); m/z 423 (M+H)$^+$ (ES$^+$); $^1$H NMR δ: 1.32 (3H, t), 3.09-3.17 (1H, m), 3.28-3.41 (assume 2H, obscured by solvent), 4.33 (2H, q), 4.83-4.92 (1H, m), 6.96 (1H, br d), 7.10 (1H, td), 7.24 (2H, br d), 7.28 (1H, td), 7.78-7.81 (2H, over-lapping s and dd), 8.06 (2H, br d).

6-(4-Nitrobenzoyl)-5,6-dihydro-4H-benzo[b]thieno[2,3-d]azepine-2-carboxylic acid

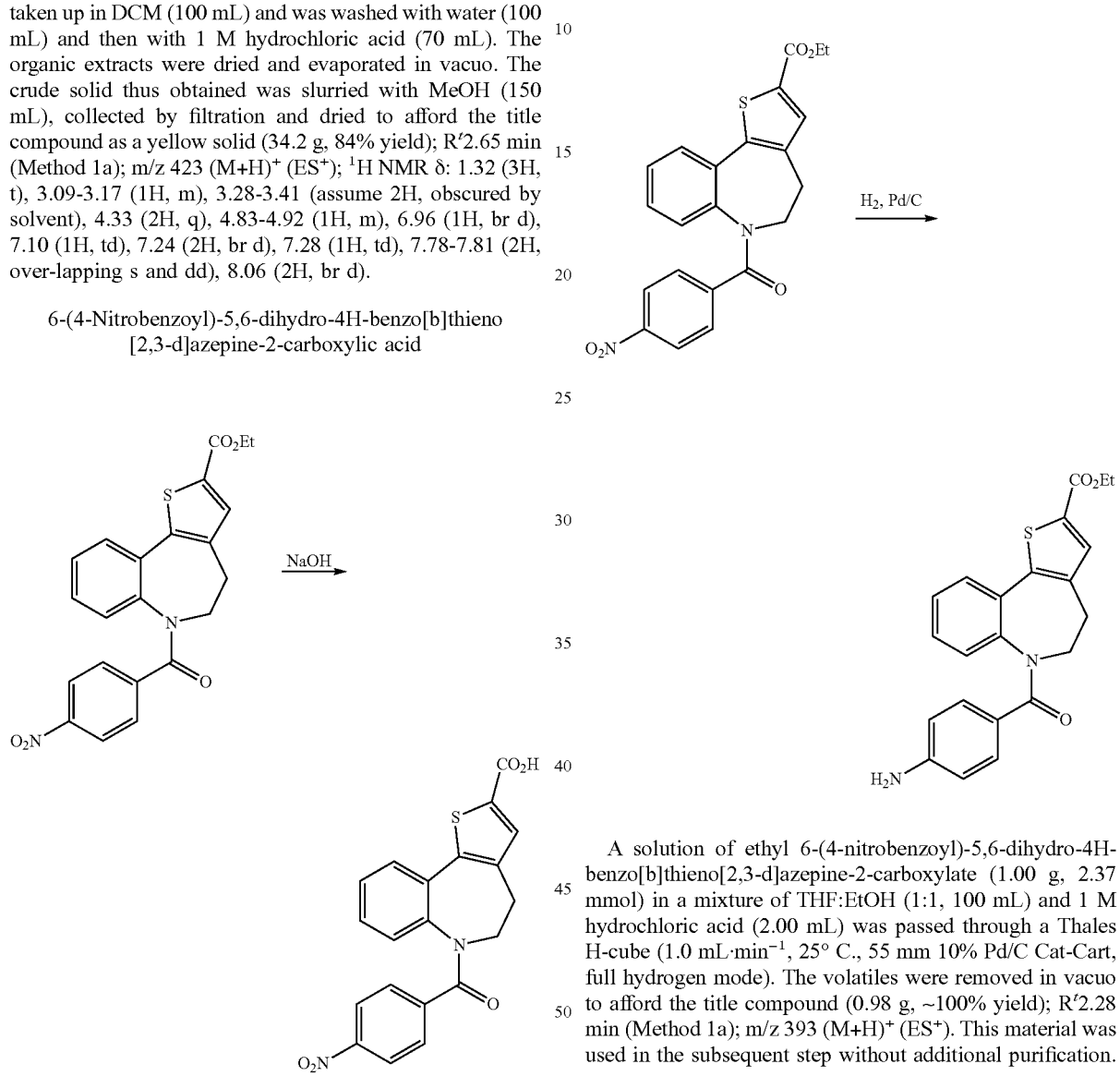

To a solution of ethyl 6-(4-nitrobenzoyl)-5,6-dihydro-4H-benzo[b]thieno[2,3-d]azepine-2-carboxylate (1.50 g, 3.55 mmol) in a mixture of THF:MeOH (1:1, 36 mL) was added 2 M aq NaOH (9.0 mL) and the mixture heated at 50° C. for 2 hr. After cooling to RT the mixture was partitioned between EtOAc (200 mL) and water (200 mL). The aq layer was separated and was acidified to pH 3 by the addition of 1 M hydrochloric acid and then extracted with EtOAc (2×150 mL). Removal of the volatiles in vacuo afforded the title compound, as a yellow solid (1.44 g, 99% yield); R$^t$ 2.24 min (Method 1a); m/z 395 (M+H)$^+$ (ES$^+$); $^1$H NMR δ: 3.06-3.17 (1H, m), 3.27-3.40 (assume 2H, obscured by solvent), 4.83-4.92 (1H, m), 6.95 (1H, br d), 7.08 (1H, br t), 7.23-7.30 (3H, over-lapping br d and br t), 7.69 (1H, s), 7.78 (1H, dd), 8.06 (2H, br d), 13.33 (1H, br s).

Ethyl 6-(4-aminobenzoyl)-5,6-dihydro-4H-benzo[b]thieno[2,3-d]azepine-2-carboxylate Catalytic Reduction Method A solution of ethyl 6-(4-nitrobenzoyl)-5,6-dihydro-4H-benzo[b]thieno[2,3-d]azepine-2-carboxylate (1.00 g, 2.37 mmol) in a mixture of THF:EtOH (1:1, 100 mL) and 1 M hydrochloric acid (2.00 mL) was passed through a Thales H-cube (1.0 mL·min$^{-1}$, 25° C., 55 mm 10% Pd/C Cat-Cart, full hydrogen mode). The volatiles were removed in vacuo to afford the title compound (0.98 g, ~100% yield); R$^t$ 2.28 min (Method 1a); m/z 393 (M+H)$^+$ (ES$^+$). This material was used in the subsequent step without additional purification.

Dissolving Metal Reduction Method

To a suspension of iron powder (5.29 g, 94.7 mmol) and ethyl 6-(4-nitrobenzoyl)-5,6-dihydro-4H-benzo[b]thieno[2,3-d]azepine-2-carboxylate (8.00 g, 18.9 mmol) in IPA (80 mL) was added saturated aq ammonium chloride (8.0 mL). The resulting mixture was stirred at 80° C. for 1 hr and was then filtered through celite. The celite pad was washed with MeOH (1.5 L) and combined filtrates were evaporated in vacuo. The resulting residue was triturated with water (400 mL) and with diethyl ether (400 mL) and was dried in vacuo to afford the title compound as a yellow solid (5.89 g, 88% pure by HPLC, 70% yield); R$^t$ 2.21 min (Method 1a); m/z 393 (M+H)$^+$ (ES$^+$). This material was used in subsequent steps without additional purification.

2-Chloronicotinoyl Chloride

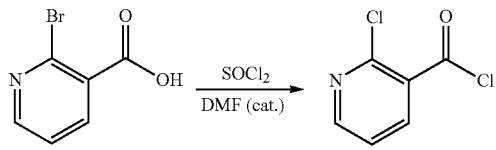

Thionyl chloride (70 mL) was added in one portion to neat 2-bromonicotinic acid (10.0 g, 49.5 mmol) at RT, followed by 2-3 drops of DMF and the mixture was heated at reflux for 4 hr. The reaction was cooled to RT and the excess thionyl chloride was removed by evaporation in vacuo. The residue was recrystallised from isohexane to afford the title compound as a light yellow solid (7.81 g, 90% pure by $^1$H-NMR, 81% yield). This material was used in subsequent steps without additional purification.

Ethyl 6-(4-2-chloronicotinamido)benzoyl)-5,6-dihydro-4H-benzo[b]thieno[2,3-d]azepine-2-carboxylate

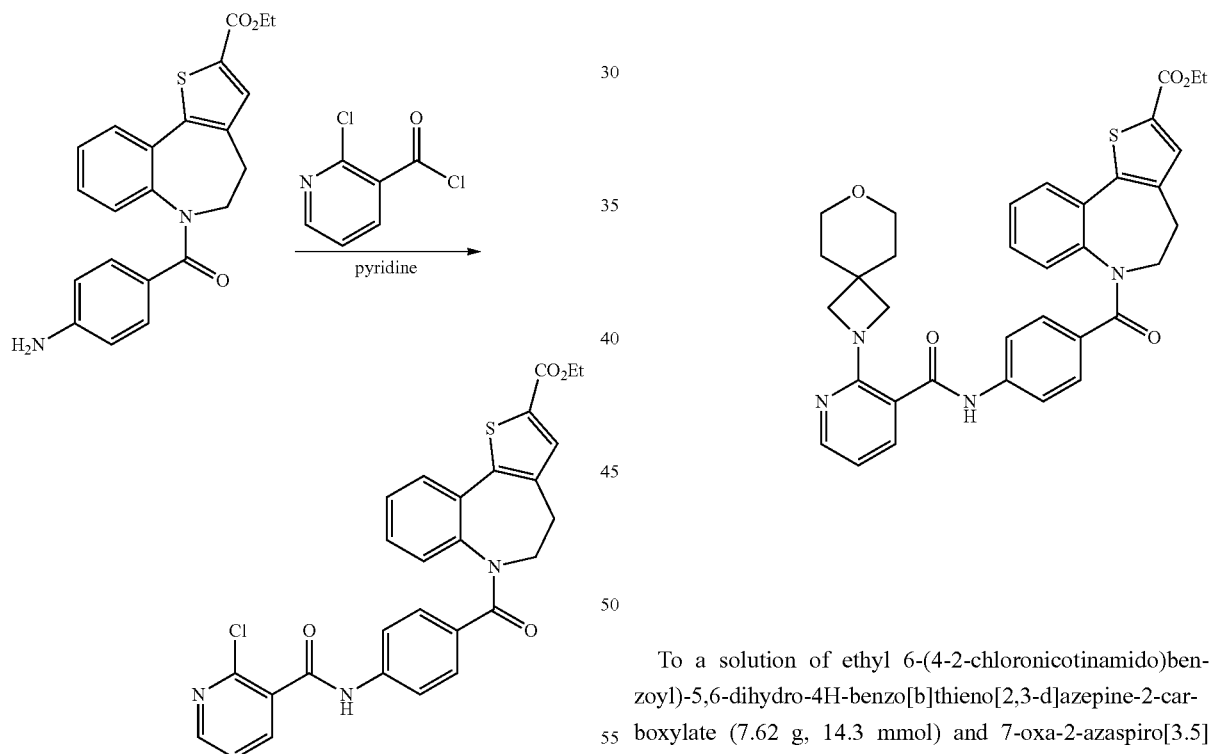

A solution of 2-chloronicotinoyl chloride (3.17 g, 18.0 mmol) in MeCN (80 mL) was added slowly to a solution of ethyl 6-(4-aminobenzoyl)-5,6-dihydro-4H-benzo[b]thieno[2,3-d]azepine-2-carboxylate (5.89 g, 15.0 mmol) in pyridine (80 mL) at RT. The resulting mixture was heated at 40° C. for 2 hr and was then cooled to RT and concentrated in vacuo. The residue was taken up into DCM:MeOH (9:1, 200 mL) and was washed with water (200 mL). The aq layer was separated and was extracted with DCM:MeOH (9:1, 2×100 mL) and the combined organic layers were dried and concentrated in vacuo to give the title compound as a yellow solid (7.62 g, 90% pure by HPLC, 91% yield); R'2.36 min (Method 1a); m/z 532 (M+H)$^+$ (ES$^+$). This material was used in subsequent steps without additional purification.

Ethyl 6-(4-(2-(7-oxa-2-azaspiro[3.5]nonan-2-yl)nicotinamido)benzoyl)-5,6-dihydro-4H-benzo[b]thieno[2,3-d]azepine-2-carboxylate

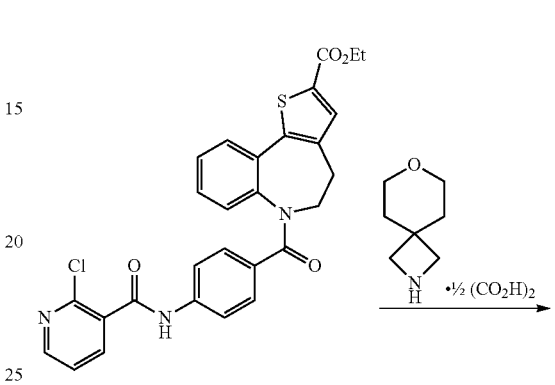

To a solution of ethyl 6-(4-2-chloronicotinamido)benzoyl)-5,6-dihydro-4H-benzo[b]thieno[2,3-d]azepine-2-carboxylate (7.62 g, 14.3 mmol) and 7-oxa-2-azaspiro[3.5]nonane hemi oxalate (4.67 g, 21.5 mmol) in NMP (36 mL) was added Et$_3$N (5.99 mL, 43.0 mmol). The reaction mixture was heated to 150° C. for 1 hr and was then cooled to RT. Water (100 mL) was added and the resulting precipitate was collected by vacuum filtration. The solid thus obtained was purified by flash column chromatography (SiO$_2$, 80 g, 0-10% MeCN in EtOAc, gradient elution) to afford the title compound as a pale yellow solid (6.23 g, 63% yield); R' 1.93 min (Method 1a); m/z 623 (M+H)$^+$ (ES$^+$).

6-(4-(2-(7-Oxa-2-azaspiro[3.5]nonan-2-yl)nicotinamido)benzoyl)-5,6-dihydro-4H-benzo[b]thieno[2,3-d]azepine-2-carboxylic acid

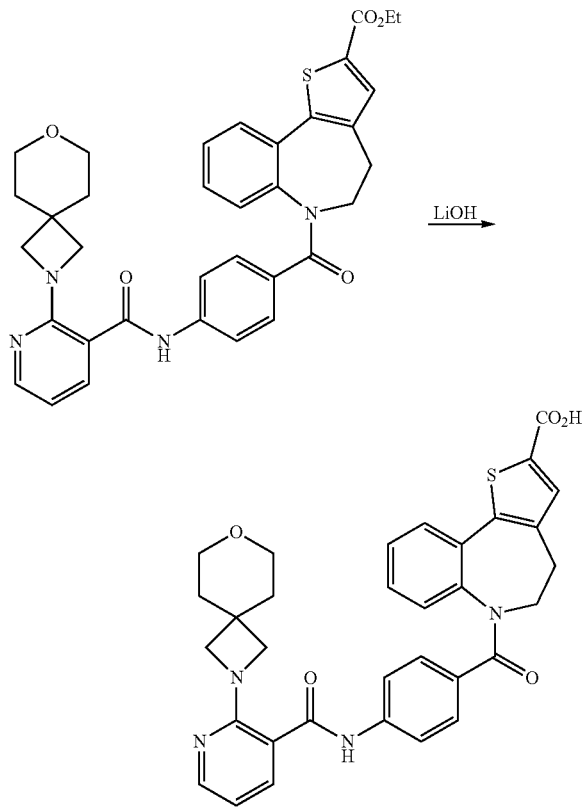

To a solution ethyl 6-(4-(2-(7-oxa-2-azaspiro[3.5]nonan-2-yl)nicotinamido)benzoyl)-5,6-dihydro-4H-benzo[b]thieno[2,3-d]azepine-2-carboxylate (4.35 g, 6.99 mmol) in THF:MeOH (1:1, 60 mL) was added a solution of lithium hydroxide (0.84 g, 34.9 mmol) in water (60 mL). The reaction mixture was heated to 50° C. for 1 hr and was then cooled to RT. The volatiles were removed in vacuo and the remaining aqueous solution was neutralised by the addition of 1 M hydrochloric acid. The resulting solid was collected by vacuum filtration and dried in vacuo to afforded the title compound as an off-white solid (3.90 g, 92% yield); R$^t$ 1.63 min (Method 1a); m/z 595 (M+H)$^+$ (ES$^+$).

6-(4-(2-(7-Oxa-2-azaspiro[3.5]nonan-2-yl)nicotinamido)benzoyl)-5,6-dihydro-4H-benzo[b]thieno[2,3-d]azepine-2-carbonyl chloride

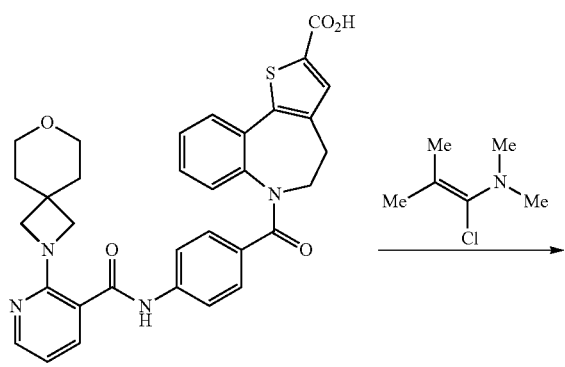

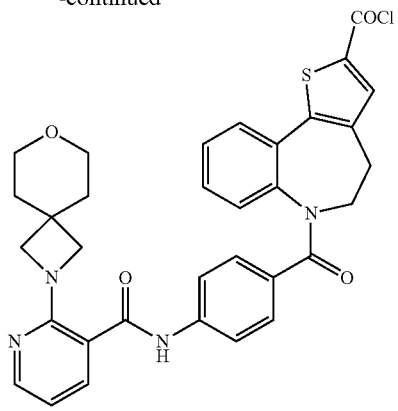

To a solution of 6-(4-(2-(7-oxa-2-azaspiro[3.5]nonan-2-yl)nicotinamido)benzoyl)-5,6-dihydro-4H-benzo[b]thieno[2,3-d]azepine-2-carboxylic acid (100 mg, 0.17 mmol) in DCM (10 mL) was added 1-chloro-N,N,2-trimethylprop-1-en-1-amine (45 μL, 0.34 mmol). The reaction mixture was stirred at RT for 30 min and was then concentrated in vacuo. The resulting residue was taken up into DCM (10 mL) to afford a stock solution of the title compound (16.80 mM). This material was used in subsequent steps without additional purification.

Ethyl 6-(4-(2-chloro-5-methylnicotinamido)benzoyl)-5,6-dihydro-4H-benzo[b]thieno[2,3-d]azepine-2-carboxylate

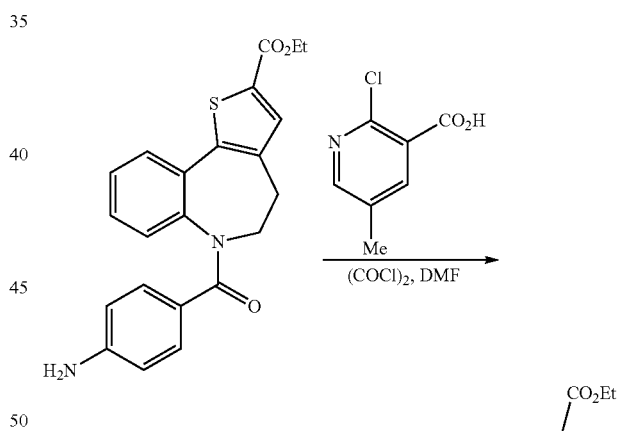

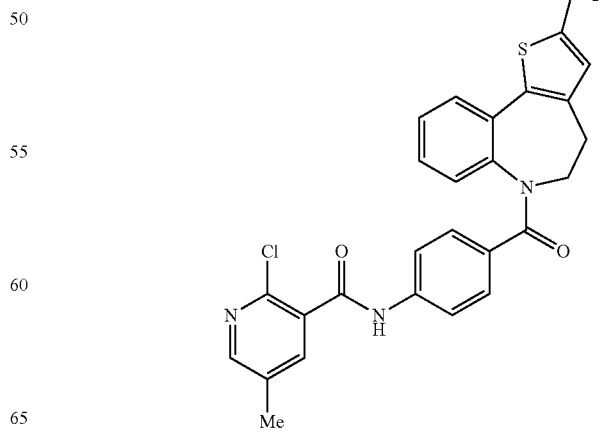

To a suspension of 2-chloro-5-methylnicotinic acid (2.49 g, 14.5 mmol) in DCM (50 mL) was added oxalyl chloride (4.24 mL, 48.4 mmol) and one drop of DMF. The resulting mixture was stirred at RT for 1 hr and was then evaporated in vacuo. The residue was taken up into DCM (25 mL) and added to a solution of ethyl 6-(4-aminobenzoyl)-5,6-dihydro-4H-benzo[b]thieno[2,3-d]azepine-2-carboxylate (3.80 g, 9.68 mmol) in pyridine (20 mL) at RT. The reaction mixture was maintained at RT for 1 hr and then quenched by the addition of water (100 mL) and extracted with EtOAc (100 mL). The aq layer was separated and was washed with EtOAc (2×100 mL). The combined organic extracts were washed with water (100 mL), evaporated in vacuo. and the resulting solid triturated with water (200 mL). This sequence was repeated on the same scale to afford the title compound as a pale yellow solid (10.0 g, 89% pure by HPLC, 95%); $R^t$ 2.51 min (Method 1a); m/z 545/547 (M+H)$^+$ (ES$^+$). This material was used in subsequent steps without additional purification.

Ethyl 6-(4-(5-methyl-2-(7-oxa-2-azaspiro[3.5]nonan-2-yl)nicotinamido)benzoyl)-5,6-dihydro-4H-benzo[b]thieno[2,3-d]azepine-2-carboxylate Method 1: Displacement of a 2-Halonicotinamide with a Spirocyclic Amine

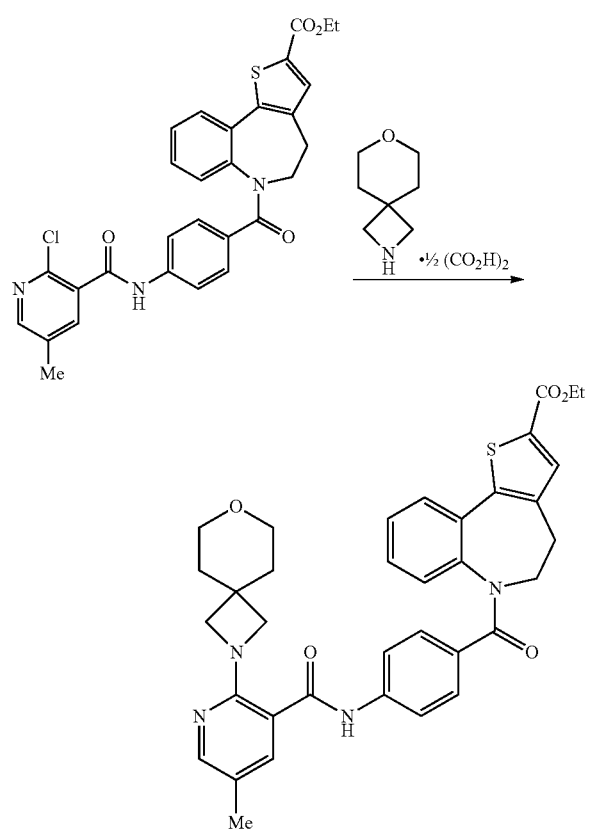

A suspension of ethyl 6-(4-(2-chloro-5-methylnicotinamido)benzoyl)-5,6-dihydro-4H-benzo[b]thieno[2,3-d]azepine-2-carboxylate (4.97 g, 9.10 mmol) and 7-oxa-2-azaspiro[3.5]nonane hemi oxalate (5.93 g, 27.3 mmol) in NMP (23 mL) and Et$_3$N (7.61 mL, 54.6 mmol) was heated at 150° C. for 7.5 hr and then cooled to RT and left to stand for 60 hr. Water (400 mL) was added and the resulting precipitate was collected by filtration. The solid thus obtained was purified by flash column chromatography (SiO$_2$, 120 g, 0-30% THF in DCM, gradient elution) to afford the title compound as a pale yellow solid (3.72 g, 64%); $R^t$ 1.94 min (Method 1a); m/z 637 (M+H)$^+$ (ES$^+$); $^1$H NMR δ: 1.32 (3H, t), 1.62 (4H, br t), 2.17 (3H, s), 3.06-3.35 (assume 3H, obscured by solvent), 3.45 (4H, br t), 3.60 (4H, s), 4.32 (2H, q), 4.81-4.97 (1H, br), 6.88 (1H, br d), 6.99 (2H, br d), 7.14 (1H, br t), 7.29 (1H, td), 7.45-7.54 (3H, over-lapping m), 7.78 (1H, s), 7.81 (1H, dd), 8.04 (1H, dd), 10.36 (1H, s).

Ethyl 2-chloro-5-methylnicotinate

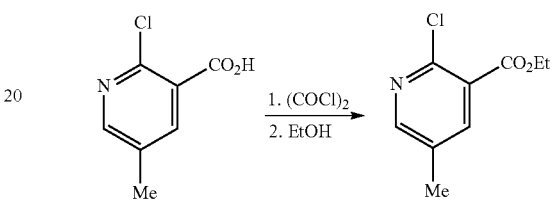

To a solution of 2-chloro-5-methylnicotinic acid (3.90 g, 22.7 mmol) in DCM (100 mL) was added oxalyl chloride (9.95 mL, 114 mmol) followed by 1 drop of DMF. The resulting mixture was stirred at RT for 30 min and evaporated in vacuo. The residue thus obtained was taken up into EtOH (66 mL), stirred for a further 2 hr and then evaporated in vacuo. The crude product obtained was purified by flash column chromatography (SiO$_2$, 120 g, 0-50% DCM in isohexane, gradient elution) to afford the title compound as a colourless oil (3.71 g, 82% yield); $^1$H NMR δ: 1.32 (3H, t), 2.34 (3H, s), 4.34 (2H, q), 8.06-8.07 (1H, m), 8.41-8.43 (1H, m). [See also: Yamamoto S. et al., *Bioorg. Med. Chem.* 2012, 20, 422-434.]

Ethyl 5-methyl-2-(7-oxa-2-azaspiro[3.5]nonan-2-yl)nicotinate

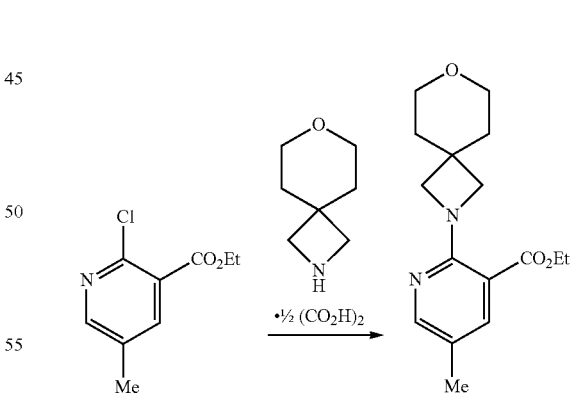

A mixture of ethyl 2-chloro-5-methylnicotinate (3.70 g, 18.5 mmol), 7-oxa-2-azaspiro[3.5]nonane hemioxalate (9.57 g, 55.6 mmol) and DIPEA (19.4 mL, 111 mmol) in NMP (50 mL) was heated at 150° C. for 2 hr. After cooling to RT the crude mixture was poured into water (200 mL) and extracted with EtOAc (3×200 mL). The combined organic extracts were washed with brine (2×100 mL), and then dried and evaporated in vacuo to afford the title compound (4.81 g, 88% yield); $R^t$ 1.32 min (Method 1a); m/z 291 (M+H)$^+$ (ES+); 1H NMR δ: 1.29 (3H, t), 1.67 (4H, br t), 2.18 (3H, s), 3.52 (4H, br t), 3.67 (4H, s), 4.25 (2H, q), 7.74 (1H, apparent dd), 8.12 (1H, apparent dd).

5-Methyl-2-(7-oxa-2-azaspiro[3.5]nonan-2-yl)nicotinic acid

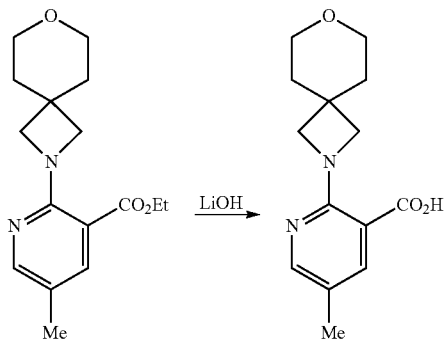

A mixture of ethyl 5-methyl-2-(7-oxa-2-azaspiro[3.5] nonan-2-yl)nicotinate (4.1 g, 14 mmol) and lithium hydroxide (0.50 g, 21 mmol) in THF:water (4:1, 50 mL) was heated at 50° C. for 18 hr and then evaporated in vacuo. The residue thus obtained was acidified to pH 4 by the addition of 1 M hydrochloric acid and the resulting mixture extracted with EtOAc (10×250 mL). The combined organic extracts were evaporated in vacuo to afford the title compound as a crystalline solid (3.4 g, 92% yield); R'0.42 min (Method 1a); m/z 263 (M+H)+ (ES+); 1H NMR δ: 1.67 (4H, br t), 2.17 (3H, s), 3.52 (4H, br t), 3.69 (4H, s), 7.74 (1H, apparent dd), 8.09 (1H, apparent dd), 12.69 (1H, br).

Ethyl 6-(4-(5-methyl-2-(7-oxa-2-azaspiro[3.5] nonan-2-yl)nicotinamido)benzoyl)-5,6-dihydro-4H-benzo[b]thieno[2,3-d]azepine-2-carboxylate Method 2: Acylation of an Aminobenzoylazepine with a 2-Aminonicotinoyl Chloride

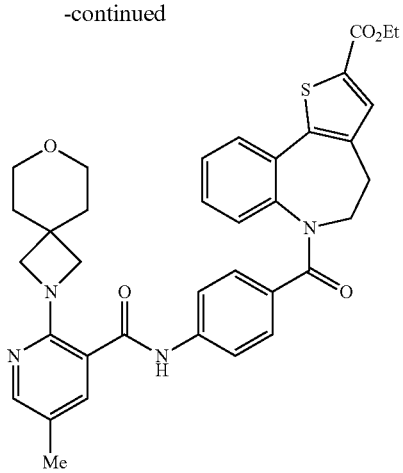

To a suspension of 5-methyl-2-(7-oxa-2-azaspiro[3.5] nonan-2-yl)nicotinic acid (2.21 g, 8.41 mmol) in DCM (50 mL) was added oxalyl chloride (0.80 mL, 9.17 mmol) followed by 1 drop of DMF. The resulting mixture was stirred at RT for 1 hr and then a second portion of oxalyl chloride (0.80 mL, 9.17 mmol) and of DMF (1 drop) were added. After a further 30 min the mixture was evaporated in vacuo and the residue thus obtained taken up into DCM (50 mL) and added to a solution of ethyl 6-(4-aminobenzoyl)-5,6-dihydro-4H-benzo[b]thieno[2,3-d]azepine-2-carboxylate (3.00 g, 7.64 mmol) in pyridine (20 mL). The resulting mixture was stirred at RT for 1 hr, then diluted with water (100 mL) and passed through a phase separator. The organic phase was evaporated in vacuo and the residue obtained purified by flash column chromatography (SiO2, 80 g, 0-100% EtOAc in isohexane, gradient elution). The pale orange residue that was isolated was triturated with acetonitrile (2×20 mL) and the solid that formed was collected by filtration and dried to afford the title compound as a white solid (2.78 g, 94% pure by HPLC, 57% yield); R' 1.95 min (Method 1a); m/z 637 (M+H)+ (ES+); 1H NMR δ: 1.32 (3H, t), 1.62 (4H, br t), 2.16 (3H, s), 3.06-3.38 (assume 3H, obscured by solvent), 3.45 (4H, br t), 3.60 (4H, s), 4.32 (2H, q), 4.85-4.95 (1H, br), 6.88 (1H, br d), 6.99 (2H, br d), 7.14 (1H, br t), 7.29 (1H, td), 7.45-7.53 (3H, over-lapping m), 7.79 (1H, s), 7.82 (1H, dd), 8.04 (1H, apparent dd), 10.37 (1H, s).

6-(4-(5-Methyl-2-(7-oxa-2-azaspiro[3.5]nonan-2-yl) nicotinamido)benzoyl)-5,6-dihydro-4H-benzo[b] thieno[2,3-d]azepine-2-carboxylic acid

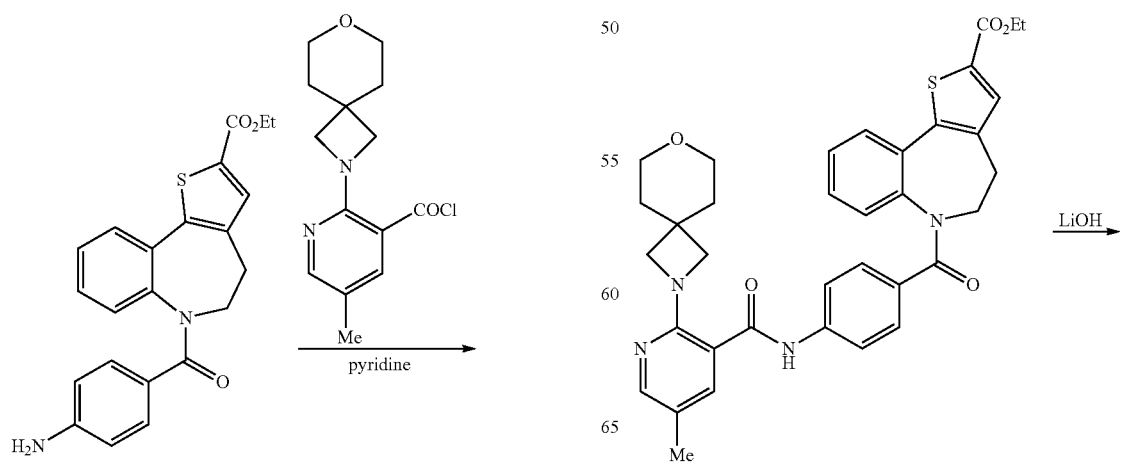

-continued

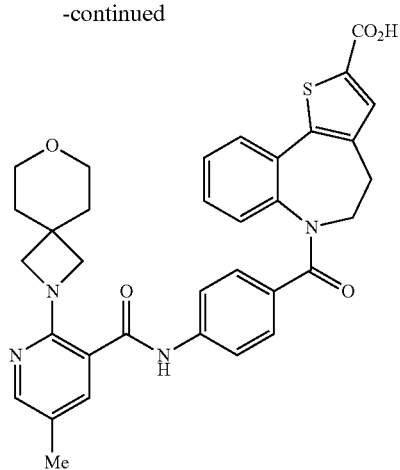

To a solution ethyl 6-(4-(5-methyl-2-(7-oxa-2-azaspiro[3.5]nonan-2-yl)nicotinamido)benzoyl)-5,6-dihydro-4H-benzo[b]thieno[2,3-d]azepine-2-carboxylate (3.72 g, 5.84 mmol) in a mixture of THF:MeOH (1:1, 40 mL) was added a solution of lithium hydroxide (700 mg, 29.2 mmol) in water (40 mL). The reaction mixture was heated to 50° C. for 1 hr and was then cooled to RT. The volatiles were removed in vacuo and the remaining aq solution was diluted with water and sonicated until the resulting precipitate dissolved. This mixture was neutralised by the addition of 1 M hydrochloric acid and the resulting solid collected by filtration and dried in vacuo to afford the title compound as an off-white solid (3.27 g, 92% yield); $R^t$ 1.64 min (Method 1a); m/z 609 (M+H)$^+$ (ES$^+$); $^1$H NMR δ: 1.62 (4H, br t), 2.16 (3H, s), 3.00-3.51 (assume 8H, obscured by solvent), 3.62 (4H, s), 4.82-4.96 (1H, br), 6.86 (1H, br d), 6.99 (2H, br d), 7.11 (1H, br t), 7.28 (1H, td), 7.46-7.54 (3H, over-lapping m), 7.62 (1H, s), 7.78 (1H, dd), 8.03 (1H, dd), 10.38 (1H, s).

Ethyl 6-(2-fluoro-4-nitrobenzoyl)-5,6-dihydro-4H-benzo[b]thieno[2,3-d]azepine-2-carboxylate

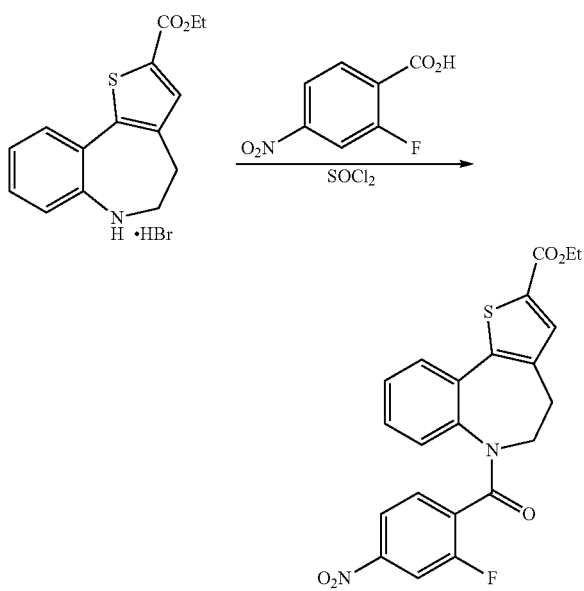

To a suspension of 2-fluoro-4-nitrobenzoic acid (1.00 g, 5.40 mmol) in DCM (30 mL) at RT was added thionyl chloride (2.87 mL, 39.3 mmol) and the resulting mixture was heated at reflux for 2 hr. The volatiles were evaporated in vacuo and the resulting residue was taken up into acetonitrile (20 mL) and was added dropwise at RT to a solution of ethyl 5,6-dihydro-4H-benzo[b]thieno[2,3-d]azepine-2-carboxylate hydrobromide (1.74 g, 4.91 mmol) in pyridine (20 mL). The mixture was stirred at RT for 4 hr and at 50° C. for 1 hr and was evaporated in vacuo.

The residue was taken up into EtOAc (200 mL) and was washed sequentially with 1 M hydrochloric acid (100 mL), sat aq NaHCO$_3$ (100 mL) and water (100 mL). The organic extracts were dried and evaporated in vacuo to afford the title compound as a brown gum (1.91 g, 88% yield, 95% pure by HPLC); $R^t$2.64 min (Method 1a); m/z 441 (M+H)$^+$ (ES$^+$). This material was used in the subsequent step without additional purification.

Ethyl 6-(4-amino-2-fluorobenzoyl)-5,6-dihydro-4H-benzo[b]thieno[2,3-d]azepine-2-carboxylate

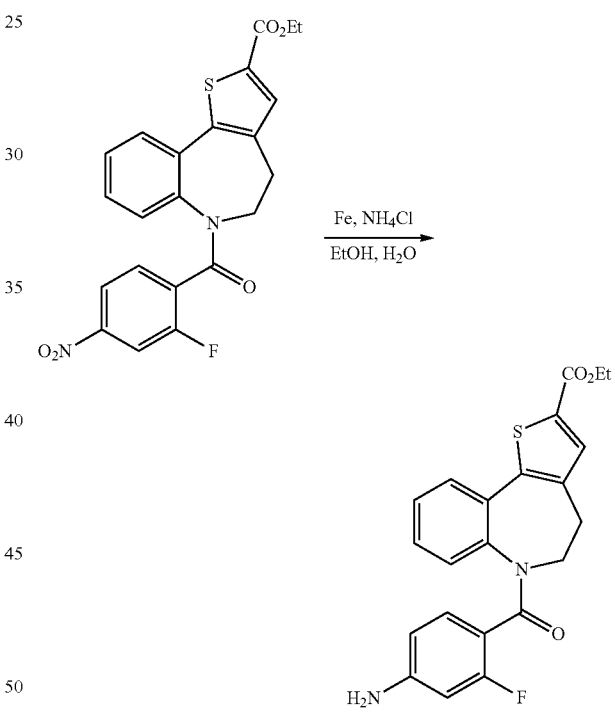

To a solution of ethyl 6-(2-fluoro-4-nitrobenzoyl)-5,6-dihydro-4H-benzo[b]thieno[2,3-d]azepine-2-carboxylate (4.55 g, 10.3 mmol) in a mixture of EtOH:water (2:1, 309 mL) at RT was added iron powder (2.88 g, 51.7 mmol) and ammonium chloride (5.53 g, 103 mmol). The resulting mixture was stirred at reflux for 2 hr, then cooled to RT and filtered through a celite pad. The pad was washed sequentially with MeOH (200 mL), DCM (100 mL) and with EtOAc (200 mL) and the combined organic filtrates were evaporated in vacuo. Water (250 mL) was added to the residue and the resulting solid was collected by filtration, washed with water (200 mL) and dried to afford the title compound (3.87 g, 89% yield); $R^t$ 2.29 min (Method 1a); m/z 411 (M+H)$^+$ (ES$^+$). This material was used in the subsequent step without additional purification.

53

Ethyl 6-(4-(2-chloro-6-methylnicotinamido)-2-fluorobenzoyl)-5,6-dihydro-4H-benzo[b]thieno[2,3-d]azepine-2-carboxylate

54

Ethyl 6-(4-(2-(7-oxa-2-azaspiro[3.5]nonan-2-yl)-6-methylnicotinamido)-2-fluorobenzoyl)-5,6-dihydro-4H-benzo[b]thieno[2,3-d]azepine-2-carboxylate

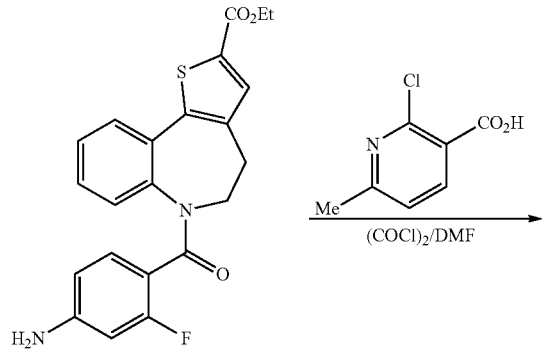

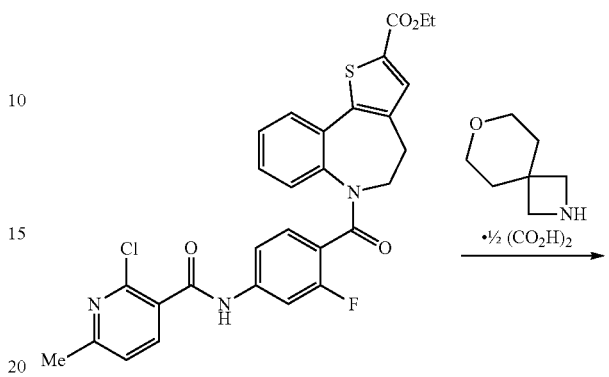

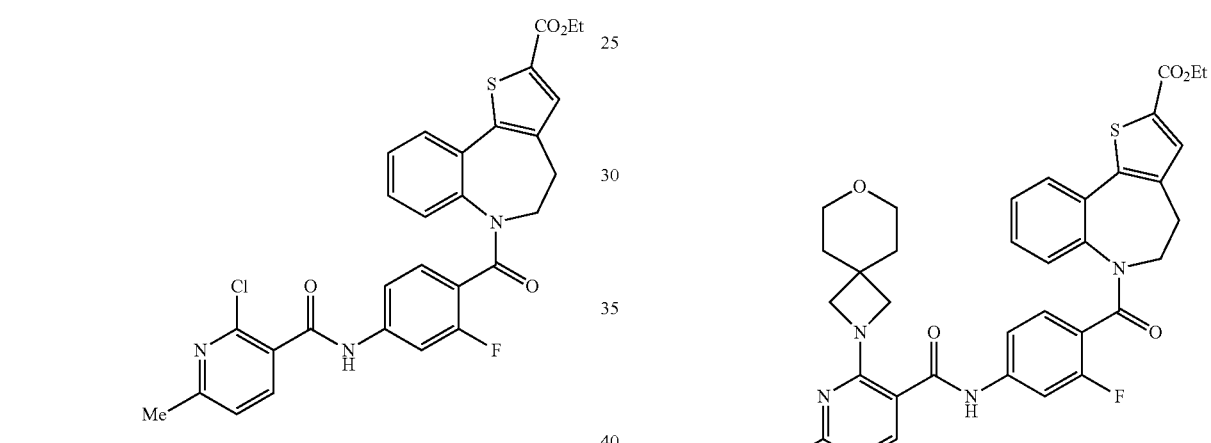

To neat DMF (40 mL) at RT was added neat oxalyl chloride (1.01 mL, 11.5 mmol) over 10 min and 10 min afterwards the resulting mixture was added to 2-chloro-6-methylnicotinic acid (0.92 g, 5.36 mmol). After an additional 10 min a solution of ethyl 6-(4-amino-2-fluoro benzoyl)-5,6-dihydro-4H-benzo[b]thieno[2,3-d]azepine-2-carboxylate (1.10 g, 2.68 mmol) in pyridine (13 mL) was added dropwise over 2 min at RT. The reaction mixture was stirred for 30 min, quenched by the addition of sat aq NaHCO$_3$ (10 mL) and then partitioned between EtOAc (10 mL) and water (10 mL). The organic layer was separated, dried and evaporated in vacuo. The solid thus obtained was purified by flash column chromatography (SiO$_2$, 12 g, 0-50% EtOAc in isohexane, gradient elution) to afford the title compound as an off-white solid (1.39 g, 88% yield); R$^t$ 2.49 min (Method 1b); m/z 564 (M+H)$^+$ (ES$^+$); $^1$H NMR δ: 1.32 (3H, t), 2.50 (assume 3H, obscured by solvent), 3.10 (1H, dt), 3.21-3.39 (assume 2H, obscured by solvent), 4.32 (2H, q), 4.81-4.86 (1H, m), 6.95 (1H, br d), 7.14 (1H, td), 7.20-7.40 (5H, over-lapping m), 7.76-7.78 (2H, over-lapping m), 7.94 (1H, d), 10.78 (1H, s).

To a solution of ethyl 6-(4-(2-chloro-6-methylnicotinamido)-2-fluorobenzoyl)-5,6-dihydro-4H-benzo[b]thieno[2,3-d]azepine-2-carboxylate (669 mg, 1.19 mmol) and 7-oxa-2-azaspiro[3.5]nonane hemioxalate (773 mg, 3.56 mmol) in NMP (6.0 mL) was added Et$_3$N (0.99 mL, 7.12 mmol). The reaction mixture was heated to 130° C. for 1 hr and was then cooled to RT and treated with water (50 mL). The resulting precipitate was collected by vacuum filtration, washed with water (50 mL) and the solid then taken up into a mixture of DCM:MeOH (9:1). The volatiles were evaporated in vacuo to afford the title compound, (826 mg, 91% pure by HPLC, containing residual NMP; R$^t$ 1.98 min (Method 1a); m/z 655 (M+H)$^+$ (ES$^+$). This material was used in the subsequent step without additional purification.

55

6-(4-(2-(7-Oxa-2-azaspiro[3.5]nonan-2-yl)-6-methylnicotinamido)-2-fluorobenzoyl)-5,6-dihydro-4H-benzo[b]thieno[2,3-d]azepine-2-carboxylic acid

56

6-(4-Nitrobenzoyl)-N-(2-fluorophenyl)-5,6-dihydro-4H-benzo[b]thieno[2,3-d]azepine-2-carboxamide

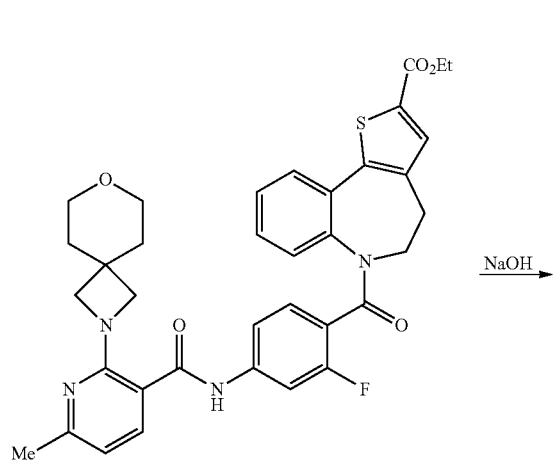

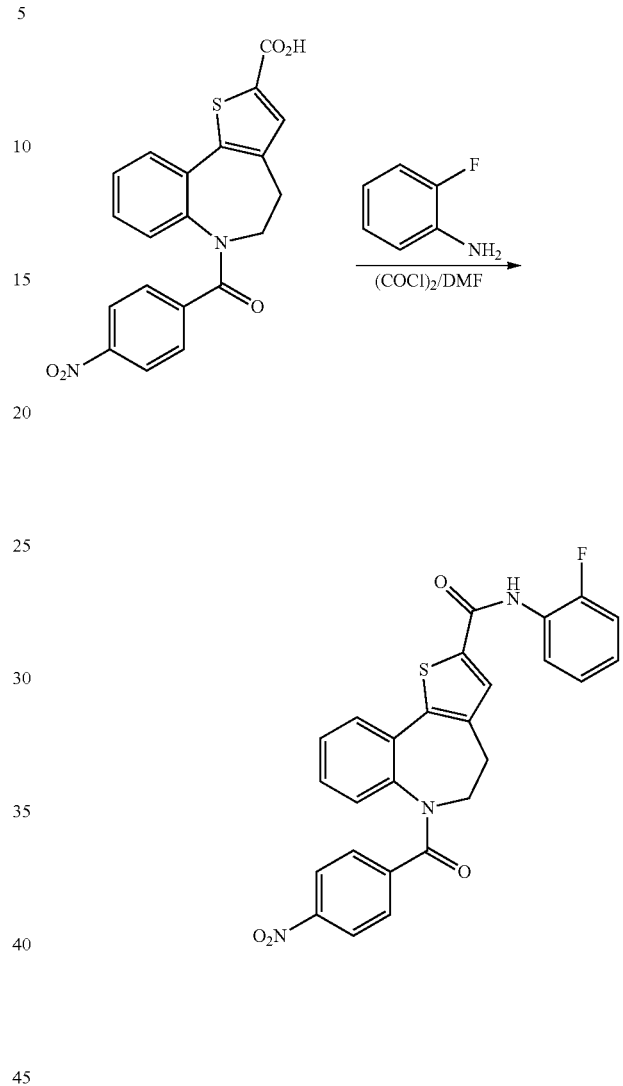

To a solution of ethyl 6-(4-(2-(7-oxa-2-azaspiro[3.5]nonan-2-yl)-6-methylnicotinamido)-2-fluorobenzoyl)-5,6-dihydro-4H-benzo[b]thieno[2,3-d]azepine-2-carboxylate (826 mg, 1.26 mmol) in a mixture of THF:MeOH (1:1, 12.6 mL) was added 2 M aq NaOH (6.3 mL) and the reaction mixture heated at 50° C. for 2 hr. After cooling to RT the mixture was acidified to pH 3 by the addition of 1 M hydrochloric acid and extracted with a mixture of DCM:MeOH (9:1, 2×75 mL). The combined organic extracts were evaporated in vacuo to afford the title compound as a off-white solid (775 mg, 90% pure by $^1$H NMR, 98%); R$^t$ 1.76 min (Method 1a); m/z 627 (M+H)$^+$ (ES$^+$). This material was used in the subsequent step without additional purification.

To neat DMF (40 mL) at RT was added oxalyl chloride (1.0 mL, 11 mmol) and the mixture stirred for 10 min. An aliquot (8.9 mL) of the resulting solution was withdrawn and added to 6-(4-nitrobenzoyl)-5,6-dihydro-4H-benzo[b]thieno[2,3-d]azepine-2-carboxylic acid (1.0 g, 2.5 mmol) and the mixture stirred at RT for 24 hr. A second aliquot (0.2 mL) of the oxalyl chloride solution was added dropwise at RT and after 2 hr a solution of 2-fluoroaniline (1.1 g, 10 mmol) in pyridine (10.0 mL) was added. The reaction mixture was kept at RT for 24 hr and was then quenched by the addition of water (100 mL). The resulting solid was filtered, washed with water (100 mL) and dried to give the title compound as a white solid (800 mg, 60% yield); R$^t$ 2.46 min (Method 1b); m/z 488 (M+H)$^+$ (ES$^+$); $^1$H NMR δ: 3.15-3.20 (1H, m), 3.29-3.44 (assume 2H, obscured by solvent), 4.88-4.93 (1H, m), 6.96 (1H, br d), 7.09 (1H, td), 7.22-7.35 (6H, overlapping m), 7.60 (1H, td), 7.81 (1H, dd), 8.00 (1H, s), 8.07 (2H, br d), 10.25 (1H, s).

57

6-(4-Aminobenzoyl)-N-(2-fluorophenyl)-5,6-dihydro-4H-benzo[b]thieno[2,3-d]azepine-2-carboxamide

58

6-(4-(2-Chloro-6-methoxynicotinamido)benzoyl)-N-(2-fluorophenyl)-5,6-dihydro-4H-benzo[b]thieno[2,3-d]azepine-2-carboxamide

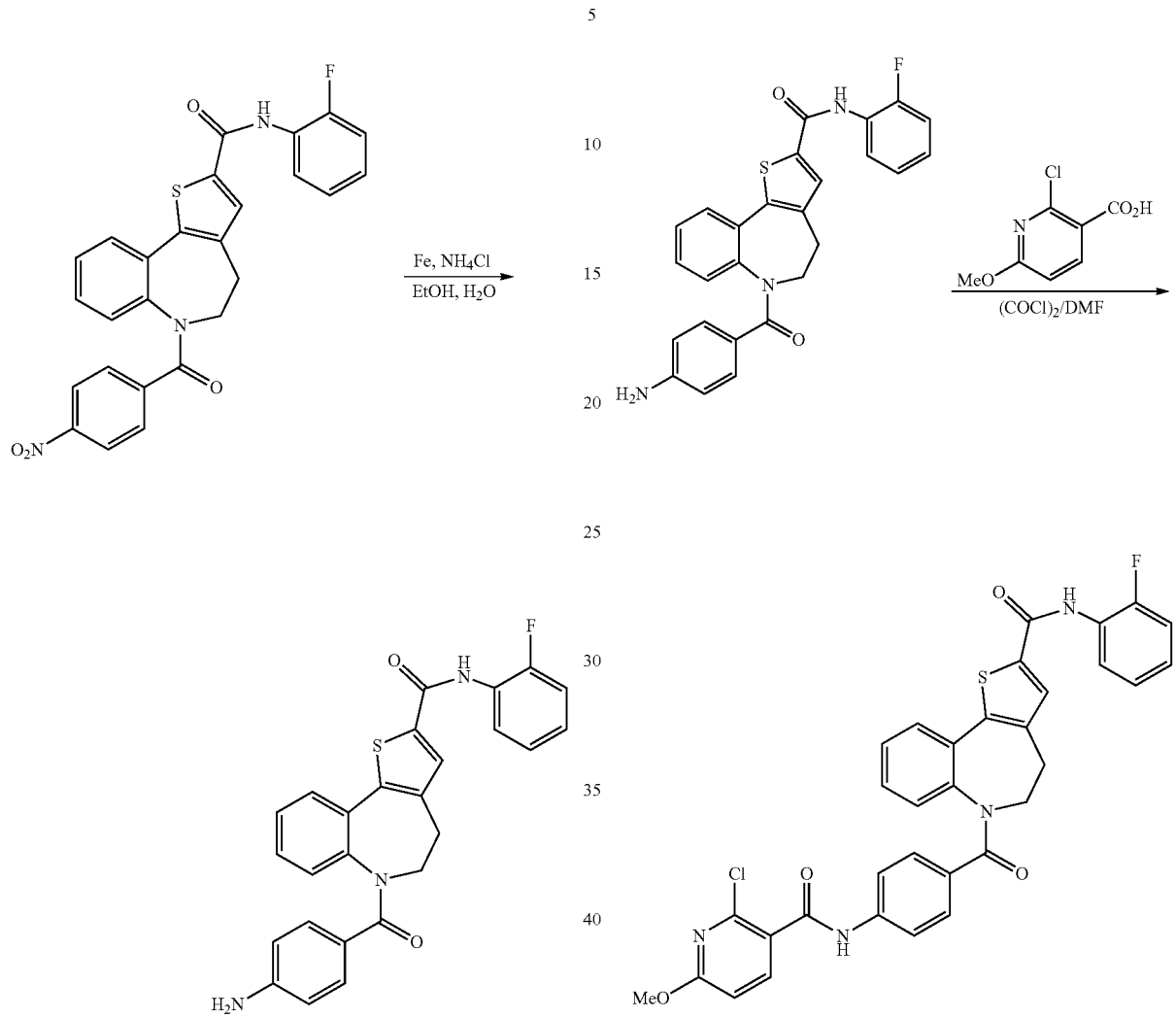

To a solution of 6-(4-nitrobenzoyl)-N-(2-fluorophenyl)-5,6-dihydro-4H-benzo[b]thieno[2,3-d]azepine-2-carboxamide (779 mg, 1.60 mmol) in a mixture of EtOH:water (2:1, 48 mL) at RT was added iron powder (447 mg, 8.00 mmol) and ammonium chloride (856 mg, 16.0 mmol).

The reaction mixture was heated at 80° C. for 2 hr, cooled to RT and was then filtered through a celite pad. The pad was washed with EtOAc (100 mL) and the combined filtrates were evaporated in vacuo. Water (50 mL) was added to the residue which was then extracted with a mixture of DCM:MeOH (9:1, 2×50 mL). The combined organic extracts were washed with saturated aq NaHCO$_3$ (50 mL) and with water (50 mL) and dried by passing the solution through a phase separator. The volatiles were evaporated in vacuo to afford the title compound as a tan solid (700 mg, 91% yield); R$^t$ 2.16 min (Method 1b); m/z 458 (M+H)$^+$ (ES$^+$); $^1$H NMR δ: 3.17 (3H, br), 4.92 (1H, br), 5.48 (2H, s), 6.27 (2H, d), 6.75 (2H, d), 6.81 (1H, dd), 7.12 (1H, td), 7.21-7.34 (4H, overlapping m), 7.59 (1H, td), 7.81 (1H, dd), 7.95 (1H, s), 10.20 (1H, s).

To DMF (20 mL) at RT was added oxalyl chloride (0.50 mL, 5.71 mmol) over 10 min and the mixture stirred for 1 hr. An aliquot (2.3 mL) of the resulting solution was withdrawn, and was added to 2-chloro-6-methoxynicotinic acid (122 mg, 0.65 mmol). This mixture was kept at RT for 3 hr and was then treated with a solution of 6-(4-aminobenzoyl)-N-(2-fluorophenyl)-5,6-dihydro-4H-benzo[b]thieno[2,3-d]azepine-2-carboxamide (149 mg, 0.33 mmol) in pyridine (1.3 mL). The reaction mixture was maintained at RT for 16 hr and was then quenched by the addition of water (20 mL). The resulting solid was collected by filtration, washed with water (25 mL) and then taken up into a mixture of DCM:MeOH (9:1). The solution was concentrated in vacuo to give the title compound as a white solid (172 mg, 81% yield); R$^t$2.55 min (Method 1a); m/z 628 (M+H)$^+$ (ES$^+$); $^1$H NMR δ: 3.11-3.36 (assume 3H, obscured by solvent), 3.89 (3H, s), 4.88-4.97 (1H, m), 6.85-6.89 (1H, m), 6.93 (1H, d), 7.02 (2H, br d), 7.13 (1H, br t), 7.21-7.35 (4H, over-lapping m), 7.50 (2H, br d), 7.59 (1H, td), 7.82 (1H, dd), 7.95 (1H, d), 7.98 (1H, s), 10.23 (1H, s), 10.57 (1H, s).

59

6-(4-(5-Bromo-2-chloronicotinamido)benzoyl)-N-(2-fluorophenyl)-5,6-dihydro-4H-benzo[b]thieno[2,3-d]azepine-2-carboxamide

60

6-(4-(5-Bromo-2-(7-oxa-2-azaspiro[3.5]nonan-2-yl)nicotinamido)benzoyl)-N-(2-fluoro phenyl)-5,6-dihydro-4H-benzo[b]thieno[2,3-d]azepine-2-carboxamide

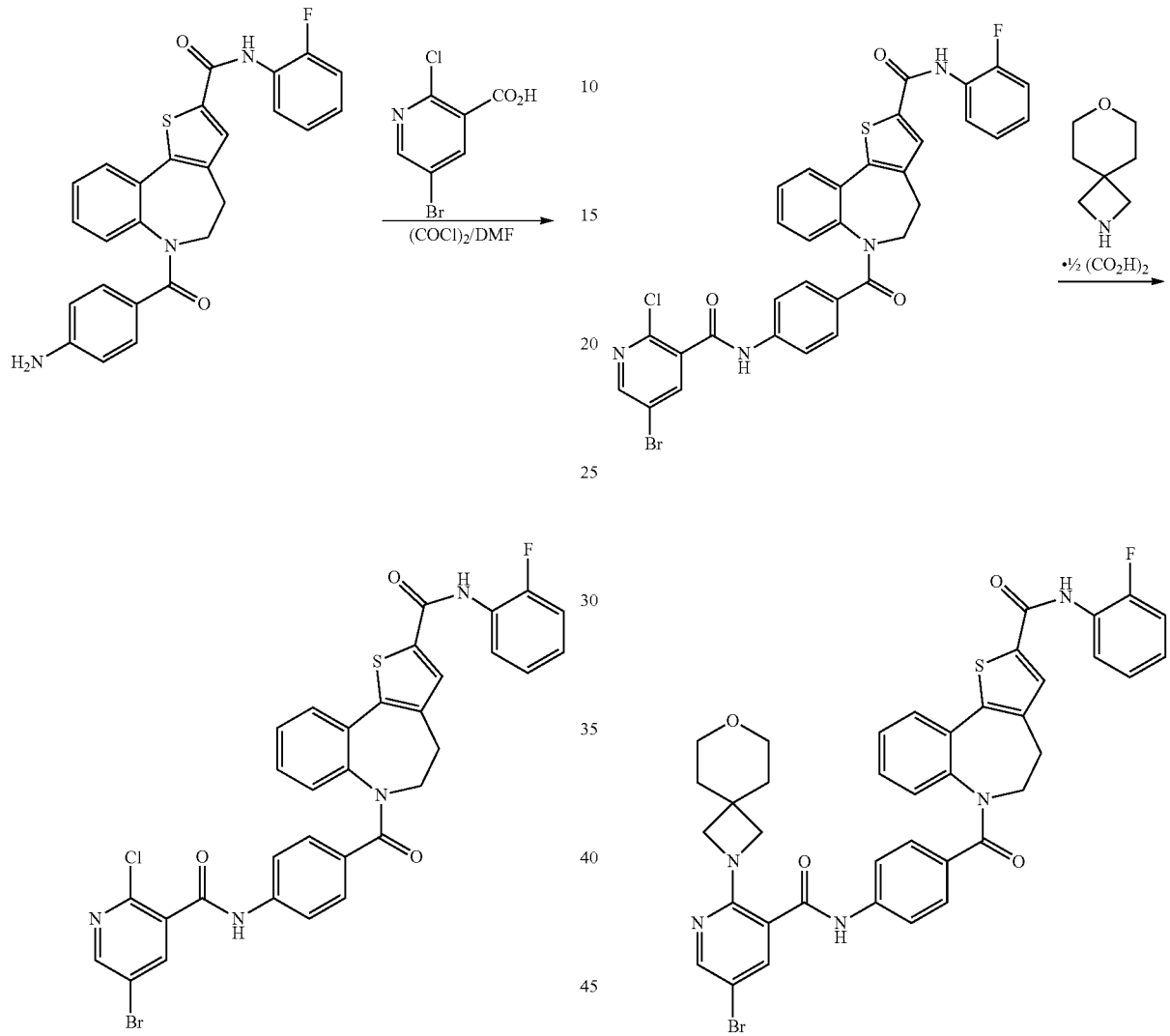

To DMF (20 mL) at RT was added oxalyl chloride (0.50 mL, 5.71 mmol) over 10 min. After an additional 10 min an aliquot (1.9 mL) of the resulting solution was withdrawn and was added to 5-bromo-2-chloronicotinic acid (260 mg, 1.10 mmol). This mixture was kept at RT for 30 min and was then treated with a solution of 6-(4-aminobenzoyl)-N-(2-fluorophenyl)-5,6-dihydro-4H-benzo[b]thieno[2,3-d]azepine-2-carboxamide (250 mg, 0.55 mmol) in pyridine (2.2 mL). The reaction mixture was maintained at RT for 16 hr and was then quenched by the addition of water (20 mL) and extracted into a mixture of DCM:MeOH (9:1). The organic extracts were evaporated in vacuo and the resulting residue was purified by flash column chromatography (SiO$_2$, 12 g, 0-10% MeOH in DCM, gradient elution) to afford the title compound as a white solid (205 mg, 83% pure by HPLC, 55% yield); R'2.60 min (Method 1a); m/z 675 (M+H)$^+$ (ES$^+$). This material was used in the subsequent step without additional purification.

To a solution of 6-(4-(5-bromo-2-chloronicotinamido)benzoyl)-N-(2-fluorophenyl)-5,6-dihydro-4H-benzo[b]thieno[2,3-d]azepine-2-carboxamide (698 mg, 1.03 mmol) and 7-oxa-2-azaspiro [3.5]nonane hemioxalate (665 mg, 3.06 mmol) in NMP (5.1 mL) was added Et$_3$N (0.85 mL, 6.12 mmol). The reaction mixture was heated to 130° C. for 1 hr and was cooled to RT and treated with water (50 mL). The resulting precipitate was collected by filtration and was purified by flash column chromatography (SiO$_2$, 40 g, 0-10% MeOH in DCM, gradient elution) to afford the title compound as a tan foam (640 mg, 81% yield); R' 2.61 min (Method 1a); m/z 767 (M+H)$^+$ (ES$^+$); $^1$H NMR δ: 1.63 (4H, br t), 3.12-3.35 (assume 3H, obscured by solvent), 3.46 (4H, br t), 3.65 (4H, s), 4.90-4.98 (1H, b), 6.88 (1H, br d), 7.02 (2H, br d), 7.12 (1H, br t), 7.21-7.35 (4H, over-lapping m), 7.50 (2H, br d), 7.59 (1H, td), 7.80-7.83 (2H, over-lapping m), 7.98 (1H, s), 8.26 (1H, d), 10.23 (1H, s), 10.48 (1H, s). This material, containing ~10% NMP and a trace of DCM was used directly in subsequent preparations.

61

N-(2-fluoro-6-methylphenyl)-6-(4-nitrobenzoyl)-5,6-dihydro-4H-benzo[b]thieno[2,3-d]azepine-2-carboxamide

62

6-(4-aminobenzoyl)-N-(2-fluoro-6-methylphenyl)-5,6-dihydro-4H-benzo[b]thieno[2,3-d]azepine-2-carboxamide

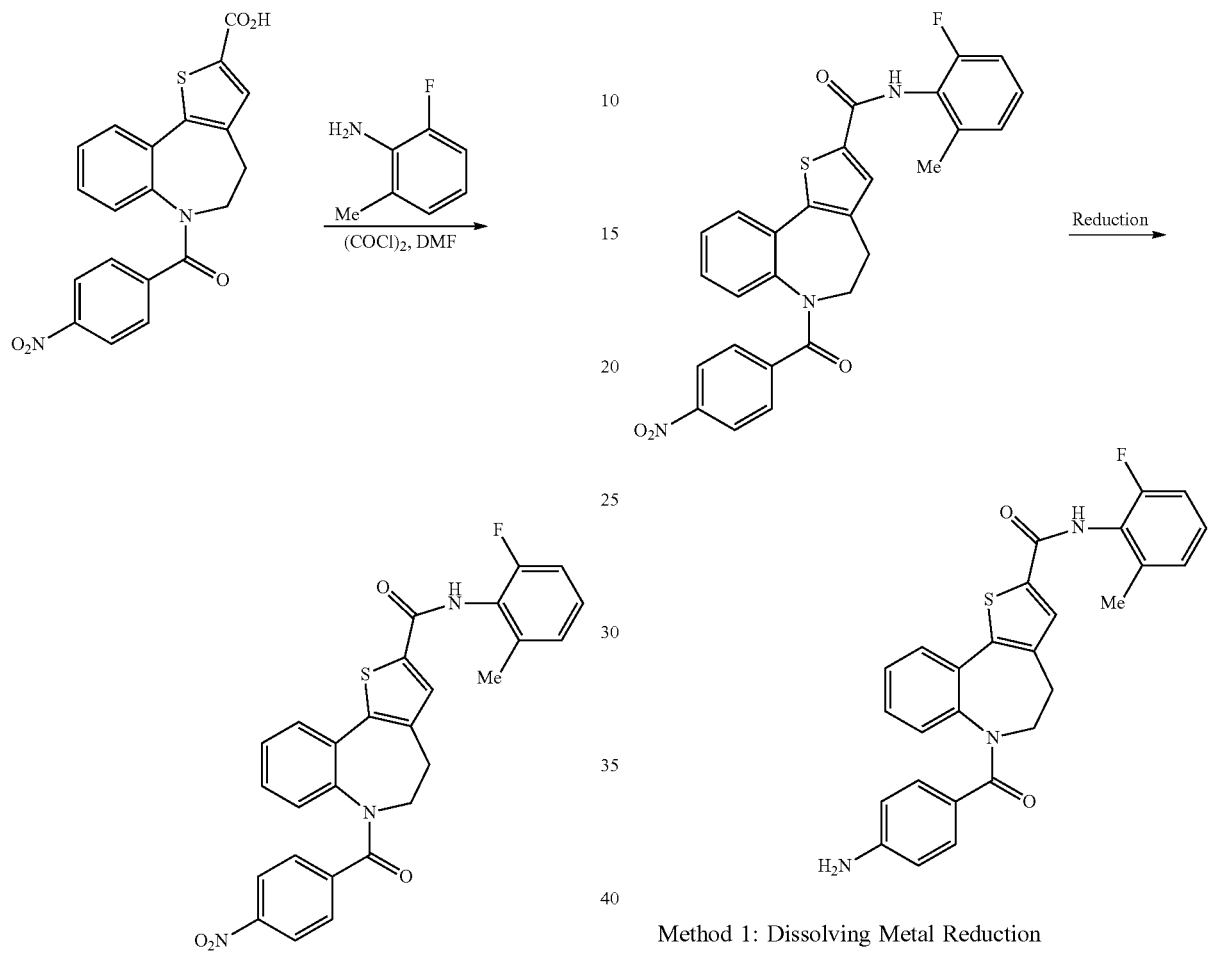

To a suspension of 6-(4-nitrobenzoyl)-5,6-dihydro-4H-benzo[b]thieno[2,3-d]azepine-2-carboxylic acid (10.0 g, 25.4 mmol) in DCM (250 mL) was added oxalyl chloride (11.1 mL, 127 mmol) followed by 1 drop of DMF. The resulting mixture was stirred at RT for 1 hr and was then evaporated in vacuo. The residue thus obtained was taken up into DCM (100 mL) and to this solution was added a solution of 2-fluoro-6-methylaniline (6.35 g, 50.7 mmol) in pyridine (100 mL). The mixture was stirred at RT for 1 hr and was then evaporated in vacuo. The residue was taken up into EtOAc (500 mL) and the solution was washed with 1 M hydrochloric acid (2×100 mL), followed by sat aq NaHCO$_3$ (100 mL) and then dried and evaporated in vacuo. This same procedure was repeated three times with additional 6-(4-nitrobenzoyl)-5,6-dihydro-4H-benzo[b]thieno[2,3-d]azepine-2-carboxylic acid (12.0 g, 30.4 mmol) to afford the title compound as a pale yellow solid (51.1 g, 93% pure by HPLC, 87% yield); R′2.46 min (Method 1a); m/z 502 (M+H)$^+$ (ES$^+$). This material was used in the subsequent step without additional purification.

Method 1: Dissolving Metal Reduction

To a solution of N-(2-fluoro-6-methylphenyl)-6-(4-nitrobenzoyl)-5,6-dihydro-4H-benzo[b]thieno[2,3-d]azepine-2-carboxamide (5.00 g, 9.97 mmol) in EtOH (100 mL) was added ammonium chloride (5.33 g, 100 mmol), water (20 mL) and then iron powder (2.78 g, 49.8 mmol). The resulting mixture was stirred at reflux for 1 hr and was then filtered through celite. The celite pad was washed with EtOH (50 mL) and the combined filtrates were evaporated in vacuo. The resulting residue was taken up into EtOAc (200 mL), washed with water (2×100 mL) and was then dried and evaporated in vacuo. This procedure was repeated three times with additional N-(2-fluoro-6-methylphenyl)-6-(4-nitrobenzoyl)-5,6-dihydro-4H-benzo[b]thieno [2,3-d]azepine-2-carboxamide (15.0 g, 29.9 mmol) and the solids that were obtained were combined and triturated with Et$_2$O (200 mL) to afford the title compound as a pale yellow solid (41.1 g, 87% yield); R′2.12 min (Method 1a); m/z 472 (M+H)$^+$ (ES$^+$); $^1$H NMR δ: 2.25 (3H, s), 3.02-3.30 (3H, br), 4.85-5.05 (1H, br), 5.51 (2H, s), 6.27 (2H, d), 6.75 (2H, d), 6.80 (1H, d), 7.10-7.15 (3H, over-lapping m), 7.24-7.30 (2H, over-lapping m), 7.81 (1H, dd), 7.93 (1H, s), 10.02 (1H, s).

Method 2: Catalytic Hydrogenation

To a solution of N-(2-fluoro-6-methylphenyl)-6-(4-nitrobenzoyl)-5,6-dihydro-4Hbenzo[b]thieno[2,3-d]azepine-2-carboxamide (100 mg, 0.199 mmol) in THF (4.0 mL) was added 5% Pd/C paste (58 wt % water, 21.0 mg, 0.100 mmol) and the mixture stirred under 5 bar of hydrogen for 18 hr. Upon completion of the reaction the mixture was passed through a Agilent 0.45 μm syringe filter and filtrate evaporated in vacuo to afford the title compound (91.0 mg, 97% yield); R'2.13 min (Method 1a); m/z 472 (M+H)$^+$ (ES$^+$).

6-(4-(2-Chloro-5-methylnicotinamido)benzoyl)-N-(2-fluoro-6-methylphenyl)-5,6-dihydro-4H-benzo[b]thieno[2,3-d]azepine-2-carboxamide

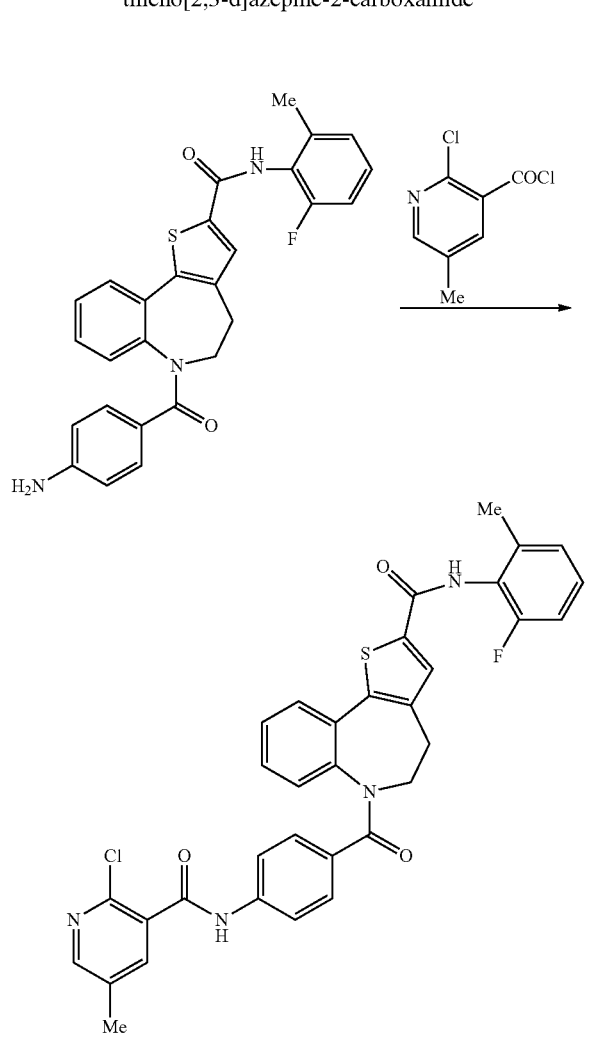

A solution of 2-chloronicotinoyl chloride (1.21 g, 3.36 mmol) in DCM (10 mL) was added to a stirred solution of 6-(4-aminobenzoyl)-N-(2-fluoro-6-methylphenyl)-5,6-dihydro-4H-benzo[b]thieno[2,3-d]azepine-2-carboxamide (2.00 g, 4.24 mmol) in pyridine (10 mL). The reaction mixture was stirred at RT for 1 hr and was then poured into water (100 mL) and extracted into EtOAc (2×50 mL) The combined organics were concentrated in vacuo to remove volatiles and the resulting solid was slurried in EtOAc (50 mL) and collected by filtration. The above procedure was repeated another three times, on an increasingly greater scale, using 5.0, 15.0 and finally 18.0 g of the aniline starting material. All batches were then combined by taking them up into DCM (300 mL). The solvent was evaporated in vacuo to give the title compound as a white solid (40.34 g, 75% yield); R' 2.39 min (Method 1a); m/z 625 (M+H)$^+$ (ES$^+$); $^1$H NMR δ: 2.26 (3H, s), 2.32 (3H, s), 3.09-3.33 (assume 3H, obscured by solvent), 4.83-5.03 (1H, m), 6.86 (1H, d), 7.04 (2H, d), 7.09-7.19 (3H, m), 7.22-7.34 (2H, m), 7.51 (2H, d), 7.83 (1H, dd), 7.91 (1H, d), 7.96 (1H, s), 8.36 (1H, dd), 10.04 (1H, s), 10.71 (1H, s).

Methyl 5-bromo-2-(7-oxa-2-azaspiro[3.5]nonan-2-yl)nicotinate

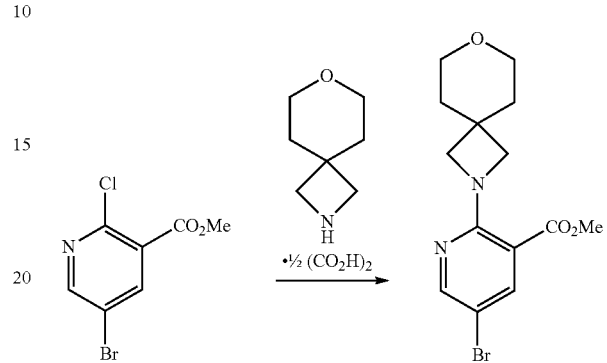

To a solution of methyl 5-bromo-2-chloronicotinate (5.75 g, 23.0 mmol) and 7-oxa-2-azaspiro[3.5]nonane hemi oxalate (5.98 g, 27.5 mmol) in NMP (55 mL) was added Et$_3$N (9.60 mL, 68.9 mmol). The reaction mixture was heated to 120° C. for 1 hr and was then cooled to RT and diluted with water (250 mL) and EtOAc (200 mL). The aq layer was separated and was extracted with EtOAc (200 mL). The combined organic layers were washed with water (3×300 mL) and then dried and evaporated in vacuo to give the title compound as a brown solid (7.22 g, 92% yield); R' 2.15 min (Method 1a); m/z 340/342 (M+H)$^+$ (ES$^+$); $^1$H NMR δ: 1.68 (4H, br t), 3.52 (4H, br t), 3.72 (4H, s), 3.81 (3H, s), 8.01 (1H, d), 8.35 (1H, d).

Methyl 5-cyclopropyl-2-(7-oxa-2-azaspiro[3.5]nonan-2-yl)nicotinate

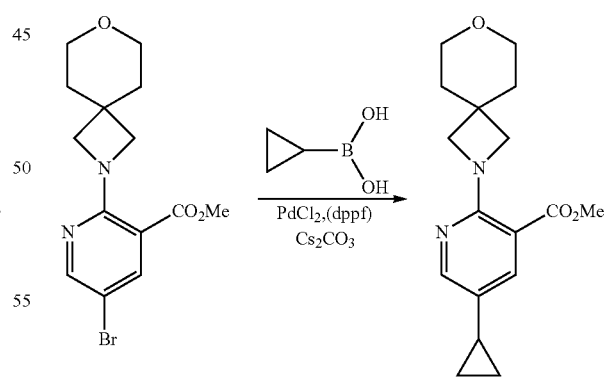

A mixture of methyl 5-bromo-2-(7-oxa-2-azaspiro[3.5]nonan-2-yl)nicotinate (1.50 g, 4.40 mmol), cyclopropylboronic acid (0.77 g, 9.00 mmol), cesium carbonate (3.23 g, 9.90 mmol) and Pd(dppf)Cl$_2$ (0.33 g, 0.45 mmol) was suspended in water (7.5 mL) and 1,4-dioxane (15.0 mL) and degassed with nitrogen for 10 min. The reaction mixture was heated at 100° C. for 6 hr, cooled to RT and was then partitioned between EtOAc (100 mL) and water (100 mL).

The organic layer was separated and was washed with brine (100 mL) and then dried and evaporated in vacuo. The crude residue thus obtained was purified by flash column chromatography (SiO$_2$, 40 g, 0-100% EtOAc in isohexane, gradient elution) to afford the title compound, as a colourless oil (1.17 g, 86% yield, 91% pure by $^1$H NMR); R$^t$ 1.44 min (Method 1a); m/z 303 (M+H)$^+$ (ES$^+$). This material was used in subsequent steps without additional purification.

5-Cyclopropyl-2-(7-oxa-2-azaspiro[3.5]nonan-2-yl) nicotinic acid

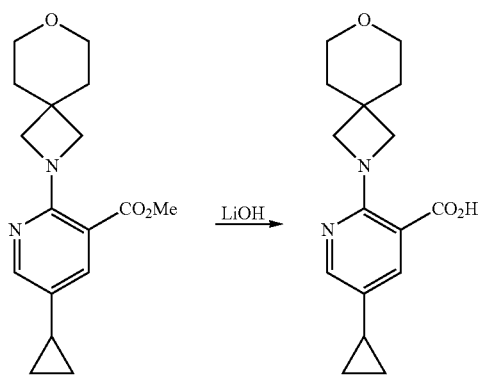 [SMILES: COC(=O)c1cc(C2CC2)cnc1N1CC2(CCOCC2)C1 ; "LiOH" ; O=C(O)c1cc(C2CC2)cnc1N1CC2(CCOCC2)C1]

To a solution of methyl 5-cyclopropyl-2-(7-oxa-2-azaspiro[3.5]nonan-2-yl)nicotinate (1.17 g, 3.87 mmol) in a mixture of THF:MeOH:water (2:1:1, 32 mL) was added lithium hydroxide (0.19 g, 7.7 mmol). The reaction mixture was heated to 50° C. for 6 hr and was then allowed to cool to RT overnight. The volatiles were removed in vacuo and the remaining aq solution acidified to pH 4 by the addition of 1 M hydrochloric acid. The mixture was extracted with EtOAc (3×100 mL) and the combined organic extracts were dried and evaporated in vacuo to afforded the title compound as a white foam (0.91 g, 95% pure by $^1$H NMR, 82% yield); R$^t$ 0.92 min (Method 1a); m/z 289 (M+H)$^+$ (ES$^+$).

2-Oxo-1,5,7,8-tetrahydro-2H-pyrano[4,3-b]pyridine-3-carboxylic acid

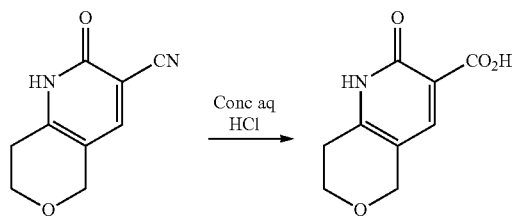 [SMILES: N#Cc1cc2c([nH]c1=O)CCOC2 ; O=C(O)c1cc2c([nH]c1=O)CCOC2]

A mixture of 2-oxo-1,5,7,8-tetrahydro-2H-pyrano[4,3-b]pyridine-3-carbonitrile (2.50 g, 14.2 mmol) and conc hydrochloric acid (28.4 mL) was heated at reflux for 6 hr. The resulting solution was concentrated to one third of the original volume and the resulting precipitate filtered and retained. The filtrate was evaporated in vacuo and the resulting solid triturated with water (20 mL) and filtered. This solid was combined with that previously obtained and partitioned between DCM:MeOH (9:1, 500 mL) and water (200 mL). The organic extracts were separated and the aq layer further extracted with DCM:MeOH (9:1, 5×300 mL). The combined organic extracts were dried and evaporated in vacuo to afford the title compound as a brown solid (2.45 g, 92% pure by HPLC, 88% yield); R$^t$ 0.70 min (Method 1a);

m/z 196 (M+H)$^+$ (ES$^+$). This material was used in subsequent steps without additional purification.

2-Chloro-7,8-dihydro-5H-pyrano[4,3-b]pyridine-3-carbonyl chloride

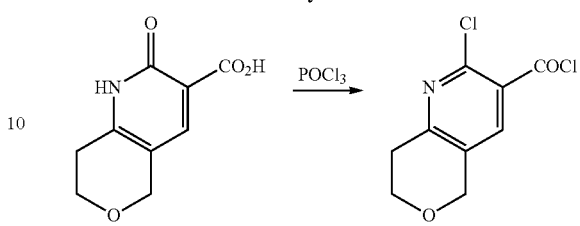

A solution of 2-oxo-1,5,7,8-tetrahydro-2H-pyrano[4,3-b]pyridine-3-carboxylic acid (500 mg, 2.56 mmol) in phosphoryl trichloride (5.12 mL, 2.56 mmol) was heated at reflux for 18 hr and then was cooled to RT and evaporated in vacuo to afford the title compound as a colourless solid (100 mg, 28% yield); R$^t$ 1.48 min (Method 1a); m/z 228 (M+H)$^+$ [methyl ester] (ES$^+$). This material was used in the subsequent step without additional purification.

2-Chloro-N-(4-(2-((2-fluoro-6-methylphenyl)car-bamoyl)-5,6-dihydro-4H-benzo[b]thieno [2,3-d] azepine-6-carbonyl)phenyl)-7,8-dihydro-5H-pyrano [4,3-b]pyridine-3-carboxamide

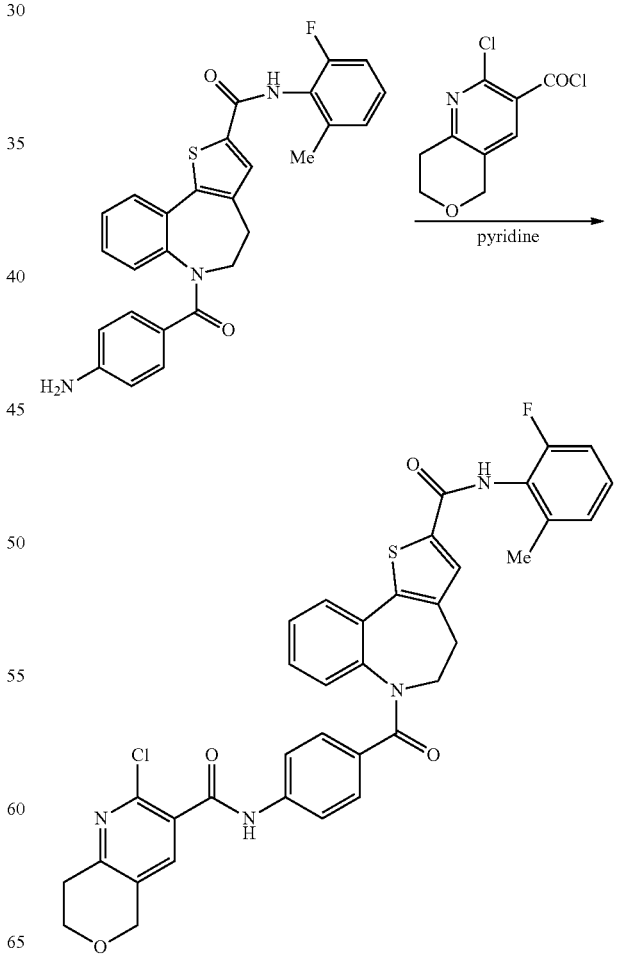

To a solution of 6-(4-aminobenzoyl)-N-(2-fluoro-6-methylphenyl)-5,6-dihydro-4H-benzo[b]thieno[2,3-d]azepine-2-carboxamide (200 mg, 0.42 mmol) in pyridine (2.9 mL) was added a solution of 2-chloro-7,8-dihydro-5H-pyrano[4,3-b]pyridine-3-carbonyl chloride (98 mg, 0.42 mmol) in DCM (5.7 mL). After 1 hr at RT the solvent was evaporated in vacuo and the resulting residue triturated with water (50 mL). The solids were collected by filtration and purified by flash column chromatography (SiO$_2$, 12 g, 0-10% MeOH in DCM, gradient elution) to afford the title compound as a white solid (76 mg, 27% yield); R$^t$ 2.28 min (Method 1b); m/z 667 (M+H)$^+$ (ES$^+$).

Ethyl 6-(4-(2-chloro-6,7-dihydro-5H-cyclopenta[b]pyridine-3-carboxamido)benzoyl)-5,6-dihydro-4H-benzo[b]thieno[2,3-d]azepine-2-carboxylate

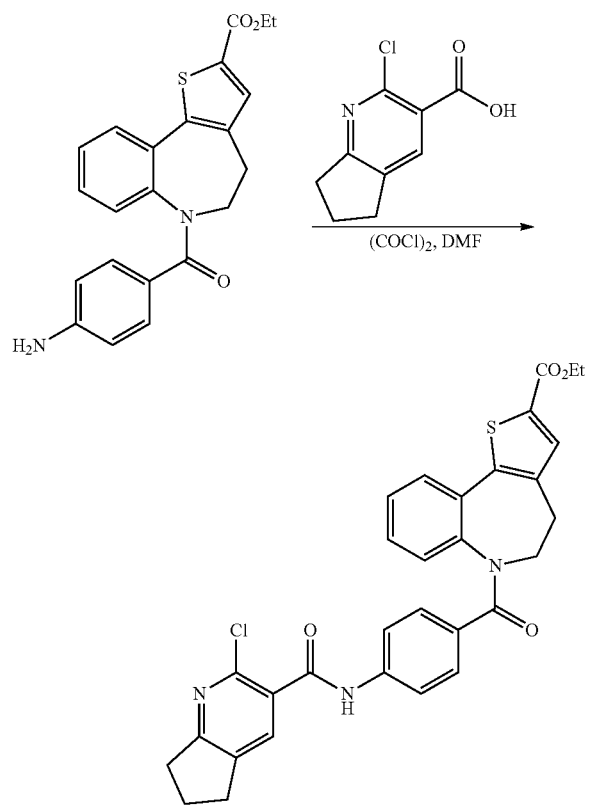

To a suspension of 2-chloro-6,7-dihydro-5H-cyclopenta[b]pyridine-3-carboxylic acid (3.78 g, 19.1 mmol) in DCM (50 mL) was added oxalyl chloride (5.58 mL, 63.7 mmol) and two drops of DMF. The resulting mixture was stirred at RT for 1 hr and then evaporated in vacuo. The residue was taken up into DCM (50 mL) and added to a solution of ethyl 6-(4-aminobenzoyl)-5,6-dihydro-4H-benzo[b]thieno[2,3-d]azepine-2-carboxylate (5.00 g, 12.7 mmol) in pyridine (20 mL) at RT. The reaction mixture was maintained at RT for 1 hr and then quenched by the addition of water (100 mL) and extracted into EtOAc (100 mL). The aq layer was separated and the organic extracts washed with brine (50 mL) and with water (50 mL), and then dried over a phase separator. After evaporating in vacuo the resulting residue was purified by flash column chromatography (SiO$_2$, 80 g, 0-10% MeOH in DCM, gradient elution). The solid thus obtained was triturated with MeCN (2×20 mL), collected by filtration and dried to afford the title compound as a pale orange solid (6.22 g, 85% yield); R$^t$2.61 min (Method 1a); m/z 572 (M+H)$^+$ (ES$^+$); $^1$H NMR δ: 1.32 (3H, t), 2.09 (2H, quint), 2.86-2.96 (4H, m), 3.04-3.30 (assume 3H, obscured by solvent), 4.32 (2H, q), 4.83-4.96 (1H, m), 6.87 (1H, d), 7.00 (2H, br d), 7.15 (1H, brt), 7.29 (1H, td), 7.49 (2H, br d), 7.78 (1H, s), 7.81 (1H, dd), 7.84 (1H, s), 10.61 (1H, s).

Ethyl 6-(4-(2-(7-oxa-2-azaspiro[3.5]nonan-2-yl)-6,7-dihydro-5H-cyclopenta[b]pyridine-3-carboxamido)benzoyl)-5,6-dihydro-4H-benzo[b]thieno[2,3-d]azepine-2-carboxylate

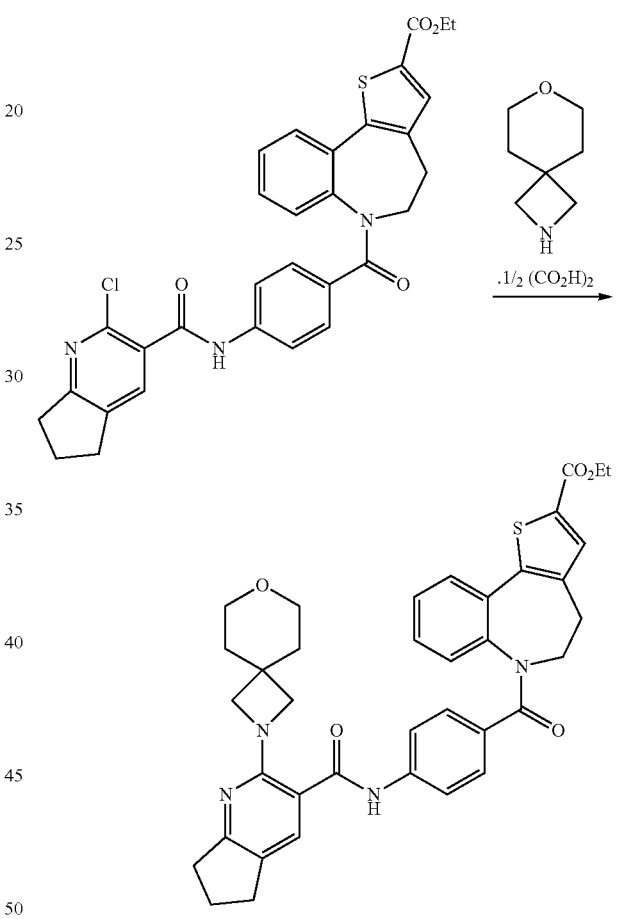

To a solution of ethyl 6-(4-(2-chloro-6,7-dihydro-5H-cyclopenta[b]pyridine-3-carboxamido) benzoyl)-5,6-dihydro-4H-benzo[b]thieno[2,3-d]azepine-2-carboxylate (1.00 g, 1.75 mmol) and 7-oxa-2-azaspiro[3.5]nonane hemioxalate (1.14 g, 5.24 mmol) in NMP (10 mL) and THF (10 mL) was added Et$_3$N (1.46 mL, 10.5 mmol). The reaction mixture was heated to 130° C. for 1 hr and then at 150° C. for 2 hr. Additional 7-oxa-2-azaspiro[3.5]nonane hemioxalate (1.14 g, 5.24 mmol) and Et$_3$N (1.46 mL, 10.5 mmol) were added and the mixture heated at 150° C. for 3 hr and then allowed to cool to RT overnight. Water (10 mL) was added and the resulting precipitate dissolved in EtOAc (20 mL). The aq layer was separated and the organic extracts were washed with water (2×10 mL), and then dried over a phase separator. After evaporation in vacuo the resulting residue was purified by flash column chromatography (SiO$_2$, 40 g, 0-10% MeOH in DCM, gradient elution) to afford the title compound as a pale yellow solid (0.98 g, 85% yield); R'2.07 min (Method 1a); m/z 663 (M+H)⁺ (ES⁺).

6-(4-(2-(7-Oxa-2-azaspiro[3.5]nonan-2-yl)-6,7-dihydro-5H-cyclopenta[b]pyridine-3-carboxamido)benzoyl)-5,6-dihydro-4H-benzo[b]thieno[2,3-d]azepine-2-carboxylic acid

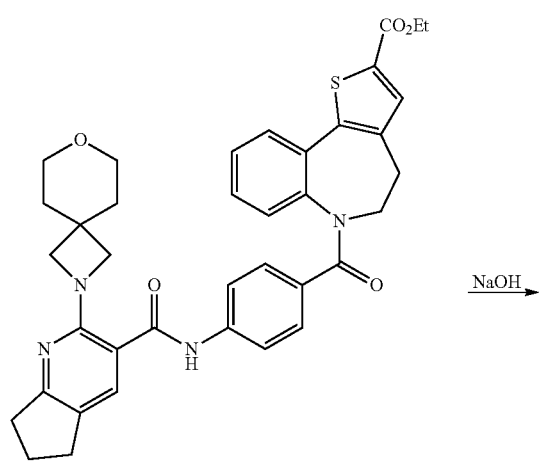

To a solution of ethyl 6-(4-(2-(7-oxa-2-azaspiro[3.5]nonan-2-yl)-6,7-dihydro-5H-cyclopenta[b]pyridine-3-carboxamido)benzoyl)-5,6-dihydro-4H-benzo[b]thieno[2,3-d]azepine-2-carboxylate (984 mg, 1.49 mmol) in a mixture of THF:MeOH (1:1, 20 mL) was added 2 M aq NaOH (3.7 mL) and the reaction mixture heated at 50° C. for 2 hr. The volatiles were evaporated in vacuo and the residue was dissolved in water (20 mL) and 1 M hydrochloric acid (1.2 mL) was added. The resulting precipitate was collected by filtration, washed with water (5 mL) and MeCN (10 mL) and dried to afforded the title compound as an off-white solid (812 mg, 86% yield); R' 1.79 min (Method 1a); m/z 635 (M+H)⁺ (ES⁺).

2-Chloro-5,6,7,8-tetrahydroquinoline-3-carbonyl chloride

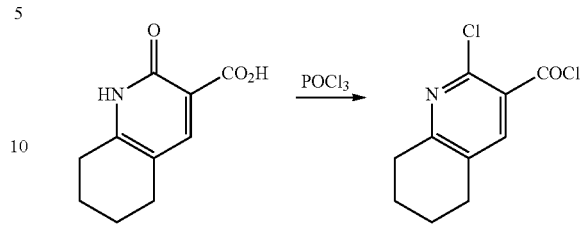

A solution of 2-oxo-1,2,5,6,7,8-hexahydroquinoline-3-carboxylic acid (1.00 g, 5.18 mmol) and phosphoryl trichloride (10.0 mL, 107 mmol) was heated at 105° C. for 18 hr and was cooled and evaporated in vacuo. To the resulting residue was added ice (5 g) and the precipitate that formed was isolated by filtration, washed with cold water (2.0 mL) and then dried to afford the title compound as an off-white solid (0.52 g, 85% pure by HPLC, 44% yield); R' 2.27 min (Method 1a); m/z 240 (M+H)⁺ [ethyl ester] (ES⁺). This material was used in the subsequent step without additional purification.

Ethyl 6-(4-(2-chloro-5,6,7,8-tetrahydroquinoline-3-carboxamido)benzoyl)-5,6-dihydro-4H-benzo[b]thieno[2,3-d]azepine-2-carboxylate

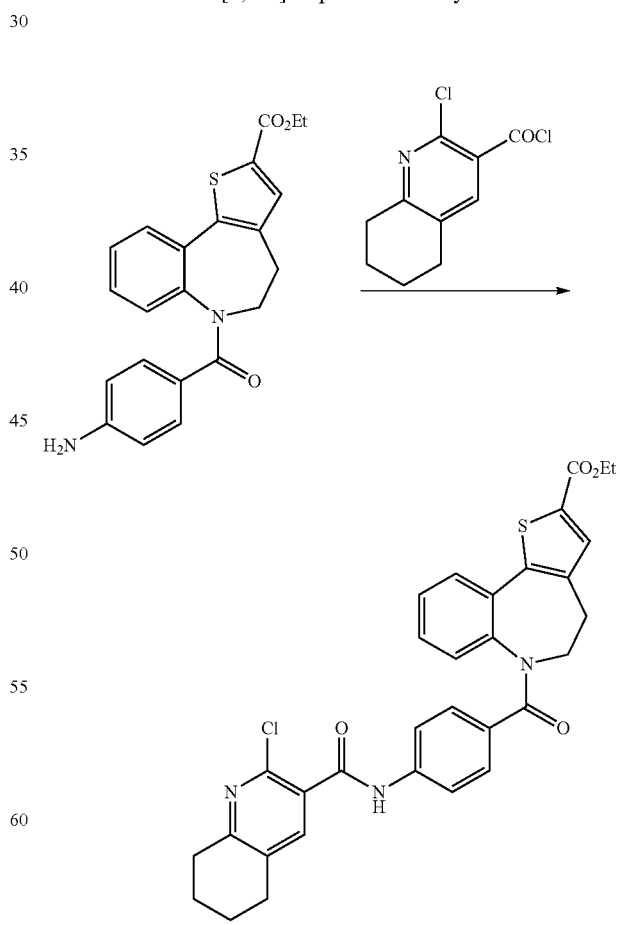

To a solution of ethyl 6-(4-aminobenzoyl)-5,6-dihydro-4H-benzo[b]thieno[2,3-d]azepine-2-carboxylate (870 mg, 2.22 mmol) in pyridine (10 mL) was added a solution of 2-chloro-5,6,7,8-tetrahydroquinoline-3-carbonyl chloride (510 mg, 2.22 mmol) in DCM (3.0 mL). After 1 hr at RT the solvent was evaporated in vacuo and the resulting residue triturated with water (10 mL) and collected by filtration. The solid thus obtained was purified by flash column chromatography (SiO$_2$, 40 g, 0-60% EtOAc in isohexane, gradient elution) to afford the title compound as a white solid (0.56 g, 43% yield); R$^t$ 2.71 min (Method 1a); m/z 586 (M+H)$^+$ (ES$^+$); $^1$H NMR δ: 1.32 (3H, t), 1.69-1.77 (3H, m), 1.77-1.85 (1H, dd), 2.73 (2H, t), 2.81 (2H, t), 3.04-3.31 (assume 3H, obscured by solvent), 4.32 (2H, q), 4.83-4.96 (1H, m), 6.87 (1H, br d), 7.00 (2H, br d), 7.14 (1H, br t), 7.29 (1H, td), 7.48 (2H, br d), 7.73 (1H, s), 7.78 (1H, s), 7.81 (1H, dd), 10.59 (1H, s).

Ethyl 6-(4-(2-(7-oxa-2-azaspiro[3.5]nonan-2-yl)-5,6,7,8-tetrahydroquinoline-3-carboxamido)benzoyl)-5,6-dihydro-4H-benzo[b]thieno[2,3-d]azepine-2-carboxylate The resulting precipitate was collected by filtration and purified by flash column chromatography (SiO$_2$, 40 g, 0-100% EtOAc in isohexane, gradient elution) to afford the title compound as a white solid (360 mg, 57% yield); R$^t$ 1.99 min (Method 1a); m/z 677 (M+H)$^+$ (ES$^+$); $^1$H NMR δ: 1.32 (3H, t), 1.61 (4H, br t), 1.65-1.73 (2H, m), 1.73-1.81 (2H, m), 2.59 (2H, t), 2.64 (2H, t), 3.04-3.30 (assume 3H, obscured by solvent), 3.46 (4H, br t), 3.58 (4H, s), 4.32 (2H, q), 4.81-4.97 (1H, m), 6.88 (1H, br d), 6.98 (2H, br d), 7.14 (1H, t), 7.29 (1H, td), 7.34 (1H, s), 7.49 (2H, d), 7.79 (1H, s), 7.81 (1H, dd), 10.27 (1H, s).

6-(4-(2-(7-Oxa-2-azaspiro[3.5]nonan-2-yl)-5,6,7,8-tetrahydroquinoline-3-carboxamido) benzoyl)-5,6-dihydro-4H-benzo[b]thieno[2,3-d]azepine-2-carboxylic acid

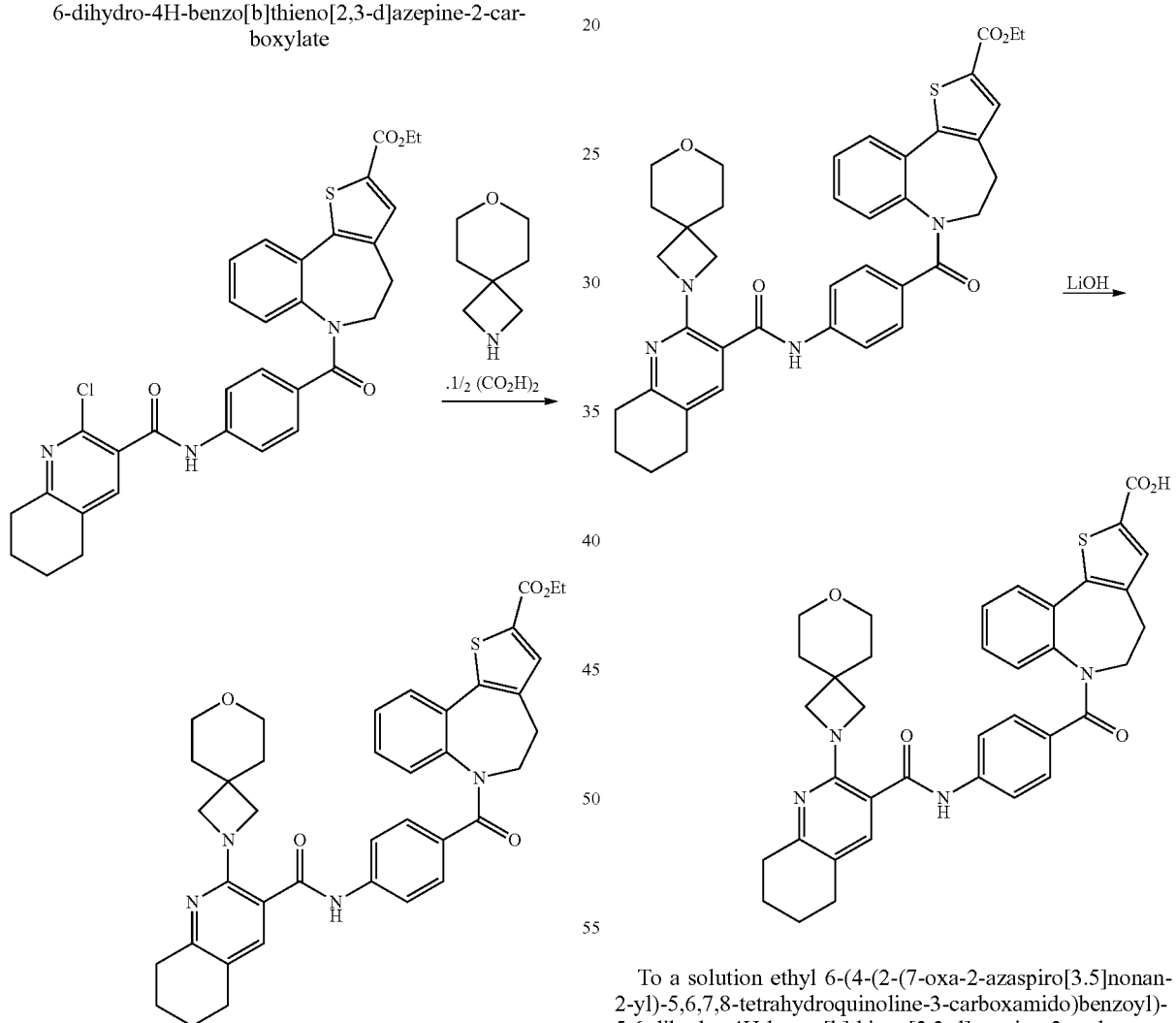

To a solution of ethyl 6-(4-(2-chloro-5,6,7,8-tetrahydroquinoline-3-carboxamido)benzoyl)-5,6-dihydro-4H-benzo[b]thieno[2,3-d]azepine-2-carboxylate (550 mg, 0.94 mmol) and 7-oxa-2-azaspiro[3.5]nonane hemioxalate (612 mg, 2.82 mmol) in NMP (10 mL) was added Et$_3$N (785 µL, 5.63 mmol). The reaction mixture was heated to 140° C. for 2 hr and was then cooled to RT and treated with water (40 mL).

To a solution ethyl 6-(4-(2-(7-oxa-2-azaspiro[3.5]nonan-2-yl)-5,6,7,8-tetrahydroquinoline-3-carboxamido)benzoyl)-5,6-dihydro-4H-benzo[b]thieno[2,3-d]azepine-2-carboxylate (510 mg, 0.75 mmol) in a mixture of THF:MeOH:water (10:1:1, 12 mL) was added lithium hydroxide (36.0 mg, 1.51 mmol) and the mixture stirred at RT for 18 hr. The volatiles were removed in vacuo and the resulting residue dissolved in water (20 mL) and acidified to pH 3 by the addition of 1 M hydrochloric acid. The solid thus formed was collected by filtration and dried to afford the title compound as a white solid (320 mg, 65% yield); R$^t$ 1.72 min (Method 1a); m/z 649 (M+H)+ (ES+); 1H NMR δ: 1.61 (4H, br t), 1.65-1.73 (2H, m), 1.73-1.81 (2H, m), 2.59 (2H, t), 2.64 (2H, t), 3.04-3.30 (assume 3H, obscured by solvent), 3.46 (4H, br t), 3.58 (4H, s), 4.83-4.96 (1H, m), 6.87 (1H, br d), 6.98 (2H, br d), 7.12 (1H, t), 7.29 (1H, td), 7.34 (1H, s), 7.49 (2H, d), 7.70 (1H, s), 7.79 (1H, dd), 10.27 (1H, s), 13.24 (1H, s).

Ethyl 6-(4-(2-chloroquinoline-3-carboxamido)benzoyl)-5,6-dihydro-4H-benzo[b]thieno [2,3-d]azepine-2-carboxylate

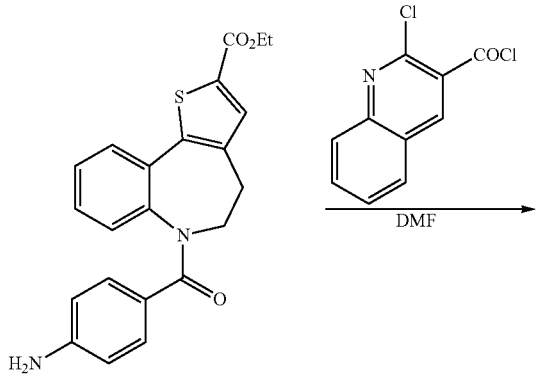

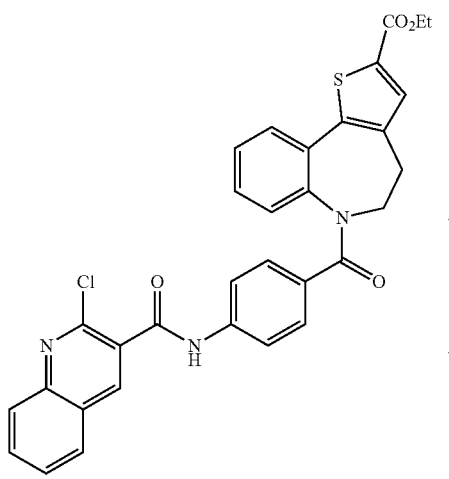

Oxalyl chloride (167 μL, 1.91 mmol) was added slowly to DMF (8.0 mL) and was stirred at RT for 10 min. The resulting solution was added to 2-chloroquinoline-3-carboxylic acid (397 mg, 1.91 mmol) and maintained at RT for 30 min and was then treated with a solution of ethyl 6-(4-aminobenzoyl)-5,6-dihydro-4H-benzo[b]thieno[2,3-d]azepine-2-carboxylate (500 mg, 1.27 mmol) in pyridine (3 mL). After stirring for 1 hr, sat aq NaHCO3 (20 mL) and water (20 mL) were added and the mixture partitioned with EtOAc (40 mL). The aq layer was separated and was extracted with EtOAc (40 mL). The combined organic layers were washed with water (30 mL) and with brine (30 mL) and then dried and evaporated in vacuo to give the title compound (719 mg, 78% pure by HPLC, 97% yield); R$^t$ 2.60 min (Method 1a); m/z 582/584 (M+H)+ (ES+). This material was used in subsequent steps without additional purification.

Ethyl 6-(4-(2-(7-oxa-2-azaspiro[3.5]nonan-2-yl)quinoline-3-carboxamido)benzoyl)-5,6-dihydro-4H-benzo[b]thieno[2,3-d]azepine-2-carboxylate

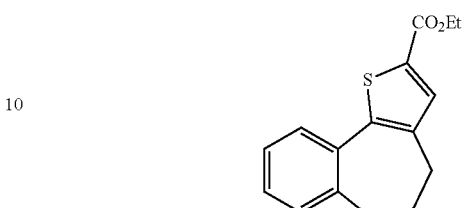 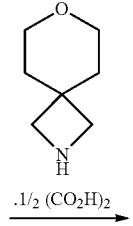

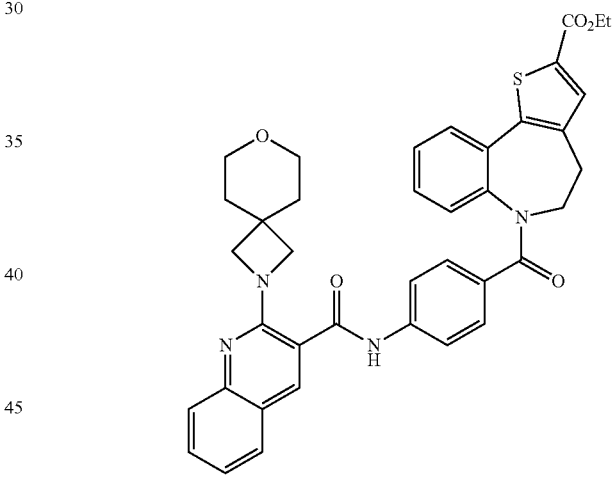

To a suspension of ethyl 6-(4-(2-chloroquinoline-3-carboxamido)benzoyl)-5,6-dihydro-4H-benzo[b]thieno[2,3-d]azepine-2-carboxylate (719 mg, 0.96 mmol) and 7-oxa-2-azaspiro[3.5]nonane hemioxalate (837 mg, 3.85 mmol) in NMP (2.4 mL) was added Et3N (1.07 mL, 7.71 mmol). The reaction mixture was heated to 150° C. for 1 hr and was cooled to RT and treated with water (150 mL). The resulting precipitate was collected by filtration and was purified by flash column chromatography (SiO2, 12 g, 0-30% THF in DCM, gradient elution) to afford the title compound as a bright yellow solid (563 mg, 87% yield); R$^t$ 1.91 min (Method 1a); m/z 673 (M+H)+ (ES+); 1H NMR δ: 1.32 (3H, t), 1.66 (4H, br t), 3.05-3.36 (assume 3H, obscured by solvent), 3.49 (4H, br t), 3.78 (4H, s), 4.33 (2H, q), 4.85-4.96 (1H, br), 6.90 (1H, br d), 7.03 (2H, br d), 7.15 (1H, br t), 7.24-7.32 (2H, over-lapping m), 7.54 (2H, br d), 7.59 (2H, apparent d), 7.75-7.80 (2H, over-lapping m), 7.82 (1H, dd), 8.21 (1H, s), 10.64 (1H, s).

75

6-(4-(2-(7-Oxa-2-azaspiro[3.5]nonan-2-yl)quinoline-3-carboxamido)benzoyl)-5,6-dihydro-4H-benzo[b]thieno[2,3-d]azepine-2-carboxylic acid

76

6-(4-(2-(7-Oxa-2-azaspiro[3.5]nonan-2-yl)quinoline-3-carboxamido)benzoyl)-5,6-dihydro-4H-benzo[b]thieno[2,3-d]azepine-2-carbonyl chloride

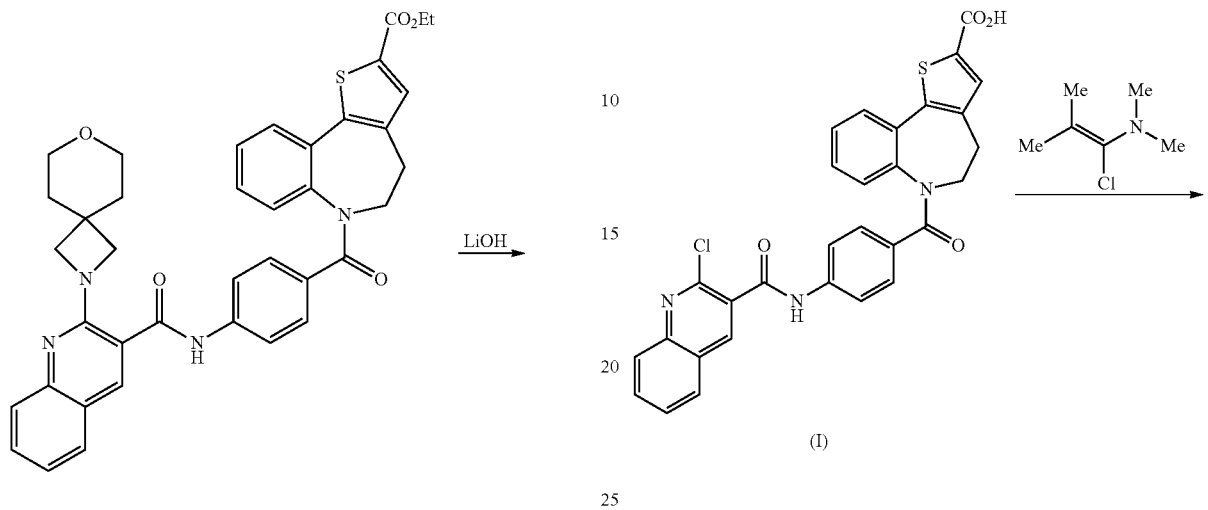

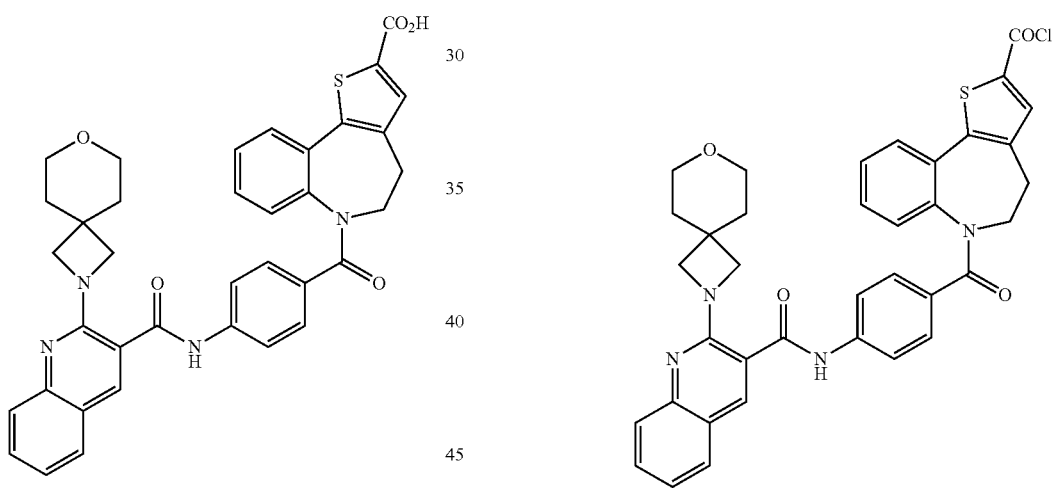

(I)

To a solution of ethyl 6-(4-(2-(7-oxa-2-azaspiro[3.5]nonan-2-yl)quinoline-3-carboxamido) benzoyl)-5,6-dihydro-4H-benzo[b]thieno[2,3-d]azepine-2-carboxylate (560 mg, 0.83 mmol) in a mixture of THF:MeOH (1:1, 14 mL) was added a solution of lithium hydroxide (100 mg, 4.16 mmol) in water (14 mL). The reaction mixture was heated to 50° C. for 1 hr and was then cooled to RT. The volatiles were removed in vacuo and the remaining aq solution was neutralised by the addition of 1 M hydrochloric acid. The resulting solid was collected by vacuum filtration and dried in vacuo to afford the title compound as a pale yellow solid (499 mg, 93% pure by HPLC, 93% yield); $R^t$ 1.63 min (Method 1a); m/z 645 (M+H)$^+$ (ES$^+$). This material was used in subsequent steps without additional purification.

To a solution of 6-(4-(2-(7-oxa-2-azaspiro[3.5]nonan-2-yl)quinoline-3-carboxamido)benzoyl)-5,6-dihydro-4H-benzo[b]thieno[2,3-d]azepine-2-carboxylic acid (100 mg, 0.16 mmol) in DCM (5.0 mL) was added 1-chloro-N,N,2-trimethylprop-1-en-1-amine (62 µL, 0.46 mmol). The reaction mixture was stirred at RT for 1 hr and was then concentrated in vacuo. The resulting residue was taken up into DCM (10 mL) to afford a stock solution of the title compound (15.0 mM). This material was used in subsequent steps without purification.

77

Ethyl 6-(4-(5-chlorothieno[3,2-b]pyridine-6-carbox-amido)benzoyl)-5,6-dihydro-4H-benzo[b]thieno[2,3-d]azepine-2-carboxylate

78

Ethyl 6-(4-(5-(7-oxa-2-azaspiro[3.5]nonan-2-yl)thieno[3,2-b]pyridine-6-carboxamido) benzoyl)-5,6-dihydro-4H-benzo[b]thieno[2,3-d]azepine-2-carboxylate

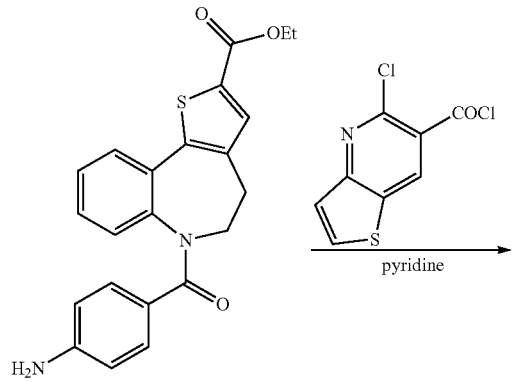

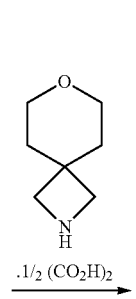

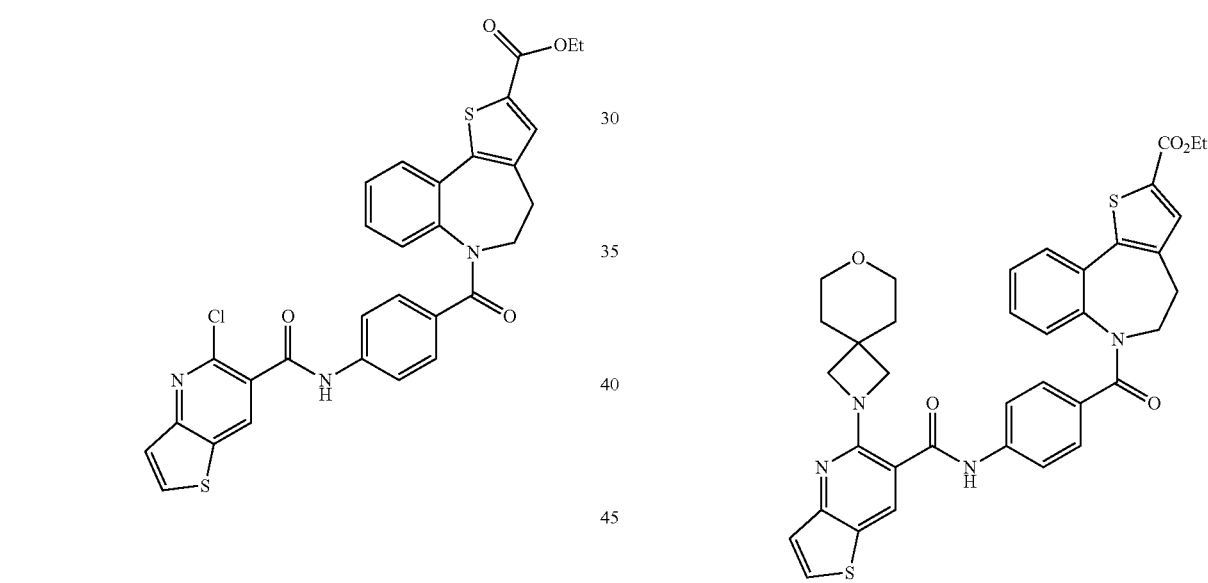

To a suspension of 5-chlorothieno[3,2-b]pyridine-6-carboxylic acid [see Cazin J., Trefouel T., Dupas G., Bourguignon J. and Queguiner G. *Tetrahedron*, 1988, 44, 1079-1090.] (362 mg, 1.70 mmol) in DCM (8.0 mL) was added oxalyl chloride (742 µL, 8.47 mmol) and 1 drop of DMF. The resulting mixture was stirred at RT for 1.5 hr and then evaporated in vacuo. The resulting residue was taken up into DCM (6.0 mL) and was added to a suspension of ethyl 6-(4-aminobenzoyl)-5,6-dihydro-4H-benzo[b]thieno[2,3-d]azepine-2-carboxylate (333 mg, 0.85 mmol) in pyridine (2.6 mL) at 0° C. After warming to RT the mixture was stirred for 1 hr and then the solvent was evaporated in vacuo. The residue thus obtained was triturated with water (20 mL), filtered and dried to afford the title compound as a yellow solid (550 mg, 74% purity by HPLC); R$^r$ 2.62 min (Method 1a); m/z 588 (M+H)$^+$ (ES$^+$). This material was used in subsequent steps without additional purification.

A mixture, comprising of ethyl 6-(4-(5-chlorothieno[3,2-b]pyridine-6-carboxamido)benzoyl)-5,6-dihydro-4H-benzo[b]thieno[2,3-d]azepine-2-carboxylate (550 mg, 0.94 mmol), 7-oxa-2-azaspiro[3.5]nonane hemioxalate (609 mg, 2.81 mmol), K$_2$CO$_3$ (776 mg, 5.61 mmol) and NMP (5.0 mL) was heated to 110° C. for 2.5 hr, then cooled to RT and treated with water (15 mL). The resulting precipitate was collected by filtration, washed with water (2×50 mL) and dried. The solid thus obtained was purified by flash column chromatography (SiO$_2$, 40 g, 0-5% MeOH in DCM, gradient elution) to afford the title compound as a yellow solid (420 mg, 66% yield); R$^r$ 2.41 min (Method 1b); m/z 679 (M+H)$^+$ (ES$^+$); $^1$H NMR δ: 1.32 (3H, t), 1.64 (4H, br t), 3.05-3.35 (assume 3H, obscured by solvent), 3.48 (4H, br t), 3.70 (4H, s), 4.33 (2H, q), 4.84-4.95 (1H, br), 6.89 (1H, br d), 7.01 (2H, br d), 7.15 (1H, br t), 7.27-7.32 (2H, over-lapping m), 7.53 (2H, br d), 7.79 (1H, s), 7.82 (1H, dd), 8.07 (1H, d), 8.32 (1H, s), 10.50 (1H, s).

6-(4-(5-(7-Oxa-2-azaspiro[3.5]nonan-2-yl)thieno[3,2-b]pyridine-6-carboxamido)benzoyl)-5,6-dihydro-4H-benzo[b]thieno[2,3-d]azepine-2-carboxylic acid

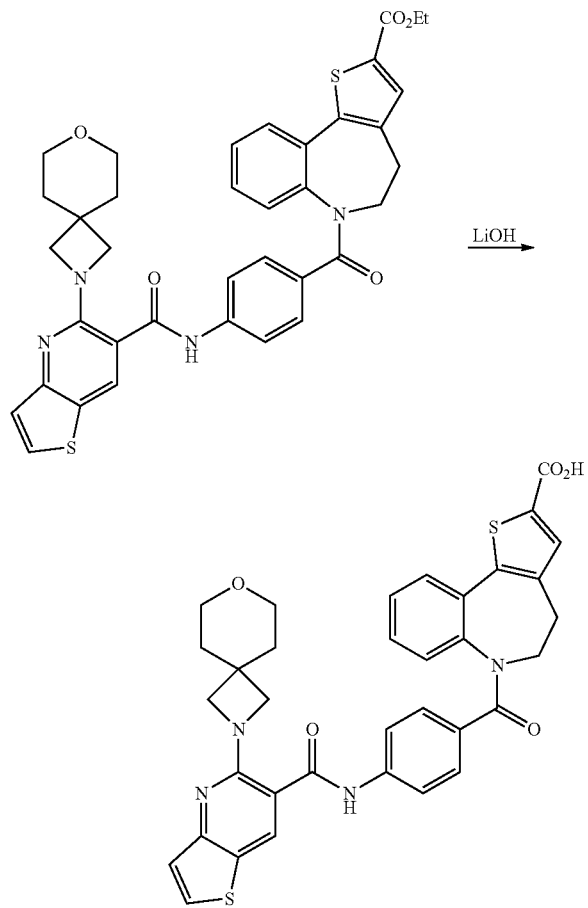

To a solution of ethyl 6-(4-(5-(7-oxa-2-azaspiro[3.5]nonan-2-yl)thieno[3,2-b]pyridine-6-carboxamido)benzoyl)-5,6-dihydro-4H-benzo[b]thieno[2,3-d]azepine-2-carboxylate (418 mg, 0.62 mmol) in THF:MeOH:water (10:1:1, 9.6 mL) was added lithium hydroxide (29 mg, 1.23 mmol). The reaction mixture was stirred at RT for 1 hr, heated to 40° C. for 2.5 hr and then cooled to RT. The volatiles were removed in vacuo and the resulting residue was dissolved in water (15 mL) and acidified to pH 1 by the addition of 1 M hydrochloric acid. The precipitate that formed was dissolved in DCM:MeOH (9:1, 20 mL), diluted with further water (15 mL) and the organic extracts separated. The aq layer was extracted with a second aliquot of DCM:MeOH: (9:1, 20 mL) and the combined organic extracts were evaporated in vacuo to afforded the title compound as a yellow solid (336 mg, 84% yield); R$^t$ 2.02 min (Method 1a); m/z 651 (M+H)$^+$ (ES$^+$); $^1$H NMR δ: 1.64 (4H, br t), 3.06-3.42 (assume 3H, obscured by solvent), 3.48 (4H, br t), 3.70 (4H, s), 4.85-4.96 (1H, br), 6.88 (1H, br d), 7.01 (2H, br d), 7.13 (1H, br t), 7.27-7.32 (2H, over-lapping m), 7.53 (2H, br d), 7.71 (1H, s), 7.80 (1H, dd), 8.08 (1H, d), 8.34 (1H, s), 10.53 (1H, s), 13.27 (1H, br).

PREPARATION OF COMPOUND EXAMPLES OF THE INVENTION

Example 1

6-(4-(2-(7-oxa-2-azaspiro[3.5]nonan-2-yl)nicotinamido)benzoyl)-N-phenyl-5,6-dihydro-4H-benzo[b]thieno[2,3-d]azepine-2-carboxamide

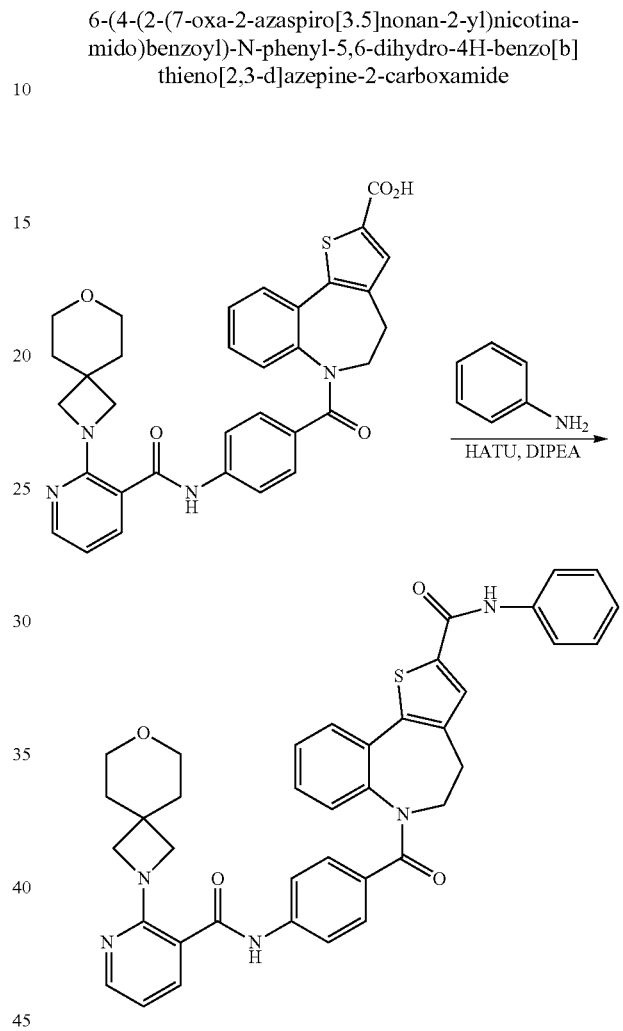

To a solution of 6-(4-(2-(7-oxa-2-azaspiro[3.5]nonan-2-yl)nicotinamido)benzoyl)-5,6-dihydro-4H-benzo[b]thieno[2,3-d]azepine-2-carboxylic acid (50 mg, 0.08 mmol), aniline (86 mg, 0.93 mmol) and DIPEA (176 μL, 1.01 mmol) in DMF (2.0 mL) at RT was added HATU (96 mg, 0.25 mmol). The reaction mixture was stirred at RT for 60 hr and was partitioned between EtOAc (5.0 mL) and brine (20 mL). The aq layer was separated and was washed with EtOAc (2×5.0 mL). The combined organic extracts were washed with saturated aq NaHCO$_3$ (10 mL) and with brine (10 mL) and then dried and evaporated in vacuo. The residue was purified by preparative HPLC (Method 3) to afford the title compound, Example 1, as a white solid (31 mg, 54% yield); R$^t$ 1.87 min (Method 1a); m/z 670 (M+H)$^+$ (ES$^+$); $^1$H NMR δ: 1.64 (4H, br t), 3.14-3.51 (assume 7H, obscured by solvent), 3.67 (4H, s), 4.89-4.98 (1H, m), 6.72 (1H, dd), 6.85-6.90 (1H, m), 7.01 (2H, br d), 7.12 (2H, tt), 7.30 (1H, td), 7.37 (2H, t), 7.51 (2H, broad t), 7.67 (1H, m), 7.74 (2H, apparent dd), 7.83 (1H, m), 7.99 (1H, s), 8.17 (1H, dd), 10.31 (1H, s), 10.42 (1H, br s).

Example 2

6-(4-(2-(7-oxa-2-azaspiro[3.5]nonan-2-yl)nicotinamido)benzoyl)-N-(2-cyano phenyl)-5,6-dihydro-4H-benzo[b]thieno[2,3-d]azepine-2-carboxamide

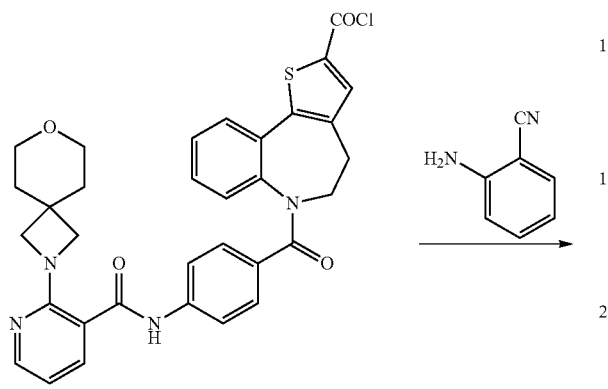

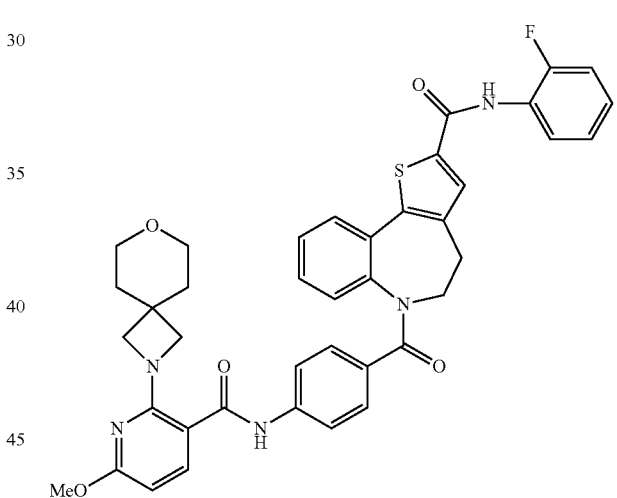

To a stock solution of 6-(4-(2-(7-oxa-2-azaspiro[3.5]nonan-2-yl)nicotinamido)benzoyl)-5,6-dihydro-4H-benzo[b]thieno[2,3-d]azepine-2-carbonyl chloride in DCM (5.0 mL, 16.80 mM) was added 2-aminobenzonitrile (99 mg, 0.84 mmol) and the resulting mixture was stirred at RT for 3 days. A few drops of methanol were added to solubilise the resulting precipitate, followed by water (5 mL) and the resulting mixture was passed through a phase separator. The volatiles were evaporated in vacuo and the crude residue purified by preparative HPLC (Method 2) to afford the title compound as a white solid (35 mg, 58% yield); $R^t$ 1.75 min (Method 1a); m/z 695 (M+H)$^+$ (ES$^+$); $^1$H NMR δ: 1.63 (4H, br t), 3.13-3.42 (3H, over-lapping m), 3.46 (4H, br t), 3.64 (4H, s), 4.95 (1H, m), 6.71 (1H, dd), 6.9 (1H, br d), 7.02 (2H, br d), 7.13 (1H, t), 7.30 (1H, td), 7.45 (1H, td), 7.52 (2H, br d), 7.58 (1H, dd), 7.62 (1H, dd), 7.77 (1H, td), 7.84 (1H, dd), 7.90 (1H, dd), 7.98 (1H, s), 8.18 (1H, dd), 10.39 (1H, s), 10.74 (1H, s).

Example 3

6-(4-(6-methoxy-2-(7-oxa-2-azaspiro[3.5]nonan-2-yl)nicotinamido)benzoyl)-N-(2-fluorophenyl)-5,6-dihydro-4H-benzo[b]thieno[2,3-d]azepine-2-carboxamide

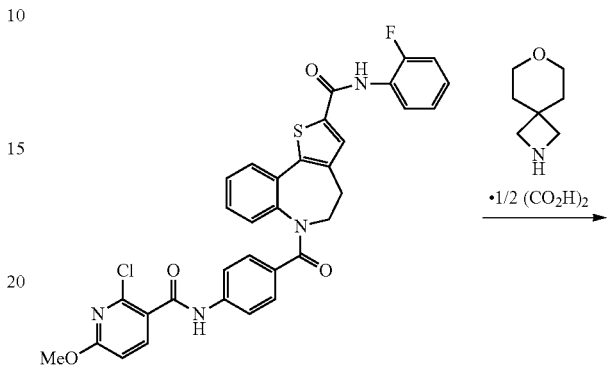

To a solution of 6-(4-(2-chloro-6-methoxynicotinamido)benzoyl)-N-(2-fluorophenyl)-5,6-dihydro-4H-benzo[b]thieno[2,3-d]azepine-2-carboxamide (172 mg, 0.27 mmol) and 7-oxa-2-azaspiro[3.5]nonane hemioxalate (179 mg, 0.82 mmol) in NMP (1.4 mL) was added Et$_3$N (0.23 mL, 1.65 mmol). The reaction mixture was heated by microwave irradiation to 120° C. for 30 min and was cooled to RT and treated with water (10 mL). The resulting precipitate was collected by vacuum filtration, washed with water (20 mL) and the solid dried to afford the title compound as a white solid (166 mg, 81% yield); $R^t$ 2.59 min (Method 1a); m/z 718 (M+H)$^+$ (ES$^+$); $^1$H NMR δ: 1.64 (4H, br t), 3.12-3.34 (assume 3H, obscured by solvent), 3.47 (4H, br t), 3.66 (4H, s), 3.82 (3H, s), 4.89-4.98 (1H, m), 6.07 (1H, d), 6.87 (1H, br d), 6.99 (2H, br d), 7.13 (1H, br t), 7.21-7.34 (4H, over-lapping m), 7.50 (2H, br d), 7.57-7.62 (2H, over-lapping td and d), 7.82 (1H, dd), 7.98 (1H, s), 10.15 (1H, s), 10.23 (1H, s).

Example 4

6-(4-(5-Cyclopropyl-2-(7-oxa-2-azaspiro[3.5]nonan-2-yl)nicotinamido) benzoyl)-N-(2-fluorophenyl)-5,6-dihydro-4H-benzo[b]thieno[2,3-d]azepine-2-carboxamide

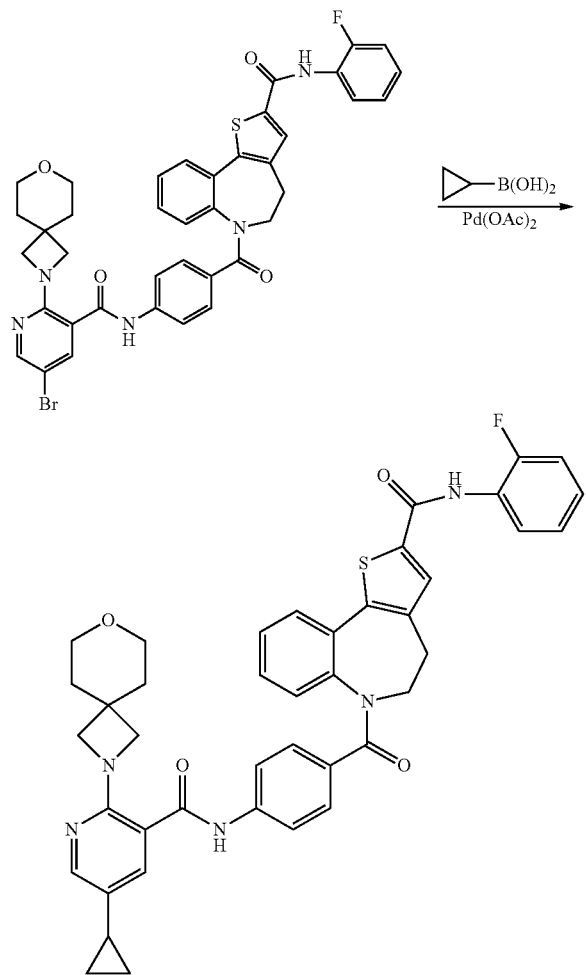

A mixture of 6-(4-(5-bromo-2-(7-oxa-2-azaspiro[3.5]nonan-2-yl)nicotinamido)benzoyl)-N-(2-fluorophenyl)-5,6-dihydro-4H-benzo[b]thieno[2,3-d]azepine-2-carboxamide (50 mg, 65 µmol), cyclopropylboronic acid (8.4 mg, 100 µmol), palladium(II) acetate (1.5 mg, 6.5 µmol) and tripotassium phosphate (62 mg, 300 µmol) in toluene (33 µL) and water (0.7 mL) was degassed with nitrogen for 15 min. Tricyclohexylphosphine (3.7 mg, 13 µmol) was added and the mixture was heated at 100° C. in a sealed vessel for 16 hr. More tripotassium phosphate (62 mg, 300 µmol), tricyclohexylphosphine (3.7 mg, 13 µmol) and toluene (33 µL) were added and the mixture heated at 100° C. for a further 3 hr. After cooling to RT, water (20 mL) was added and resulting precipitate was collected by filtration, and washed with water (10 mL) and Et$_2$O (10 mL). The solid was taken up into a mixture of DCM:MeOH (9:1, 10 mL) and the volatiles were evaporated in vacuo. The residue was purified by preparative HPLC (Method 5) to afford the title compound, as a white solid (17 mg, 35%); R$^t$ 3.15 min (Method 1b); m/z 728 (M+H)$^+$ (ES$^+$); $^1$H NMR δ: 0.61-0.64 (2H, m), 0.84-0.88 (2H, m), 1.61 (4H, brt), 1.80-1.87 (1H, m), 3.12-3.36 (assume 3H, obscured by solvent), 3.45 (4H, br t), 3.59 (4H, s), 4.90-4.97 (1H, b), 6.88 (1H, br d), 7.01 (2H, br d), 7.12 (1H, br t), 7.21-7.34 (5H, over-lapping m), 7.50 (2H, br d), 7.60 (1H, td), 7.82 (1H, dd), 7.97 (1H, s), 8.04 (1H, d), 10.25 (1H, s), 10.35 (1H, s).

Example 5

N-(2-Fluoro-6-methylphenyl)-6-(4-(5-methyl-2-(7-oxa-2-azaspiro[3.5]nonan-2-yl)nicotinamido)benzoyl)-5,6-dihydro-4H-benzo[b]thieno[2,3-d]azepine-2-carboxamide

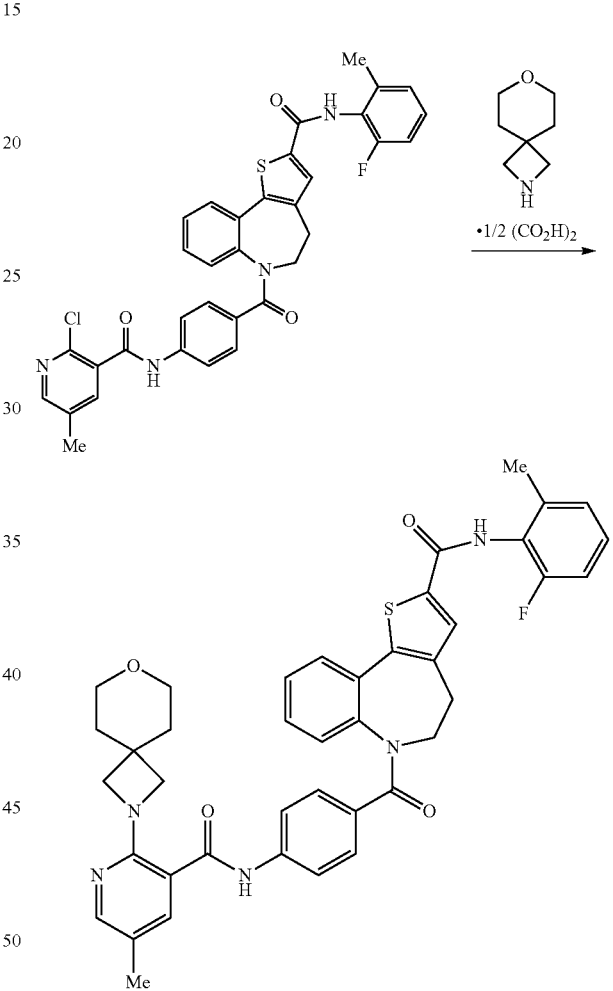

To a solution of 6-(4-(2-chloro-5-methylnicotinamido) benzoyl)-N-(2-fluoro-6-methylphenyl)-5,6-dihydro-4H-benzo[b]thieno[2,3-d]azepine-2-carboxamide (10.0 g, 16.0 mmol) and 7-oxa-2-azaspiro[3.5]nonane hemi oxalate (10.4 g, 48.0 mmol) in NMP (125 mL) was added triethylamine (13 mL, 96 mmol) and the reaction mixture heated at 145° C. for 7 hr. After cooling to RT, the mixture was poured into water (800 mL) and the resulting solids were collected by vacuum filtration, washed with water (2×100 mL) and then taken up in DCM (400 mL). The solution was washed with water (100 mL), dried over sodium sulphate and evaporated in vacuo. The solid residue thus obtained was purified by flash column chromatography (SiO$_2$, 220 g, 20-100% EtOAc in diethyl ether, gradient elution) [an earlier batch was purified by preparative HPLC, Method 3] to afford a batch of the title compound as a white solid.

This procedure was repeated on additional 5 and 10 g batches of the chloronicotinamide starting material. The three batches were combined by dissolution in EtOAc (500 mL) and evaporation of the solvent in vacuo. The resulting solid was triturated with diethyl ether (200 mL) and the solid collected by filtration and dried to afford the title compound, Example 5, as a white solid (24 g, 82% yield); $R^t$ 1.85 min (Method 1a); m/z 716 (M+H)$^+$ (ES$^+$). $^1$H NMR δ: 1.62 (4H, br t), 2.17 (3H, s), 2.26 (3H, s), 3.14-3.37 (assume 3H, obscured by solvent), 3.46 (4H, br t), 3.60 (4H, s), 4.90-4.98 (1H, br), 6.88 (1H, br d), 7.02 (2H, br d), 7.10-7.16 (3H, over-lapping m), 7.25-7.31 (2H, over-lapping m), 7.48 (1H, d), 7.52 (2H, br d), 7.82 (1H, dd), 7.95 (1H, s), 8.04 (1H, dd), 10.03 (1H, s), 10.37 (1H, s).

Example 6

N-(2-Fluoro-6-iodophenyl)-6-(4-(5-methyl-2-(7-oxa-2-azaspiro[3.5]nonan-2-yl)nicotinamido)benzoyl)-5,6-dihydro-4H-benzo[b]thieno[2,3-d]azepine-2-carboxamide To a solution of 6-(4-(5-methyl-2-(7-oxa-2-azaspiro[3.5]nonan-2-yl)nicotinamido)benzoyl)-5,6-dihydro-4H-benzo[b]thieno[2,3-d]azepine-2-carboxylic acid (200 mg, 0.33 mmol) in DCM (10 mL) at RT was added 1-chloro-N,N,2-trimethylprop-1-en-1-amine (87 μL, 0.66 mmol). The reaction mixture was stirred at RT for 30 min and was then concentrated in vacuo. The residue was taken up into DCM (3.0 mL) and to this was added a solution of 2-fluoro-6-iodoaniline (389 mg, 1.64 mmol) in pyridine (2.0 mL) at RT. The resulting mixture was stirred at RT for 2 hr and was then diluted with DCM (20 mL) and water (20 mL) and was passed through a phase separator. The organic phase was evaporated in vacuo and the residue thus obtained was purified by flash column chromatography (SiO$_2$, 12 g, 0-3% MeOH in DCM, gradient elution). The product so obtained was taken up into MeOH and subject to SCX capture and release. After evaporation in vacuo the title compound Example 6, was obtained as an off-white solid (179 mg, 66%); $R^t$ 1.92 min (Method 1a); m/z 828 (M+H)$^+$ (ES$^+$); $^1$H NMR δ: 1.62 (4H, br t), 2.17 (3H, s), 3.12-3.38 (assume 3H, obscured by solvent), 3.46 (4H, br t), 3.60 (4H, s), 4.90-5.00 (1H, br), 6.88 (1H, br d), 7.02 (2H, br d), 7.12 (1H, br t), 7.17-7.23 (1H, m), 7.30 (1H, td), 7.39 (1H, over-lapping dd), 7.49 (1H, d), 7.52 (2H, br d), 7.79 (1H, dt), 7.83 (1H, dd), 7.98 (1H, s), 8.04 (1H, over-lapping dd), 10.26 (1H, br), 10.38 (1H, s).

Example 7

N-(2-Cyclopropyl-6-fluorophenyl)-6-(4-(5-methyl-2-(7-oxa-2-azaspiro[3.5]nonan-2-yl)nicotinamido)benzoyl)-5,6-dihydro-4H-benzo[b]thieno[2,3-d]azepine-2-carboxamide

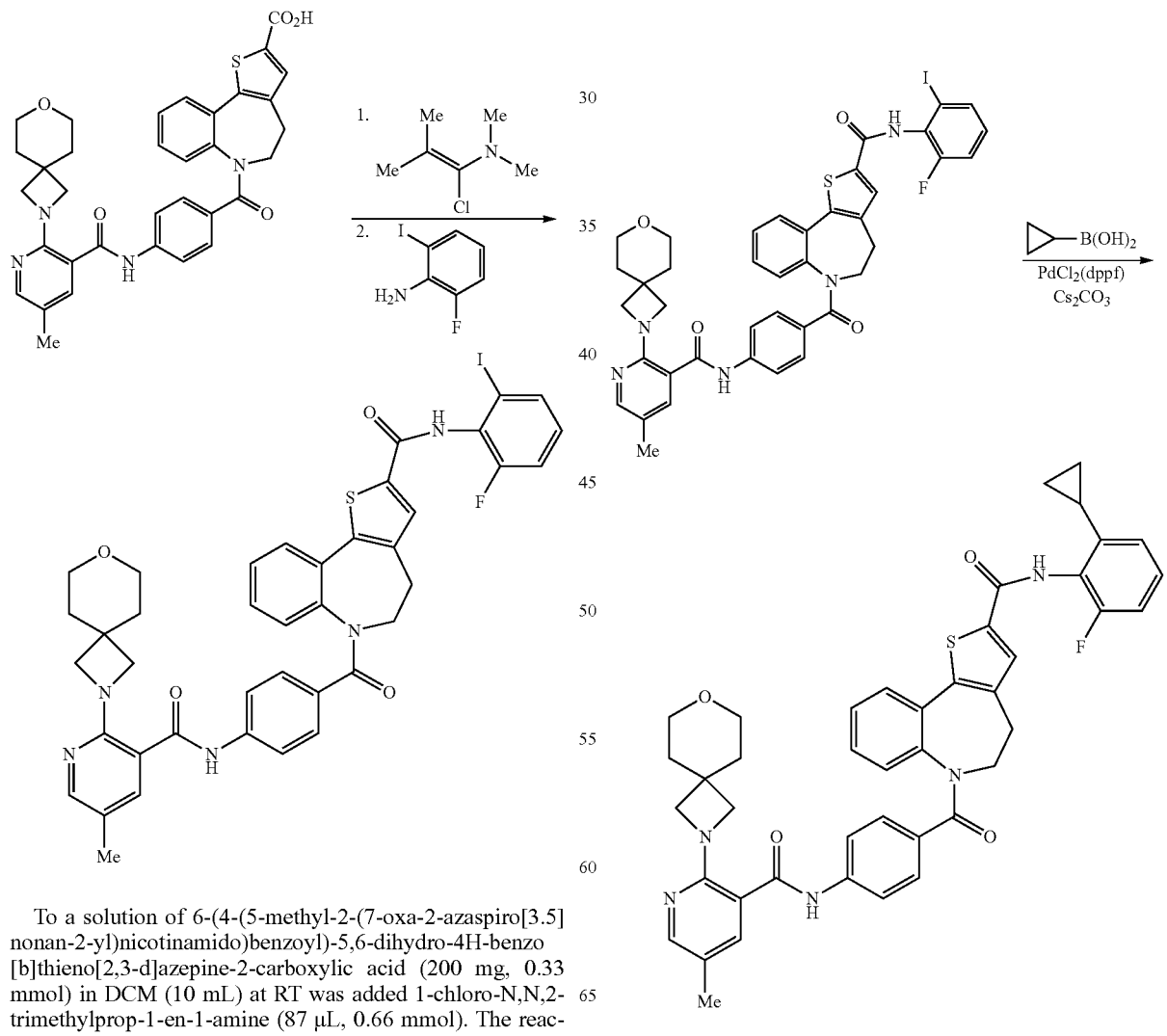

A solution of N-(2-fluoro-6-iodophenyl)-6-(4-(5-methyl-2-(7-oxa-2-azaspiro[3.5]nonan-2-yl) nicotinamido)benzoyl)-5,6-dihydro-4H-benzo[b]thieno[2,3-d]azepine-2-carboxamide (50 mg, 60 μmol), cyclopropylboronic acid (10 mg, 120 μmol) and cesium carbonate (39 mg, 120 μmol) in 1,4-dioxane:water (7:3, 5.0 mL) was degassed with nitrogen for 10 min and then Pd(dppf)Cl$_2$ (4.4 mg, 6.0 μmol) was added. The reaction mixture was heated at 95° C. for 2 hr and then additional cyclopropylboronic acid (10 mg, 120 μmol) and Pd(dppf)Cl$_2$ (4.4 mg, 6.0 μmol) were added. After stirring at 95° C. for a further 18 hr the mixture was cooled and partitioned between EtOAc (15 mL) and water (15 mL). The organic phase was separated and the aq layer was extracted with EtOAc (3×10 mL). The combined organic extracts were washed with water (15 mL) and with brine (2×15 mL), then dried and evaporated in vacuo. The residue thus obtained was purified by preparative HPLC (Method 7) to afford the title compound, Example 7, as a white solid (8 mg, 18%); R$^t$ 1.93 min (Method 1a); m/z 742 (M+H)$^+$ (ES$^+$); $^1$H NMR δ: 0.66-0.70 (2H, m), 0.93-0.97 (2H, m), 1.62 (4H, br t), 2.01-2.08 (1H, m), 2.17 (3H, s), 3.12-3.40 (assume 3H, obscured by solvent), 3.46 (4H, br t), 3.60 (4H, s), 4.88-5.00 (1H, br), 6.79 (1H, d), 6.88 (1H, br d), 7.02 (2H, br d), 7.07-7.14 (2H, over-lapping m), 7.24-7.31 (2H, over-lapping m), 7.48 (1H, d), 7.51 (2H, br d), 7.82 (1H, dd), 7.98 (1H, s), 8.04 (1H, dd), 10.10 (1H, s), 10.37 (1H, s).

Example 8

6-(4-(2-(7-Oxa-2-azaspiro[3.5]nonan-2-yl)-6,7-dihydro-5H-cyclopenta[b]pyridine-3-carboxamido)benzoyl)-N-(2-fluoro-6-methylphenyl)-5,6-dihydro-4H-benzo[b]thieno[2,3-d]azepine-2-carboxamide To a solution of 6-(4-(2-(7-oxa-2-azaspiro[3.5]nonan-2-yl)-6,7-dihydro-5H-cyclopenta[b]pyridine-3-carboxamido)benzoyl)-5,6-dihydro-4H-benzo[b]thieno[2,3-d]azepine-2-carboxylic acid (50 mg, 0.1 mmol) in DCM (5.0 mL) was added 1-chloro-N,N,2-trimethylprop-1-en-1-amine (21 μL, 0.2 mmol). The reaction mixture was stirred at RT for 30 min and was then concentrated in vacuo. The resulting residue was taken up into DCM (1.0 mL) and a solution of 2-fluoro-6-methylaniline (49 mg, 0.4 mmol) in pyridine (0.5 mL) was added. After stirring for 2 hr the mixture was partitioned between DCM (5.0 mL) and water (5.0 mL) and passed through a phase separator. The organic phase was evaporated in vacuo and the residue was purified by preparative HPLC (Method 4) to afford the title compound, Example 8, as an off-white solid (29 mg, 50% yield); R$^t$ 1.98 min (Method 1a); m/z 742 (M+H)$^+$ (ES$^+$); $^1$H NMR δ: 1.62 (4H, br t), 2.02 (2H, m), 2.27 (3H, s), 2.78 (4H, t), 3.12-3.31 (assume 3H, obscured by solvent), 3.47 (4H, br t), 3.61 (4H, s), 4.87-5.02 (1H, m), 6.88 (1H, d), 7.02 (2H, d), 7.10-7.18 (3H, m), 7.24-7.33 (2H, m), 7.49 (1H, s), 7.52 (2H, d), 7.83 (1H, dd), 7.96 (1H, s), 10.03 (1H, s), 10.29 (1H, s).

Example 9

6-(4-(2-(7-Oxa-2-azaspiro[3.5]nonan-2-yl)-5,6,7,8-tetrahydroquinoline-3-carboxamido)benzoyl)-N-(2-fluoro-6-methylphenyl)-5,6-dihydro-4H-benzo[b]thieno[2,3-d]azepine-2-carboxamide

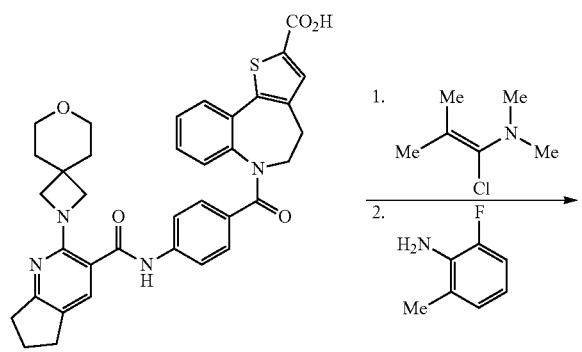

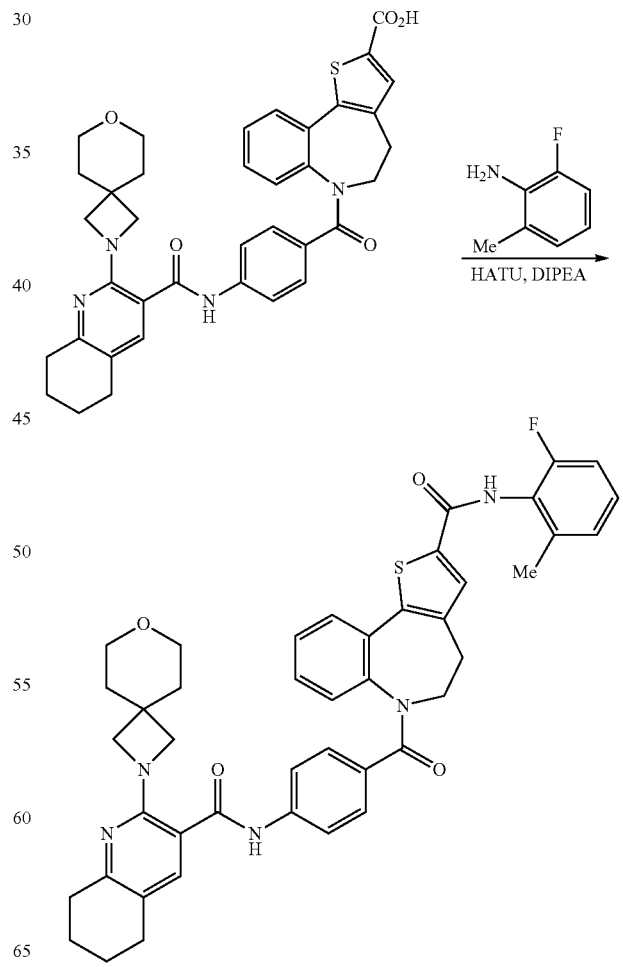

To a solution of 6-(4-(2-(7-oxa-2-azaspiro[3.5]nonan-2-yl)-5,6,7,8-tetrahydroquinoline-3-carboxamido)benzoyl)-5,6-dihydro-4H-benzo[b]thieno[2,3-d]azepine-2-carboxylic acid (100 mg, 0.15 mmol), 2-fluoro-6-methylaniline (96.0 mg, 0.77 mmol) and DIPEA (162 µL, 0.93 mmol) in DMF (2.0 mL) at RT was added HATU (176 mg, 0.46 mmol). The reaction mixture was stirred at 50° C. for 4 hr then at RT for 48 hr. The mixture was poured into water (15 mL) and the precipitate so formed was collected by filtration and washed with water (2×5 mL). The crude product thus obtained was purified by flash column chromatography (SiO$_2$, 40 g, 0-3% MeOH in DCM, gradient elution) to afford the title compound, Example 9, as a cream solid (57 mg, 49% yield); R$^t$ 1.94 min (Method 1a); m/z 756 (M+H)$^+$ (ES$^+$); $^1$H NMR δ: 1.61 (4H, br t), 1.65-1.73 (2H, m), 1.73-1.81 (2H, m), 2.26 (3H, s), 2.60 (2H, t), 2.65 (2H, t), 3.10-3.30 (assume 3H, obscured by solvent), 3.46 (4H, br t), 3.59 (4H, s), 4.86-5.01 (1H, m), 6.87 (1H, d), 7.01 (2H, d), 7.09-7.18 (3H, m), 7.23-7.32 (2H, m), 7.34 (1H, s), 7.51 (2H, d), 7.82 (1H, dd), 7.95 (1H, s), 10.02 (1H, s), 10.28 (1H, s).

Example 10

6-(4-(2-(7-Oxa-2-azaspiro[3.5]nonan-2-yl)quinoline-3-carboxamido) benzoyl)-N-(2-fluoro-6-methyl phenyl)-5,6-dihydro-4H-benzo[b]thieno[2,3-d]azepine-2-carboxamide To a stock solution of 6-(4-(2-(7-oxa-2-azaspiro[3.5]nonan-2-yl)quinoline-3-carboxamido) benzoyl)-5,6-dihydro-4H-benzo[b]thieno[2,3-d]azepine-2-carbonyl chloride in DCM (5.0 mL, 15 mM) was added 2-fluoro-6-methylaniline (48 mg, 0.4 mmol) and the resulting mixture was stirred at RT for 3 days. The volatiles were evaporated in vacuo and the crude residue purified by preparative HPLC (Method 2) to afford the title compound, Example 10, as a pale yellow solid (11 mg, 19% yield); R$^t$ 1.85 min (Method 1a); m/z 752 (M+H)$^+$ (ES$^+$); $^1$H NMR δ: 1.66 (4H, br t), 2.26 (3H, s), 3.12-3.30 (assume 3H, obscured by solvent), 3.49 (4H, br t), 3.78 (4H, s), 4.90-5.00 (1H, m), 6.89 (1H, d), 7.06 (2H, d), 7.11-7.17 (3H, m), 7.21-7.34 (3H, m), 7.56 (2H, d), 7.59 (2H, d), 7.78 (1H, d), 7.83 (1H, dd), 7.96 (1H, s), 8.21 (1H, s), 10.03 (1H, s), 10.65 (1H, s).

Example 11

6-(4-(5-Cyclopropyl-2-(7-oxa-2-azaspiro[3,5]nonan-2-yl)nicotinamido) benzoyl)-N-(2-fluoro-6-methyl phenyl)-5,6-dihydro-4H-benzo[b]thieno[2,3-d]azepine-2-carboxamide

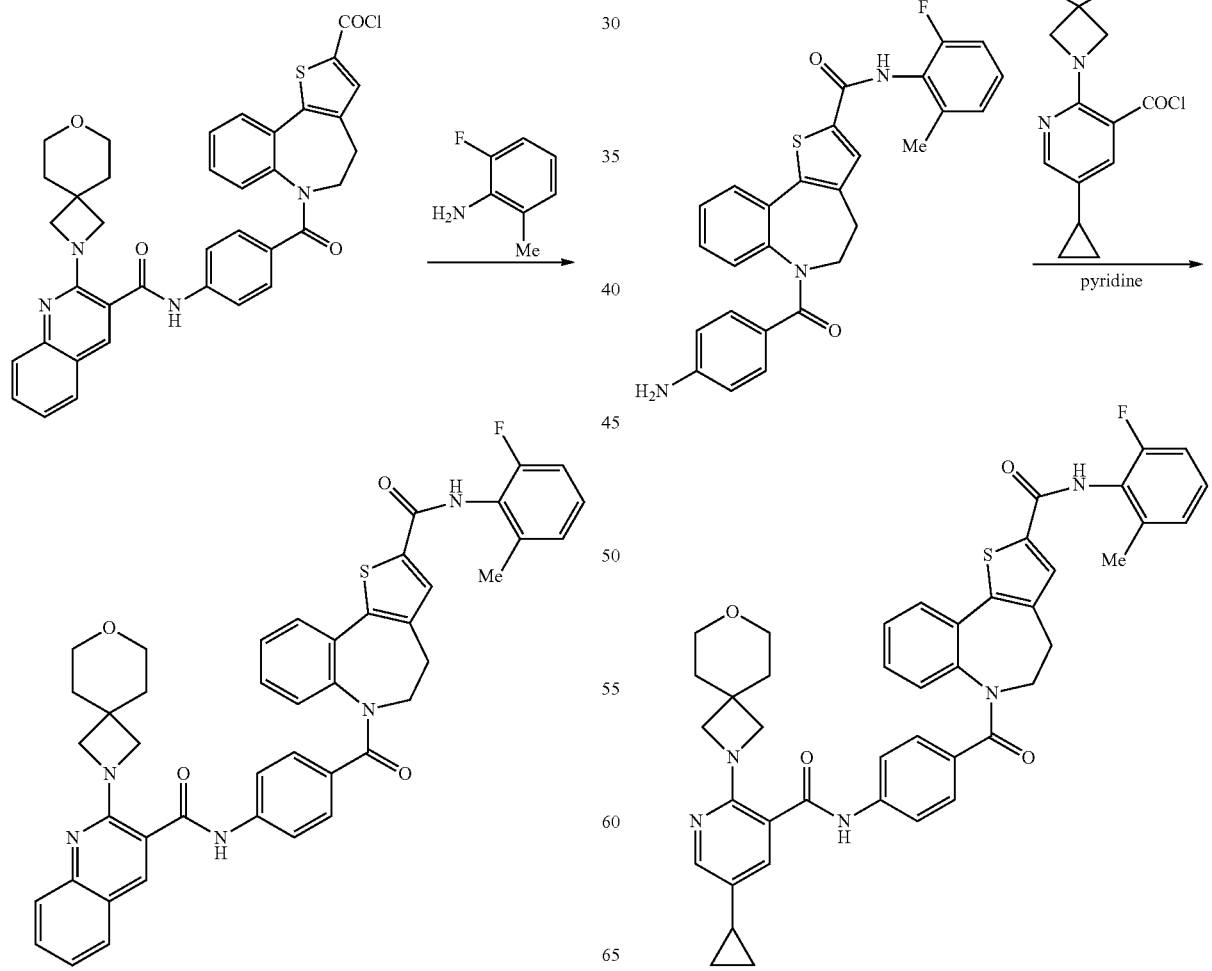
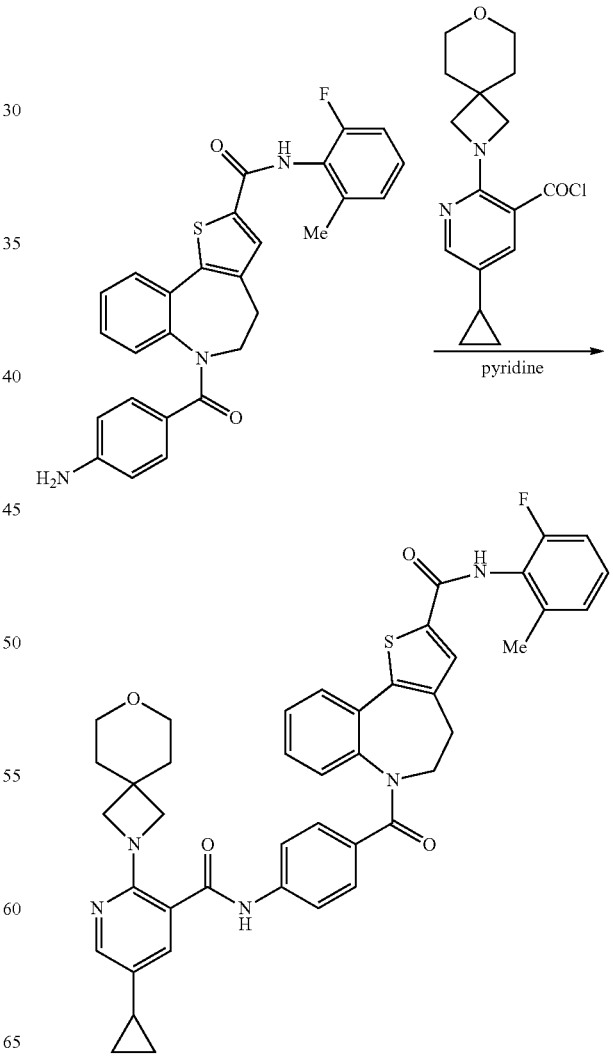

To a suspension of 5-cyclopropyl-2-(7-oxa-2-azaspiro[3.5]nonan-2-yl)nicotinic acid (109 mg, 0.38 mmol) in DCM (0.5 mL) was added 1-chloro-N,N,2-trimethylprop-1-en-1-amine (106 μL, 0.80 mmol) and the resulting mixture was stirred at RT for 1 hr. This solution was added to 6-(4-aminobenzoyl)-N-(2-fluoro-6-methylphenyl)-5,6-dihydro-4H-benzo[b]thieno[2,3-d]azepine-2-carboxamide (94 mg, 0.20 mmol) in pyridine (0.5 mL) and the mixture stirred at RT for 16 hr. Water (5.0 mL) and DCM:MeOH (9:1, 15.0 mL) were added and the resulting biphasic mixture was passed through a phase separator. The organic phase was evaporated in vacuo and the residue was purified by preparative HPLC (Method 11). The material thus obtained was further purified by flash column chromatography (SiO$_2$, 12 g, 0-10% MeOH in DCM, gradient elution) to afford the title compound, Example 11, as a white solid (54 mg, 36% yield); R$^t$ 2.02 min (Method 1a); m/z 742 (M+H)$^+$ (ES$^+$); $^1$H NMR δ: 0.60-0.65 (2H, m), 0.83-0.89 (2H, m), 1.62 (4H, br t), 1.84 (1H, tt), 2.26 (3H, s), 3.11-3.37 (assume 3H, obscured by solvent), 3.45 (4H, br t), 3.60 (4H, s), 4.88-5.01 (1H, m), 6.87 (1H, br d), 7.02 (2H, br d), 7.08-7.19 (3H, m), 7.20-7.34 (3H, m), 7.51 (2H, d), 7.82 (1H, dd), 7.95 (1H, s), 8.04 (1H, d), 10.02 (1H, s), 10.34 (1H, s).

Example 12

N-(4-(2-((2-Fluoro-6-methylphenyl)carbamoyl)-5,6-dihydro-4H-benzo[b]thieno[2,3-d]azepine-6-carbonyl)phenyl)-2-(7-oxa-2-azaspiro[3.5]nonan-2-yl)-7,8-di hydro-5H-pyrano[4,3-b]pyridine-3-carboxamide A mixture, comprising of 2-chloro-N-(4-(2-((2-fluoro-6-methylphenyl)carbamoyl)-5,6-dihydro-4H-benzo[b]thieno[2,3-d]azepine-6-carbonyl) phenyl)-7, 8-dihydro-5H-pyrano[4, 3-b]pyridine-3-carboxamide (75 mg, 0.11 mmol), 7-oxa-2-azaspiro[3.5]nonane hemioxalate (75 mg, 0.34 mmol), K$_2$CO$_3$ (94 mg, 0.68 mmol) and NMP (3.0 mL) was heated to 130° C. for 1.5 hr and was then cooled to RT and treated with water (30 mL). The resulting precipitate was collected by filtration and retained. The filtrate was diluted with EtOAc (50 mL) and the aq layer was separated and extracted with EtOAc (50 mL). The solid previously obtained was taken up in the combined organic extracts and the resulting solution was washed with water (5×100 mL) and then dried and evaporated in vacuo. The residue so obtained was purified by flash column chromatography (SiO$_2$, 12 g, 0-10% MeOH in DCM, gradient elution) to provide an oil that was triturated with water (2.0 mL). The solid that formed was collected by filtration and dried to afford the title compound, Example 12, as a white solid (45 mg, 53% yield); R$^t$ 2.28 min (Method 1b); m/z 758 (M+H)$^+$ (ES$^+$); $^1$H NMR δ: 1.62 (4H, br t), 2.26 (3H, s), 2.72 (2H, br t), 3.12-3.42 (assume 3H, obscured by solvent), 3.45 (4H, br t), 3.63 (4H, s), 3.91 (2H, apparent t), 4.57 (2H, s), 4.90-4.98 (1H, br), 6.87 (1H, br d), 7.01 (2H, br d), 7.08-7.18 (3H, over-lapping m), 7.24-7.32 (2H, over-lapping m), 7.39 (1H, s), 7.50 (2H, br d), 7.82 (1H, dd), 7.95 (1H, s), 10.03 (1H, s), 10.35 (1H, s).

Example 13

6-(4-(5-(7-Oxa-2-azaspiro[3.5]nonan-2-yl)thieno[3,2-b]pyridine-6-carboxamido)benzoyl)-N-(2,6-difluorophenyl)-5,6-dihydro-4H-benzo[b]thieno[2,3-d]azepine-2-carboxamide

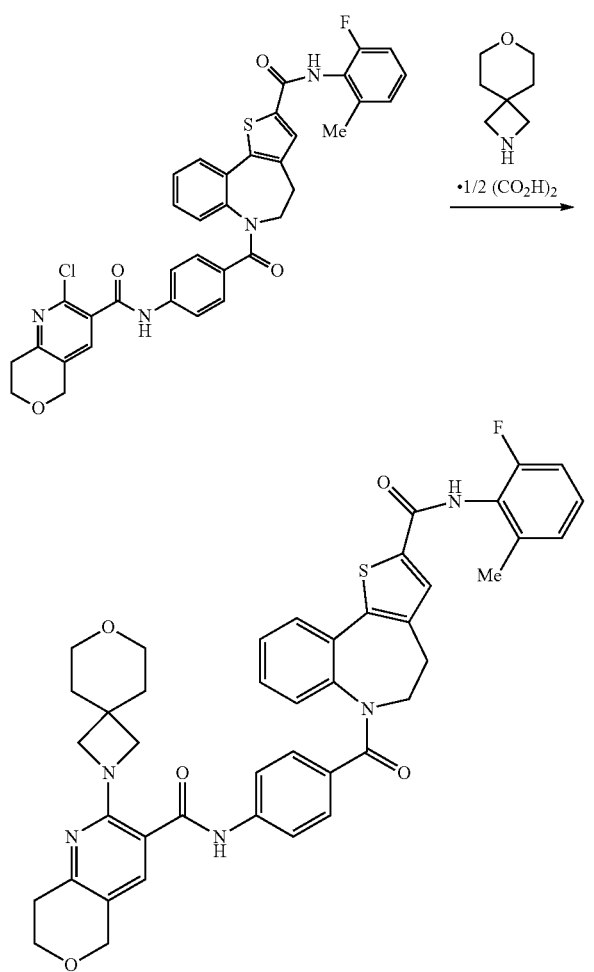

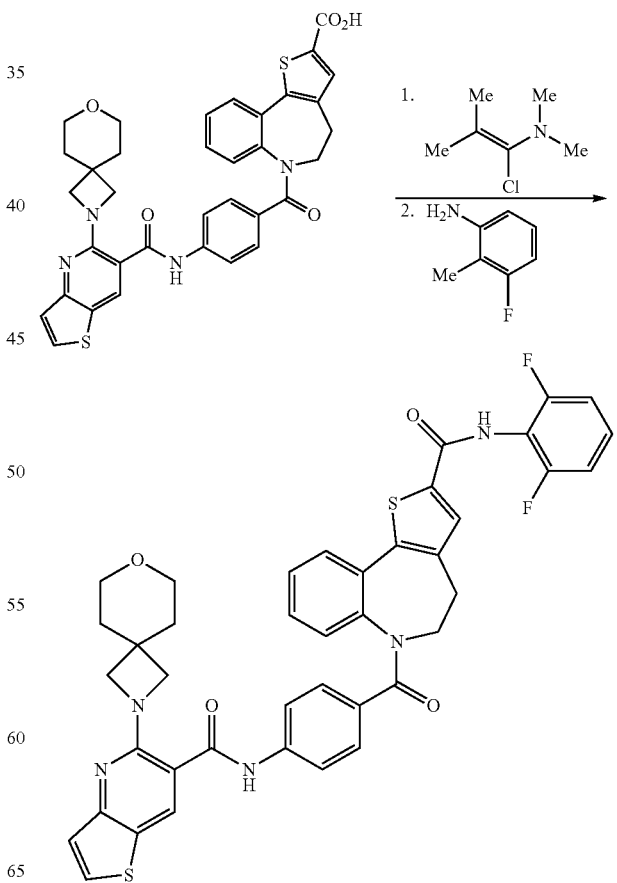

To a suspension of 6-(4-(5-(7-oxa-2-azaspiro[3.5]nonan-2-yl)thieno[3,2-b]pyridine-6-carboxamido)benzoyl)-5,6-dihydro-4H-benzo[b]thieno[2,3-d]azepine-2-carboxylic acid (196 mg, 0.30 mmol) in DCM (3.0 mL) at RT was added 1-chloro-N,N,2-trimethylprop-1-en-1-amine (120 μL, 0.90 mmol). The reaction mixture was kept at RT for 30 min and was then concentrated in vacuo. The residue was taken up into DCM (3.0 mL) and an aliquot (1.5 mL) was added to a solution of 2,6-difluoroaniline (58 mg, 0.45 mmol) in pyridine (1.5 mL) at RT. The resulting mixture was stirred at RT for 1 hr, heated to 40° C. for 2 hr and then allowed to cool to RT over 16 hr. After evaporation in vacuo the resulting residue was triturated with water (10 mL) and the precipitate that formed was collected by filtration and dried. The solid was purified by flash column chromatography (SiO$_2$, 24 g, 0-5% MeOH in DCM, gradient elution) to afford the title compound, Example 13, as a light yellow solid (34 mg, 30% yield); R$^t$ 2.21 min (Method 1a); m/z 762 (M+H)$^+$ (ES$^+$); $^1$H NMR δ: 1.64 (4H, br t), 3.12-3.36 (assume 3H, obscured by solvent), 3.48 (4H, br t), 3.70 (4H, s), 4.90-5.00 (1H, br), 6.89 (1H, br d), 7.04 (2H, br d), 7.13 (1H, br t), 7.20-7.33 (4H, over-lapping m), 7.39-7.48 (1H, m), 7.54 (2H, br d), 7.83 (1H, dd), 7.97 (1H, s), 8.07 (1H, d), 8.33 (1H, s), 10.29 (1H, s), 10.52 (1H, s).

The following compound examples (Table 2) may be prepared by similar synthetic methods to the aforementioned examples or by methods described elsewhere herein:

TABLE 2

Additional Compound Examples of the Invention

Structure, Example No., Name, Preparative HPLC or Column Chromatography Purification Method (where employed), LC-MS Analysis and $^1$HNMR Spectral Data

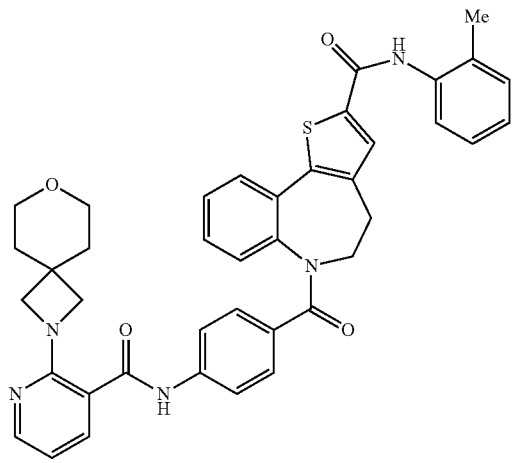 [SMILES: Cc1ccccc1NC(=O)c1cc2c(s1)-c1ccccc1N(C(=O)c1ccc(NC(=O)c3cccnc3N3CC4(CCOCC4)C3)cc1)CC2]

14: 6-(4-(2-(7-oxa-2-azaspiro[3.5]nonan-2-yl)nicotinamido)benzoyl)-N-(o-tolyl)-5,6-dihydro-4H-benzo[b]thieno[2,3-d]azepine-2-carboxamide.
Prep HPLC Method 3
R$^t$ 1.86 min (Method 1a); m/z 684 (M + H)$^+$ (ES$^+$);
$^1$H NMR δ: 1.63 (4H, br t), 2.25 (3H, s), 3.14-3.33 (assume 3H, obscured by solvent), 3.46 (4H, br t), 3.64 (4H, s), 4.80-4.98 (1H, m), 6.70 (1H, dd), 6.87 (1H, br d), 7.02 (2H, br d), 7.12 (1H, br t), 7.16-7.23 (2H, m), 7.27-7.33 (3H, m), 7.52 (2H, br d), 7.62 (1H, dd), 7.82 (1H, dd), 7.94 (1H, s), 8.17-8.19 (assume 1H, obscured by solvent) 9.99 (1H, s), 10.40 (1H, s).

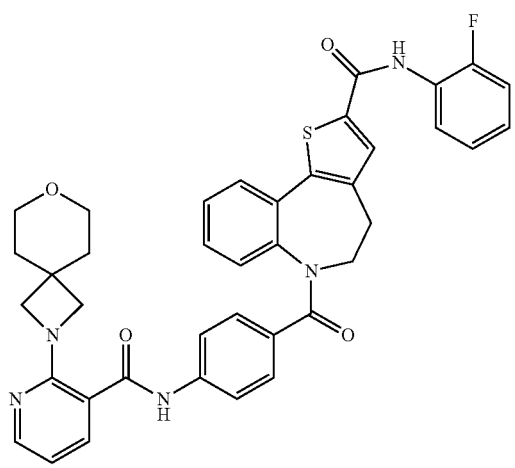 [SMILES: O=C(Nc1ccccc1F)c1cc2c(s1)-c1ccccc1N(C(=O)c1ccc(NC(=O)c3cccnc3N3CC4(CCOCC4)C3)cc1)CC2]

15: 6-(4-(2-(7-oxa-2-azaspiro[3.5]nonan-2-yl)nicotinamido)benzoyl)-N-(2-fluorophenyl)-5,6-dihydro-4H-benzo[b]thieno[2,3-d]azepine-2-carboxamide.
Prep HPLC Method 4;
R$^t$ 1.87 min (Method 1a); m/z 688 (M + H)$^+$ (ES$^+$);
$^1$H NMR δ: 1.63 (4H, br t), 3.11-3.24 (assume 3H, obscured by solvent), 3.46 (4H, br t), 3.64 (4H, s), 4.80-4.98 (1H, m), 6.70 (1H, dd), 6.88 (1H, br d), 7.01 (2H, br d), 7.12 (1H, broad t), 7.21-7.29 (4H, m), 7.52 (2H, br d), 7.58-7.64, (2H, m), 7.82 (1H, dd), 7.98 (1H, s), 8.18 (1H, dd), 10.23 (1H, s), 10.39 (1H, s).

TABLE 2-continued

Additional Compound Examples of the Invention

Structure, Example No., Name, Preparative HPLC or Column Chromatography
Purification Method (where employed), LC-MS Analysis and ¹HNMR Spectral Data

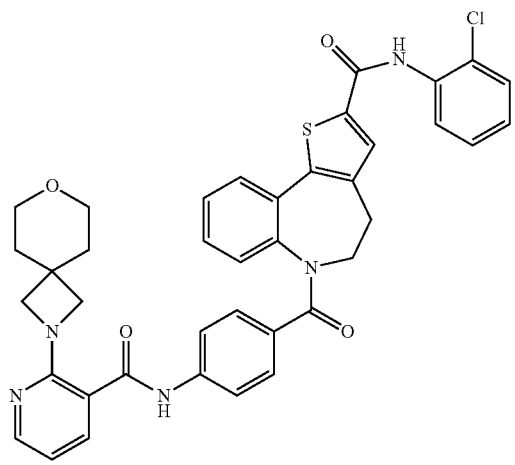 [SMILES: CCc1ccccc1NC(=O)c1cc2c(s1)-c1ccccc1N(C(=O)c1ccc(NC(=O)c3cccnc3N3CC4(CCOCC4)C3)cc1)CC2]

16: 6-(4-(2-(7-oxa-2-azaspiro[3.5]nonan-2-yl)nicotinamido)benzoyl)-N-(2-chlorophenyl)-5,6-dihydro-4H-benzo[b]thieno[2,3-d]azepine-2-carboxamide.
Prep HPLC Method 4;
$R^r$ 1.99 min (Method 1a); m/z 704 (M + H)⁺ (ES⁺);
¹H NMR δ: 1.63 (4H, br t), 3.14-3.34 (assume 3H, obscured by solvent), 3.46 (4H, br t), 3.64 (4H, s), 4.80-4.98 (1H, m), 6.71 (1H, dd), 6.88 (1H, br d), 7.02 (2H, br d), 7.13 (1H, br t), 7.27-7.32 (2H, m), 7.40 (1H, td), 7.52 (2H, br d), 7.57 (2H, dt), 7.62 (1H, dd), 7.83 (1H, dd), 7.98 (1H, s), 8.18 (1H, dd), 10.19 (1H, s), 10.39 (1H, s).

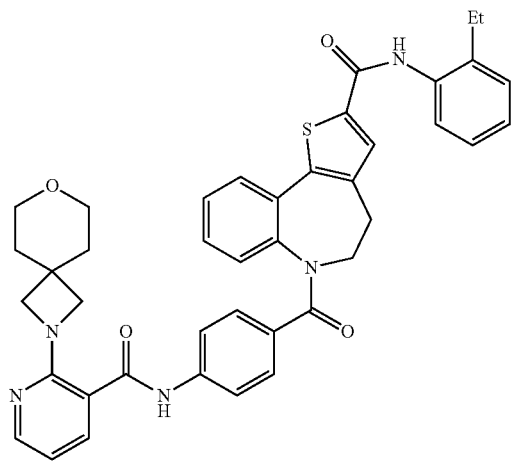

17: 6-(4-(2-(7-oxa-2-azaspiro[3.5]nonan-2-yl)nicotinamido)benzoyl)-N-(2-ethylphenyl)-5,6-dihydro-4H-benzo[b]thieno[2,3-d]azepine-2-carboxamide.
Prep HPLC Method 3;
$R^r$ 1.95 min (Method 1a); m/z 698 (M + H)⁺ (ES⁺);
¹H NMR δ: 1.14 (3H, t), 1.63 (4H, br t), 2.64 (2H, q), 3.14-3.22 (assume 3H, obscured by solvent), 3.46 (4H, br t), 3.64 (4H, s), 4.80-4.98 (1H, m), 6.70 (1H, dd), 6.87 (1H, br d), 7.02 (2H, br d), 7.11 (1H, br t), 7.23-7.29 (5H, m), 7.52 (2H, br d), 7.62 (1H, dd), 7.82 (1H, dd), 7.93 (1H, s), 8.18 (1H, dd), 9.99 (1H, s), 10.39 (1H, s).

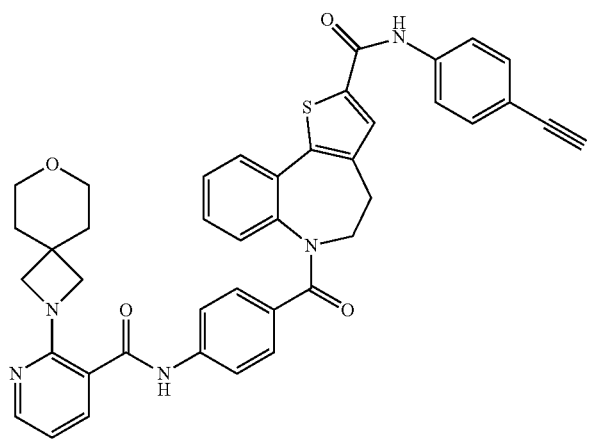 [SMILES: C#Cc1ccc(NC(=O)c2cc3c(s2)-c2ccccc2N(C(=O)c2ccc(NC(=O)c4cccnc4N4CC5(CCOCC5)C4)cc2)CC3)cc1]

18: 6-(4-(2-(7-oxa-2-azaspiro[3.5]nonan-2-yl)nicotinamido)benzoyl)-N-(4-ethynylphenyl)-5,6-dihydro-4H-benzo[b]thieno[2,3-d]azepine-2-carboxamide.
Prep HPLC Method 3;
Rt 1.98 min (Method 1a); m/z 694 (M + H)⁺ (ES⁺);
¹H NMR δ: 1.63 (4H, br t), 3.12-3.36 (assume 3H, obscured by solvent), 3.46(4H, br t), 3.64 (4H, s), 4.12 (1H, s), 4.90-4.99 (1H, b), 6.70 (1H, dd), 6.88 (1H, br d), 7.01 (2H, br d), 7.13 (1H, br t), 7.30 (1H, td), 7.47-7.52 (4H, over-lapping m), 7.62 (1H, dd), 7.79 (2H, d), 7.83 (1H, dd), 8.00 (1H, s), 8.18 (1H, dd), 10.39 (1H, s), 10.45 (1H, s).

TABLE 2-continued

Additional Compound Examples of the Invention

Structure, Example No., Name, Preparative HPLC or Column Chromatography Purification Method (where employed), LC-MS Analysis and ¹HNMR Spectral Data

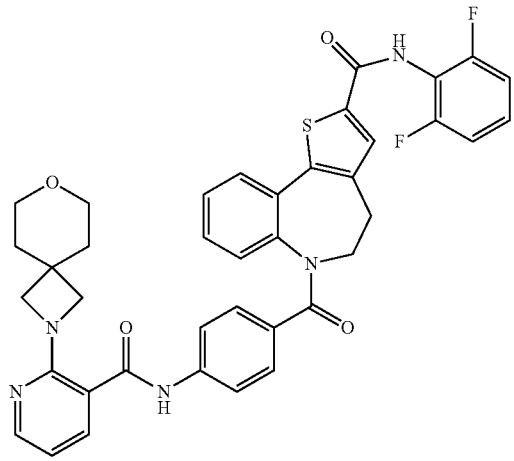 [SMILES: O=C(Nc1c(F)cccc1F)c1cc2c(s1)-c1ccccc1N(C(=O)c1ccc(NC(=O)c3cccnc3N3CC4(CCOCC4)C3)cc1)CC2]

19: 6-(4-(2-(7-oxa-2-azaspiro[3.5]nonan-2-yl)nicotinamido)benzoyl)-N-(2,6-difluorophenyl)-5,6-dihydro-4H-benzo[b]thieno[2,3-d]azepine-2-carboxamide.
Prep HPLC Method 2;
$R^r$ 1.80 min (Method 1a); m/z 706 (M + H)⁺ (ES⁺);
¹H NMR δ: 1.63 (4H, br t), 3.14-3.34 (assume 3H, obscured by solvent), 3.46 (4H, br t), 3.64 (4H, s), 4.80-4.98 (1H, m), 6.72(1H, dd), 6.88 (1H, br d), 7.02(2H, br d), 7.13(1H, br t), 7.23 (2H, t), 7.29 (1H, t), 7.45 (1H, quin), 7.52 (2H, br d), 7.62 (1H, dd), 7.83 (1H, dd), 7.97 (1H, s), 8.19 (assume 1H obscured by solvent, d), 10.28 (1H, s), 10.39 (1H, s).

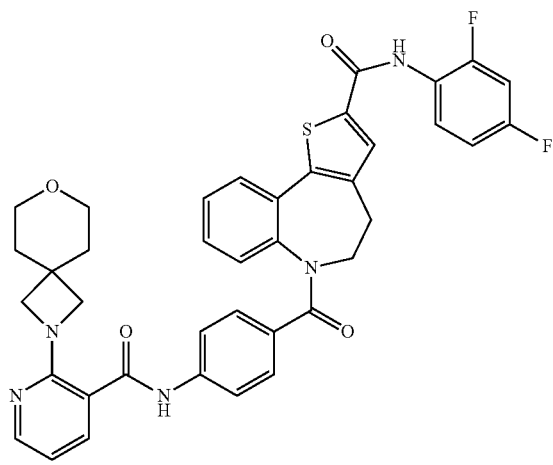 [SMILES: O=C(Nc1ccc(F)cc1F)c1cc2c(s1)-c1ccccc1N(C(=O)c1ccc(NC(=O)c3cccnc3N3CC4(CCOCC4)C3)cc1)CC2]

20: 6-(4-(2-(7-oxa-2-azaspiro[3.5]nonan-2-yl)nicotinamido)benzoyl)-N-(2,4-difluorophenyl)-5,6-dihydro-4H-benzo[b]thieno[2,3-d]azepine-2-carboxamide.
Prep HPLC Method 3;
$R^r$ 1.90 min (Method 1a); m/z 706 (M + H)⁺ (ES⁺);
¹H NMR δ: 1.63 (4H, t), 3.10-3.38 (assume 3H, obscured by solvent, m), 3.46 (4H, t), 3.64 (4H, s), 4.86-5.02 (1H, m), 6.70 (1H, dd), 6.88 (1H, d), 7.01 (2H, d), 7.09-7.19 (2H, m), 7.29 (1H, td), 7.38 (1H, ddd), 7.51 (2H, d), 7.55-7.65 (2H, m), 7.82 (1H, dd), 7.96 (1H, s), 8.18 (1H, dd), 10.25 (1H, s), 10.39 (1H, s).

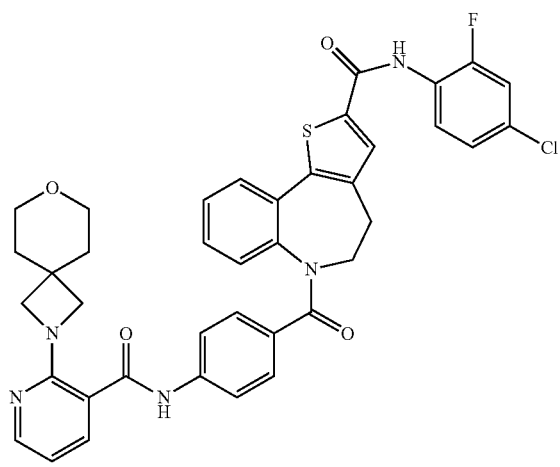 [SMILES: O=C(Nc1ccc(Cl)cc1F)c1cc2c(s1)-c1ccccc1N(C(=O)c1ccc(NC(=O)c3cccnc3N3CC4(CCOCC4)C3)cc1)CC2]

21: 6-(4-(2-(7-oxa-2-azaspiro[3.5]nonan-2-yl)nicotinamido)benzoyl)-N-(4-chloro-2-fluorophenyl)-5,6-dihydro-4H-benzo[b]thieno[2,3-d]azepine-2-carboxamide.
Prep HPLC Method 3;
$R^r$ 2.06 min (Method 1a); m/z 722 (M + H)⁺ (ES⁺);
¹H NMR δ: 1.63 (4H, br t), 3.12-3.37 (assume 3H, obscured by solvent), 3.46 (4H, br t), 3.64 (4H, s), 4.93 (1H, b), 6.70 (1H, dd), 6.88 (1H, br d), 7.01 (2H, br d), 7.13 (1H, br t), 7.27-7.35 (2H, over-lapping m), 7.51 (2H, br d), 7.57 (1H, dd), 7.61-7.66 (2H, over-lapping m), 7.82 (1H, dd), 7.98 (1H, s), 8.18 (1H, dd), 10.31 (1H, s), 10.39 (1H, s).

TABLE 2-continued

Additional Compound Examples of the Invention

Structure, Example No., Name, Preparative HPLC or Column Chromatography
Purification Method (where employed), LC-MS Analysis and ¹HNMR Spectral Data

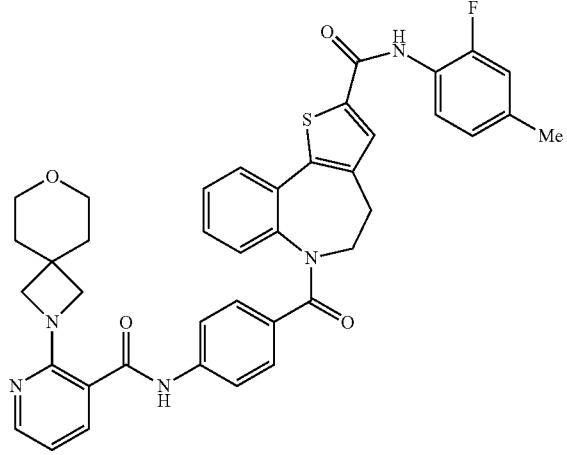 [SMILES: Cc1ccc(NC(=O)c2cc3c(s2)-c2ccccc2N(C(=O)c2ccc(NC(=O)c4cccnc4N4CC5(CCOCC5)C4)cc2)CC3)c(F)c1]

22: 6-(4-(2-(7-oxa-2-azaspiro[3.5]nonan-2-yl)nicotinamido)benzoyl)-N-(2-fluoro-4-methylphenyl)-5,6-dihydro-4H-benzo[b]thieno[2,3-d]azepine-2-carboxamide.
Prep HPLC Method 3;
$R^t$ 1.97 min (Method 1a); m/z 702 (M + H)⁺ (ES⁺);
¹H NMR δ: 1.63 (4H, t), 2.33 (3H, s), 3.08-3.38 (assume 3H, obscured by solvent, m), 3.46 (4H, t), 3.64 (4H, s), 4.86-4.98 (1H, m), 6.70 (1H, dd), 6.88 (1H, d), 6.96-7.08 (3H, over-lapping m), 7.09-7.17 (2H, over-lapping m), 7.29 (1H, td), 7.43 (1H, t), 7.51 (2H, d), 7.62 (1H, dd), 7.82 (1H, dd), 7.96 (1H, s), 8.18 (1H, dd), 10.14 (1H, s), 10.39 (1H, s).

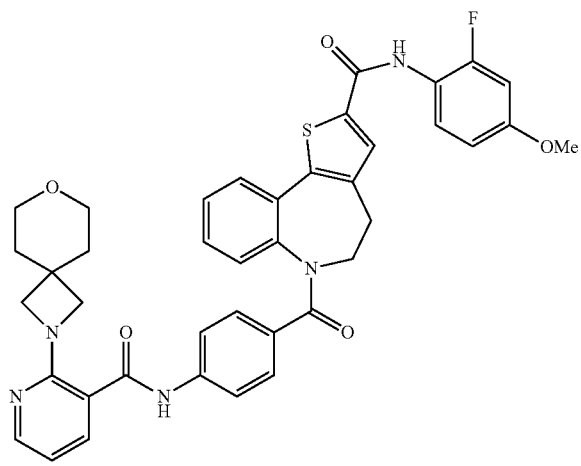 [SMILES: COc1ccc(NC(=O)c2cc3c(s2)-c2ccccc2N(C(=O)c2ccc(NC(=O)c4cccnc4N4CC5(CCOCC5)C4)cc2)CC3)c(F)c1]

23: 6-(4-(2-(7-oxa-2-azaspiro[3.5]nonan-2-yl)nicotinamido)benzoyl)-N-(2-fluoro-4-methoxyphenyl)-5,6-dihydro-4H-benzo[b]thieno[2,3-d]azepine-2-carboxamide.
Prep HPLC Method 2;
$R^t$ 1.86 min (Method 1a); m/z 718 (M + H)⁺ (ES⁺);
¹H NMR δ: 1.63 (4H, t), 3.09-3.42 (assume 3H, obscured by solvent, m), 3.46 (4H, t), 3.64 (4H, s), 3.79 (3H, s), 4.88-5.02 (1H, m), 6.70 (1H, dd), 6.82 (1H, ddd), 6.88 (1H, d), 6.95 (1H, dd), 7.01 (2H, d), 7.12 (1H, t), 7.29 (1H, td), 7.41 (1H, t), 7.51 (2H, d), 7.62 (1H, dd), 7.81 (1H, dd), 7.93 (1H, s), 8.12-8.26 (1H, m), 10.08 (1H, s), 10.39 (1H, s).

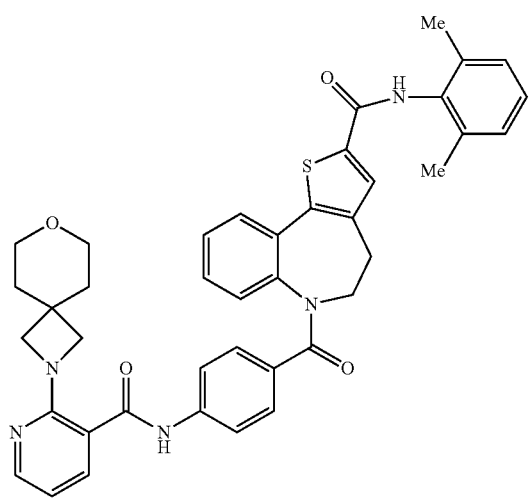 [SMILES: Cc1cccc(C)c1NC(=O)c1cc2c(s1)-c1ccccc1N(C(=O)c1ccc(NC(=O)c3cccnc3N3CC4(CCOCC4)C3)cc1)CC2]

24: 6-(4-(2-(7-oxa-2-azaspiro[3.5]nonan-2-yl)nicotinamido)benzoyl)-N-(2,6-dimethylphenyl)-5,6-dihydro-4H-benzo[b]thieno[2,3-d]azepine-2-carboxamide.
Prep HPLC Method 3;
$R^t$ 1.91 min (Method 1a); m/z 350 (M + 2H)²⁺ (ES⁺);
¹H NMR δ: 1.63 (4H, t), 2.21 (6H, s), 3.11-3.38 (assume 3H, obscured by solvent, m), 3.46 (4H, t), 3.65 (4H, s), 4.94 (1H, m), 6.70 (1H, dd), 6.87 (1H, d), 7.03 (2H, d), 7.08-7.16 (4H, m), 7.29 (1H, m), 7.52 (2H, d), 7.62 (1H, dd), 7.82 (1H, dd), 7.94 (1H, s), 8.18 (1H, dd), 9.88 (1H, s), 10.39 (1H, s).

TABLE 2-continued

Additional Compound Examples of the Invention

Structure, Example No., Name, Preparative HPLC or Column Chromatography
Purification Method (where employed), LC-MS Analysis and ¹HNMR Spectral Data

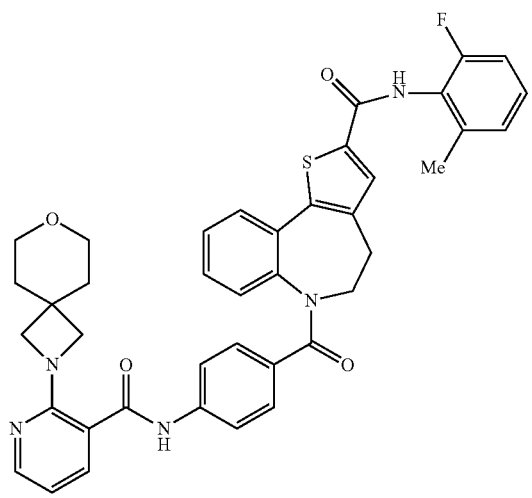 [SMILES: Cc1cccc(F)c1NC(=O)c1cc2c(s1)-c1ccccc1N(C(=O)c1ccc(NC(=O)c3cccnc3N3CC4(CCOCC4)C3)cc1)CC2]

25: 6-(4-(2-(7-oxa-2-azaspiro[3.5]nonan-2-yl)nicotinamido)benzoyl)-N-(2-fluoro-6-methylphenyl)-5,6-dihydro-4H-benzo[b]thieno[2,3-d]azepine-2-carboxamide.
Prep HPLC Method 3;
R$^r$ 1.86 min (Method 1a); m/z 352 (M + 2H)$^{2+}$ (ES$^+$);
¹H NMR δ: 1.63 (4H, t), 2.26 (3H, s), 3.33 (assume 3H, obscured by solvent, m), 3.46 (4H, t), 3.65 (4H, s), 4.94 (1H, m), 6.71 (1H, dd), 6.87(1H d), 7.02(2H d), 7.09-7.17 (3H, over-lapping m), 7.24-7.34 (2H, m), 7.52(2H, d), 7.63 (1H, dd), 7.82 (1H, dd), 7.95 (1H, s), 8.18 (1H, dd), 10.02 (1H, s), 10.40 (1H, s).

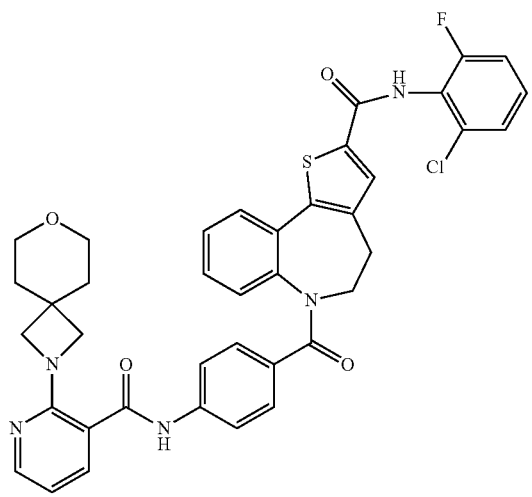 [SMILES: O=C(Nc1c(F)cccc1Cl)c1cc2c(s1)-c1ccccc1N(C(=O)c1ccc(NC(=O)c3cccnc3N3CC4(CCOCC4)C3)cc1)CC2]

26: 6-(4-(2-(7-oxa-2-azaspiro[3.5]nonan-2-yl)nicotinamido)benzoyl)-N-(2-chloro-6-fluorophenyl)-5,6-dihydro-4H-benzo[b]thieno[2,3-d]azepine-2-carboxamide.
Prep HPLC Method 3;
R$^r$ 1.85 min (Method 1a); m/z 722 (M + H)$^+$ (ES$^+$);
¹H NMR δ: 1.63 (4H, br t), 3.16-3.25 (assume 3H, obscured by solvent), 3.46 (4H, br t), 3.64 (4H, s), 4.94 (1H, m), 6.71 (1H, dd), 6.88 (1H, br d), 7.02 (2H, br d), 7.13 (1H, br t), 7.29 (1H, t), 7.35-7.41 (1H, m), 7.42-7.48 (2H, m), 7.52 (2H, br d), 7.63 (1H, dd), 7.83 (1H, dd), 7.98 (1H, s), 8.18 (1H, dd), 10.34 (1H, s), 10.41 (1H, s).

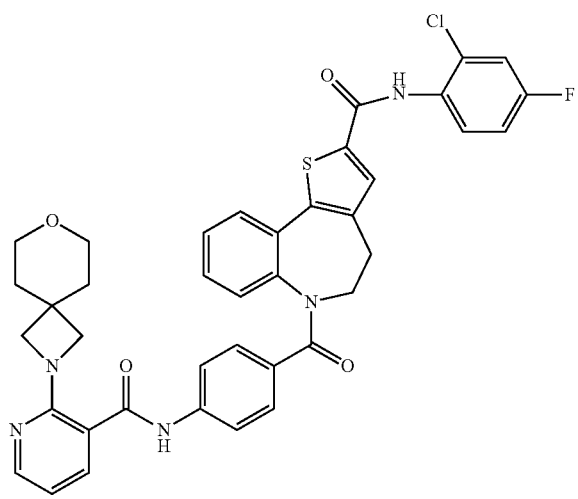 [SMILES: O=C(Nc1ccc(F)cc1Cl)c1cc2c(s1)-c1ccccc1N(C(=O)c1ccc(NC(=O)c3cccnc3N3CC4(CCOCC4)C3)cc1)CC2]

27: 6-(4-(2-(7-oxa-2-azaspiro[3.5]nonan-2-yl)nicotinamido)benzoyl)-N-(2-chloro-4-fluorophenyl)-5,6-dihydro-4H-benzo[b]thieno[2,3-d]azepine-2-carboxamide.
Prep HPLC Method 3;
R$^r$ 1.98 min (Method 1a); m/z 722 (M + H)$^+$ (ES$^+$);
¹H NMR δ: 1.63 (4H, t), 3.11-3.38 (assume 3H, obscured by solvent, m), 3.46 (4H, t), 3.64 (4H, s), 4.88-4.98 (1H, m), 6.70 (1H, dd), 6.88 (1H, d), 7.01 (2H, d), 7.12 (1H, t), 7.29 (2H, td), 7.52 (2H, d), 7.55-7.65 (3H, m), 7.82 (1H, dd), 7.95 (1H, s), 8.18 (1H, dd), 10.25 (1H, s), 10.41 (1H, s).

TABLE 2-continued

Additional Compound Examples of the Invention

Structure, Example No., Name, Preparative HPLC or Column Chromatography
Purification Method (where employed), LC-MS Analysis and ¹HNMR Spectral Data

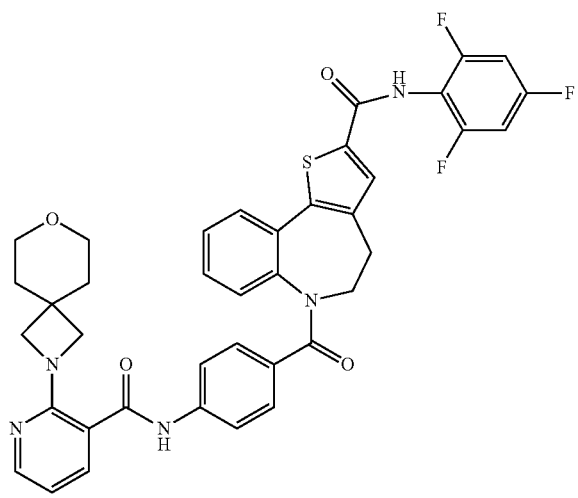 [SMILES: O=C(Nc1c(F)cc(F)cc1F)c1cc2c(s1)-c1ccccc1N(C(=O)c1ccc(NC(=O)c3cccnc3N3CC4(CCOCC4)C3)cc1)CC2]

28: 6-(4-(2-(7-oxa-2-azaspiro[3.5]nonan-2-yl)nicotinamido)
benzoyl)-N-(2,4,6-trifluorophenyl)-5,6-dihydro-4H-benzo[b]
thieno[2,3-d]azepine-2-carboxamide.
Prep HPLC Method 4;
$R^r$ 1.87 min (Method 1a); m/z 362 (M + 2H)$^{2+}$ (ES$^+$);
¹H NMR δ: 1.63 (4H, br t), 3.12-3.37 (assume 3H, obscured
by solvent), 3.46 (4H, br t), 3.64 (4H, s), 4.89-4.98 (1H, b),
6.70 (1H, dd), 6.88 (1H, br d), 7.02 (2H, br d), 7.13 (1H, br
t), 7.29 (1H, td), 7.34-7.38 (2H, over-lapping m), 7.52 (2H,
br d), 7.62 (1H, dd), 7.82 (1H, dd), 7.96 (1H, s), 8.18 (1H,
dd), 10.26 (1H, s), 10.39 (1H, s).

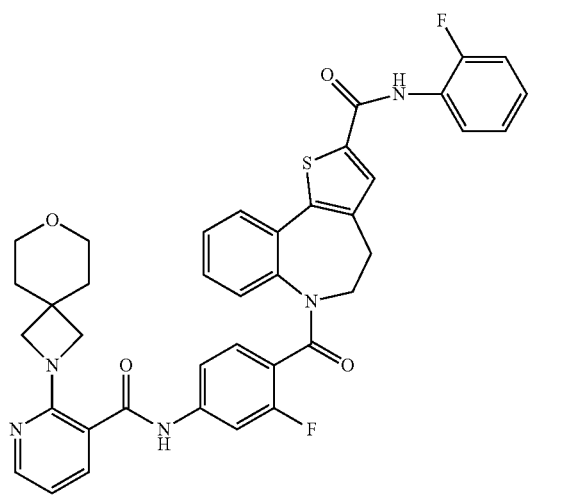 [SMILES: O=C(Nc1ccccc1F)c1cc2c(s1)-c1ccccc1N(C(=O)c1ccc(NC(=O)c3cccnc3N3CC4(CCOCC4)C3)cc1F)CC2]

29: 6-(4-(2-(7-oxa-2-azaspiro[3.5]nonan-2-yl)nicotinamido)-
2-fluorobenzoyl)-N-(2-fluorophenyl)-5,6-dihydro-4H-
benzo[b]thieno[2,3-d]azepine-2-carboxamide.
Prep HPLC Method 4;
$R^r$ 1.94 min (Method 1a); m/z 706 (M + H)$^+$ (ES$^+$);
¹H NMR δ: 1.64 (4H, t), 3.07-3.43 (assume 3H, obscured
by solvent, m), 3.47 (4H, t), 3.63 (4H, s), 4.78-4.94 (1H, m),
6.71 (1H, dd), 6.95 (1H, dd), 7.11 (1H, td), 7.16-7.34 (5H,
m), 7.37 (2H, t), 7.59 (1H, td), 7.64 (1H, dd), 7.78 (1H, dd),
7.96 (1H, s), 8.19 (1H, dd), 10.24 (1H, s), 10.55 (1H, s).

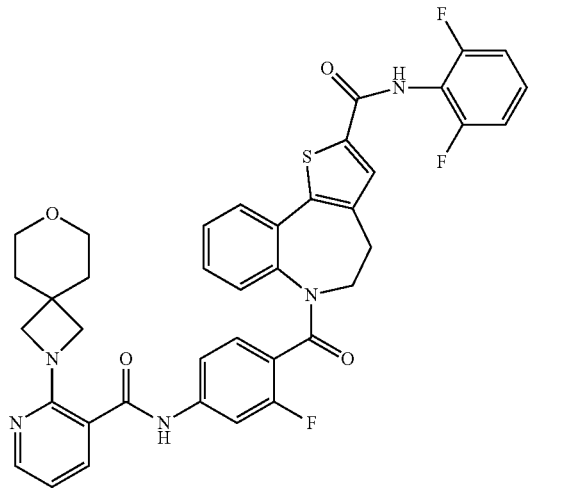 [SMILES: O=C(Nc1c(F)cccc1Cl)c1cc2c(s1)-c1ccccc1N(C(=O)c1ccc(NC(=O)c3cccnc3N3CC4(CCOCC4)C3)cc1F)CC2]

30: 6-(4-(2-(7-oxa-2-azaspiro[3.5]nonan-2-yl)nicotinamido)-
2-fluorobenzoyl)-N-(2,6-difluorophenyl)-5,6-dihydro-4H-
benzo[b]thieno[2,3-d]azepine-2-carboxamide.
Prep HPLC Method 2
$R^r$ 1.85 min (Method 1a); m/z 724 (M + H)$^+$ (ES$^+$);
¹H NMR δ: 1.64 (4H, br t), 3.13-3.19 (1H, m), 3.23-3.42
(assume 2H, obscured by solvent), 3.47 (4H, br t), 3.64
(4H, s), 4.84-4.90 (1H, m), 6.71 (1H, dd), 6.95 (1H, dd),
7.12 (1H, td), 7.17-7.30 (4H, over-lapping m), 7.34-7.47
(3H, over-lapping m), 7.64 (1H, dd), 7.78 (1H, dd), 7.95
(1H, s), 8.19 (1H, dd), 10.28 (1H, s), 10.54 (1H, s).

TABLE 2-continued

Additional Compound Examples of the Invention

Structure, Example No., Name, Preparative HPLC or Column Chromatography Purification Method (where employed), LC-MS Analysis and ¹HNMR Spectral Data

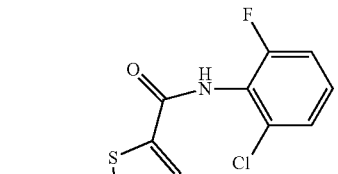

31: 6-(4-(2-(7-oxa-2-azaspiro[3.5]nonan-2-yl)nicotinamido)-2-fluorobenzoyl)-N-(2-chloro-6-fluorophenyl)-5,6-dihydro-4H-benzo[b]thieno[2,3-d]azepine-2-carboxamide.
Prep HPLC Method 6;
$R^t$ 2.29 min (Method 1b); m/z 740 (M + H)⁺ (ES⁺);
¹H NMR δ: 1.64 (4H, br t), 3.16 (1H, dt), 3.23-3.42 (assume 2H, obscured by solvent), 3.47 (4H, br t), 3.64 (4H, s), 4.85-4.90 (1H, m), 6.71 (1H, dd), 6.95 (1H, d), 7.12 (1H, td), 7.20 (1H, br t), 7.28 (1H, td), 7.35-7.48 (5H, over-lapping m), 7.64 (1H, dd), 7.78 (1H, dd), 7.96 (1H, s), 8.19 (1H, dd), 10.31 (1H, s), 10.53 (1H, s).

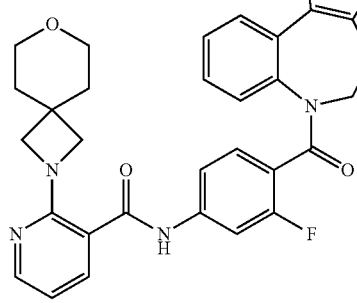

32: 6-(4-(5-methyl-2-(7-oxa-2-azaspiro[3.5]nonan-2-yl)nicotinamido)benzoyl)-N-phenyl-5,6-dihydro-4H-benzo[b]thieno[2,3-d]azepine-2-carboxamide.
Prep HPLC Method 3;
$R^t$ 1.90 min (Method 1a); m/z 684 (M + H)⁺ (ES⁺);
¹H NMR δ: 1.62 (4H, br t), 2.17 (3H, s), 3.13-3.36 (assume 3H, obscured by solvent), 3.45 (4H, br t), 3.60 (4H, s), 4.89-4.98 (1H, b), 6.87-6.89 (1H, m), 7.01 (2H, br d), 7.10-7.14 (2H, over-lapping m), 7.30 (1H, td), 7.35-7.39 (2H, over-lapping m), 7.48-7.52 (3H, over-lapping m), 7.73-7.76 (2H, over-lapping m), 7.83 (1H, dd), 7.99 (1H, s), 8.03 (1H, dd), 10.30 (1H, s), 10.36 (1H, s).

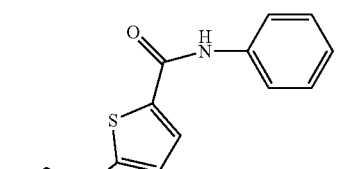

33: N-(2-fluorophenyl)-6-(4-(5-methyl-2-(7-oxa-2-azaspiro[3.5]nonan-2-yl)nicotinamido)benzoyl)-5,6-dihydro-4H-benzo[b]thieno[2,3-d]azepine-2-carboxamide.
Prep HPLC Method 3;
$R^t$ 1.88 min (Method 1a); m/z 702 (M + H)⁺ (ES⁺);
¹H NMR δ: 1.62 (4H, br t), 2.17 (3H, s), 3.11-3.38 (assume 3H, obscured by solvent), 3.46 (4H, br t), 3.60 (4H, s), 4.90-4.97 (1H, b), 6.88 (1H, br d), 7.01 (2H, br d), 7.12 (1H, br t), 7.21-7.34 (4H, over-lapping m), 7.48 (1H, d), 7.51 (2H, br d), 7.60 (1H, td), 7.82 (1H, dd), 7.98 (1H, s), 8.04 (1H, dd), 10.23 (1H, s), 10.37 (1H, s).

TABLE 2-continued

Additional Compound Examples of the Invention

Structure, Example No., Name, Preparative HPLC or Column Chromatography
Purification Method (where employed), LC-MS Analysis and ¹HNMR Spectral Data

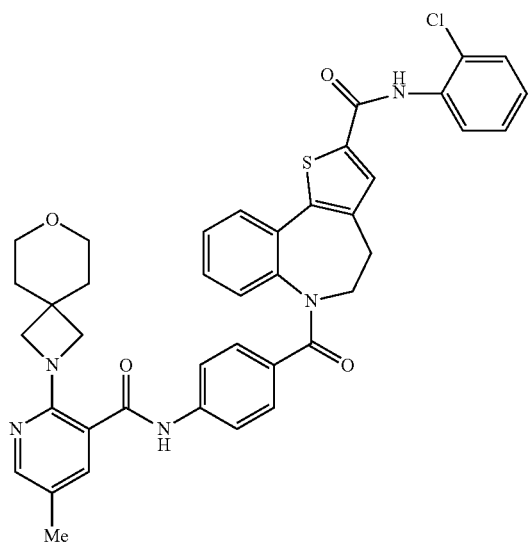 [SMILES: Cc1cnc(N2CC3(CCOCC3)C2)c(C(=O)Nc2ccc(C(=O)N3CCc4cc(C(=O)Nc5ccccc5F)sc4-c4ccccc43)cc2)c1]

34: N-(2-chlorophenyl)-6-(4-(5-methyl-2-(7-oxa-2-azaspiro
[3.5]nonan-2-yl)nicotinamido)benzoyl)-5,6-dihydro-4H-
benzo[b]thieno[2,3-d]azepine-2-carboxamide.
Prep HPLC Method 3;
$R^r$ 1.99 min (Method 1a); m/z 718 (M + H)⁺ (ES⁺);
¹H NMR δ: 1.62 (4H, br t), 2.17 (3H, s), 3.12-3.40 (assume
3H, obscured by solvent), 3.46 (4H, br t), 3.60 (4H, s), 4.90-
4.98 (1H, b), 6.88 (1H, br t), 7.01 (2H, br d), 7.12 (1H, br t),
7.27-7.34 (2H, over-lapping m), 7.41 (1H, td), 7.48 (1H, d),
7.51 (2H, br d), 7.58 (2H, dt), 7.83 (1H, dd), 7.98 (1H, s),
8.04 (1H, dd), 10.19 (1H, s), 10.37 (1H, s).

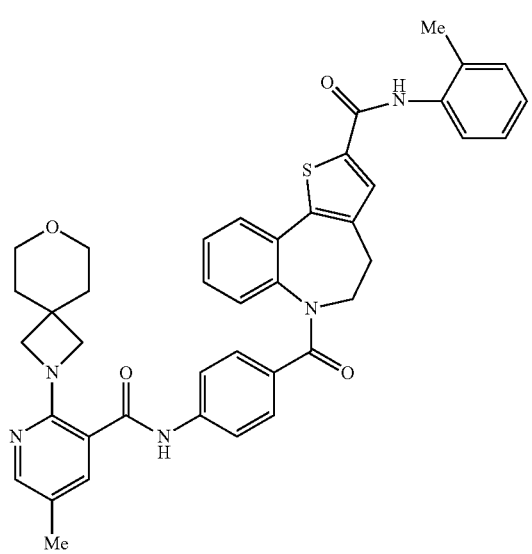 [SMILES: Cc1cnc(N2CC3(CCOCC3)C2)c(C(=O)Nc2ccc(C(=O)N3CCc4cc(C(=O)Nc5ccccc5C)sc4-c4ccccc43)cc2)c1]

35: 6-(4-(5-methyl-2-(7-oxa-2-azaspiro[3.5]nonan-2-yl)
nicotinamido)benzoyl)-N-(o-tolyl)-5,6-dihydro-4H-benzo[b]
thieno[2,3-d]azepine-2-carboxamide.
Prep HPLC Method 3;
$R^r$ 1.88 min (Method 1a); m/z 698 (M + H)⁺ (ES⁺);
¹H NMR δ: 1.62 (4H, br t), 2.17 (3H, s), 2.26 (3H, s), 3.12-
3.38 (assume 3H, obscured by solvent), 3.46 (4H, br t),
3.60 (4H, s), 4.90-4.97 (1H, br), 6.87 (1H, br d), 7.01 (2H,
br d), 7.12 (1H, br t), 7.16-7.34 (5H, over-lapping m), 7.48
(1H, d), 7.51 (2H, br d), 7.82 (1H, dd), 7.94 (1H, s), 8.04
(1H, dd), 9.98 (1H, s), 10.37 (1H, s).

TABLE 2-continued

Additional Compound Examples of the Invention

Structure, Example No., Name, Preparative HPLC or Column Chromatography
Purification Method (where employed), LC-MS Analysis and ¹HNMR Spectral Data

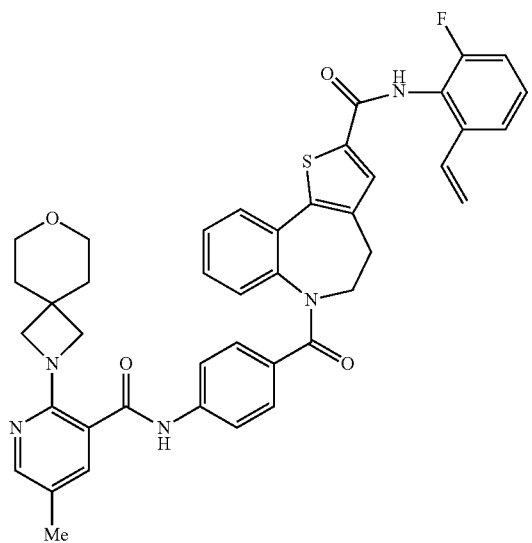 [SMILES: C=Cc1cccc(F)c1NC(=O)c1cc2c(s1)-c1ccccc1N(C(=O)c1ccc(NC(=O)c3cc(C)cnc3N3CC4(CCOCC4)C3)cc1)CC2]

36: N-(2-fluoro-6-vinylphenyl)-6-(4-(5-methyl-2-(7-oxa-2-azaspiro[3.5]nonan-2-yl)nicotinamido)benzoyl)-5,6-dihydro-4H-benzo[b]thieno[2,3-d]azepine-2-carboxamide.
$R^t$ 1.91 min (Method 1a); m/z 728 (M + H)⁺ (ES⁺);
¹H NMR δ: 1.62 (4H, t), 2.17 (3H, s), 3.11-3.31 (assume 3H, obscured by solvent), 3.46 (4H, t), 3.60 (4H, s), 4.93 (1H, bs), 5.38-5.45 (1H, m), 5.92 (1H, dd), 6.81-6.92 (2H, m), 7.02 (2H, d), 7.12 (1H, t), 7.22-7.33 (2H, m), 7.38 (1H, td), 7.43-7.61 (4H, m), 7.82 (1H, dd), 7.94-8.09 (2H, m), 10.17 (1H, s), 10.38 (1H, s).

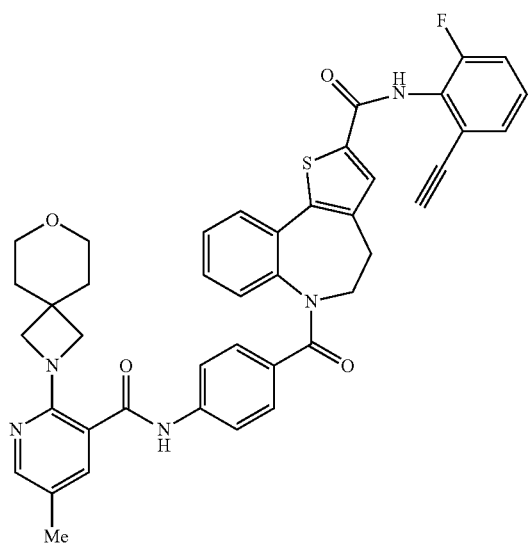 [SMILES: C#Cc1cccc(F)c1NC(=O)c1cc2c(s1)-c1ccccc1N(C(=O)c1ccc(NC(=O)c3cc(C)cnc3N3CC4(CCOCC4)C3)cc1)CC2]

37: N-(2-ethynyl-6-fluorophenyl)-6-(4-(5-methyl-2-(7-oxa-2-azaspiro[3.5]nonan-2-yl)nicotinamido)benzoyl)-5,6-dihydro-4H-benzo[b]thieno[2,3-d]azepine-2-carboxamide.
$R^t$ 1.86 min (Method 1a); m/z 726 (M + H)⁺ (ES⁺);
¹H NMR δ: 1.62 (4H, t), 2.17 (3H, s), 3.15-3.23 (assume 3H, obscured by solvent), 3.45 (4H, t), 3.60 (4H, s), 4.45 (1H, s), 4.93 (1H, s), 6.87 (1H, d), 7.02 (2H, d), 7.12 (1H, t), 7.29 (1H, td), 7.34-7.57 (6H, m), 7.83 (1H, dd), 7.98 (1H, s), 8.03 (1H, dd), 10.31 (1H, s), 10.38 (1H, s).

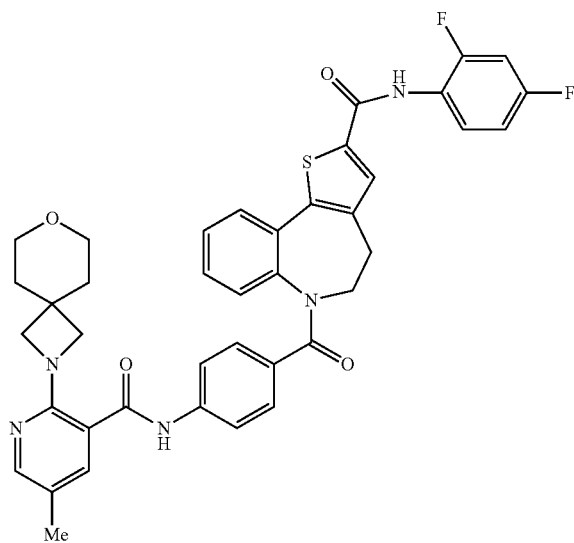 [SMILES: Cc1cnc(N2CC3(CCOCC3)C2)c(C(=O)Nc2ccc(C(=O)N3CCc4cc(C(=O)Nc5ccc(F)cc5F)sc4-c4ccccc43)cc2)c1]

38: N-(2,4-difluorophenyl)-6-(4-(5-methyl-2-(7-oxa-2-aza-spiro[3.5]nonan-2-yl)nicotinamido)benzoyl)-5,6-dihydro-4H-benzo[b]thieno[2,3-d]azepine-2-carboxamide.
Prep HPLC Method 3;
R$^r$ 1.91 min (Method 1a); m/z 720 (M + H)$^+$ (ES$^+$);
$^1$H NMR δ: 1.62 (4H, br t), 2.17 (3H, s), 3.12-3.37 (assume 3H, obscured by solvent), 3.46 (4H, br t), 3.60 (4H, s), 4.90-4.98 (1H, b), 6.88 (1H, br d), 7.01 (2H, br d), 7.11-7.17 (2H, over-lapping m), 7.29 (1H, td), 7.39 (1H, over-lapping dd), 7.48 (1H, d), 7.51 (2H, br d), 7.59 (1H, over-lapping dd), 7.82 (1H, dd), 7.96 (1H, s), 8.04 (1H, dd), 10.25 (1H, s), 10.37 (1H, s).

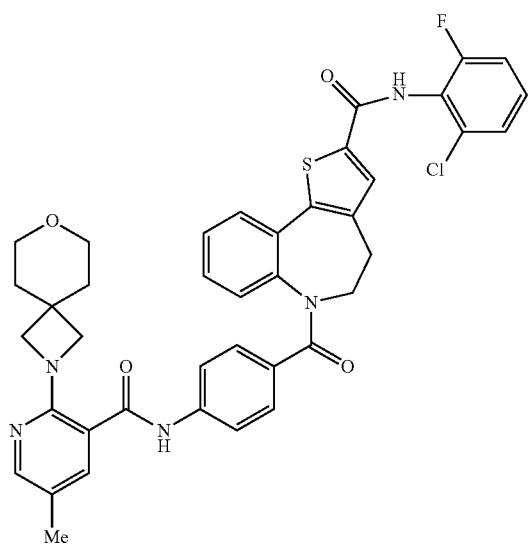

39: N-(2-chloro-6-fluorophenyl)-6-(4-(5-methyl-2-(7-oxa-2-azaspiro[3.5]nonan-2-yl)nicotinamido)benzoyl)-5,6-dihydro-4H-benzo[b]thieno[2,3-d]azepine-2-carboxamide.
Prep HPLC Method 4;
R$^r$ 1.87 min (Method 1a); m/z 736 (M + H)$^+$ (ES$^+$);
$^1$H NMR δ: 1.62 (4H, br t), 2.17 (3H, s), 3.12-3.27 (3H, m), 3.46 (4H, br t), 3.60 (4H, s), 4.94 (1H, m), 6.88 (1H, d),7.02 (2H, d), 7.12 (1H, t), 7.28 (1H, dt), 7.35-7.40 (1H, m), 7.40-7.45 (1H, m), 7.45-7.48 (2H, m), 7.51-7.53 (2H, br d), 7.82 (1H, dd), 7.98 (1H, s), 8.03 (1H, dd), 10.32 (1H, s), 10.37(1H, s).

TABLE 2-continued

Additional Compound Examples of the Invention

Structure, Example No., Name, Preparative HPLC or Column Chromatography Purification Method (where employed), LC-MS Analysis and ¹HNMR Spectral Data 40: N-(2-fluoro-6-methylphenyl)-6-(4-(6-methyl-2-(7-oxa-2-azaspiro[3.5]nonan-2-yl)nicotinamido)benzoyl)-5,6-dihydro-4H-benzo[b]thieno[2,3-d]azepine-2-carboxamide.
Prep HPLC Method 3;
R$^r$ 1.82 min (Method 1a); m/z 716 (M + H)$^+$ (ES$^+$);
¹H NMR δ: 1.62 (4H, br t), 2.26 (3H, s), 2.32 (3H, s), 3.12-3.36 (assume 3H, obscured by solvent), 3.47 (4H, br t), 3.63 (4H, s), 4.89-4.98 (1H, b), 6.56 (1H, d), 6.87 (1H, br d), 7.01 (2H, br d), 7.10-7.16 (3H, over-lapping m), 7.25-7.31 (2H, over-lapping m), 7.50-7.53 (3H, over-lapping m), 7.82 (1H, dd), 7.95 (1H, s), 10.02 (1H, s), 10.29 (1H, s).

41: N-(2-chloro-6-fluorophenyl)-6-(4-(6-methyl-2-(7-oxa-2-azaspiro[3.5]nonan-2-yl)nicotinamido)benzoyl)-5,6-dihydro-4H-benzo[b]thieno[2,3-d]azepine-2-carboxamide.
Prep HPLC Method 1;
R$^r$ 1.85 min (Method 1a); m/z 736 (M + H)$^+$ (ES$^+$);
¹H NMR δ: 1.62 (4H, br t), 2.32 (3H, s), 3.14-3.37 (assume 3H, obscured by solvent), 3.47 (4H, br t), 3.63 (4H, s), 4.90-4.98 (1H, b), 6.56 (1H, d), 6.87 (1H, br d), 7.01 (2H, br d), 7.13 (1H, br t), 7.29 (1H, td), 7.35-7.53 (6H, over-lapping m), 7.83 (1H, dd), 7.98 (1H, s), 10.29 (1H, s), 10.32 (1H, s)

42: 6-(4-(5,6-dimethyl-2-(7-oxa-2-azaspiro[3.5]nonan-2-yl)nicotinamido)benzoyl)-N-(o-tolyl)-5,6-dihydro-4H-benzo[b]thieno[2,3-d]azepine-2-carboxamide.
Prep HPLC Method 3;
R$^r$ 1.88 min (Method 1a); m/z 712 (M + H)$^+$ (ES$^+$);
¹H NMR δ: 1.61 (4H, br t), 2.13 (3H, s), 2.26 (3H, s), 2.30 (3H, s), 3.12-3.36 (assume 3H, obscured by solvent), 3.46 (4H, br t), 3.59 (4H, s), 4.89-4.98 (1H, b), 6.87 (1H, br d), 7.00 (2H, br d), 7.12 (1H, br t), 7.16-7.34 (5H, over-lapping m), 7.40 (1H, s), 7.51 (2H, br d), 7.82 (1H, dd), 7.94 (1H, s), 9.98 (1H, s), 10.26 (1H, s)

US 10,189,863 B2

TABLE 2-continued

Additional Compound Examples of the Invention

Structure, Example No., Name, Preparative HPLC or Column Chromatography Purification Method (where employed), LC-MS Analysis and ¹HNMR Spectral Data

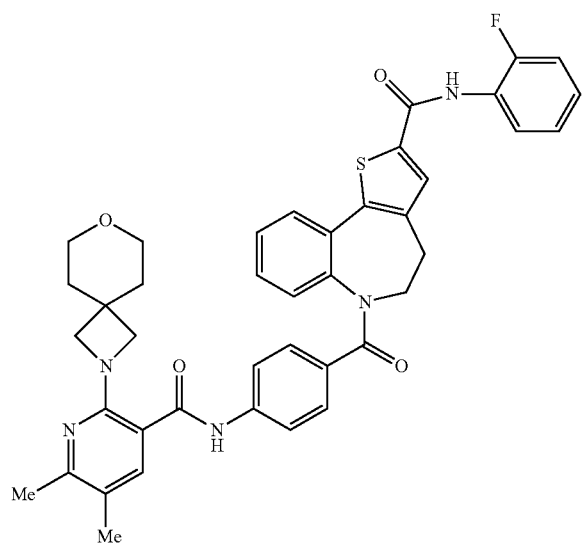 [SMILES: Cc1cc(C(=O)Nc2ccc(C(=O)N3CCc4cc(C(=O)Nc5ccccc5F)sc4-c4ccccc43)cc2)c(N2CC3(CCOCC3)C2)nc1C]

43: 6-(4-(5,6-dimethyl-2-(7-oxa-2-azaspiro[3.5]nonan-2-yl)nicotinamido)benzoyl)-N-(2-fluorophenyl)-5,6-dihydro-4H-benzo[b]thieno[2,3-d]azepine-2-carboxamide.
Prep HPLC Method 5;
R$^r$ 2.52 min (Method 1a); m/z 716 (M + H)$^+$ (ES$^+$);
¹H NMR δ: 1.62 (4H, br t), 2.13 (3H, s), 2.31(3H, s), 3.14-3.29 (3H, m), 3.47 (4H, br t), 3.60 (4H, br s), 4.93 (1H, br s), 6.88 (1H, d), 7.00 (2H, d), 7.13 (1H, t), 7.22-7.30(4H, m), 7.41(1H, s), 7.51 (2H, d), 7.60 (1H, dt), 7.83 (1H, dd), 7.99 (1H, br s), 10.25 (1H, s), 10.28 (1H, s).

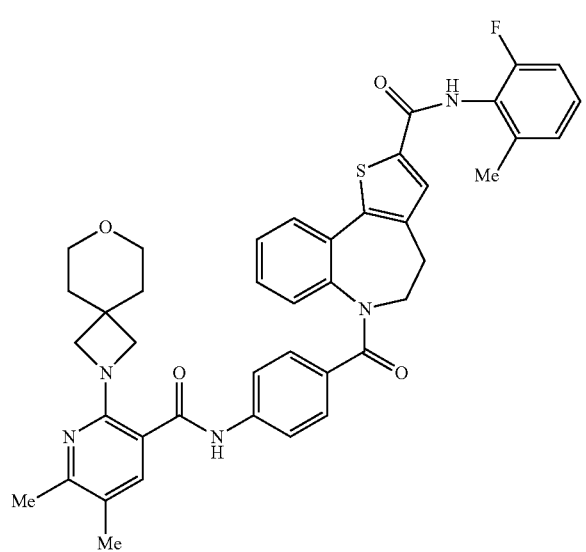 [SMILES: Cc1cc(C(=O)Nc2ccc(C(=O)N3CCc4cc(C(=O)Nc5c(C)cccc5F)sc4-c4ccccc43)cc2)c(N2CC3(CCOCC3)C2)nc1C]

44: 6-(4-(5,6-dimethyl-2-(7-oxa-2-azaspiro[3.5]nonan-2-yl)nicotinamido)benzoyl)-N-(2-fluoro-6-methylphenyl)-5,6-dihydro-4H-benzo[b]thieno[2,3-d]azepine-2-carboxamide.
Prep HPLC Method 3;
R$^r$ 1.85 min (Method 1a); m/z 730 (M + H)$^+$ (ES$^+$);
¹H NMR δ: 1.61 (4H, br t), 2.13 (3H, s), 2.26 (3H, s), 2.30 (3H, s), 3.13-3.36 (assume 3H, obscured by solvent), 3.46 (4H, br t), 3.59 (4H, s), 4.90-4.98 (1H, b), 6.87 (1H, br d), 7.01 (2H, br d), 7.10-7.16 (3H, over-lapping m), 7.25-7.31 (2H, over-lapping m), 7.40 (1H, s), 7.51 (2H, br d), 7.82 (1H, dd), 7.95 (1H, s), 10.02 (1H, s), 10.26 (1H, s).

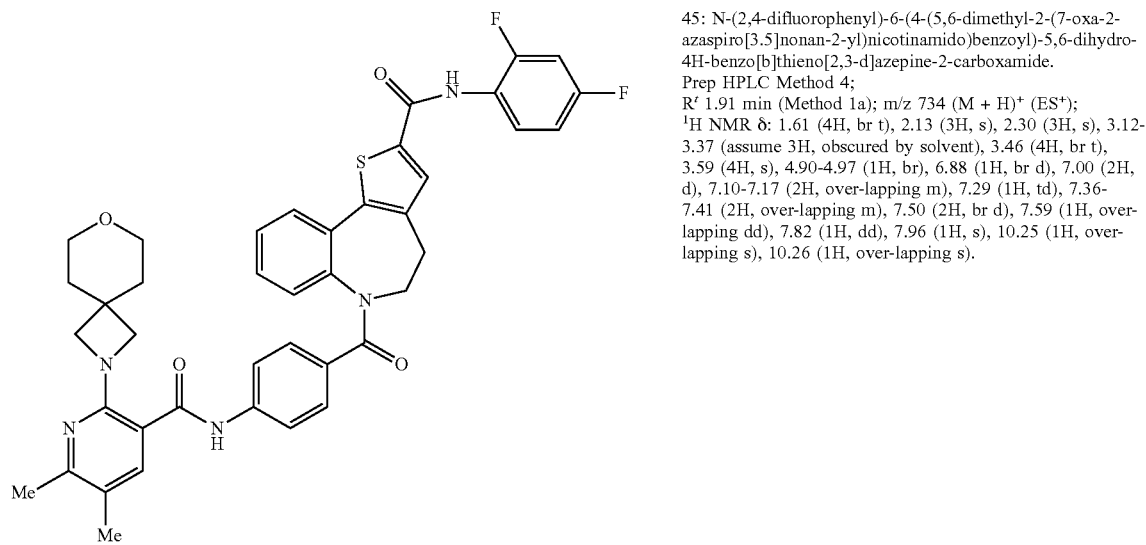

45: N-(2,4-difluorophenyl)-6-(4-(5,6-dimethyl-2-(7-oxa-2-azaspiro[3.5]nonan-2-yl)nicotinamido)benzoyl)-5,6-dihydro-4H-benzo[b]thieno[2,3-d]azepine-2-carboxamide.
Prep HPLC Method 4;
$R^r$ 1.91 min (Method 1a); m/z 734 (M + H)$^+$ (ES$^+$);
$^1$H NMR δ: 1.61 (4H, br t), 2.13 (3H, s), 2.30 (3H, s), 3.12-3.37 (assume 3H, obscured by solvent), 3.46 (4H, br t), 3.59 (4H, s), 4.90-4.97 (1H, br), 6.88 (1H, br d), 7.00 (2H, d), 7.10-7.17 (2H, over-lapping m), 7.29 (1H, td), 7.36-7.41 (2H, over-lapping m), 7.50 (2H, br d), 7.59 (1H, over-lapping dd), 7.82 (1H, dd), 7.96 (1H, s), 10.25 (1H, over-lapping s), 10.26 (1H, over-lapping s).

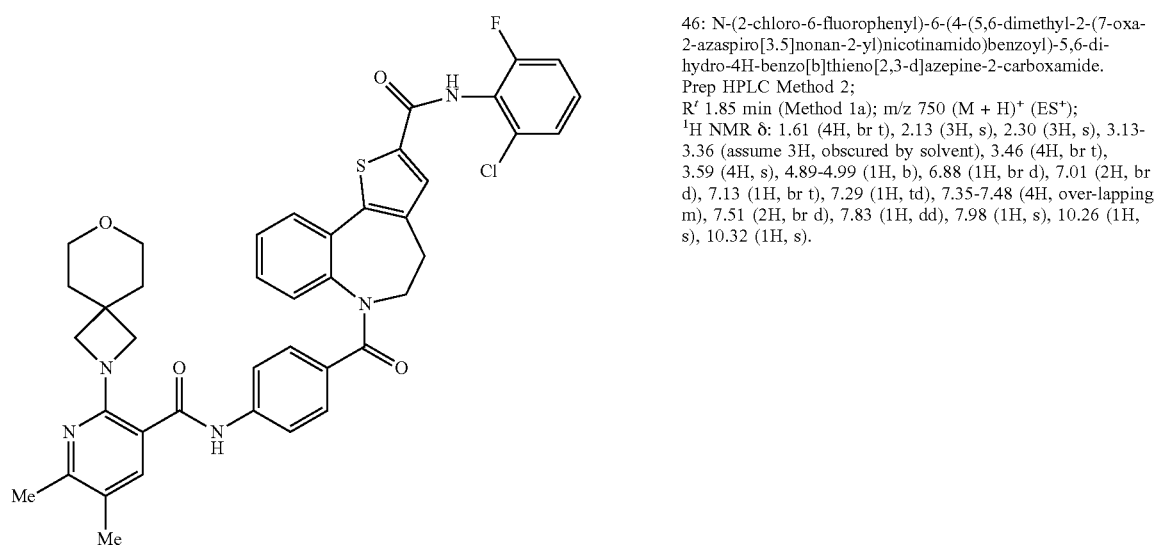

46: N-(2-chloro-6-fluorophenyl)-6-(4-(5,6-dimethyl-2-(7-oxa-2-azaspiro[3.5]nonan-2-yl)nicotinamido)benzoyl)-5,6-dihydro-4H-benzo[b]thieno[2,3-d]azepine-2-carboxamide.
Prep HPLC Method 2;
$R^r$ 1.85 min (Method 1a); m/z 750 (M + H)$^+$ (ES$^+$);
$^1$H NMR δ: 1.61 (4H, br t), 2.13 (3H, s), 2.30 (3H, s), 3.13-3.36 (assume 3H, obscured by solvent), 3.46 (4H, br t), 3.59 (4H, s), 4.89-4.99 (1H, b), 6.88 (1H, br d), 7.01 (2H, br d), 7.13 (1H, br t), 7.29 (1H, td), 7.35-7.48 (4H, over-lapping m), 7.51 (2H, br d), 7.83 (1H, dd), 7.98 (1H, s), 10.26 (1H, s), 10.32 (1H, s).

TABLE 2-continued

Additional Compound Examples of the Invention

Structure, Example No., Name, Preparative HPLC or Column Chromatography Purification Method (where employed), LC-MS Analysis and ¹HNMR Spectral Data

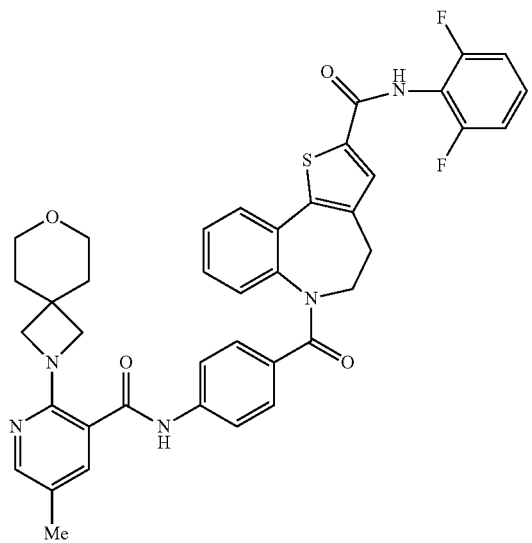 [SMILES: Cc1cnc(N2CC3(CCOCC3)C2)c(C(=O)Nc2ccc(C(=O)N3CCc4cc(C(=O)Nc5c(F)cccc5F)sc4-c4ccccc43)cc2)c1]

47: N-(2,6-difluorophenyl)-6-(4-(5-methyl-2-(7-oxa-2-azaspiro[3.5]nonan-2-yl)nicotinamido)benzoyl)-5,6-dihydro-4H-benzo[b]thieno[2,3-d]azepine-2-carboxamide.
Prep HPLC Method 2;
$R^r$ 1.81 min (Method 1a); m/z 720 (M + H)⁺ (ES⁺);
¹H NMR δ: 1.62 (4H, br t), 2.17 (3H, s), 3.14-3.25 (assume 3H, obscured by solvent), 3.46 (4H, br t), 3.60 (4H, s), 4.88-5.00 (1H, m), 6.88 (1H, br d), 7.02 (2H, br d), 7.13 (1H, br t), 7.23 (2H, t), 7.29 (1H, td), 7.39-7.48 (2H, m), 7.51 (2H, br d), 7.82 (1H, dd), 7.97 (1H, s), 8.03 (1H, dd), 10.28 (1H, s), 10.37 (1H, s).

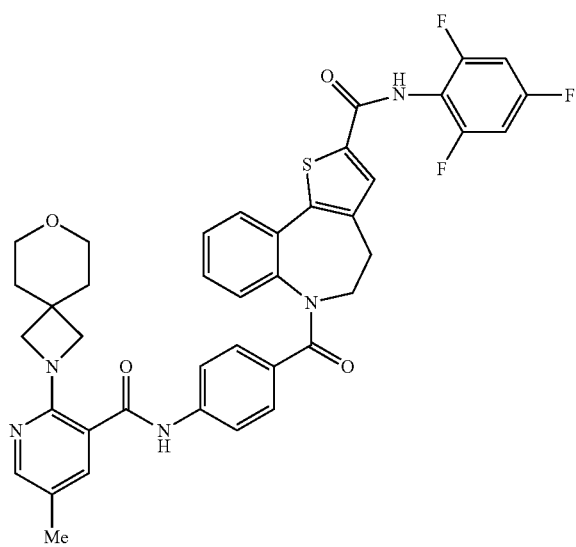 [SMILES: Cc1cnc(N2CC3(CCOCC3)C2)c(C(=O)Nc2ccc(C(=O)N3CCc4cc(C(=O)Nc5c(F)cc(F)cc5F)sc4-c4ccccc43)cc2)c1]

48: 6-(4-(5-methyl-2-(7-oxa-2-azaspiro[3.5]nonan-2-yl)nicotinamido)benzoyl)-N-(2,4,6-trifluorophenyl)-5,6-dihydro-4H-benzo[b]thieno[2,3-d]azepine-2-carboxamide.
Prep HPLC Method 3;
$R^r$ 1.87 min (Method 1a); m/z 738 (M + H)⁺ (ES⁺);
¹H NMR δ: 1.62 (4H, br t), 2.17 (3H, s), 3.14-3.25 (assume 3H, obscured by solvent), 3.46 (4H, br t), 3.60 (4H, s), 4.88-5.00 (1H, m), 6.88 (1H, br d), 7.01 (2H, br d), 7.13 (1H, br t), 7.29 (assume 1H, obscured by minor impurity), 7.36 (2H, app. t), 7.48 (1H, d), 7.51 (2H, br d), 7.82 (1H, dd), 7.95 (1H, s), 8.03 (1H, dd), 10.26 (1H, s), 10.37 (1H, s).

TABLE 2-continued

Additional Compound Examples of the Invention

Structure, Example No., Name, Preparative HPLC or Column Chromatography
Purification Method (where employed), LC-MS Analysis and ¹HNMR Spectral Data

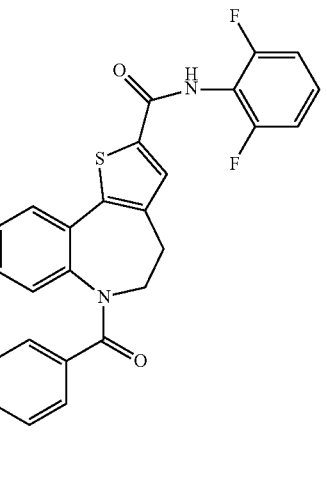

49: N-(2,6-difluorophenyl)-6-(4-(6-methyl-2-(7-oxa-2-aza-spiro[3.5]nonan-2-yl)nicotinamido)benzoyl)-5,6-dihydro-4H-benzo[b]thieno[2,3-d]azepine-2-carboxamide.
Prep HPLC Method 2;
R$^r$ 1.79 min (Method 1a); m/z 720 (M + H)$^+$ (ES$^+$);
¹H NMR δ: 1.62 (4H, br t), 2.32 (3H, s), 3.14-3.25 (assume 3H, obscured by solvent), 3.47 (4H, br t), 3.63 (4H, s), 4.89-4.97 (1H, m), 6.56 (1H, d), 6.87 (1H, br d), 7.01 (2H, br d), 7.12 (1H, br t), 7.23 (2H, app.t), 7.29 (1H, app. td), 7.39-7.47 (1H, m), 7.49-7.53 (3H, m), 7.82 (1H, dd), 7.96 (1H, s) 10.28-10.29 (2H, m).

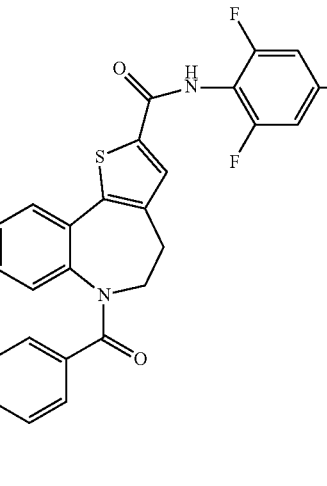

50: 6-(4-(6-methyl-2-(7-oxa-2-azaspiro[3.5]nonan-2-yl) nicotinamido)benzoyl)-N-(2,4,6-trifluorophenyl)-5,6-dihydro-4H-benzo[b]thieno[2,3-d]azepine-2-carboxamide.
Prep HPLC Method 2;
R$^r$ 1.84 min (Method 1a); m/z 738 (M + H)$^+$ (ES$^+$);
¹H NMR δ: 1.62 (4H, br t), 2.32 (3H, s), 3.14-3.25 (assume 3H, obscured by solvent), 3.47 (4H, br t), 3.63 (4H, s), 4.89-4.97 (1H, m), 6.56 (1H, d), 6.88 (1H, br d), 7.00 (2H, br d), 7.13 (1H, br t), 7.29 (1H, t), 7.36 (2H, app. t), 7.49-7.53 (3H, m), 7.82 (1H, dd), 7.95 (1H, s) 10.26 (1H, s), 10.29 (1H. s).

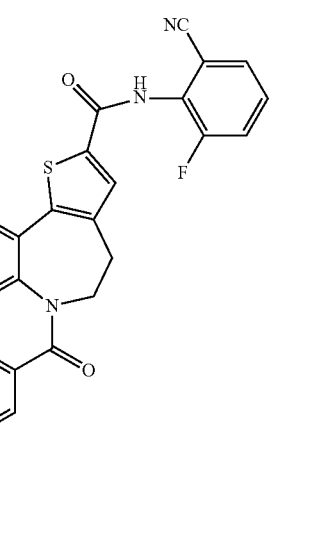

51: N-(2-cyano-6-fluorophenyl)-6-(4-(5-methyl-2-(7-oxa-2-azaspiro[3.5]nonan-2-yl)nicotinamido)benzoyl)-5,6-dihydro-4H-benzo[b]thieno[2,3-d]azepine-2-carboxamide.
Prep HPLC Method 2;
R$^r$ 1.76 min (Method 1a); m/z 727 (M + H)$^+$ (ES$^+$);
¹H NMR δ: 1.62 (4H, t), 2.17 (3H, s), 3.19 (assume 3H, obscured by solvent), 3.45 (4H, d), 3.60 (4H, s), 4.95 (1H, s), 6.88 (1H, s), 7.03 (2H, d), 7.13 (1H, t), 7.30 (1H, td), 7.44-7.62 (4H, m), 7.71-7.87 (3H, m), 8.00 (1H, s), 8.03 (1H, dd), 10.37 (1H, s), 10.72 (1H, s).

TABLE 2-continued

Additional Compound Examples of the Invention

Structure, Example No., Name, Preparative HPLC or Column Chromatography
Purification Method (where employed), LC-MS Analysis and ¹HNMR Spectral Data

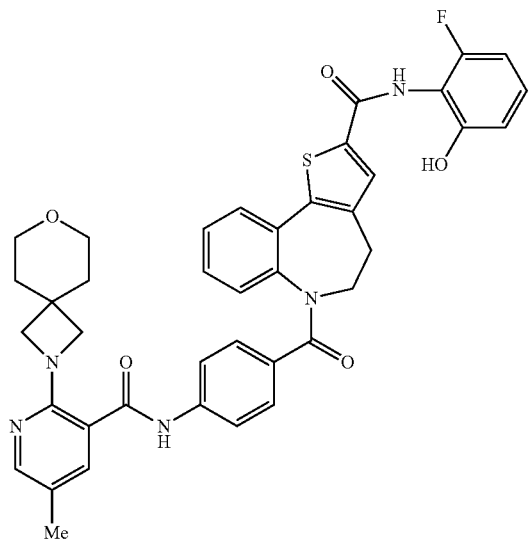

52: N-(2-fluoro-6-hydroxyphenyl)-6-(4-(5-methyl-2-(7-oxa-2-azaspiro[3.5]nonan-2-yl)nicotinamido)benzoyl)-5,6-dihydro-4H-benzo[b]thieno[2,3-d]azepine-2-carboxamide.
Prep HPLC Method 2;
$R^r$ 1.78 min (Method 1a); m/z 718 (M + H)⁺ (ES⁺);
¹H NMR δ: 1.62 (4H, t), 2.17 (3H, s), 3.14-3.25 (assume 3H, obscured by solvent), 3.46 (4H, t), 3.60 (4H, s), 4.93 (1H, s), 6.66-6.80 (2H, m), 6.87 (1H, d), 7.01 (2H, d), 7.08-7.21 (2H, m), 7.29 (1H, td), 7.50 (3H, dd), 7.81 (1H, dd), 7.94 (1H, s), 8.03 (1H, d), 9.77 (1H, s), 10.04 (1H, s), 10.38 (1H, s).

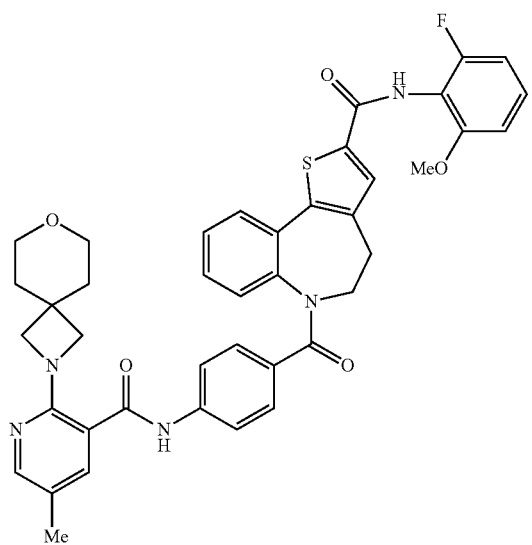 [SMILES: COc1cccc(F)c1NC(=O)c1cc2c(s1)-c1ccccc1N(C(=O)c1ccc(NC(=O)c3cc(C)cnc3N3CC4(CCOCC4)C3)cc1)CC2]

53: N-(2-fluoro-6-methoxyphenyl)-6-(4-(5-methyl-2-(7-oxa-2-azaspiro[3.5]nonan-2-yl)nicotinamido)benzoyl)-5,6-dihydro-4H-benzo[b]thieno[2,3-d]azepine-2-carboxamide.
Prep HPLC Method 2;
$R^r$ 1.79 min (Method 1a); m/z 732 (M + H)⁺ (ES⁺);
¹H NMR δ: 1.62 (4H, t), 2.17 (3H, s), 3.15 (assume 3H, obscured by solvent), 3.46 (4H, t), 3.60 (4H, s), 3.82 (3H, s), 4.93 (1H, s), 6.83-7.05 (5H, m), 7.12 (1H, t), 7.24-7.38 (2H, m), 7.45-7.56 (3H, m), 7.81 (1H, dd), 7.95 (1H, s), 8.03 (1H, dd), 9.85 (1H, s), 10.37 (1H, s).

TABLE 2-continued

Additional Compound Examples of the Invention

Structure, Example No., Name, Preparative HPLC or Column Chromatography
Purification Method (where employed), LC-MS Analysis and ¹HNMR Spectral Data

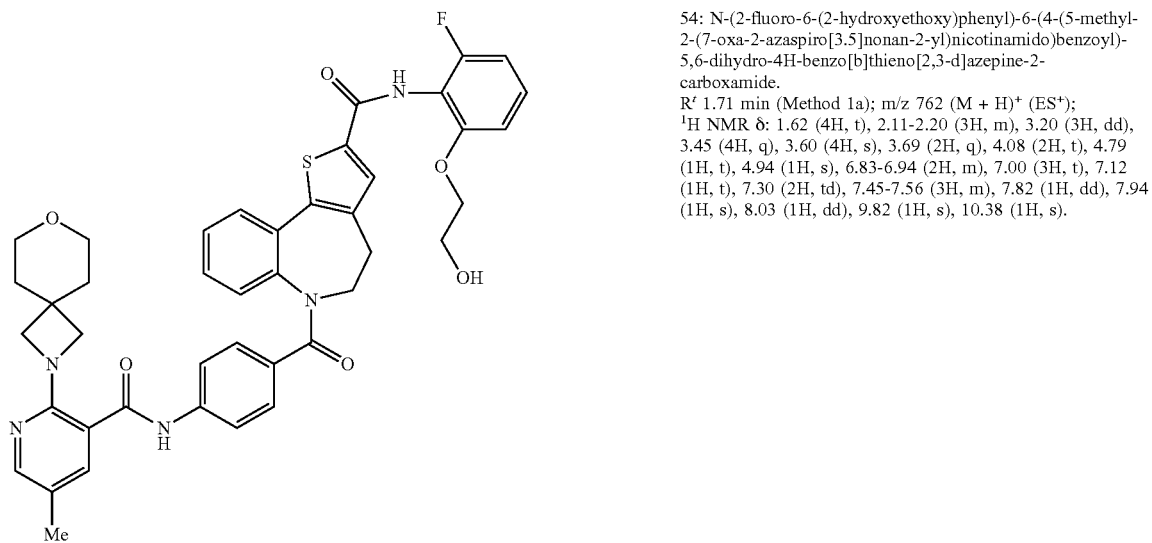

54: N-(2-fluoro-6-(2-hydroxyethoxy)phenyl)-6-(4-(5-methyl-2-(7-oxa-2-azaspiro[3.5]nonan-2-yl)nicotinamido)benzoyl)-5,6-dihydro-4H-benzo[b]thieno[2,3-d]azepine-2-carboxamide.
$R^t$ 1.71 min (Method 1a); m/z 762 (M + H)⁺ (ES⁺);
¹H NMR δ: 1.62 (4H, t), 2.11-2.20 (3H, m), 3.20 (3H, dd), 3.45 (4H, q), 3.60 (4H, s), 3.69 (2H, q), 4.08 (2H, t), 4.79 (1H, t), 4.94 (1H, s), 6.83-6.94 (2H, m), 7.00 (3H, t), 7.12 (1H, t), 7.30 (2H, td), 7.45-7.56 (3H, m), 7.82 (1H, dd), 7.94 (1H, s), 8.03 (1H, dd), 9.82 (1H, s), 10.38 (1H, s).

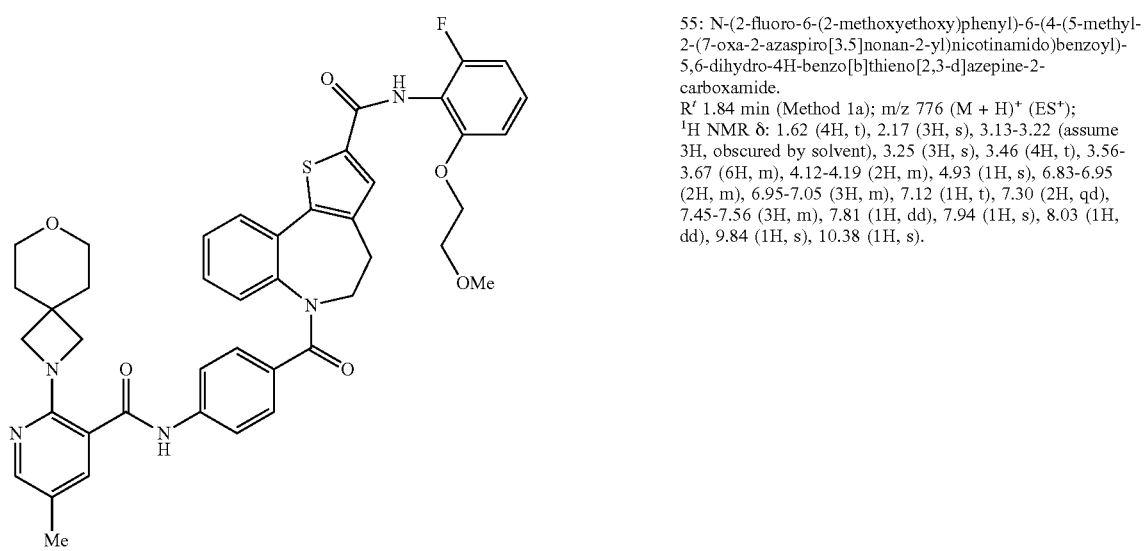

55: N-(2-fluoro-6-(2-methoxyethoxy)phenyl)-6-(4-(5-methyl-2-(7-oxa-2-azaspiro[3.5]nonan-2-yl)nicotinamido)benzoyl)-5,6-dihydro-4H-benzo[b]thieno[2,3-d]azepine-2-carboxamide.
$R^t$ 1.84 min (Method 1a); m/z 776 (M + H)⁺ (ES⁺);
¹H NMR δ: 1.62 (4H, t), 2.17 (3H, s), 3.13-3.22 (assume 3H, obscured by solvent), 3.25 (3H, s), 3.46 (4H, t), 3.56-3.67 (6H, m), 4.12-4.19 (2H, m), 4.93 (1H, s), 6.83-6.95 (2H, m), 6.95-7.05 (3H, m), 7.12 (1H, t), 7.30 (2H, qd), 7.45-7.56 (3H, m), 7.81 (1H, dd), 7.94 (1H, s), 8.03 (1H, dd), 9.84 (1H, s), 10.38 (1H, s).

TABLE 2-continued

Additional Compound Examples of the Invention

Structure, Example No., Name, Preparative HPLC or Column Chromatography Purification Method (where employed), LC-MS Analysis and ¹HNMR Spectral Data

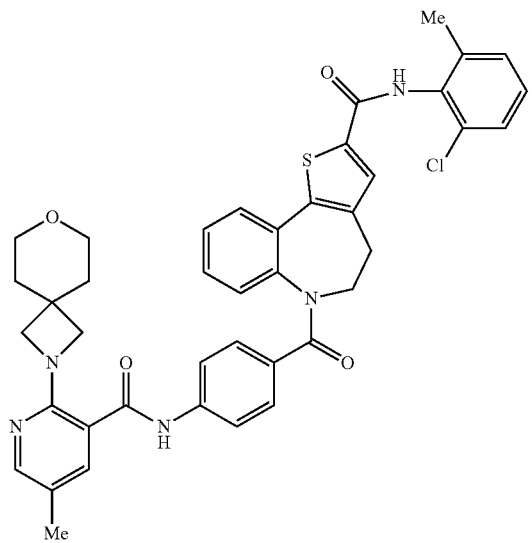

56: N-(2-chloro-6-methylphenyl)-6-(4-(5-methyl-2-(7-oxa-2-azaspiro[3.5]nonan-2-yl)nicotinamido)benzoyl)-5,6-dihydro-4H-benzo[b]thieno[2,3-d]azepine-2-carboxamide.
Prep HPLC Method 2;
$R^t$ 1.91 min (Method 1a); m/z 732 (M + H)⁺ (ES⁺);
¹H NMR δ: 1.62 (4H, t), 2.17 (3H, s), 2.26 (3H, s), 3.17-3.29 (assume 3H, obscured by solvent), 3.46 (4H, t), 3.60 (4H, s), 4.97 (1H, s), 6.87 (1H, d), 7.02 (2H, d), 7.12 (1H, t), 7.24-7.33 (3H, m), 7.42 (1H, dd), 7.46-7.57 (3H, m), 7.82 (1H, dd), 7.96 (1H, s), 8.03 (1H, dd), 10.16 (1H, s), 10.38 (1H, s).

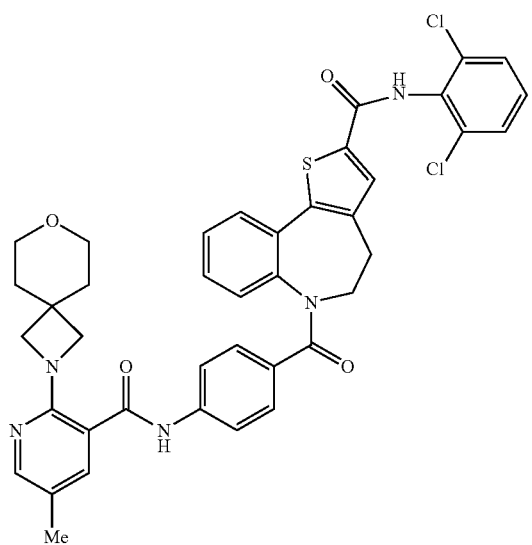 [SMILES: Cc1cnc(N2CC3(CCOCC3)C2)c(C(=O)Nc2ccc(C(=O)N3CCc4cc(C(=O)Nc5c(Cl)cccc5Cl)sc4-c4ccccc43)cc2)c1]

57: N-(2,6-dichlorophenyl)-6-(4-(5-methyl-2-(7-oxa-2-azaspiro[3.5]nonan-2-yl)nicotinamido)benzoyl)-5,6-dihydro-4H-benzo[b]thieno[2,3-d]azepine-2-carboxamide.
Prep HPLC Method 2;
$R^t$ 1.91 min (Method 1a); m/z 752 (M + H)⁺ (ES⁺);
¹H NMR δ: 1.62 (4H, t), 2.17 (3H, s), 3.16-3.29 (3H, m), 3.46 (4H, t), 3.60 (4H, s), 4.94 (1H, s), 6.88 (1H, d), 7.02 (2H, d), 7.13 (1H, t), 7.30 (1H, td), 7.38-7.46 (1H, m), 7.46-7.56 (3H, m), 7.61 (2H, d), 7.83 (1H, dd), 7.98 (1H, s), 8.03 (1H, dd), 10.38 (1H, s), 10.45 (1H, s).

TABLE 2-continued

Additional Compound Examples of the Invention

Structure, Example No., Name, Preparative HPLC or Column Chromatography
Purification Method (where employed), LC-MS Analysis and ¹HNMR Spectral Data

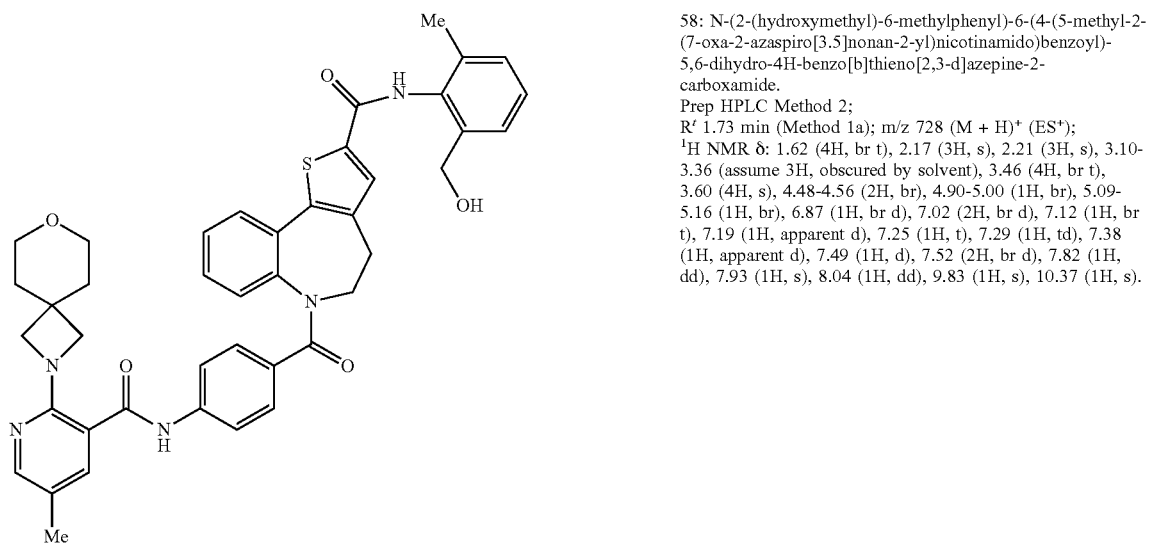

58: N-(2-(hydroxymethyl)-6-methylphenyl)-6-(4-(5-methyl-2-(7-oxa-2-azaspiro[3.5]nonan-2-yl)nicotinamido)benzoyl)-5,6-dihydro-4H-benzo[b]thieno[2,3-d]azepine-2-carboxamide.
Prep HPLC Method 2;
$R^t$ 1.73 min (Method 1a); m/z 728 (M + H)⁺ (ES⁺);
¹H NMR δ: 1.62 (4H, br t), 2.17 (3H, s), 2.21 (3H, s), 3.10-3.36 (assume 3H, obscured by solvent), 3.46 (4H, br t), 3.60 (4H, s), 4.48-4.56 (2H, br), 4.90-5.00 (1H, br), 5.09-5.16 (1H, br), 6.87 (1H, br d), 7.02 (2H, br d), 7.12 (1H, br t), 7.19 (1H, apparent d), 7.25 (1H, t), 7.29 (1H, td), 7.38 (1H, apparent d), 7.49 (1H, d), 7.52 (2H, br d), 7.82 (1H, dd), 7.93 (1H, s), 8.04 (1H, dd), 9.83 (1H, s), 10.37 (1H, s).

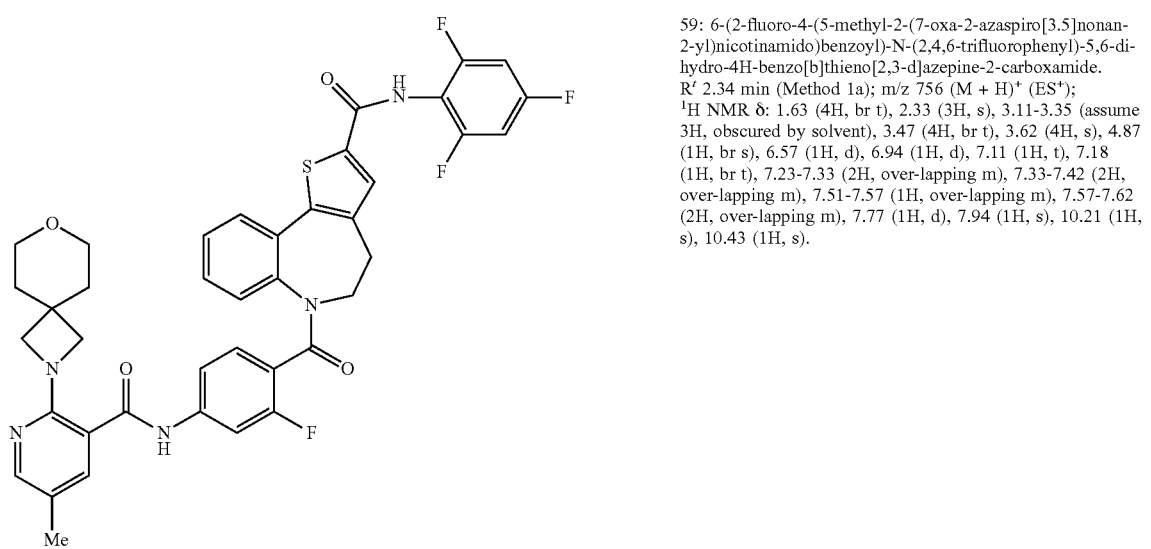

59: 6-(2-fluoro-4-(5-methyl-2-(7-oxa-2-azaspiro[3.5]nonan-2-yl)nicotinamido)benzoyl)-N-(2,4,6-trifluorophenyl)-5,6-dihydro-4H-benzo[b]thieno[2,3-d]azepine-2-carboxamide.
$R^t$ 2.34 min (Method 1a); m/z 756 (M + H)⁺ (ES⁺);
¹H NMR δ: 1.63 (4H, br t), 2.33 (3H, s), 3.11-3.35 (assume 3H, obscured by solvent), 3.47 (4H, br t), 3.62 (4H, s), 4.87 (1H, br s), 6.57 (1H, d), 6.94 (1H, d), 7.11 (1H, t), 7.18 (1H, br t), 7.23-7.33 (2H, over-lapping m), 7.33-7.42 (2H, over-lapping m), 7.51-7.57 (1H, over-lapping m), 7.57-7.62 (2H, over-lapping m), 7.77 (1H, d), 7.94 (1H, s), 10.21 (1H, s), 10.43 (1H, s).

TABLE 2-continued

Additional Compound Examples of the Invention

Structure, Example No., Name, Preparative HPLC or Column Chromatography Purification Method (where employed), LC-MS Analysis and ¹HNMR Spectral Data

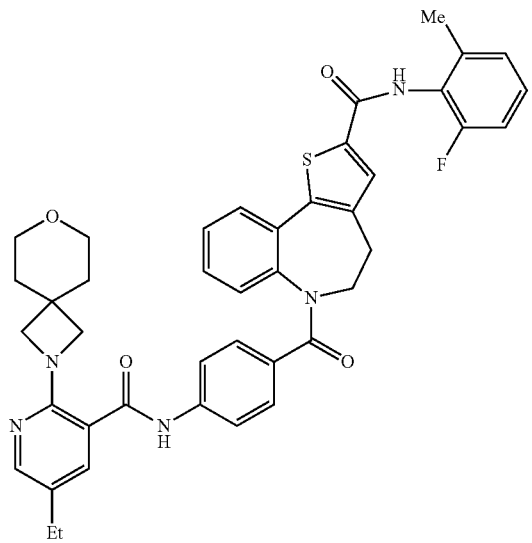

60: 6-(4-(5-ethyl-2-(7-oxa-2-azaspiro[3.5]nonan-2-yl) nicotinamido)benzoyl)-N-(2-fluoro-6-methylphenyl)-5,6-dihydro-4H-benzo[b]thieno[2,3-d]azepine-2-carboxamide.
Prep HPLC Method 8;
$R^t$ 1.96 min (Method 1a); m/z 730 (M + H)⁺ (ES⁺);
¹H NMR δ: 1.14 (3H, t), 1.62 (4H, br t), 2.26 (3H, s), 3.1-3.38 (assume 5H, obscured by solvent), 3.46 (4H, br t), 3.61 (4H, s), 4.86-5.03 (1H, m), 6.87 (1H, br d), 7.02 (2H, br d), 7.08-7018 (3H, overlaping m), 7.24-7.33 (2H, m), 7.50 (1H, d), 7.52 (2H, br d), 7.82 (1H, dd), 7.96 (1H, s), 8.06 (1H, d), 10.03 (1H, s), 10.37 (1H, s).

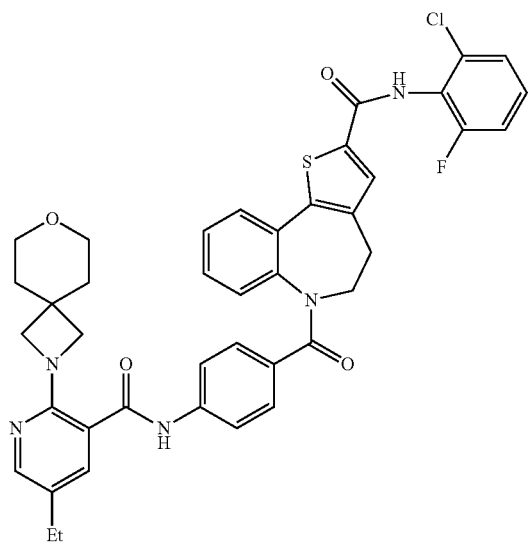 [SMILES: CCc1cnc(N2CC3(CCOCC3)C2)c(C(=O)Nc2ccc(C(=O)N3CCc4cc(C(=O)Nc5c(F)cccc5Cl)sc4-c4ccccc43)cc2)c1]

61: N-(2-chloro-6-fluorophenyl)-6-(4-(5-ethyl-2-(7-oxa-2-azaspiro[3.5]nonan-2-yl)nicotinamido)benzoyl)-5,6-dihydro-4H-benzo[b]thieno[2,3-d]azepine-2-carboxamide.
Prep HPLC Method 8;
$R^t$ 1.97 min (Method 1a); m/z 750 (M + H)⁺ (ES⁺);
¹H NMR δ: 1.14 (3H, t), 1.62 (4H, br t), 3.10-3.41 (assume 5H, obscured by solvent), 3.46 (4H, br t), 3.61 (4H, s), 4.87-5.02 (1H, m), 6.88 (1H, br d), 7.02 (2H, br d), 7.13 (1H, br t), 7.29 (1H, td), 7.33-7.50 (4H, overlapping m), 7.52 (2H, overlapping br d), 7.83 (1H, dd), 7.98 (1H, s), 8.06 (1H, d), 10.32 (1H, overlapping s), 10.37 (1H, overlapping s).

TABLE 2-continued

Additional Compound Examples of the Invention

Structure, Example No., Name, Preparative HPLC or Column Chromatography
Purification Method (where employed), LC-MS Analysis and ¹HNMR Spectral Data

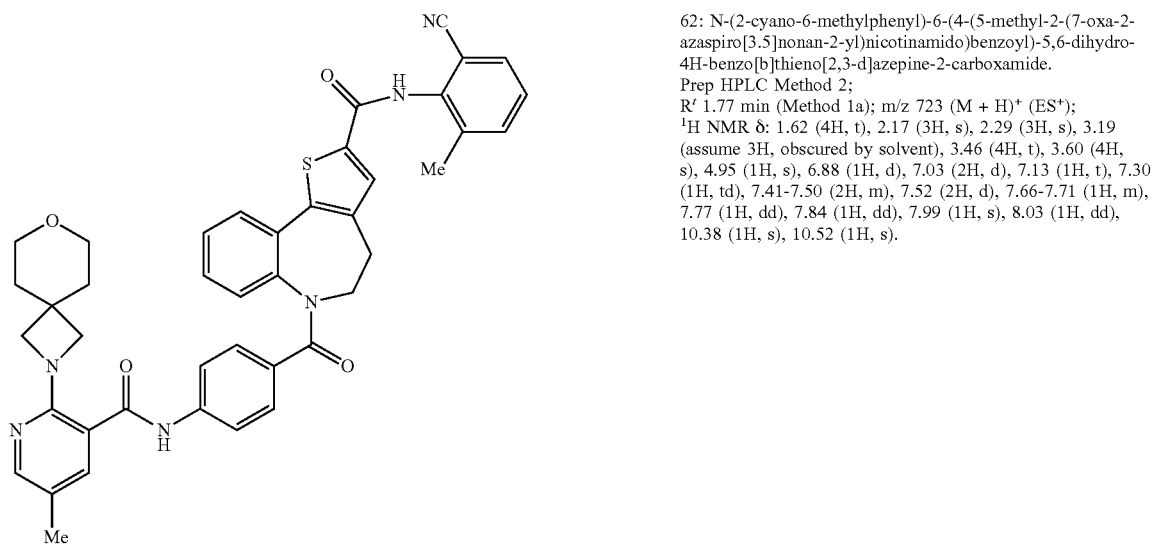

62: N-(2-cyano-6-methylphenyl)-6-(4-(5-methyl-2-(7-oxa-2-azaspiro[3.5]nonan-2-yl)nicotinamido)benzoyl)-5,6-dihydro-4H-benzo[b]thieno[2,3-d]azepine-2-carboxamide.
Prep HPLC Method 2;
$R^r$ 1.77 min (Method 1a); m/z 723 (M + H)⁺ (ES⁺);
¹H NMR δ: 1.62 (4H, t), 2.17 (3H, s), 2.29 (3H, s), 3.19 (assume 3H, obscured by solvent), 3.46 (4H, t), 3.60 (4H, s), 4.95 (1H, s), 6.88 (1H, d), 7.03 (2H, d), 7.13 (1H, t), 7.30 (1H, td), 7.41-7.50 (2H, m), 7.52 (2H, d), 7.66-7.71 (1H, m), 7.77 (1H, dd), 7.84 (1H, dd), 7.99 (1H, s), 8.03 (1H, dd), 10.38 (1H, s), 10.52 (1H, s).

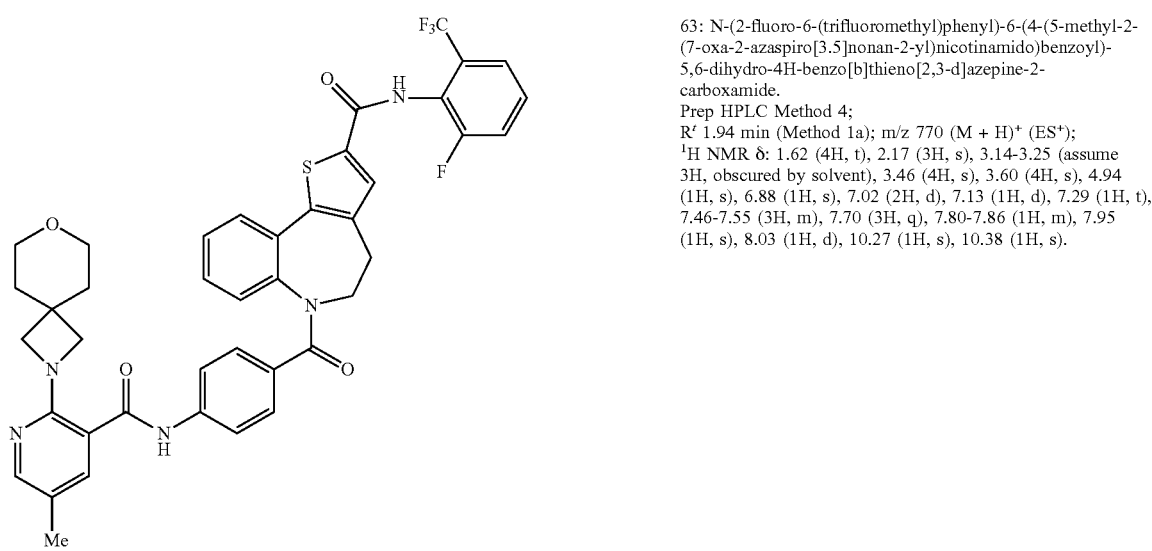

63: N-(2-fluoro-6-(trifluoromethyl)phenyl)-6-(4-(5-methyl-2-(7-oxa-2-azaspiro[3.5]nonan-2-yl)nicotinamido)benzoyl)-5,6-dihydro-4H-benzo[b]thieno[2,3-d]azepine-2-carboxamide.
Prep HPLC Method 4;
$R^r$ 1.94 min (Method 1a); m/z 770 (M + H)⁺ (ES⁺);
¹H NMR δ: 1.62 (4H, t), 2.17 (3H, s), 3.14-3.25 (assume 3H, obscured by solvent), 3.46 (4H, s), 3.60 (4H, s), 4.94 (1H, s), 6.88 (1H, s), 7.02 (2H, d), 7.13 (1H, d), 7.29 (1H, t), 7.46-7.55 (3H, m), 7.70 (3H, q), 7.80-7.86 (1H, m), 7.95 (1H, s), 8.03 (1H, d), 10.27 (1H, s), 10.38 (1H, s).

TABLE 2-continued

Additional Compound Examples of the Invention

Structure, Example No., Name, Preparative HPLC or Column Chromatography
Purification Method (where employed), LC-MS Analysis and ¹HNMR Spectral Data

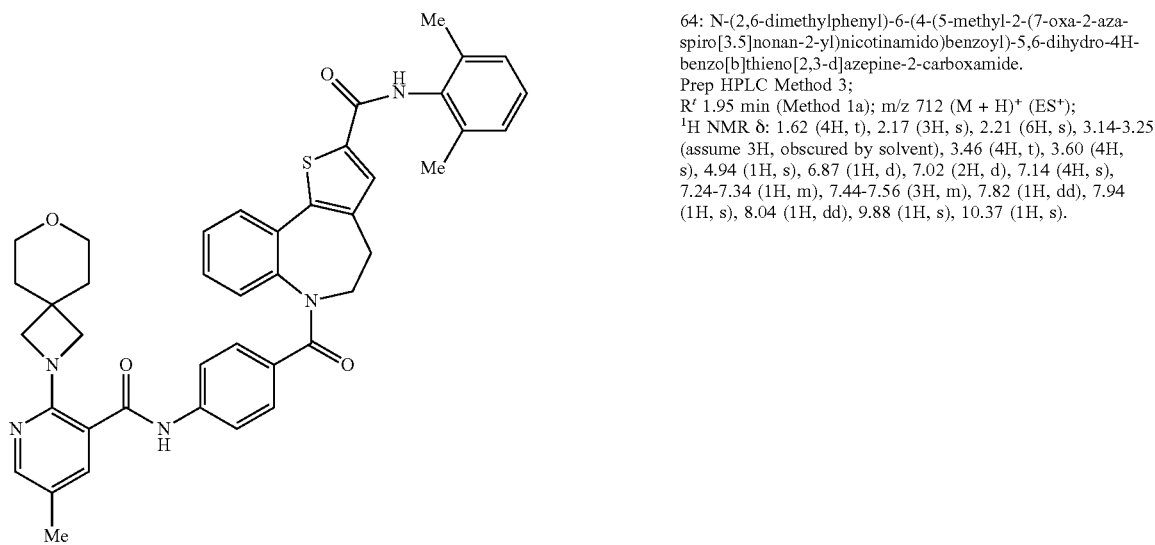

64: N-(2,6-dimethylphenyl)-6-(4-(5-methyl-2-(7-oxa-2-aza-spiro[3.5]nonan-2-yl)nicotinamido)benzoyl)-5,6-dihydro-4H-benzo[b]thieno[2,3-d]azepine-2-carboxamide.
Prep HPLC Method 3;
R$^t$ 1.95 min (Method 1a); m/z 712 (M + H)$^+$ (ES$^+$);
¹H NMR δ: 1.62 (4H, t), 2.17 (3H, s), 2.21 (6H, s), 3.14-3.25 (assume 3H, obscured by solvent), 3.46 (4H, t), 3.60 (4H, s), 4.94 (1H, s), 6.87 (1H, d), 7.02 (2H, d), 7.14 (4H, s), 7.24-7.34 (1H, m), 7.44-7.56 (3H, m), 7.82 (1H, dd), 7.94 (1H, s), 8.04 (1H, dd), 9.88 (1H, s), 10.37 (1H, s).

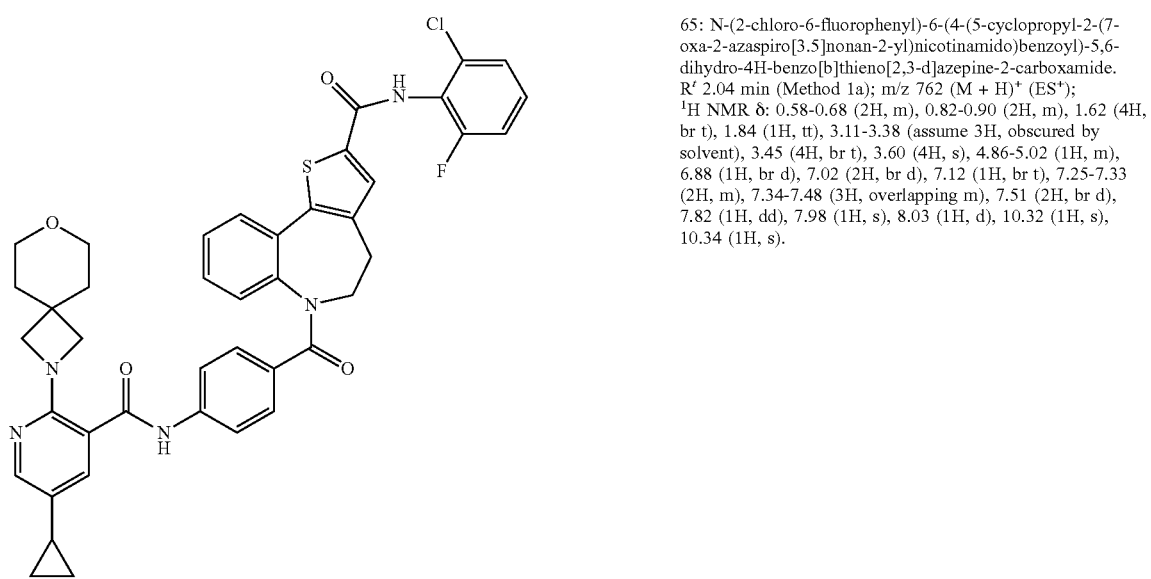

65: N-(2-chloro-6-fluorophenyl)-6-(4-(5-cyclopropyl-2-(7-oxa-2-azaspiro[3.5]nonan-2-yl)nicotinamido)benzoyl)-5,6-dihydro-4H-benzo[b]thieno[2,3-d]azepine-2-carboxamide.
R$^t$ 2.04 min (Method 1a); m/z 762 (M + H)$^+$ (ES$^+$);
¹H NMR δ: 0.58-0.68 (2H, m), 0.82-0.90 (2H, m), 1.62 (4H, br t), 1.84 (1H, tt), 3.11-3.38 (assume 3H, obscured by solvent), 3.45 (4H, br t), 3.60 (4H, s), 4.86-5.02 (1H, m), 6.88 (1H, br d), 7.02 (2H, br d), 7.12 (1H, br t), 7.25-7.33 (2H, m), 7.34-7.48 (3H, overlapping m), 7.51 (2H, br d), 7.82 (1H, dd), 7.98 (1H, s), 8.03 (1H, d), 10.32 (1H, s), 10.34 (1H, s).

TABLE 2-continued

Additional Compound Examples of the Invention

Structure, Example No., Name, Preparative HPLC or Column Chromatography
Purification Method (where employed), LC-MS Analysis and ¹HNMR Spectral Data 66: N-(2-chloro-6-fluorophenyl)-6-(4-(5-ethynyl-2-(7-oxa-2-azaspiro[3.5]nonan-2-yl)nicotinamido)benzoyl)-5,6-dihydro-4H-benzo[b]thieno[2,3-d]azepine-2-carboxamide.
R$^r$ 2.40 min (Method 1a); m/z 746 (M + H)$^+$ (ES$^+$);
¹H NMR δ: 1.64 (4H, br t), 3.12-3.28 (3H, m), 3.46 (4H, br t), 3.70 (4H, s), 4.14 (1H, s), 4.94 (1H, br s), 6.88 (1H, br d), 7.03 (2H, br d), 7.13 (1H, br t), 7.25-7.43 (2H, m), 7.40-7.51 (2H, m), 7.51 (2H, d), 7.71 (1H, d), 7.83 (1H, d), 7.98 (1H, s), 8.28 (1H, d), 10.32 (1H, s), 10.46 (1H, s).

67: N-(2-chloro-6-fluorophenyl)-6-(4-(5-(methoxymethyl)-2-(7-oxa-2-azaspiro[3.5]nonan-2-yl)nicotinamido)benzoyl)-5,6-dihydro-4H-benzo[b]thieno[2,3-d]azepine-2-carboxamide.
R$^r$ 1.96 min (Method 1a); m/z 766 (M + H)$^+$ (ES$^+$);
¹H NMR δ: 1.64 (4H, br t), 3.11-3.29 (assume 3H, obscured by solvent), 3.25 (3H, over-lapping s), 3.47 (4H, br t), 3.66 (4H, s), 4.30 (2H, s), 4.85-5.04 (1H, m), 6.89 (1H, br d), 7.03 (2H, br d), 7.14 (1H, br t), 7.30 (1H, td), 7.35-7.50 (3H, m), 7.53 (2H, br d), 7.59 (1H, br d), 7.83 (1H, dd), 7.99 (1H, s), 8.15 (1H, d), 10.33 (1H, s), 10.43 (1H, s).

TABLE 2-continued

Additional Compound Examples of the Invention

Structure, Example No., Name, Preparative HPLC or Column Chromatography
Purification Method (where employed), LC-MS Analysis and $^1$HNMR Spectral Data

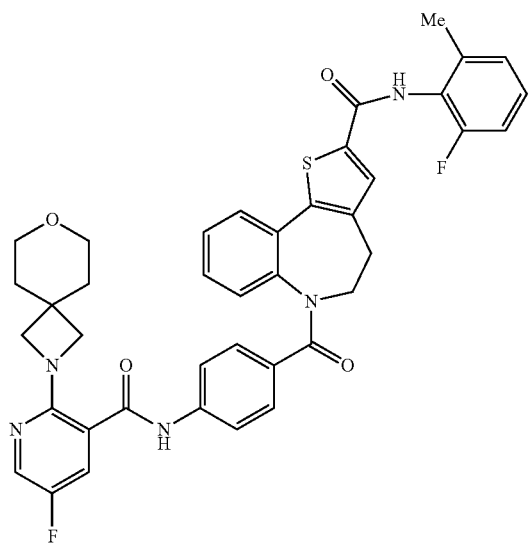 [SMILES: Cc1cccc(F)c1NC(=O)c1cc2c(s1)-c1ccccc1N(C(=O)c1ccc(NC(=O)c3cc(F)cnc3N3CC4(CCOCC4)C3)cc1)CC2]

68: 6-(4-(5-fluoro-2-(7-oxa-2-azaspiro[3.5]nonan-2-yl)nicotinamido)benzoyl)-N-(2-fluoro-6-methylphenyl)-5,6-dihydro-4H-benzo[b]thieno[2,3-d]azepine-2-carboxamide.
Prep HPLC Method 9;
$R^t$ 2.42 min (Method 1a); m/z 720 (M + H)$^+$ (ES$^+$);
$^1$H NMR δ: 1.63 (4H, t), 2.26 (3H, s), 3.14-3.25 (assume 3H, obscured by solvent), 3.45 (4H, t), 3.63 (4H, s), 4.94 (1H, s), 6.87 (1H, d), 7.03 (2H, d), 7.14 (3H, t), 7.23-7.33 (2H, m), 7.51 (2H, d), 7.69 (1H, dd), 7.82 (1H, dd), 7.95 (1H, s), 8.21 (1H, d), 10.03 (1H, s), 10.47 (1H, s).

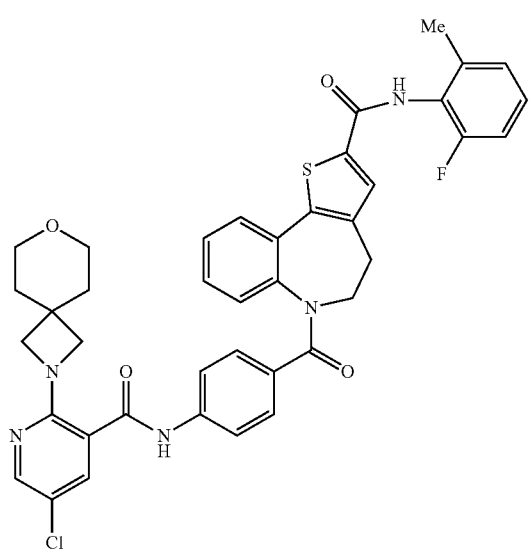 [SMILES: Cc1cccc(F)c1NC(=O)c1cc2c(s1)-c1ccccc1N(C(=O)c1ccc(NC(=O)c3cc(Cl)cnc3N3CC4(CCOCC4)C3)cc1)CC2]

69: 6-(4-(5-chloro-2-(7-oxa-2-azaspiro[3.5]nonan-2-yl)nicotinamido)benzoyl)-N-(2-fluoro-6-methylphenyl)-5,6-dihydro-4H-benzo[b]thieno[2,3-d]azepine-2-carboxamide.
Prep HPLC Method 10;
$R^t$ 2.52 min (Method 1a); m/z 737 (M + H)$^+$ (ES$^+$);
$^1$H NMR δ: 1.63 (4H, t), 2.26 (3H, s), 3.14-3.25 (assume 3H, obscured by solvent), 3.46 (4H, t), 3.65 (4H, s), 4.94 (1H, s), 6.88 (1H, s), 7.03 (2H, d), 7.14 (3H, t), 7.22-7.34 (2H, m), 7.51 (2H, d), 7.75 (1H, d), 7.82 (1H, dd), 7.95 (1H, s), 8.20 (1H, d), 10.02 (1H, s), 10.49 (1H, s).

TABLE 2-continued

Additional Compound Examples of the Invention

Structure, Example No., Name, Preparative HPLC or Column Chromatography
Purification Method (where employed), LC-MS Analysis and ¹HNMR Spectral Data 70: N-2-fluoro-6-methylphenyl)-6-(4-(5-methyl-2-(7-oxa-2-azaspiro[3.5]nonan-2-yl)nicotinamido)benzoyl-2,3,5,6-d4)-5,6-dihydro-4H-benzo[b]thieno[2,3-d]azepine-2-carboxamide.
R$^t$ 2.34 min (Method 1a); m/z 720 (M + H)⁺ (ES⁺);
¹H NMR δ: 1.62 (5H, br t), 2.17 (3H, s), 2.26 (3H, s), 3.12-3.28 (3H, m), 3.45 (4H, br t), 3.60 (4H, s), 4.96 (1H, br s), 6.88 (1H, br s), 7.14 (3H, t), 7.24-7.33 (2H, m), 7.48 (1H, d), 7.80-7.84 (1H, m), 7.95 (1H, s), 8.03 (1H, d), 10.03 (1H, s), 10.38 (1H, s).

71: N-(2-fluoro-6-methylphenyl)-6-(4-(5-methoxy-2-(7-oxa-2-azaspiro[3.5]nonan-2-yl)nicotinamido)benzoyl)-5,6-dihydro-4H-benzo[b]thieno[2,3-d]azepine-2-carboxamide.
R$^t$ 2.18 min (Method 1a); m/z 732 (M + H)⁺ (ES⁺);
¹H NMR δ: 1.62 (4H, br t), 2.26 (3H, s), 2.69 (2H, s), 3.11-3.27 (2H, m), 3.45 (4H, br t), 3.58 (4H, s), 3.75 (3H, s), 4.94 (1H, br s), 6.87 (1H, d), 7.02 (2H, d), 7.14 (3H, t), 7.24-7.32 (2H, m), 7.37 (1H, d), 7.52 (2H, d), 7.82 (1H, d), 7.95 (1H, s), 7.98 (1H, d), 10.03 (1H, s), 10.41 (1H, s).

| | |
|---|---|
| 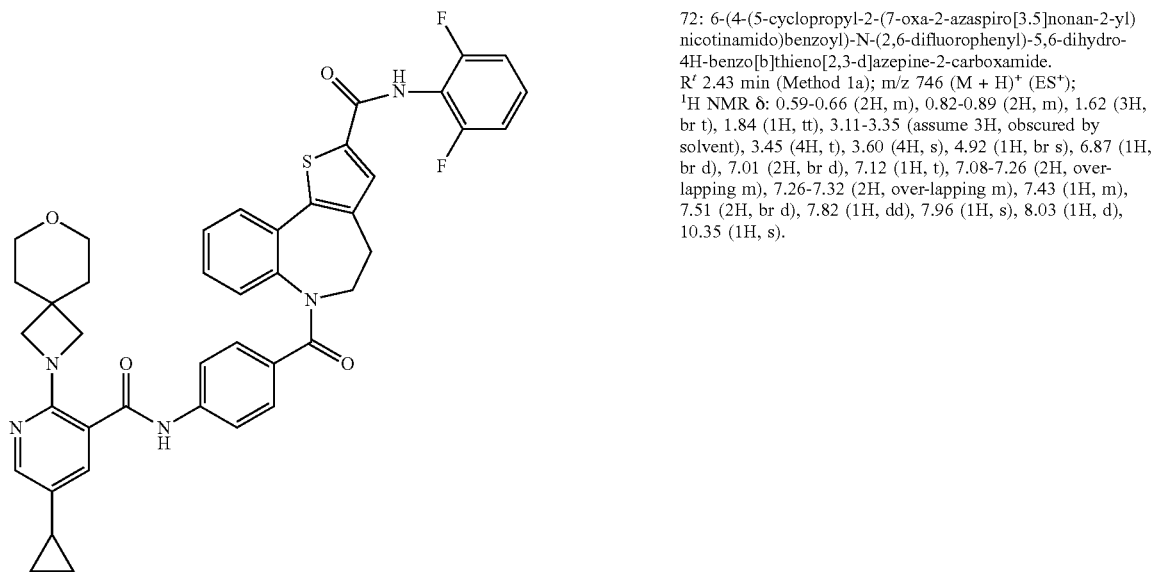 | 72: 6-(4-(5-cyclopropyl-2-(7-oxa-2-azaspiro[3.5]nonan-2-yl)nicotinamido)benzoyl)-N-(2,6-difluorophenyl)-5,6-dihydro-4H-benzo[b]thieno[2,3-d]azepine-2-carboxamide.<br>R$^f$ 2.43 min (Method 1a); m/z 746 (M + H)$^+$ (ES$^+$);<br>$^1$H NMR δ: 0.59-0.66 (2H, m), 0.82-0.89 (2H, m), 1.62 (3H, br t), 1.84 (1H, tt), 3.11-3.35 (assume 3H, obscured by solvent), 3.45 (4H, t), 3.60 (4H, s), 4.92 (1H, br s), 6.87 (1H, br d), 7.01 (2H, br d), 7.12 (1H, t), 7.08-7.26 (2H, overlapping m), 7.26-7.32 (2H, over-lapping m), 7.43 (1H, m), 7.51 (2H, br d), 7.82 (1H, dd), 7.96 (1H, s), 8.03 (1H, d), 10.35 (1H, s). |
| 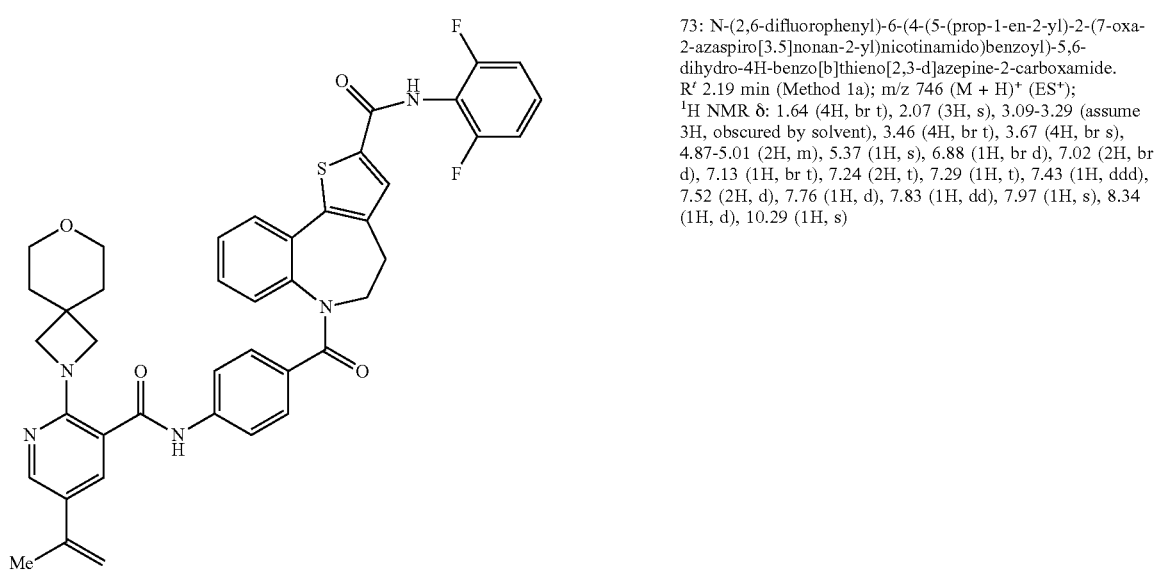 | 73: N-(2,6-difluorophenyl)-6-(4-(5-(prop-1-en-2-yl)-2-(7-oxa-2-azaspiro[3.5]nonan-2-yl)nicotinamido)benzoyl)-5,6-dihydro-4H-benzo[b]thieno[2,3-d]azepine-2-carboxamide.<br>R$^f$ 2.19 min (Method 1a); m/z 746 (M + H)$^+$ (ES$^+$);<br>$^1$H NMR δ: 1.64 (4H, br t), 2.07 (3H, s), 3.09-3.29 (assume 3H, obscured by solvent), 3.46 (4H, br t), 3.67 (4H, br s), 4.87-5.01 (2H, m), 5.37 (1H, s), 6.88 (1H, br d), 7.02 (2H, br d), 7.13 (1H, br t), 7.24 (2H, t), 7.29 (1H, t), 7.43 (1H, ddd), 7.52 (2H, d), 7.76 (1H, d), 7.83 (1H, dd), 7.97 (1H, s), 8.34 (1H, d), 10.29 (1H, s) |

TABLE 2-continued

Additional Compound Examples of the Invention

Structure, Example No., Name, Preparative HPLC or Column Chromatography
Purification Method (where employed), LC-MS Analysis and $^1$HNMR Spectral Data

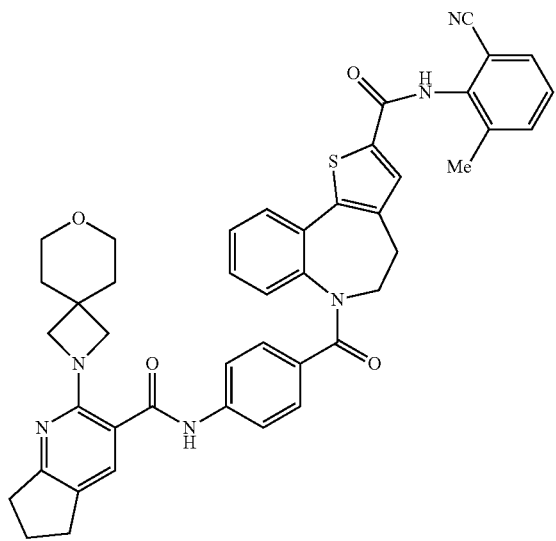 [SMILES: Cc1cccc(C#N)c1NC(=O)c1cc2c(s1)-c1ccccc1N(C(=O)c1ccc(NC(=O)c3cc4c(nc3N3CC5(CCOCC5)C3)CCC4)cc1)CC2]

74: 6-(4-(2-(7-oxa-2-azaspiro[3.5]nonan-2-yl)-6,7-dihydro-5H-cyclopenta[b]pyridine-3-carboxamido)benzoyl)-N-(2-cyano-6-methylphenyl)-5,6-dihydro-4H-benzo[b]thieno[2,3-d]azepine-2-carboxamide.
$R^t$ 1.89 min (Method 1a); m/z 749 (M + H)$^+$ (ES$^+$);
$^1$H NMR δ: 1.62 (4H, br t), 2.02 (2H, m), 2.29 (3H, s), 2.78 (4H, t), 3.13-3.28 (assumed 3H, obscured by solvent), 3.47 (4H, br t), 3.61 (4H, s), 4.88-5.02 (1H, m), 6.88 (1H, d), 7.03 (2H, d), 7.14 (1H, t), 7.31 (1H, td), 7.46 (1H, t), 7.49 (1H, s), 7.52 (2H, d), 7.69 (1H, d), 7.77 (1H, d), 7.85 (1H, dd), 7.99 (1H, s), 10.29 (1H, s), 10.52 (1H, s).

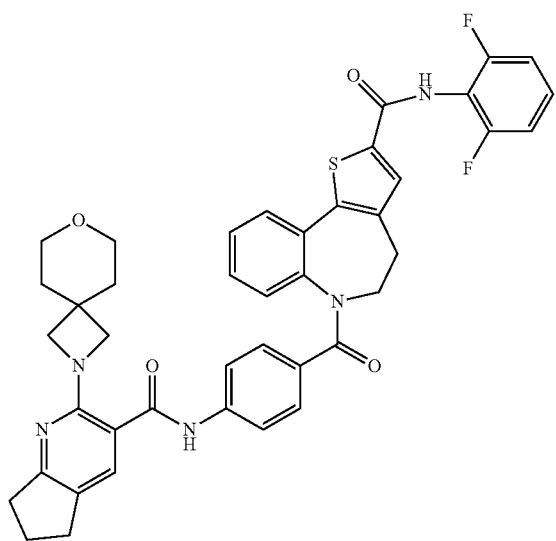 [SMILES: O=C(Nc1c(F)cccc1F)c1cc2c(s1)-c1ccccc1N(C(=O)c1ccc(NC(=O)c3cc4c(nc3N3CC5(CCOCC5)C3)CCC4)cc1)CC2]

75: 6-(4-(2-(7-oxa-2-azaspiro[3.5]nonan-2-yl)-6,7-dihydro-5H-cyclopenta[b]pyridine-3-carboxamido)benzoyl)-N-(2,6-difluorophenyl)-5,6-dihydro-4H-benzo[b]thieno[2,3-d]azepine-2-carboxamide.
$R^t$ 2.05 min (Method 1a); m/z 746 (M + H)$^+$ (ES$^+$);
$^1$H NMR δ: 1.62 (4H, br t), 2.02 (2H, m), 2.77 (4H, t), 3.06-3.33 (assume 3H, obscured by solvent), 3.45 (4H, br t), 3.61 (4H, s), 4.84-5.02 (1H, m), 6.88 (1H, d), 7.00 (2H, d), 7.09-7.18 (2H, m), 7.29 (1H, t), 7.34-7.43 (1H, m), 7.46-7.53 (3H, m), 7.59 (1H, td), 7.82 (1H, dd), 7.96 (1H, s), 10.24 (1H, s), 10.28 (1H, s).

TABLE 2-continued

Additional Compound Examples of the Invention

Structure, Example No., Name, Preparative HPLC or Column Chromatography
Purification Method (where employed), LC-MS Analysis and ¹HNMR Spectral Data

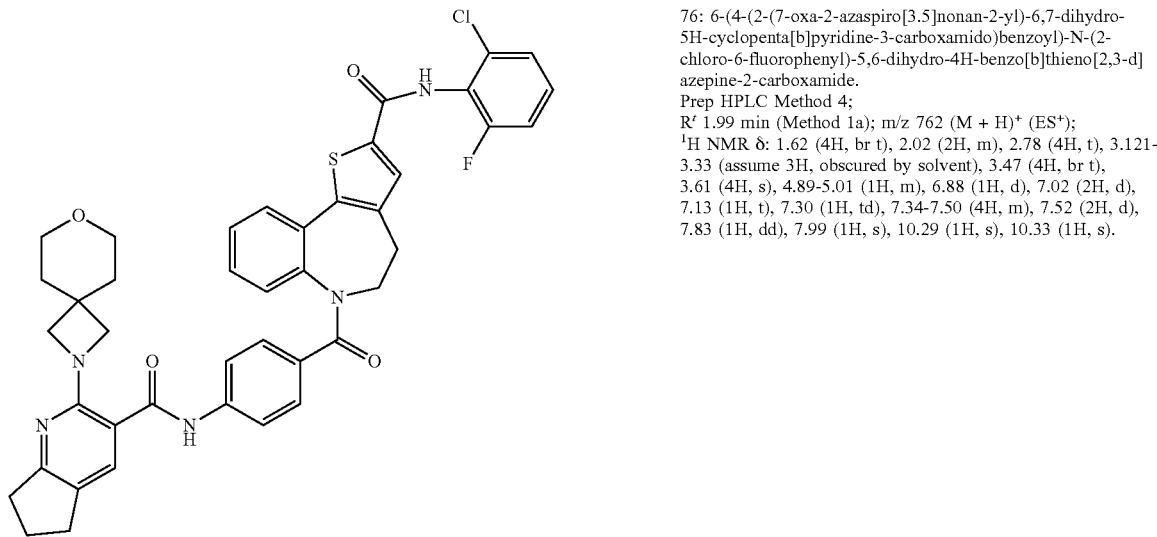

76: 6-(4-(2-(7-oxa-2-azaspiro[3.5]nonan-2-yl)-6,7-dihydro-5H-cyclopenta[b]pyridine-3-carboxamido)benzoyl)-N-(2-chloro-6-fluorophenyl)-5,6-dihydro-4H-benzo[b]thieno[2,3-d]azepine-2-carboxamide.
Prep HPLC Method 4;
R$^r$ 1.99 min (Method 1a); m/z 762 (M + H)$^+$ (ES$^+$);
¹H NMR δ: 1.62 (4H, br t), 2.02 (2H, m), 2.78 (4H, t), 3.121-3.33 (assume 3H, obscured by solvent), 3.47 (4H, br t), 3.61 (4H, s), 4.89-5.01 (1H, m), 6.88 (1H, d), 7.02 (2H, d), 7.13 (1H, t), 7.30 (1H, td), 7.34-7.50 (4H, m), 7.52 (2H, d), 7.83 (1H, dd), 7.99 (1H, s), 10.29 (1H, s), 10.33 (1H, s).

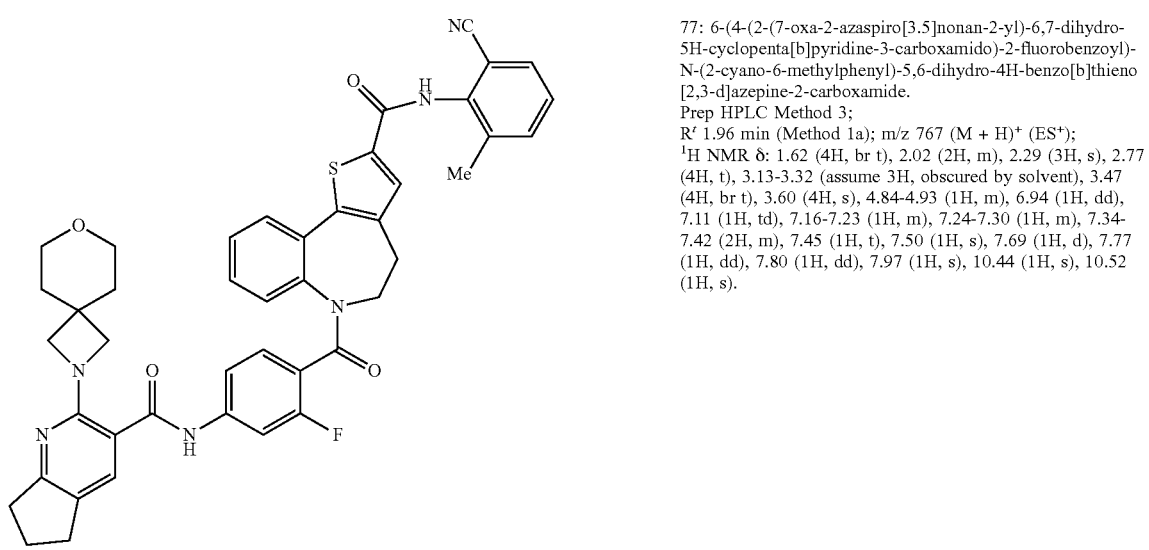

77: 6-(4-(2-(7-oxa-2-azaspiro[3.5]nonan-2-yl)-6,7-dihydro-5H-cyclopenta[b]pyridine-3-carboxamido)-2-fluorobenzoyl)-N-(2-cyano-6-methylphenyl)-5,6-dihydro-4H-benzo[b]thieno[2,3-d]azepine-2-carboxamide.
Prep HPLC Method 3;
R$^r$ 1.96 min (Method 1a); m/z 767 (M + H)$^+$ (ES$^+$);
¹H NMR δ: 1.62 (4H, br t), 2.02 (2H, m), 2.29 (3H, s), 2.77 (4H, t), 3.13-3.32 (assume 3H, obscured by solvent), 3.47 (4H, br t), 3.60 (4H, s), 4.84-4.93 (1H, m), 6.94 (1H, dd), 7.11 (1H, td), 7.16-7.23 (1H, m), 7.24-7.30 (1H, m), 7.34-7.42 (2H, m), 7.45 (1H, t), 7.50 (1H, s), 7.69 (1H, d), 7.77 (1H, dd), 7.80 (1H, dd), 7.97 (1H, s), 10.44 (1H, s), 10.52 (1H, s).

TABLE 2-continued

Additional Compound Examples of the Invention

Structure, Example No., Name, Preparative HPLC or Column Chromatography Purification Method (where employed), LC-MS Analysis and $^1$HNMR Spectral Data

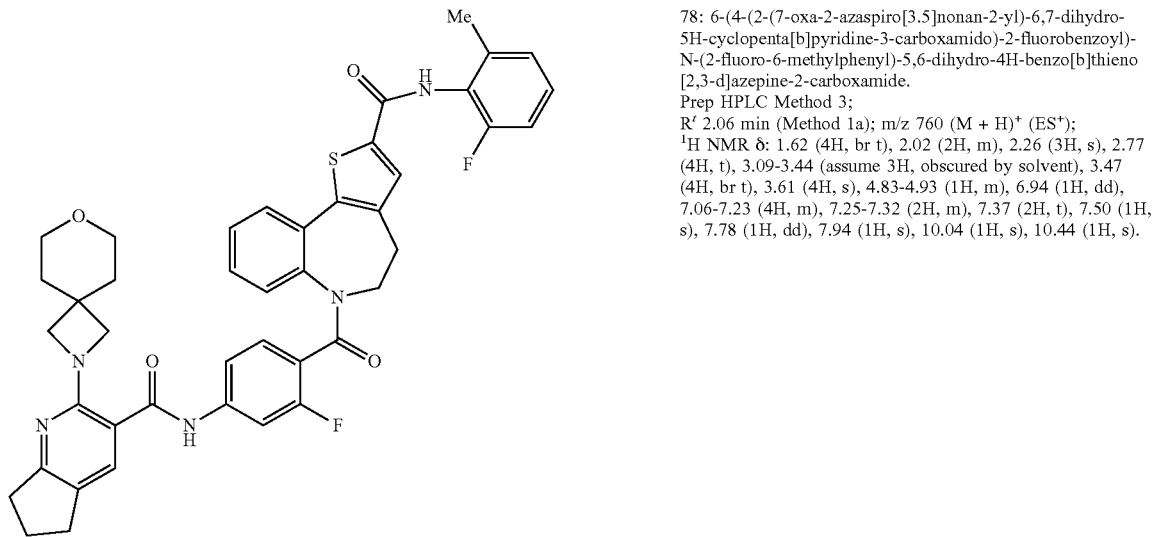

78: 6-(4-(2-(7-oxa-2-azaspiro[3.5]nonan-2-yl)-6,7-dihydro-5H-cyclopenta[b]pyridine-3-carboxamido)-2-fluorobenzoyl)-N-(2-fluoro-6-methylphenyl)-5,6-dihydro-4H-benzo[b]thieno[2,3-d]azepine-2-carboxamide.
Prep HPLC Method 3;
R$^t$ 2.06 min (Method 1a); m/z 760 (M + H)$^+$ (ES$^+$);
$^1$H NMR δ: 1.62 (4H, br t), 2.02 (2H, m), 2.26 (3H, s), 2.77 (4H, t), 3.09-3.44 (assume 3H, obscured by solvent), 3.47 (4H, br t), 3.61 (4H, s), 4.83-4.93 (1H, m), 6.94 (1H, dd), 7.06-7.23 (4H, m), 7.25-7.32 (2H, m), 7.37 (2H, t), 7.50 (1H, s), 7.78 (1H, dd), 7.94 (1H, s), 10.04 (1H, s), 10.44 (1H, s).

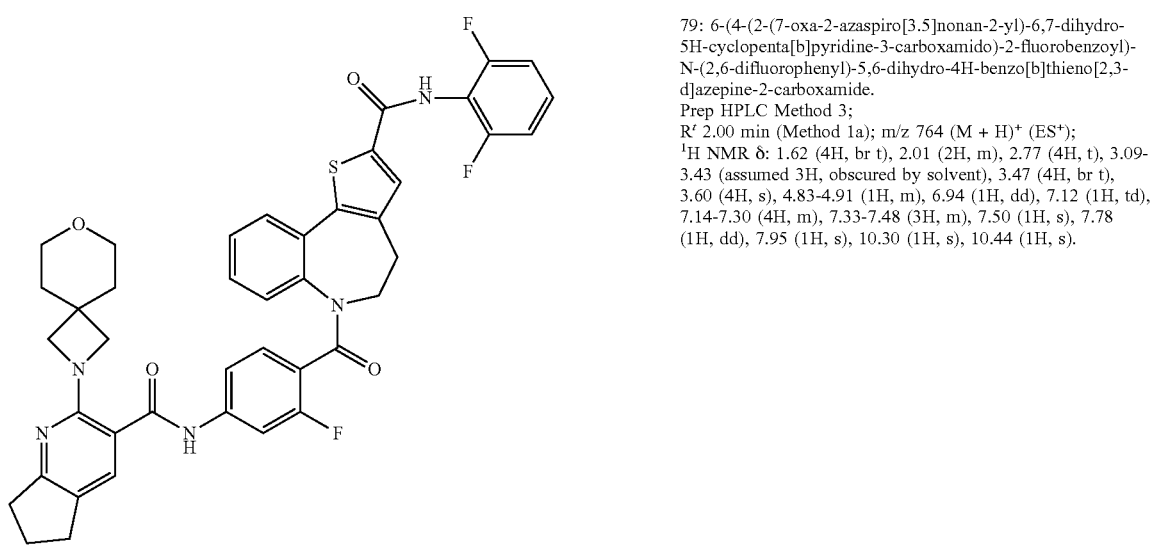

79: 6-(4-(2-(7-oxa-2-azaspiro[3.5]nonan-2-yl)-6,7-dihydro-5H-cyclopenta[b]pyridine-3-carboxamido)-2-fluorobenzoyl)-N-(2,6-difluorophenyl)-5,6-dihydro-4H-benzo[b]thieno[2,3-d]azepine-2-carboxamide.
Prep HPLC Method 3;
R$^t$ 2.00 min (Method 1a); m/z 764 (M + H)$^+$ (ES$^+$);
$^1$H NMR δ: 1.62 (4H, br t), 2.01 (2H, m), 2.77 (4H, t), 3.09-3.43 (assumed 3H, obscured by solvent), 3.47 (4H, br t), 3.60 (4H, s), 4.83-4.91 (1H, m), 6.94 (1H, dd), 7.12 (1H, td), 7.14-7.30 (4H, m), 7.33-7.48 (3H, m), 7.50 (1H, s), 7.78 (1H, dd), 7.95 (1H, s), 10.30 (1H, s), 10.44 (1H, s).

| | |
|---|---|
| 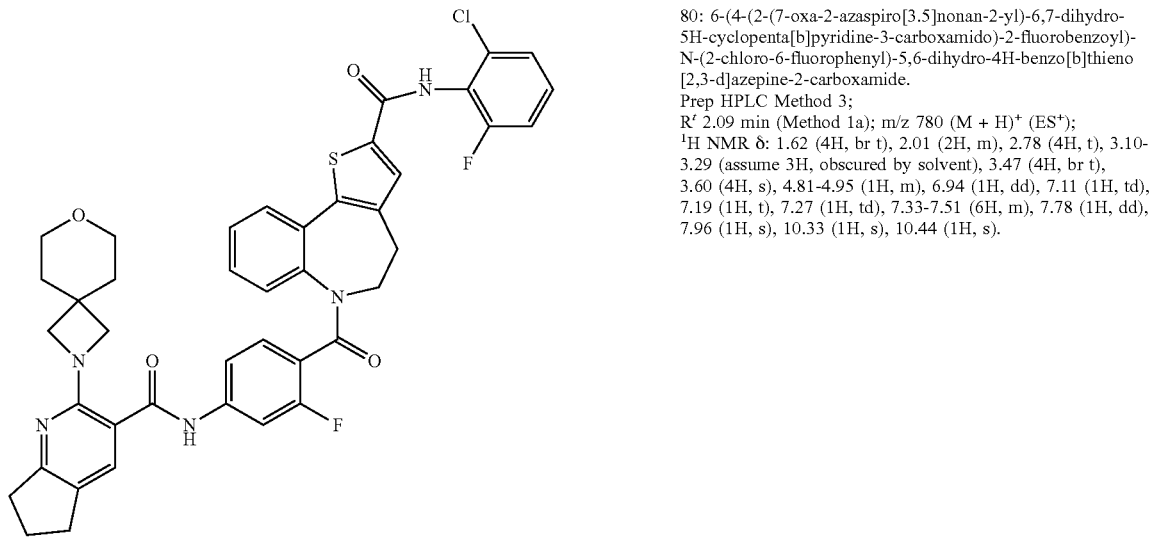 | 80: 6-(4-(2-(7-oxa-2-azaspiro[3.5]nonan-2-yl)-6,7-dihydro-5H-cyclopenta[b]pyridine-3-carboxamido)-2-fluorobenzoyl)-N-(2-chloro-6-fluorophenyl)-5,6-dihydro-4H-benzo[b]thieno[2,3-d]azepine-2-carboxamide.<br>Prep HPLC Method 3;<br>$R^r$ 2.09 min (Method 1a); m/z 780 (M + H)⁺ (ES⁺);<br>¹H NMR δ: 1.62 (4H, br t), 2.01 (2H, m), 2.78 (4H, t), 3.10-3.29 (assume 3H, obscured by solvent), 3.47 (4H, br t), 3.60 (4H, s), 4.81-4.95 (1H, m), 6.94 (1H, dd), 7.11 (1H, td), 7.19 (1H, t), 7.27 (1H, td), 7.33-7.51 (6H, m), 7.78 (1H, dd), 7.96 (1H, s), 10.33 (1H, s), 10.44 (1H, s). |
| 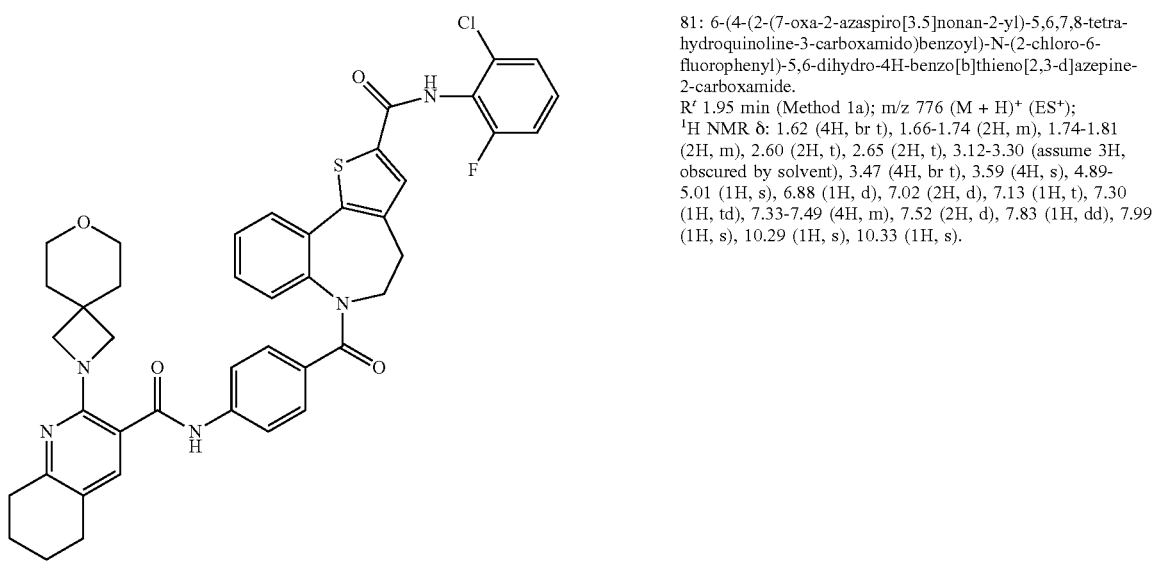 | 81: 6-(4-(2-(7-oxa-2-azaspiro[3.5]nonan-2-yl)-5,6,7,8-tetrahydroquinoline-3-carboxamido)benzoyl)-N-(2-chloro-6-fluorophenyl)-5,6-dihydro-4H-benzo[b]thieno[2,3-d]azepine-2-carboxamide.<br>$R^r$ 1.95 min (Method 1a); m/z 776 (M + H)⁺ (ES⁺);<br>¹H NMR δ: 1.62 (4H, br t), 1.66-1.74 (2H, m), 1.74-1.81 (2H, m), 2.60 (2H, t), 2.65 (2H, t), 3.12-3.30 (assume 3H, obscured by solvent), 3.47 (4H, br t), 3.59 (4H, s), 4.89-5.01 (1H, s), 6.88 (1H, d), 7.02 (2H, d), 7.13 (1H, t), 7.30 (1H, td), 7.33-7.49 (4H, m), 7.52 (2H, d), 7.83 (1H, dd), 7.99 (1H, s), 10.29 (1H, s), 10.33 (1H, s). |

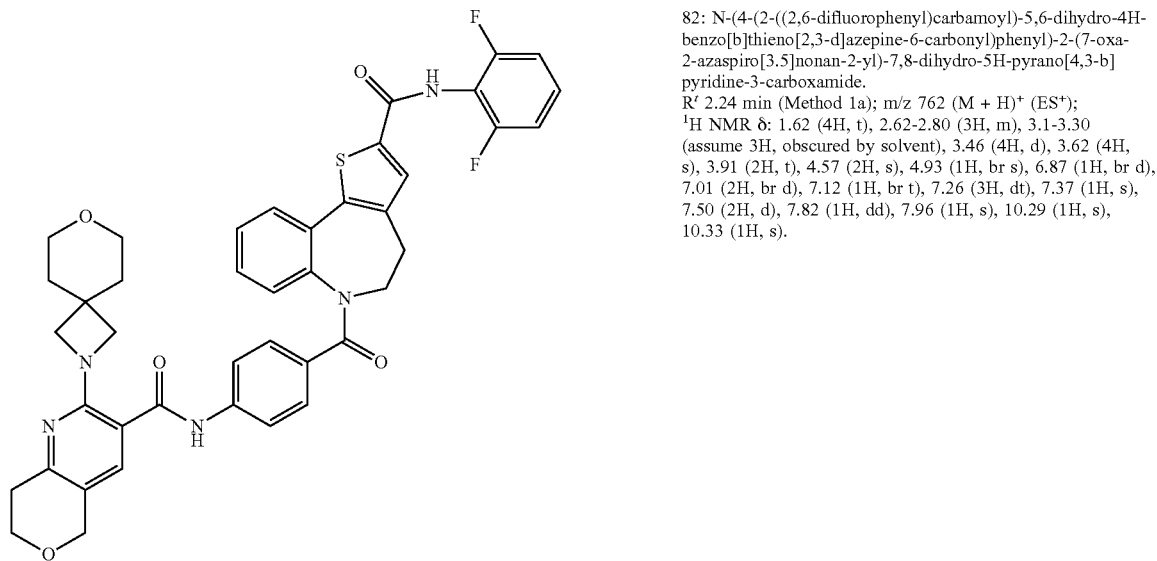

82: N-(4-(2-((2,6-difluorophenyl)carbamoyl)-5,6-dihydro-4H-benzo[b]thieno[2,3-d]azepine-6-carbonyl)phenyl)-2-(7-oxa-2-azaspiro[3.5]nonan-2-yl)-7,8-dihydro-5H-pyrano[4,3-b]pyridine-3-carboxamide.
$R^f$ 2.24 min (Method 1a); m/z 762 (M + H)$^+$ (ES$^+$);
$^1$H NMR δ: 1.62 (4H, t), 2.62-2.80 (3H, m), 3.1-3.30 (assume 3H, obscured by solvent), 3.46 (4H, d), 3.62 (4H, s), 3.91 (2H, t), 4.57 (2H, s), 4.93 (1H, br s), 6.87 (1H, br d), 7.01 (2H, br d), 7.12 (1H, br t), 7.26 (3H, dt), 7.37 (1H, s), 7.50 (2H, d), 7.82 (1H, dd), 7.96 (1H, s), 10.29 (1H, s), 10.33 (1H, s).

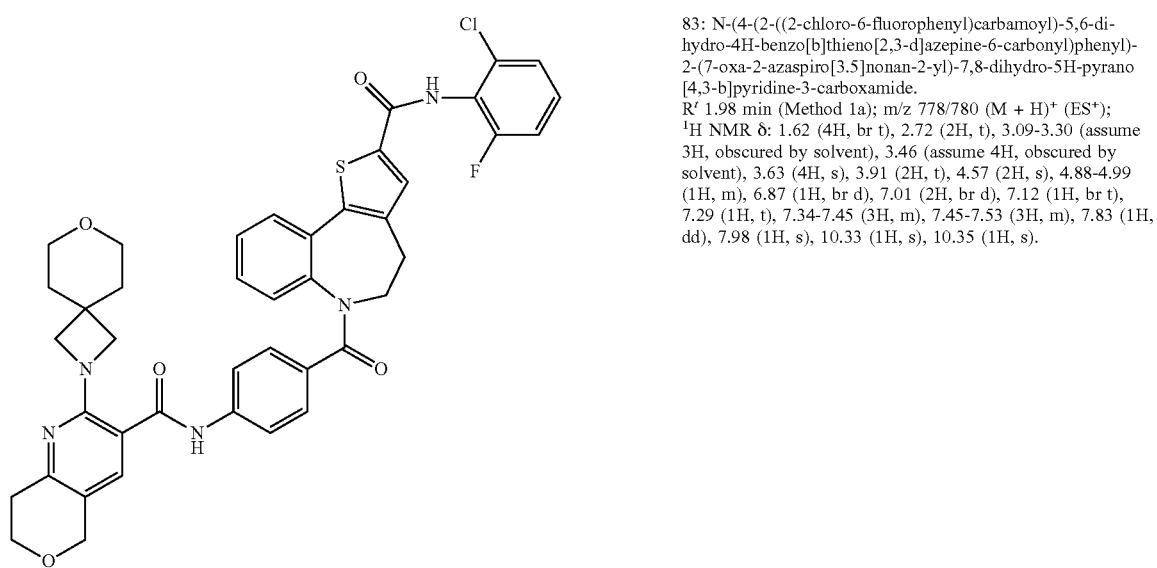

83: N-(4-(2-((2-chloro-6-fluorophenyl)carbamoyl)-5,6-dihydro-4H-benzo[b]thieno[2,3-d]azepine-6-carbonyl)phenyl)-2-(7-oxa-2-azaspiro[3.5]nonan-2-yl)-7,8-dihydro-5H-pyrano[4,3-b]pyridine-3-carboxamide.
$R^f$ 1.98 min (Method 1a); m/z 778/780 (M + H)$^+$ (ES$^+$);
$^1$H NMR δ: 1.62 (4H, br t), 2.72 (2H, t), 3.09-3.30 (assume 3H, obscured by solvent), 3.46 (assume 4H, obscured by solvent), 3.63 (4H, s), 3.91 (2H, t), 4.57 (2H, s), 4.88-4.99 (1H, m), 6.87 (1H, br d), 7.01 (2H, br d), 7.12 (1H, br t), 7.29 (1H, t), 7.34-7.45 (3H, m), 7.45-7.53 (3H, m), 7.83 (1H, dd), 7.98 (1H, s), 10.33 (1H, s), 10.35 (1H, s).

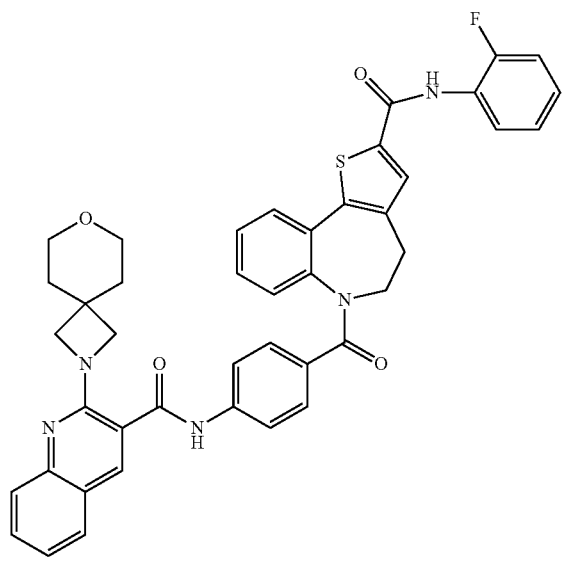 [SMILES: O=C(Nc1ccccc1F)c1cc2c(s1)-c1ccccc1N(C(=O)c1ccc(NC(=O)c3cc4ccccc4nc3N3CC4(CCOCC4)C3)cc1)CC2]

84: 6-(4-(2-(7-oxa-2-azaspiro[3.5]nonan-2-yl)quinoline-3-carboxamido)benzoyl)-N-(2-fluorophenyl)-5,6-dihydro-4H-benzo[b]thieno[2,3-d]azepine-2-carboxamide.
R$^t$ 1.93 min (Method 1a); m/z 738 (M + H)$^+$ (ES$^+$);
$^1$H NMR δ: 1.65 (4H, br t), 3.05-3.33 (assume 3H, obscured by solvent), 3.49 (4H, br t), 3.78 (4H, br s), 4.88-4.98 (1H, m), 6.88 (1H, d), 7.03 (2H, d), 7.13 (1H, t), 7.19-7.36 (5H, m), 7.50-7.63 (5H, m), 7.78 (1H, d), 7.82 (1H, dd), 7.98 (1H, s), 8.21 (1H, s), 10.24 (1H, s), 10.66 (1H, s).

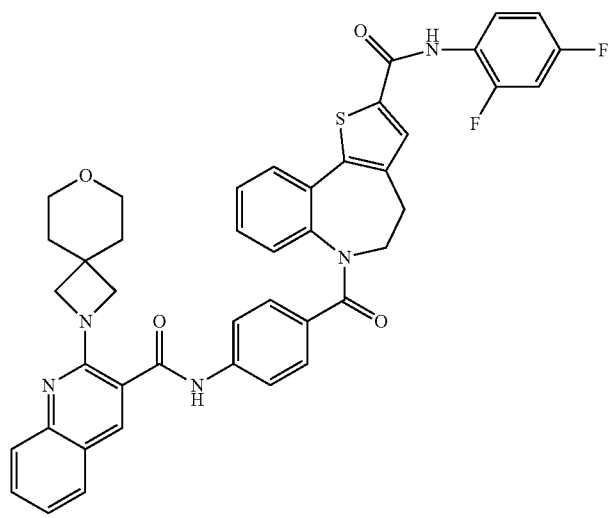 [SMILES: O=C(Nc1ccc(F)cc1F)c1cc2c(s1)-c1ccccc1N(C(=O)c1ccc(NC(=O)c3cc4ccccc4nc3N3CC4(CCOCC4)C3)cc1)CC2]

85: 6-(4-(2-(7-oxa-2-azaspiro[3.5]nonan-2-yl)quinoline-3-carboxamido)benzoyl)-N-(2,4-difluorophenyl)-5,6-dihydro-4H-benzo[b]thieno[2,3-d]azepine-2-carboxamide.
Prep HPLC Method 3;
R$^t$ 1.90 min (Method 1a); m/z 756 (M + H)$^+$ (ES$^+$);
$^1$H NMR δ: 1.66 (4H, br t), 3.21 (assume 3H, obscured by solvent), 3.49 (4H, br t), 3.79 (4H, br s), 4.88-5.00 (1H, s), 6.89 (1H, d), 7.04 (2H, d), 7.11-7.17 (2H, m), 7.23-7.28 (1H, m), 7.30 (1H, td), 7.38 (1H, ddd), 7.50-7.66 (5H, m), 7.78 (1H, d), 7.83 (1H, dd), 7.96 (1H, s), 8.21 (1H, s), 10.25 (1H, s), 10.65 (1H, s).

TABLE 2-continued

Additional Compound Examples of the Invention

Structure, Example No., Name, Preparative HPLC or Column Chromatography
Purification Method (where employed), LC-MS Analysis and $^1$HNMR Spectral Data

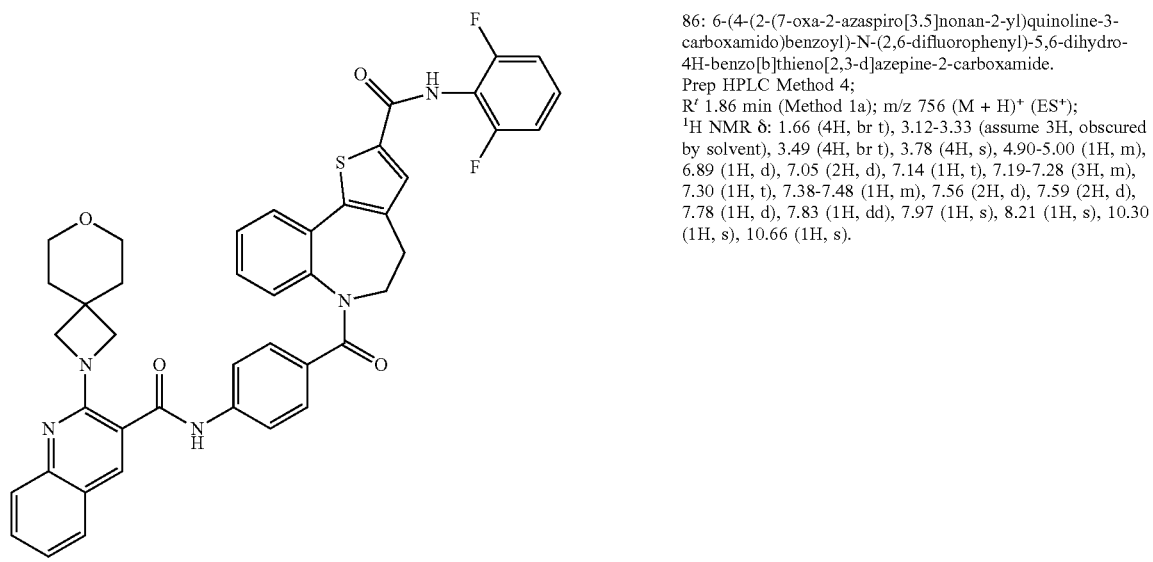

86: 6-(4-(2-(7-oxa-2-azaspiro[3.5]nonan-2-yl)quinoline-3-carboxamido)benzoyl)-N-(2,6-difluorophenyl)-5,6-dihydro-4H-benzo[b]thieno[2,3-d]azepine-2-carboxamide.
Prep HPLC Method 4;
$R^t$ 1.86 min (Method 1a); m/z 756 (M + H)$^+$ (ES$^+$);
$^1$H NMR δ: 1.66 (4H, br t), 3.12-3.33 (assume 3H, obscured by solvent), 3.49 (4H, br t), 3.78 (4H, s), 4.90-5.00 (1H, m), 6.89 (1H, d), 7.05 (2H, d), 7.14 (1H, t), 7.19-7.28 (3H, m), 7.30 (1H, t), 7.38-7.48 (1H, m), 7.56 (2H, d), 7.59 (2H, d), 7.78 (1H, d), 7.83 (1H, dd), 7.97 (1H, s), 8.21 (1H, s), 10.30 (1H, s), 10.66 (1H, s).

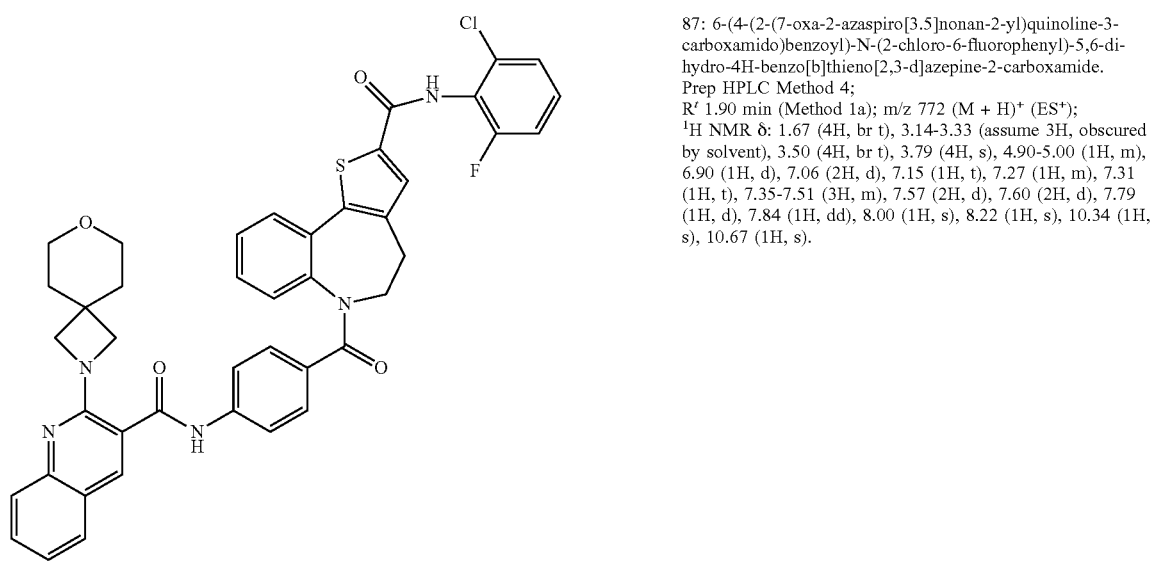

87: 6-(4-(2-(7-oxa-2-azaspiro[3.5]nonan-2-yl)quinoline-3-carboxamido)benzoyl)-N-(2-chloro-6-fluorophenyl)-5,6-dihydro-4H-benzo[b]thieno[2,3-d]azepine-2-carboxamide.
Prep HPLC Method 4;
$R^t$ 1.90 min (Method 1a); m/z 772 (M + H)$^+$ (ES$^+$);
$^1$H NMR δ: 1.67 (4H, br t), 3.14-3.33 (assume 3H, obscured by solvent), 3.50 (4H, br t), 3.79 (4H, s), 4.90-5.00 (1H, m), 6.90 (1H, d), 7.06 (2H, d), 7.15 (1H, t), 7.27 (1H, m), 7.31 (1H, t), 7.35-7.51 (3H, m), 7.57 (2H, d), 7.60 (2H, d), 7.79 (1H, d), 7.84 (1H, dd), 8.00 (1H, s), 8.22 (1H, s), 10.34 (1H, s), 10.67 (1H, s).

TABLE 2-continued

Additional Compound Examples of the Invention

Structure, Example No., Name, Preparative HPLC or Column Chromatography
Purification Method (where employed), LC-MS Analysis and ¹HNMR Spectral Data

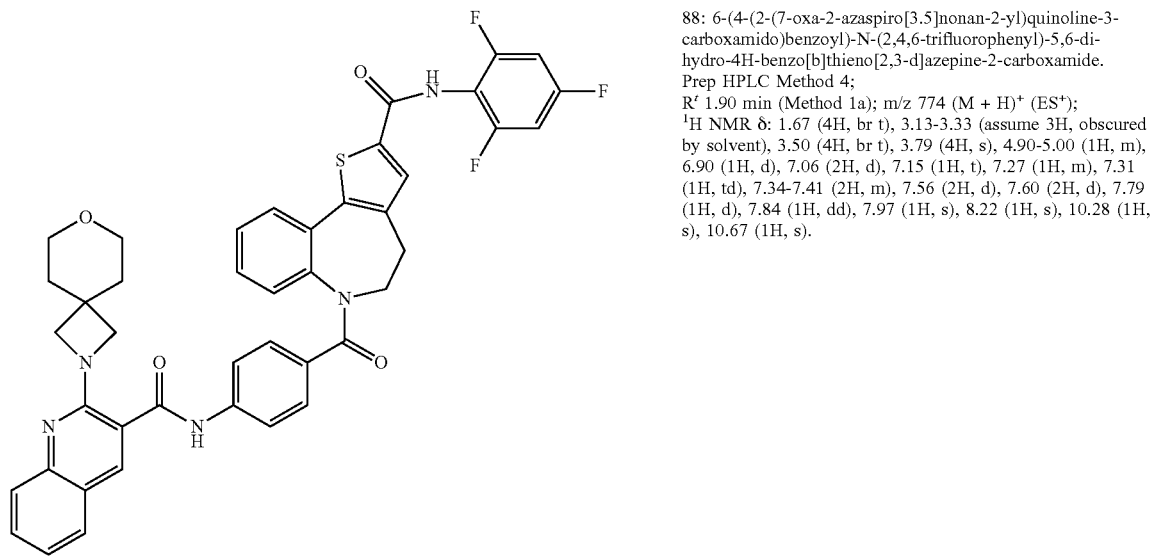

88: 6-(4-(2-(7-oxa-2-azaspiro[3.5]nonan-2-yl)quinoline-3-carboxamido)benzoyl)-N-(2,4,6-trifluorophenyl)-5,6-dihydro-4H-benzo[b]thieno[2,3-d]azepine-2-carboxamide.
Prep HPLC Method 4;
R$^t$ 1.90 min (Method 1a); m/z 774 (M + H)⁺ (ES⁺);
¹H NMR δ: 1.67 (4H, br t), 3.13-3.33 (assume 3H, obscured by solvent), 3.50 (4H, br t), 3.79 (4H, s), 4.90-5.00 (1H, m), 6.90 (1H, d), 7.06 (2H, d), 7.15 (1H, t), 7.27 (1H, m), 7.31 (1H, td), 7.34-7.41 (2H, m), 7.56 (2H, d), 7.60 (2H, d), 7.79 (1H, d), 7.84 (1H, dd), 7.97 (1H, s), 8.22 (1H, s), 10.28 (1H, s), 10.67 (1H, s).

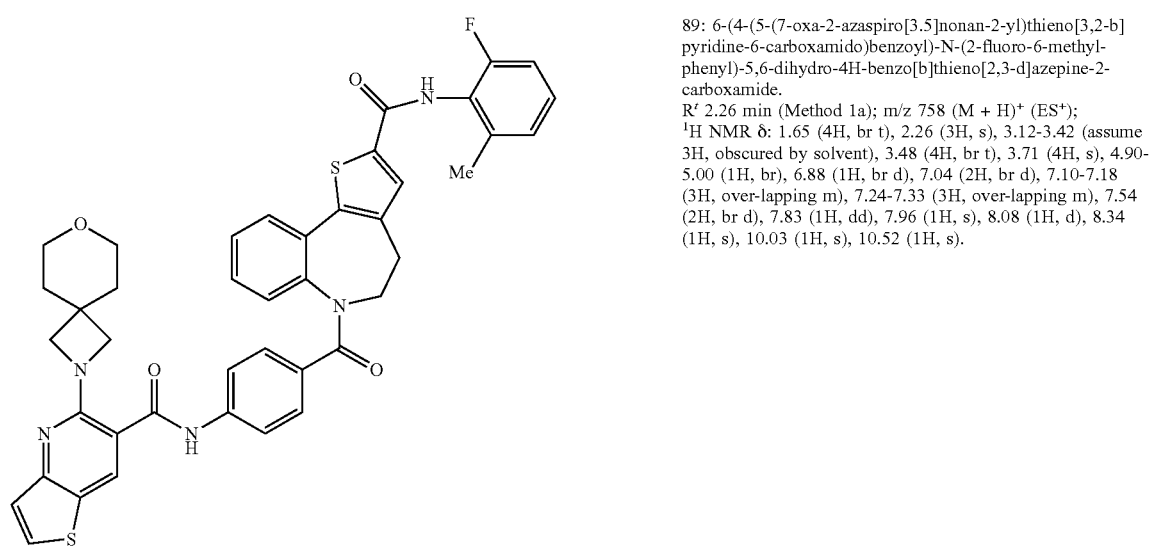

89: 6-(4-(5-(7-oxa-2-azaspiro[3.5]nonan-2-yl)thieno[3,2-b]pyridine-6-carboxamido)benzoyl)-N-(2-fluoro-6-methylphenyl)-5,6-dihydro-4H-benzo[b]thieno[2,3-d]azepine-2-carboxamide.
R$^t$ 2.26 min (Method 1a); m/z 758 (M + H)⁺ (ES⁺);
¹H NMR δ: 1.65 (4H, br t), 2.26 (3H, s), 3.12-3.42 (assume 3H, obscured by solvent), 3.48 (4H, br t), 3.71 (4H, s), 4.90-5.00 (1H, br), 6.88 (1H, br d), 7.04 (2H, br d), 7.10-7.18 (3H, over-lapping m), 7.24-7.33 (3H, over-lapping m), 7.54 (2H, br d), 7.83 (1H, dd), 7.96 (1H, s), 8.08 (1H, d), 8.34 (1H, s), 10.03 (1H, s), 10.52 (1H, s).

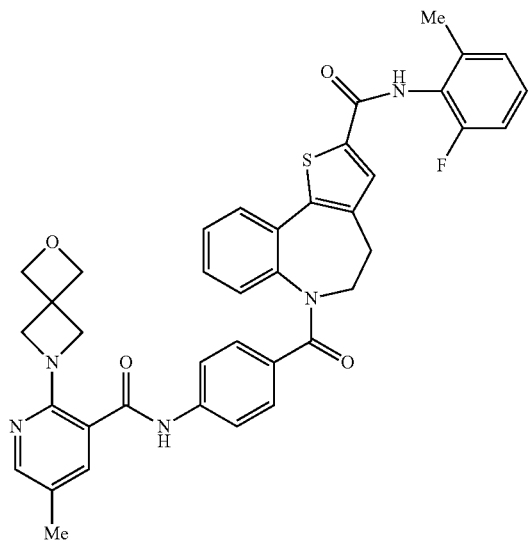 [SMILES: Cc1cnc(N2CC3(COC3)C2)c(C(=O)Nc2ccc(C(=O)N3CCc4cc(C(=O)Nc5c(C)cccc5F)sc4-c4ccccc43)cc2)c1]

90: N-(2-fluoro-6-methylphenyl)-6-(4-(5-methyl-2-(2-oxa-6-azaspiro[3.3]heptan-6-yl)nicotinamido)benzoyl)-5,6-dihydro-4H-benzo[b]thieno[2,3-d]azepine-2-carboxamide.
Prep HPLC Method 4;
$R^r$ 1.85 min (Method 1a); m/z 688 (M + H)$^+$ (ES$^+$);
$^1$H NMR δ: 2.17 (3H, s), 2.26 (3H, s), 3.12-3.40 (assume 3H, obscured by solvent), 3.99 (4H, s), 4.63 (4H, s), 4.90-5.00 (1H, br), 6.89 (1H, br d), 7.03 (2H, br d), 7.11-7.17 (3H, over-lapping m), 7.24-7.33 (2H, over-lapping m), 7.50 (1H, d), 7.53 (2H, br d), 7.83 (1H, dd), 7.96 (1H, s), 8.04 (1H, dd), 10.03 (1H, s), 10.37 (1H, s).

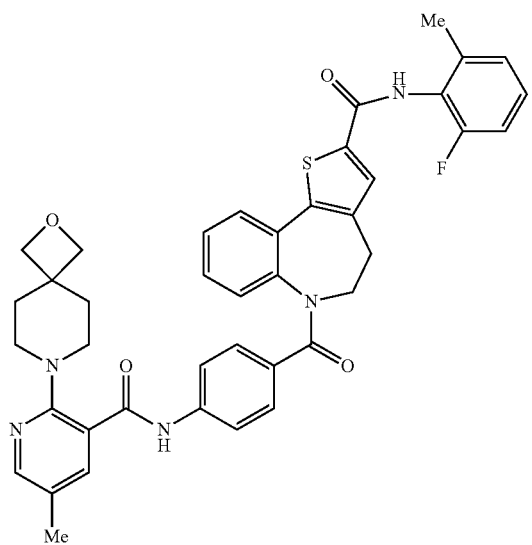 [SMILES: Cc1cnc(N2CCC3(CC2)COC3)c(C(=O)Nc2ccc(C(=O)N3CCc4cc(C(=O)Nc5c(C)cccc5F)sc4-c4ccccc43)cc2)c1]

91: N-(2-fluoro-6-methylphenyl)-6-(4-(5-methyl-2-(2-oxa-7-azaspiro[3.5]nonan-7-yl)nicotinamido)benzoyl)-5,6-dihydro-4H-benzo[b]thieno[2,3-d]azepine-2-carboxamide.
Prep HPLC Method 11;
$R^r$ 2.43 min (Method 1a); m/z 716 (M + H)$^+$ (ES$^+$);
$^1$H NMR δ: 1.75 (4H, br t), 2.22 (3H, s), 2.26 (3H, s), 3.05 (4H, apparent br t), 3.10-3.39 (assume 3H, obscured by solvent), 4.27 (4H, s), 4.88-5.00 (1H, br), 6.86 (1H, br d), 7.02 (2H, br d), 7.08-7.17 (3H, over-lapping), 7.24-7.31 (2H, over-lapping m), 7.53 (2H, br d), 7.69 (1H, d), 7.82 (1H, dd), 7.96 (1H, s), 8.14 (1H, dd), 10.05 (1H, s), 10.70 (1H, s).

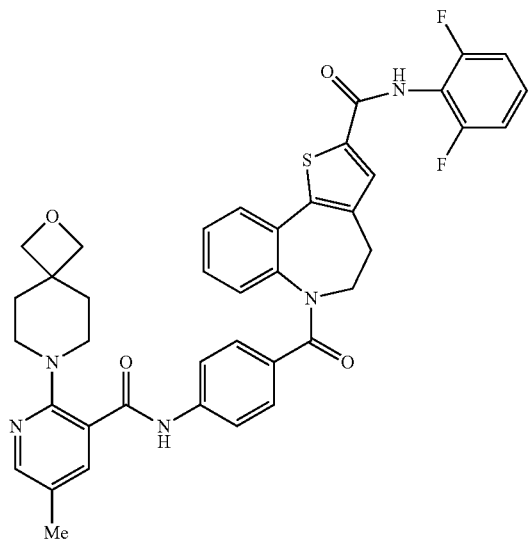 [SMILES: Cc1cnc(N2CCC3(CC2)COC3)c(C(=O)Nc2ccc(C(=O)N3CCc4cc(C(=O)Nc5c(F)cccc5F)sc4-c4ccccc43)cc2)c1]

92: N-(2,6-difluorophenyl)-6-(4-(5-methyl-2-(2-oxa-7-azaspiro[3.5]nonan-7-yl)nicotinamido)benzoyl)-5,6-dihydro-4H-benzo[b]thieno[2,3-d]azepine-2-carboxamide.
$R^r$ 2.34 min (Method 1a); m/z 720 (M + H)$^+$ (ES$^+$);
$^1$H NMR δ: 1.75 (4H, br t), 2.22 (3H, s), 3.04 (4H, br t), 3.11-3.32 (assume 3H, obscured by solvent), 4.27 (4H, s), 4.87-5.01 (1H, m), 6.86 (1H, br d), 7.02 (2H, br d), 7.12 (1H, br t), 7.19-7.33 (3H, over-lapping m), 7.37-7.48 (1H, m), 7.53 (2H, br d), 7.69 (1H, d), 7.83 (1H, dd), 7.97 (1H, s), 8.14 (1H, dd), 10.30 (1H, s), 10.70 (1H, s).

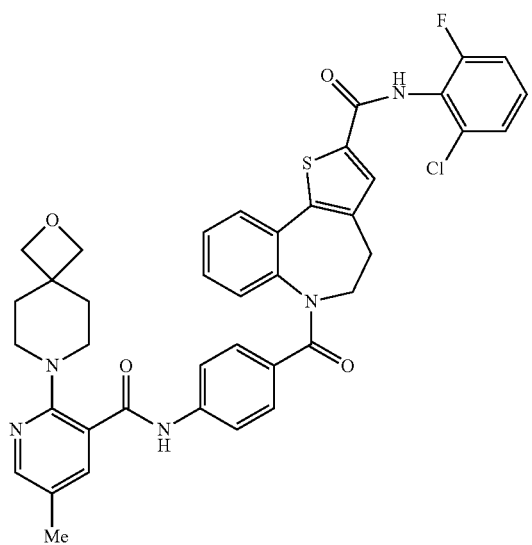

93: N-(2-chloro-6-fluorophenyl)-6-(4-(5-methyl-2-(2-oxa-7-azaspiro[3.5]nonan-7-yl)nicotinamido)benzoyl)-5,6-dihydro-4H-benzo[b]thieno[2,3-d]azepine-2-carboxamide.
$R^r$ 2.39 min (Method 1a); m/z 736 (M + H)$^+$ (ES$^+$);
$^1$H NMR δ: 1.76 (4H, br t), 2.21 (3H, s), 3.05 (4H, br t), 3.11-3.33 (assume 3H, obscured by solvent), 4.27 (4H, s), 4.88-5.03 (1H, m), 6.86 (1H, br d), 7.03 (2H, d), 7.12 (1H, br t), 7.29 (1H, td), 7.33-7.50 (3H, over-lapping m), 7.54 (2H, d), 7.69 (1H, d), 7.83 (1H, dd), 7.98 (1H, s), 8.14 (1H, dd), 10.34 (1H, s), 10.71 (1H, s).

TABLE 2-continued

Additional Compound Examples of the Invention

Structure, Example No., Name, Preparative HPLC or Column Chromatography
Purification Method (where employed), LC-MS Analysis and $^1$HNMR Spectral Data

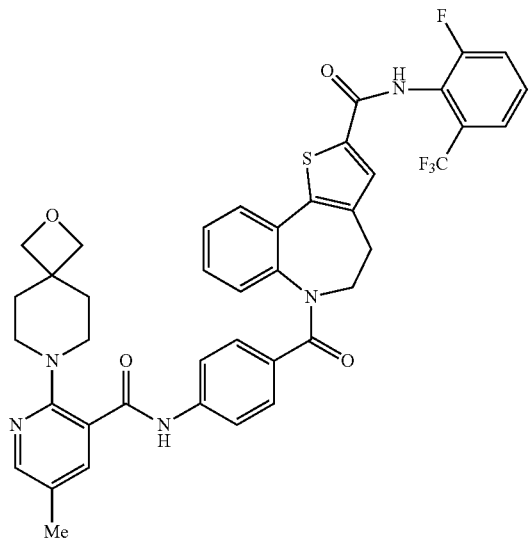 [SMILES: Cc1cnc(N2CCC3(CC2)COC3)c(C(=O)Nc2ccc(C(=O)N3CCc4cc(C(=O)Nc5c(F)cccc5C(F)(F)F)sc4-c4ccccc43)cc2)c1]

94: N-(2-fluoro-6-(trifluoromethyl)phenyl)-6-(4-(5-methyl-2-(2-oxa-7-azaspiro[3.5]nonan-7-yl)nicotinamido)benzoyl)-5,6-dihydro-4H-benzo[b]thieno[2,3-d]azepine-2-carboxamide.
$R^r$ 2.44 min (Method 1a); m/z 770 (M + H)$^+$ (ES$^+$);
$^1$H NMR δ: 1.76 (4H, br t), 2.22 (3H, s), 3.05 (4H, br t), 3.12-3.32 (assume 3H, obscured by solvent), 4.27 (4H, s), 4.84-5.02 (1H, m), 6.86 (1H, br d), 7.03 (2H, br d), 7.12 (1H, br t), 7.29 (1H, td), 7.54 (2H, d), 7.70 (4H, overlapping m), 7.83 (1H, dd), 7.96 (1H, s), 8.14 (1H, dd), 10.27 (1H, s), 10.71 (1H, s).

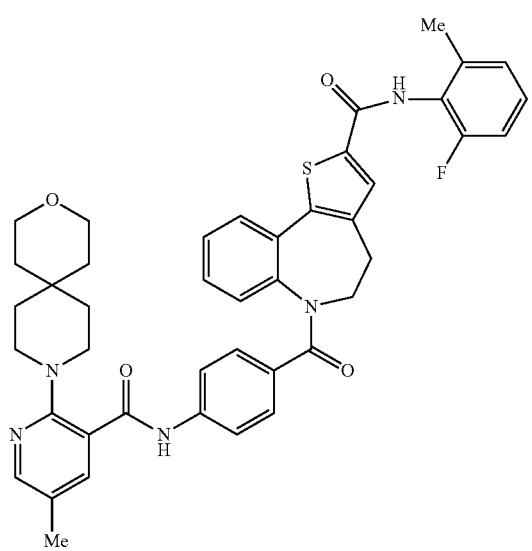 [SMILES: Cc1cnc(N2CCC3(CCOCC3)CC2)c(C(=O)Nc2ccc(C(=O)N3CCc4cc(C(=O)Nc5c(C)cccc5F)sc4-c4ccccc43)cc2)c1]

95: N-(2-fluoro-6-methylphenyl)-6-(4-(5-methyl-2-(3-oxa-9-azaspiro[5.5]undecan-9-yl)nicotinamido)benzoyl)-5,6-dihydro-4H-benzo[b]thieno[2,3-d]azepine-2-carboxamide.
Prep HPLC Method 11;
$R^r$ 2.49 min (Method 1a); m/z 744 (M + H)$^+$ (ES$^+$);
$^1$H NMR δ: 1.37 (4H, br t), 1.47 (4H, br t), 2.22 (3H, s), 2.26 (3H, s), 3.09-3.35 (assume 7H, obscured by solvent), 3.52 (4H, br t), 4.90-5.00 (1H, br), 6.85 (1H, br d), 7.03 (2H, br d), 7.07-7.17 (3H, over-lapping m), 7.24-7.31 (2H, overlapping m), 7.54 (2H, br d), 7.69 (1H, d), 7.82 (1H, dd), 7.95 (1H, s), 8.15 (1H, dd), 10.03 (1H, s), 10.75 (1H, s).

Biological Testing: Experimental Methods

Assessment of RSV Induced CPE in HEp2 Cells

HEp2 cells were seeded (10$^3$/well/50 μL) in 384-well plates (Catalogue number 353962, BD Falcon, Oxford, UK) in 5% serum free-DMEM containing 2 mM L-glutamine and 1 mM sodium pyruvate one day before infection. RSV A2 strain (#0709161v, NCPV, Public Health England, Wiltshire) or RSV B Washington strain (VR-1580, ATCC, Manassas, Va. 20108) virus solutions were prepared in serum free-DMEM with 2 mM L-glutamine and 1 mM sodium pyruvate, and then added (50 μL/well) to achieve a final virus concentration of 1 MOI. Simultaneously test compounds (0.5 μL DMSO solution) were added to 100 μL of HEp2 cell culture with virus solution to provide a final DMSO solution of 0.5%. Plates were incubated (37° C./5% CO$_2$) for 5 days for studies using RSV A2 strain or 6 days for those using RSV B strain, and then resazurin sodium salt (5 μL of 0.03% solution; Sigma-Aldrich, Dorset, UK) was added to each well and the plate incubated for a further 6 hr (37° C./5% CO$_2$). The fluorescence of each well [545 nm (excitation)/590 nm (emission)] was determined using a multi-scanner (Clariostar: BMG, Buckinghamshire, UK). The percentage inhibition for each well was calculated and the IC$_{50}$, IC$_{75}$ and IC$_{90}$ values were calculated from the concentration-response curve generated for each test compound.

Assessment of RSV F Protein Expression in BEAS2B Bronchial Epithelial Cells

An early event which follows the infection of epithelial cells by RSV is the expression of RSV F-protein on the cells' surface. BEAS2B cells (SV40-immortalised human bronchial epithelial cell line) were grown in 96 well plates. Once more than 70% confluent, cells were infected with RSV A2 (#0709161v, NCPV, Public Health England, Wiltshire) at an MOI of 0.01 in clear RPMI-1640 medium (Life technologies, Paisley, UK) with 2% FBS (Life technologies, Paisley, UK), and incubated for 3 days (37° C./5% $CO_2$).

Supernatant was aspirated and the cells were fixed with 4% formaldehyde (100 µL in PBS solution) for 20 min, washed 3 times with washing buffer (200 µL; PBS containing 0.05% Tween-20) and incubated with blocking solution (100 µL; 5% Marvel milk in PBS) for 1 hr. Cells were then washed with washing buffer (200 µL) and incubated for 1 hr at 37° C. with anti-RSV (2F7; mouse monoclonal, lot 160290, Cat. No. ab43812, Abcam plc, Cambridge, UK) F-fusion protein antibody (50 µL; prepared at a 1:1000 dilution in 5% milk/PBS-tween). After washing, cells were incubated with an HRP-conjugated anti-mouse IgG antibody (50 µL prepared at a 1:2000 dilution in 5% milk in PBS; lot 00095437, Cat.No. P0447, Dako UK Ltd, Cambridgeshire, UK) for 1 hr. Cells were washed twice with washing buffer and once with PBS. TMB substrate (100 µL; substrate reagent pack lot 320436, Cat. No. DY999, R&D Systems, Inc. Abingdon, UK) was then added and the reaction was stopped by the addition of aq sulfuric acid (50 µL; 2N). The resultant signal was determined colourimetrically (OD: 450 nm with a reference wavelength of 655 nm) in a microplate reader (Multiskan FC®, ThermoFisher Scientific). Cells were then washed and 1% crystal violet solution (50 µL; lot SLB4576, Cat. No. HT90132-1L, Sigma-Aldrich) was applied for 30 min. After washing with PBS (200 µL) 3 times, 1% SDS (100 µL) was added to each well, and plates were shaken lightly for 1 hr prior to reading the absorbance at 595 nm. The measured $OD_{450-655}$ readings were corrected for cell number by dividing the $OD_{450-655}$ by the $OD_{595}$ readings. The percentage inhibition for each well was calculated and the $IC_{50}$ value derived from the concentration-response curve generated for each test compound.

Cell Viability: Resazurin Assay

HEp2 cells were seeded in 384-well plates ($10^3$/well/50 µL; BD Falcon Ref 353962) in FBS DMEM (5%, containing 2 mM L-glutamine and 1 mM sodium pyruvate) one day before experimentation. Serum-free DMEM (50 µL) was added to test wells while for control wells the media was removed and sterile water (100 µL) was added. Test compounds (0.5 µL DMSO solution) were added to give a final DMSO concentration of 0.5%. Hep2 cells were incubated with each test compound for 5 days (37° C./5% $CO_2$ in 5% FBS) and then resazurin stock solution (5 µL; 0.03%) was added to each well and the plate incubated for a further 6 hr (37° C./5% $CO_2$). The fluorescence of each well at 545 nm (excitation) and 590 nm (emission) was determined using a multi-scanner (Clariostar: BMG Labtech). The percentage loss of cell viability was calculated for each well relative to vehicle (0.5% DMSO) treatment.

Any apparent increase in cell viability associated with test compound treatment relative to vehicle is consequently tabulated as a negative percentage. Where appropriate, a $CC_{50}$ value was calculated from the concentration-response curve generated from the concentration-response curve for each test compound.

Assessment of Virus Titre in Air-liquid Interface (ALI) Cultured Bronchial Epithelial Cells ALI cultured human bronchial epithelial cells were sourced from Epithelix Sarl (Geneva, Switzerland) and maintained by changing the basal media every 3-4 days, whilst the apical surface was washed once weekly with PBS. On Day 0, the apical surface of each well was washed once with sterile PBS (300 µL) and the inserts were transferred to new 24-well plates containing fresh MucilAir culture medium (780 µL; EP04MM). RSV A2 (50 µL; diluted in MucilAir culture medium to give a final MOI of 0.01) was added to cells for one hr (37° C./5% $CO_2$). For the purposes of standardizing MOI calculations, each MucilAir insert was estimated to contain $2 \times 10^5$ apical facing cells per well. Virus inoculum was removed with a pipette and inserts were washed twice with sterile PBS (300 µL).

Sampling was conducted by adding sterile PBS (300 µL) to the apical surface of each well for 5 min. The apical sample was then removed and transferred to tubes containing 50% sucrose dissolved in PBS (100 µL) before being stored at −80° C. This harvesting procedure was repeated daily beginning on day 0 and concluding on day 7.

ALI cultures were dosed apically with test compound on days 0-7 for "early intervention" protocols, or days 3-7 for "late intervention" protocols. The test compound (50 µL in 0.5% DMSO/PBS) was added to the apical surface and incubated (37° C./5% $CO_2$) for 1 hr before being removed. Vehicle treatments (0.5% DMSO/PBS) were performed on the corresponding apical surfaces to ensure each well received the same number of manipulations. On day 5, the basal media was removed from each well and replenished with fresh MucilAir culture media as a necessary maintenance step for ALI culture cells.

Virus titre was quantified by plaque assay. HEp2 cells were grown in 24-well plates (Corning) for 48 hr prior to infection in DMEM containing 10% FBS until they attained 100% confluency. Collected samples were thawed at RT and ten-fold serial dilutions were prepared in serum-free DMEM. The growth medium from HEp2 cells was aspirated and replaced with 300 µL of serially diluted virus collections and left to infect at 37° C./5% $CO_2$ for 4 hr. The infectious media was aspirated and replaced with Plaque Assay Overlay (500 µL; 1% methylcellulose in MEM, 2% FBS, 1% Pen Strep, 0.5 µg/mL amphotericin B), and left for 7 days at 37° C./5% $CO_2$. Cells were fixed with ice-cold methanol for 10 min and blocked with 5% powdered milk (Marvel) in 0.05% PBS-tween ('blocking buffer') for 1 hr at RT. Anti-RSV F-protein antibody (2F7; Abcam: ab43812) was diluted to a 1:100 concentration in blocking buffer and added to cells for 1 hr at RT with shaking. Cells were washed using PBS and incubated with the secondary antibody (HRP conjugated goat anti-mouse secondary antibody (Dako P044701-2) diluted in 1:400 with blocking buffer) for 1 hr at RT with shaking. The secondary antibody solution was removed and cells were washed with PBS before the metal-enhanced development substrate DAB was prepared in ultra-pure water (according to manufacturer's instructions). Each well received 300 µL of development substrate (sigmaFAST D0426) until plaques were visible. Plaques were counted by eye and confirmed using light microscopy, allowing the calculation of plaque forming units per mL.

RSV Infection in Mice

Non-fasted mice (male BALB/C, 20-30 g) were infected intranasally with RSV A2 or virus diluent (DMEM, 2% FBS, 12.5% sucrose) under isoflurane (5% in $O_2$) anaesthesia. The A2 strain of RSV (50 µL of $1.3 \times 10^6$ PFU/mL: final $0.65 \times 10^5$ PFU/mouse) was instilled into each nostril in a drop wise fashion alternating between the two until a volume of 50 µL was delivered. Following infection each animal was weighed on a daily basis to monitor changes. Test compounds were dissolved in 100% DMSO (at 20 mg/mL and/or 2 mg/mL), then diluted at 1:10 in isotonic saline to achieve 10% DMSO in all treatments. Formulations were then sonicated to produce a suspension. The suspension was administered intratracheally (20 µL) with a FMJ-250 Penn-Century device or intranasally (40 µL) with a pipette on 1 day and 1 hr before infection (day 0), and then on days 1, 2 and 3 post infection. Four days after RSV challenge, the animals were euthanised (by intraperitoneal injection of a pentobarbitone overdose), the trachea cannulated and BALF extracted for total and differential cell counts. Following BALF collection, the right lung was removed from each animal and homogenised in ice-cold Dulbecco's modified Eagles medium (using 10 times the lung weight of DMEM containing 1% BSA and 25% sucrose) for 2×20 second bursts. The homogenate was then transferred into a sterile tube and spun at 4° C. (2000 rpm; for 5 min). The clarified homogenate was transferred to a chilled cryovial, snap frozen and stored at −80° C. The supernatants from lung homogenates were used for Plaque assay.

HEp2 cells were grown in 24-well plates (Corning) for 48 hr prior to infection in DMEM containing 10% FBS until they attained 100% confluency. Lung homogenate was thawed at RT and ten-fold serial dilutions were prepared in serum-free DMEM. The growth medium from HEp2 cells was aspirated and replaced with 300 µL of serially diluted lung homogenate and left to infect (4 hr; 37° C./5% $CO_2$). The infectious media were aspirated and replaced with Plaque Assay Overlay (500 µL; 1% methylcellulose in MEM, 2% FBS, 1% Pen Strep, 0.5 µg/mL amphotericin B), and left for 7 days (37° C./5% $CO_2$). Cells were fixed with ice-cold methanol for 10 min and blocked with 5% powdered milk (Marvel) in 0.05% PBS-tween (blocking buffer) for 1 hr at RT.

Anti-RSV F-protein antibody [2F7] (Abcam: ab43812) was diluted to a 1:100 concentration in blocking buffer and added to cells for 1 hr at RT with shaking. Cells were washed using PBS and then incubated with the secondary antibody (HRP conjugated goat anti-mouse secondary antibody (Dako P044701-2) diluted in 1:400 with blocking buffer) for 1 hr at RT with shaking. The secondary antibody solution was removed and cells were washed with PBS before the metal-enhanced development substrate DAB was prepared in ultra-pure water (according to manufacturer's instructions). Each well received 300 µL of development substrate (sigmaFAST D0426) until plaques were visible. Plaques were counted by eye and confirmed using light microscopy, allowing the calculation of plaque forming units per mL of lung homogenate supernatant.

RSV Infection in Cotton Rats

Male *Sigmodon hispidus* cotton rats between 6 and 8 weeks of age were infected with hRSV/A/Long (ATCC, Manassas, Va.; $10^5$ pfu) in a volume of 0.1 mL of sucrose stabilizing media. Test compounds were dissolved in 100% DMSO (at 3.3, 10, 33 and 100 mg/mL), then diluted at 1:10 in isotonic saline to achieve 10% DMSO in all treatments. Formulations were then sonicated to produce suspensions. The resulting suspensions were administered intranasally (50 µL) by pipette 4 hr before infection (on day 0), and then on days 1, 2 and 3 post infection. Four days after RSV challenge, the animals were euthanised and the lungs were removed. The left lobe was used for viral titration via plaque assay and the lingular lobe for RSV/A/Long NS-1 qRT-PCR and cytokine qRT-PCR.

The supernatant of lung homogenates were diluted 1:10 and 1:100 in Eagle (E)-MEM. Confluent HEp2 monolayers in 24-well plates were infected in duplicate (50 µL of sample per well) starting with undiluted (neat) samples followed by diluted homogenates. After incubation for 1 hr (37° C./5% $CO_2$) wells were overlaid with the 0.75% methylcellulose medium and plates replaced at the 37° C. incubator. After incubation (for 4 days), the overlay was removed, the cells fixed with 0.1% crystal violet stain (for 1 hr) and then rinsed and air-dried. Plaques were counted and viral titers were expressed as plaque forming units per gram ($pfu \cdot g^{-1}$) of tissue.

Total RNA was also extracted from homogenized lung tissue (RNeasy purification kit; Qiagen) and a sample (1 µg) was used to prepare cDNA using QuantiTect Reverse Transcription Kit (Qiagen). For real-time PCR reactions (RSV NS-1 and RANTES genes) the QuantiFast SYBR® Green PCR Kit (Qiagen) was used in a final volume of 25 µL, with final primer concentrations of 0.5 µM. Amplifications were performed on a Bio-Rad iCycler for 1 cycle of 95° C. for 3 min, followed by 40 cycles of 95° C. for 10 sec, 60° C. for 10 sec, and 72° C. for 15 sec. Baseline cycles and cycle threshold (Ct) were calculated by the iQ5 software in the PCR Base Line Subtracted Curve Fit mode. The standard curves were developed using serially diluted cDNA sample most enriched in the transcript of interest (e.g., lungs from day 4 post-primary RSV infection). The Ct values were plotted against $log_{10}$ cDNA dilution factor. These curves were used to convert the Ct values obtained for different samples to relative expression units which were then normalized to the level of β-actin mRNA ("housekeeping gene") expressed in the corresponding sample. The mRNA levels were expressed as the geometric mean±SEM for all animals in a group.

In vitro Screening Results

The profiles of the compounds of the invention, as disclosed herein, are summarised below (Table 3) and demonstrate potent inhibitory activities against both RSV A2-induced CPE and (in many cases) RSV B-induced CPE in HEp2 cells. Furthermore, the compounds of the invention exhibit potent inhibition of RSV A2 F-protein expression in BEAS2B bronchial epithelial cells. Little or no effect on cell viability, resulting from incubation with the compounds of the formula (I), was detected.

TABLE 3

The effects of treatment with compounds of formula (I) on RSV A2- and RSV B- induced CPE in Hep2 cells, on RSV A2 F-protein expression in BEAS2B bronchial epithelial cells and on cell viability.

$IC_{50}/CC_{50}$ Values (nM) or Inhibition (%) at indicated concentration

| Compound Example No. | RSV A2 CPE $IC_{50}$ (nM) | RSV A2 CPE % Inhibition[2] | RSV B CPE $IC_{50}$ (nM) | RSV B CPE % Inhibition[3] | RSV A2 F-protein $IC_{50}$ (nM) | Cell Viability $CC_{50}$ (nM) |
|---|---|---|---|---|---|---|
| 1 | 0.50 | 98 | 166 | 77 | nt | >14900 |
| 2 | 0.16 | 91 | 314 | 69 | nt | >14400 |
| 3 | 1.3 | 100 | 195 | 58 | nt | >13900 |
| 4 | 2.1 | 100[1] | 49.3 | 83 | nt | >13700 |
| 5 | 0.017 | 100 | 10.2 | 72 | 0.17 | >14000 |
| 6 | 0.13 | 100[1] | 4.2 | 100 | nt | >12100 |
| 7 | 0.15 | 100 | 98.6 | 94 | nt | >13500 |
| 8 | 0.27 | 88[1] | 1.3 | 100[2] | 0.13 | >13500 |
| 9 | 0.39 | 92[1] | 1.4 | 100[2] | 0.034 | 12500 |
| 10 | 0.11 | 100 | 1.5 | 100[2] | 0.48 | >13300 |
| 11 | 0.28 | 93 | 25.9 | 95 | nt | >13500 |
| 12 | 0.42 | 100[1] | 1.3 | 98 | nt | >13200 |
| 13 | 0.45 | 100[1] | 0.96 | 100 | nt | >13100 |
| 14 | 0.65 | 100 | 54.5 | 92 | 0.41 | >14600 |
| 15 | 0.40 | 100 | 20.4 | 85 | 0.36 | >14500 |
| 16 | 0.76 | 100 | 142 | 63 | 0.93 | >14200 |
| 17 | 0.66 | 100 | 204 | 77 | nt | >14300 |
| 18 | 0.16 | 75 | >1440 | 18 | nt | >14400 |
| 19 | 0.14 | 88 | 28 | 100[2] | nt | >14200 |
| 20 | 0.36 | 100 | 129 | 80 | nt | >14200 |
| 21 | 1.3 | 100 | 100 | 73 | nt | >13800 |

TABLE 3-continued

The effects of treatment with compounds of formula (I) on RSV A2- and RSV B- induced CPE in Hep2 cells, on RSV A2 F-protein expression in BEAS2B bronchial epithelial cells and on cell viability.

| Compound Example No. | RSV A2 CPE IC$_{50}$ (nM) | RSV A2 CPE % Inhibition[2] | RSV B CPE IC$_{50}$ (nM) | RSV B CPE % Inhibition[3] | RSV A2 F-protein IC$_{50}$ (nM) | Cell Viability CC$_{50}$ (nM) |
|---|---|---|---|---|---|---|
| 22 | 0.96 | 96 | 37.3 | 77 | nt | >14200 |
| 23 | 1.1 | 100 | 16.3 | 55 | nt | >13900 |
| 24 | 0.57 | 88 | 19.6 | 65 | nt | >14300 |
| 25 | 0.18 | 99 | 20.6 | 71 | nt | >14200 |
| 26 | 0.12 | 95 | 9.3 | 73 | 0.14 | >13800 |
| 27 | 0.17 | 100 | 37.4 | 100 | 0.51 | >13800 |
| 28 | 0.17 | 96 | 41.4 | 66 | nt | >13800 |
| 29 | 0.13 | 97 | 27.9 | 73 | nt | >14200 |
| 30 | 0.12 | 100 | 27.3 | 94 | 0.27 | >13800 |
| 31 | 0.10 | 100 | 49.6 | 90 | nt | >13500 |
| 32 | <0.015 | 100 | 38.2 | 81 | nt | >14600 |
| 33 | <0.014 | 100 | 9.7 | 74 | 0.19 | >14200 |
| 34 | 0.11 | 100 | 38.5 | 86 | nt | >13900 |
| 35 | 0.14 | 100 | 62.8 | 70 | nt | >14300 |
| 36 | 0.16 | 95[1] | 13.4 | 99 | nt | >13700 |
| 37 | 0.15 | 100[1] | 7.2 | 100 | nt | >13800 |
| 38 | <0.014 | 100 | 18.4 | 73 | nt | >13900 |
| 39 | <0.014 | 100 | 17.3 | 77 | 0.057 | >13600 |
| 40 | 0.15 | 100 | 41.3 | 80 | nt | >14000 |
| 41 | 0.11 | 100 | 15.4 | 79 | nt | >13600 |
| 42 | 0.14 | 97 | 60.5 | 80 | nt | >14000 |
| 43 | 0.12 | 100 | 59.4 | 72 | nt | >14000 |
| 44 | 0.13 | 100 | 16.2 | 76 | nt | >13700 |
| 45 | 0.11 | 100 | 84.0 | 68 | nt | >13600 |
| 46 | 0.069 | 100 | 7.0 | 86 | nt | >13300 |
| 47 | 0.13 | 100[1] | 5.7 | 100[2] | nt | >13900 |
| 48 | 0.14 | 100 | 1.5 | 100 | nt | >13600 |
| 49 | 0.13 | 100 | 1.3 | 100 | nt | >13900 |
| 50 | 0.13 | 100 | 1.7 | 100 | nt | >13600 |
| 51 | 1.1 | 98 | 10.1 | 99 | nt | >13800 |
| 52 | 0.067 | 96 | 3.3 | 100 | nt | >13900 |
| 53 | 0.23 | 94 | 14.6 | 96 | nt | >13700 |
| 54 | 1.5 | 100[1] | 89.8 | 100 | nt | >13100 |
| 55 | 0.15 | 100[1] | 16.2 | 100 | nt | >12900 |
| 56 | 0.14 | 94 | 4.1 | 89 | nt | >13700 |
| 57 | 0.13 | 91 | 1.4 | 74 | nt | >13300 |
| 58 | 0.32 | 100[1] | 8.6 | 100 | nt | >13700 |
| 59 | 0.23 | 100 | 13.8 | 93 | nt | >13200 |
| 60 | 0.14 | 92 | 9.5 | 100 | nt | >13700 |
| 61 | 0.13 | 97 | 4.1 | 100 | nt | >13300 |
| 62 | 0.13 | 89[1] | 0.90 | 100 | nt | >13800 |
| 63 | 0.058 | 95[1] | 1.6 | 100 | nt | >13000 |
| 64 | 0.25 | 100[1] | 1.1 | 100 | nt | >14000 |
| 65 | 0.13 | 100[1] | 1.6 | 100 | 0.59 | >13100 |
| 66 | 0.15 | 95[1] | 4.8 | 95 | nt | >13400 |
| 67 | 0.17 | 100[1] | 6.5 | 100 | nt | >13100 |
| 68 | 0.087 | 90[1] | 17.1 | 100 | nt | >13900 |
| 69 | 0.45 | 96[1] | 15.3 | 100 | nt | >13600 |
| 70 | 0.18 | 76[1] | 1.2 | 100 | nt | >13900 |
| 71 | 0.61 | 100[1] | 15.5 | 100[2] | nt | >13700 |
| 72 | 0.32 | 100[1] | 3.3 | 89 | nt | >13400 |
| 73 | 2.6 | 84[1] | 14.8 | 98 | nt | >13400 |
| 74 | 0.88 | 100[1] | 3.8 | 77 | nt | >13400 |
| 75 | 0.10 | 84[1] | 2.3 | 100 | 0.25 | >13400 |
| 76 | 0.15 | 100[1] | 1.4 | 100 | 0.32 | >13100 |
| 77 | 4.9 | 94[1] | 19.2 | 92 | nt | >13000 |
| 78 | 2.4 | 89[1] | 1.3 | 94 | nt | >13200 |
| 79 | 2.3 | 92[1] | 1.8 | 93 | nt | >13100 |
| 80 | 2.0 | 91[1] | 1.6 | 93 | nt | >12800 |
| 81 | 0.18 | 77[1] | 10.2 | 100[2] | 0.13 | >12900 |
| 82 | 0.78 | 97[1] | 7.6 | 100[2] | nt | >13100 |
| 83 | 0.15 | 100[1] | 6.2 | 95 | nt | >12800 |
| 84 | 0.13 | 97 | 11.0 | 68 | nt | >13600 |
| 85 | 3.5 | 95 | 13.5 | 91 | nt | >13200 |
| 86 | 0.17 | 85[1] | 23.0 | 100[2] | nt | >13200 |
| 87 | 0.54 | 94[1] | 15.8 | 100[2] | 0.49 | >12900 |
| 88 | 0.58 | 93[1] | 3.0 | 93 | nt | >12900 |
| 89 | 0.50 | 100[1] | 19.4 | 100[2] | nt | >13200 |
| 90 | 1.8 | 100[1] | 508 | 99 | nt | >14500 |
| 91 | 1.3 | 100[1] | 393 | 100 | nt | >14000 |
| 92 | 0.17 | 93[1] | 60.8 | 100 | nt | >13900 |
| 93 | 0.56 | 98[1] | 59.3 | 100 | nt | >13600 |
| 94 | 1.4 | 100[1] | 811 | 54 | nt | >13000 |
| 95 | 2.4 | 100[1] | >1340 | 27 | nt | >13400 |

Table Footnotes:

[1]Inhibition (%) at 0.01 μg/mL;

[2]Inhibition (%) at 0.1 μg/mL;

[3]Inhibition (%) at 1 μg/mL;

NT = not tested.

Figure 2:
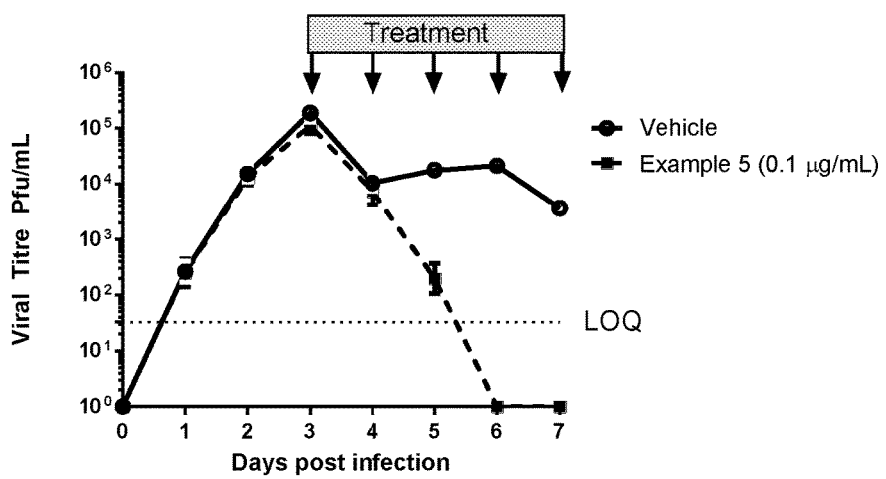
FIG. 2 shows the effect of Example 5 on virus titre in RSV A2 infected air-liquid interface (ALI) cultured epithelial cells following late intervention with test compound

Anti-viral effects were also evaluated using air-liquid cultured human primary bronchial epithelial cells. The cells undergo extensive mucociliary differentiation, resulting in cultures with morphological characteristics similar to those observed in the normal human respiratory epithelium. As a result, this cell model closely mimics RSV infections in human airways. The RSV titre increased from day 1, peaked at day 3 and then gradually and moderately reduced up to day 7. Treatment with compound Example 5 to an apical well daily from day 0 to day 7 (early intervention, see Table 4, FIG. 1) induced concentration dependent inhibition, and showed complete inhibition at 0.1 μg/mL over 7 days. The test compound also produced a dramatic reduction of virus titre on days 6 and 7 post infection when it was administered from day 3 after the virus peak (Late intervention, see Table 5, FIG. 2).

TABLE 4

The effects of early intervention (days 0-7) with compound Example 5 on RSV A2 viral titre in apical wash from RSV A2 infected, air-liquid interface cultured, bronchial epithelial cells.

| Treatment | Drug Conc. mg/mL | Virus titre in apical wash on days indicated expressed as the geometric mean (log PFU/mL) ± SD[1,2] | | | | | | | |
|---|---|---|---|---|---|---|---|---|---|
| | | 0 | 1 | 2 | 3 | 4 | 5 | 6 | 7 |
| Vehicle plus virus | none | 0.0 ± 0.0 | 0.94 ± 1.3 | 4.0 ± 0.18 | 4.5 ± 0.15 | 3.7 ± 0.22 | 4.1 ± 0.22 | 4.1 ± 0.22 | 3.5 ± 0.31 |
| Compound Example 5 | 0.004 | 0.0 ± 0.0 | 0.61 ± 0.86 | 3.1 ± 0.22 | 3.9 ± 0.18 | 4.1 ± 0.16 | 4.2 ± 0.12 | 3.2 ± 0.26 | 2.8 ± 0.43 |
| | 0.02 | 0.0 ± 0.0 | 0.0 ± 0.0 | 0.0 ± 0.0 | 0.0 ± 0.0 | 1.4 ± 1.1 | 1.9 ± 1.4 | 0.0 ± 0.0 | 0.0 ± 0.0 |
| | 0.1 | 0.0 ± 0.0 | 0.0 ± 0.0 | 0.0 ± 0.0 | 0.0 ± 0.0 | 0.0 ± 0.0 | 0.0 ± 0.0 | 0.0 ± 0.0 | 0.0 ± 0.0 |

[1]Allocated 1 PFU/mL if any plaque was detected in the assay with ×10 diluted apical wash;
[2]The n values were 3 for all experiments.

TABLE 5

The effects of late intervention (days 3-7) with compound Example 5 on RSV A2 viral titre in apical wash from RSV A2 infected air-liquid interface cultured bronchial epithelial cells.

| Treatment | Drug Conc. mg/mL | Virus titre in apical wash on days indicated expressed as the geometric mean (log PFU/mL) ± SD[1,2] | | | | | | | |
|---|---|---|---|---|---|---|---|---|---|
| | | 0 | 1 | 2 | 3 | 4 | 5 | 6 | 7 |
| Vehicle plus virus | none | 0.0 ± 0.0 | 2.4 ± 0.26 | 4.2 ± 0.12 | 5.2 ± 0.18 | 4.0 ± 0.14 | 4.2 ± 0.17 | 4.0 ± 0.50 | 3.5 ± 0.22 |
| Compound Example 5 | 0.02 | 0.0 ± 0.0 | 1.6 ± 1.1 | 3.9 ± 0.15 | 5.2 ± 0.04 | 3.8 ± 0.50 | 3.6 ± 0.13 | 0.0 ± 0.0 | 1.3 ± 0.94 |
| | 0.1 | 0.0 ± 0.0 | 2.3 ± 0.35 | 4.1 ± 0.14 | 5.0 ± 0.14 | 3.8 ± 0.31 | 1.7 ± 1.2 | 0.0 ± 0.0 | 0.0 ± 0.0 |

[1]Allocated 1 PFU/mL if any plaque was detected in the assay with ×10 diluted apical wash;
[2]The n values were 3 for all experiments.

In Vivo Testing

Human RSV is able to infect and replicate in a number of animal species used for pre-clinical screening, thereby enabling the performance and profiles of novel anti-infective agents to be assessed and compared in vivo (Bern, et al., 2011). Although primate species can also be infected and studied, most work of this nature is conducted in mice or cotton rats. Both standard, inbred mouse strains and cotton rats are characterised as "semi-permissive" for the replication of human RSV, although significantly greater viral replication is seen in cotton rats compared to inbred mouse strains. Compound Example 5 was therefore tested in the above mentioned in vivo systems.

Figure 3:
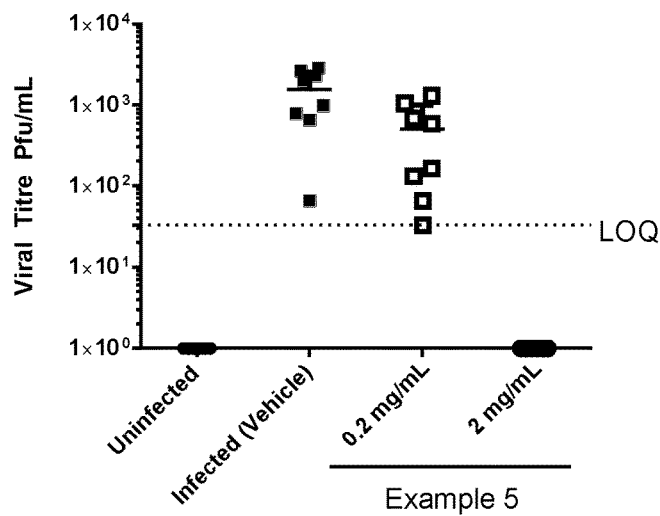
FIG. 3 shows the effect of Example 5 on virus titre in the lungs of RSV A2 infected mice

In RSV A2 infected mice, virus titre peaked on day 4 following inoculation. Test compound was administered 1 day and 1 hr before inoculation, (day 0) and then 2 and 3 days after virus infection either intranasally (Table 6, FIG. 3) or intratracheally (Table 7) and in both cases demonstrated potent dose-dependent inhibition of viral titre in lung homogenates.

TABLE 6

The effects of intranasal treatment with compound Example 5 on RSV A2 viral titre in lung from RSV A2 infected mice.

| Treatment | Drug Conc (mg/mL) | Virus titre (log PFU/lung)[1] | | |
|---|---|---|---|---|
| | | Geometric mean | Median | Interquartile range |
| Vehicle plus virus | none | 3.0 | 3.2 | 2.8-3.4 |
| Compound Example 5 | 0.2 | 2.4 | 2.5 | 1.9-3.0 |
| | 2 | <1.5[2] | <1.5[2] | |

[1]n values were 8 for all experiments;
[2]Lower limit of quantitation (LOQ).

TABLE 7

The effects of intratracheal treatment with compound Example 5 on RSV A2 viral titre in lung from RSV A2 infected mice.

| Treatment | Drug Conc (mg/mL) | Virus titre (log PFU/lung)[1] | | |
|---|---|---|---|---|
| | | Geometric mean | Median | Interquartile range |
| Vehicle plus virus | none | 3.1 | 3.1 | 2.7-3.4 |
| Compound Example 5 | 0.2 | <1.5[2] | <1.5[2] | |

[1]n values were 8 for all experiments;
[2]Lower limit of quantitation (LOQ).

Figure 4:
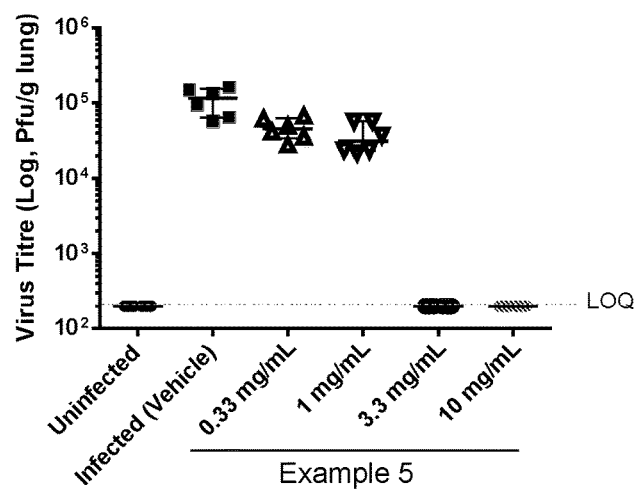
FIG. 4 shows the effect of Example 5 on virus titre in the lungs of RSV A2 infected cotton rats

The potent dose-dependent inhibition of virus titre by compound Example 5 was also seen in lung homogenates from RSV/S/Long infected cotton rats on day4 (Table 8, FIG. 4). In addition, the drug substance displayed a dose-dependent inhibition of RSV NS-1 gene transcripts (Table 9) and of RANTES transcripts in lung (Table 10).

TABLE 8

The effects of intranasal treatment with compound Example 5 on RSV A2 viral titre in lung from RSV A2 infected cotton rats.

| Treatment | Drug Conc (mg/mL) | Virus titre (log, PFU/lung)[1] | | |
|---|---|---|---|---|
| | | Geometric mean | Median | Interquartile range |
| Vehicle | none | <2.3[2] | <2.3[2] | — |
| Vehicle plus virus | None | 5.0 | 5.1 | 4.8-5.2 |
| Compound Example 5 plus virus | 0.33 | 4.7 | 4.7 | 4.5-4.8 |
| | 1.0 | 4.5 | 4.5 | 4.4-4.8 |
| | 3.3 | <2.3[2] | <2.3[2] | — |
| | 10 | <2.3[2] | <2.3[2] | — |

[1]n values were 6 for all experiments;
[2]Lower limit of quantitation (LOQ).

TABLE 9

The effects of intranasal treatment with compound Example 5 on RSV A2 NS-1 gene expression in lung from RSV A2 infected cotton rats.

| Treatment | Drug Conc (mg/mL) | RSV NS1 gene transcript (/β-actin)[1] | | % inhibition |
|---|---|---|---|---|
| | | Median | Interquartile range | |
| Vehicle | none | 0 | 0-0 | — |
| Vehicle + virus | none | 4.4 | 2.4-6.4 | — |
| Compound Example 5 plus virus | 0.33 | 2.0 | 1.7-2.5 | 55% |
| | 1.0 | 1.6 | 1.2-3.0 | 64% |
| | 3.3 | 1.0 | 0.33-2.4 | 77% |
| | 10 | 1.0 | 0.36-2.2 | 77% |

[1]n values were 6 for all experiments.

TABLE 10

The Effects of intranasal treatment with compound Example 5 on RANTES gene expression in lung from RSV A2 infected cotton rats.

| Treatment | Drug Conc (mg/mL) | RANTES gene transcript (/β-actin)[1] | | % inhibition |
|---|---|---|---|---|
| | | Median | Interquartile range | |
| Vehicle | none | 0.088 | 0.046-0.090 | — |
| Vehicle + virus | none | 0.29 | 0.21-0.40 | — |
| Compound Example 5 plus virus | 0.33 | 0.21 | 0.16-0.33 | 28 |
| | 1.0 | 0.16 | 0.15-0.25 | 45 |
| | 3.3 | 0.11 | 0.075-0.15 | 62 |
| | 10 | 0.13 | 0.13-0.17 | 55 |

[1]n values were 6 for all experiments.

SUMMARY

The in vitro antiviral activity of the compounds of the invention has been demonstrated by their cytoprotective effect on HEp2 cells infected with RSV. In this assay system the inhibition of virus replication was detected and quantified from the resulting inhibition of virus-mediated CPE. It is particularly noteworthy that compounds of the invention are potent inhibitors of the CPE induced by the RSV A strain and (in most cases) the RSV B strain studied. The potent antiviral activity of compounds of formula (I) was further evidenced by their inhibition of RSV A2 F-protein expression in BEAS2B cells.

The compounds of the invention demonstrate low mammalian cell toxicity as measured by their lack of any significant effects in the cell viability assay. Furthermore, in an in vitro model of human lung epithelium, comprising an air-liquid interface culture of bronchial epithelial cells, compound Example 5 of the invention completely inhibited virus titre when administered by either early or late stage intervention. The latter observation is particularly significant for the treatment of established disease.

The in vivo antiviral activity of the compounds of the invention has been demonstrated in mice and cotton rats infected with RSV. In the assay systems the inhibition of virus replication was detected and quantified from the RSV titre in lung homogenates as measured in a plaque assay. In keeping with the data obtained from the studies conducted in ALI-cultured human bronchial cells, compound Example 5 completely inhibited virus titre in the lungs of RSV A2 infected mice and cotton rats. The compounds of the present invention thus have the necessary attributes to be effective medicines for the treatment and/or prevention of RSV infection and associated disease.

REFERENCES

Abman S. H., Ogle J. W., Butler-Simon N., Rumack C. M., and Accurso F. J. Role of respiratory syncytial virus in early hospitalizations for respiratory distress of young infants with cystic fibrosis. *J. Pediatr.*, 1988, 113, 826-30.

Bem R. A., Domachowske J. B. and Rosenberg, H. F. Animal models of human respiratory syncytial disease. *Am. J. Physiol.*, 2011. 301, L148-L156.

Hall C. B., Douglas R. G. Jr., Schnabel K. C. and Geiman J. M. Infectivity of respiratory syncytial virus by various routes of inoculation. *Infect. Immun.*, 1981, 33, 779-83.

Holt P. G. and Sly P. D. Interactions between RSV infection, asthma, and atopy: unravelling the complexities. *J. Exp. Med.*, 2002, 196, 1271-1275.

Johnson J. E., Gonzales R. A., Olson S. J., Wright P. F. and Graham, B. S. The histopathology of fatal untreated human respiratory syncytial virus infection. *Modern Pathology*, 2007, 20, 108-119.

Lee N., Lui G. C., Wong K. T., Li T. C., Tse E. C., Chan J. Y., Yu J., Wong S. S., Choi K. W., Wong R. Y., Ngai K. L., Hui D. S. and Chan P. K. High morbidity and mortality in adults hospitalized for respiratory syncytial virus infections. *Clin. Infect. Dis.*, 2013, 57, 1069-77.

Mohan A., Chandra S., Agarwal D., Guleria R., Broor S., Gaur B. and Pandey R. M. Prevalence of viral infection detected by PCR and RT-PCR in patients with acute exacerbation of COPD: A systematic review. *Respirology*, 2010, 15, 536-542.

Newcomb D. C. and Peebles R. S. Jr. Bugs and asthma: a different disease? *Proc. Am. Thorac. Soc.*, 2009, 1; 6, 266-71.

Olivier A., Gallup J., de Macedo M. M. M. A., Varga S. M. and Ackermann M. Human respiratory syncytial virus A2 strain replicates and induces innate immune responses by respiratory epithelia of neonatal lambs. *Int. J. Exp. Pathol.*, 2009, 90, 431-438.

Panayiotou C., Richter J., Koliou M., Kalogirou N., Georgiou E. and Christodoulou C. Epidemiology of respiratory syncytial virus in children in Cyprus during three consecutive winter seasons (2010-2013): age distribution, seasonality and association between prevalent genotypes and disease severity. *Epidemiol. Infect.*, 2014, January 24, 1-6.

Walsh E. E., McConnochie K. M., Long C. E. and Hall C. B. Severity of respiratory syncytial virus infection is related to virus strain. *J. Infect. Dis.*, 1997, 175, 814-20.

Zhang Z-Y., Du L-N., Chen X., Zhao Y., Liu, E-M., Yang X-Q. and Zhao X-D Genetic variability of respiratory syncytial viruses (RSV) prevalent in Southwestern China from 2006 to 2009: emergence of subgroup B and A RSV as dominant strains. *J. Clin. Microbiol.*, 2010, 48, 1201-7.

Zhu Q., McAuliffe J. M., Patel N. K., Palmer-Hill F. J., Yang C. F., Liang B., Su L., Zhu W., Wachter L., Wilson S., MacGill R. S., Krishnan S., McCarthy M. P., Losonsky G. A. and Suzich J. A. Analysis of respiratory syncytial virus preclinical and clinical variants resistant to neutralization by monoclonal antibodies palivizumab and/or motavizumab. *J Infect. Dis.*, 2011, 203, 674-82.

Throughout the specification and the claims which follow, unless the context requires otherwise, the word 'comprise', and variations such as 'comprises' and 'comprising', will be understood to imply the inclusion of a stated integer, step, group of integers or group of steps but not to the exclusion of any other integer, step, group of integers or group of steps.

All patents and patent applications referred to herein are incorporated by reference in their entirety.

The invention claimed is:

1. A compound of formula (I),

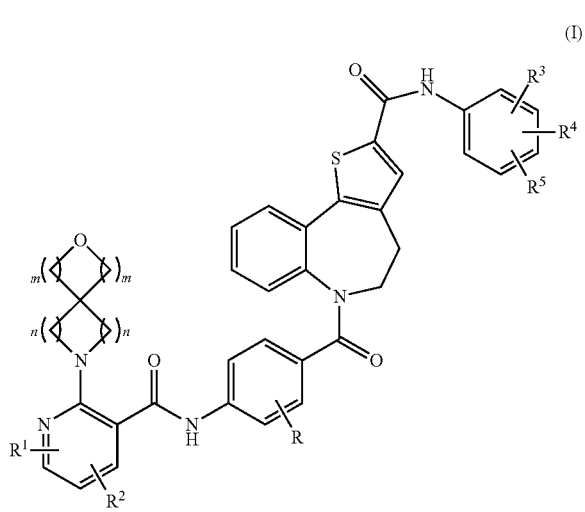

(I)

wherein:
R represents hydrogen or halo;
$R^3$ represents hydrogen, hydroxy, halo, cyano, $C_{1-4}$ alkyl, $C_{2-4}$ alkenyl, $C_{2-4}$ alkynyl, $C_{1-4}$ haloalkyl, $C_{3-6}$ cycloalkyl, $C_{1-4}$ alkoxy, $C_{1-4}$ hydroxyalkyl, $C_{1-4}$ haloalkoxy, —O(CH$_2$)$_2$OH or —O(CH$_2$)$_2$O $C_{1-2}$ alkyl;
$R^4$ represents hydrogen, halo, cyano, $C_{1-4}$ alkyl, $C_{2-4}$ alkenyl, $C_{2-4}$ alkynyl, $C_{1-4}$ haloalkyl, $C_{3-6}$ cycloalkyl, $C_{1-4}$ alkoxy or $C_{1-4}$ haloalkoxy;
$R^5$ represents hydrogen, halo, cyano, $C_{1-4}$ alkyl, $C_{2-4}$ alkenyl, $C_{2-4}$ alkynyl, $C_{1-4}$ haloalkyl, $C_{3-6}$ cycloalkyl, $C_{1-4}$ alkoxy or $C_{1-4}$ haloalkoxy;
m and n represent integers which may be independently selected from 1 and 2; and either
(a) $R^1$ represents hydrogen, $C_{1-4}$ alkyl, $C_{2-4}$ alkenyl, $C_{2-4}$ alkynyl, $C_{1-4}$ haloalkyl, $C_{3-6}$ cycloalkyl, $C_{1-4}$ alkoxy, $C_{1-2}$ alkoxy $C_{1-2}$ alkyl or $C_{1-4}$ haloalkoxy; and $R^2$ represents hydrogen, halo, $C_{1-4}$ alkyl, $C_{2-4}$ alkenyl, $C_{2-4}$ alkynyl, $C_{1-4}$ haloalkyl, $C_{3-6}$ cycloalkyl, $C_{1-4}$ alkoxy, $C_{1-4}$ haloalkoxy, $C_{1-2}$ alkoxy $C_{1-2}$ alkyl, $C_{1-4}$ hydroxyalkyl or cyano; or (b) $R^1$ and $R^2$ are in positions 6 and 5 respectively of the pyridine nucleus and are joined to form a bicyclic system comprising either a 5- or 6-membered carbocyclic ring or a 5- or 6- membered heterocyclic ring which contains heteroatoms selected only from O and S, which is fused to said pyridine nucleus;

or a pharmaceutically acceptable salt thereof.

2. A compound according to claim 1 wherein n represents 1 and m represents 2.

3. A compound according to claim 2 which is a compound of formula (Ib)

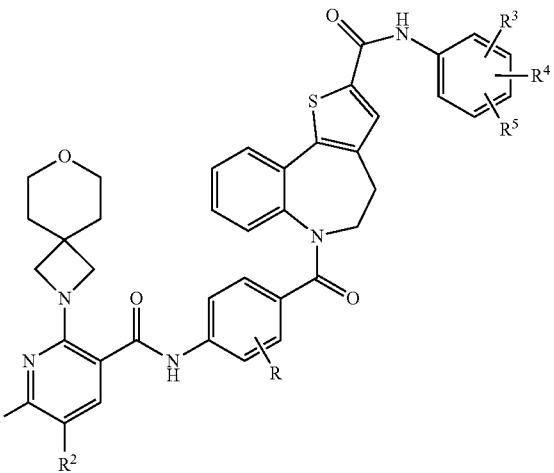

(Ib)

wherein R, $R^1$, $R^2$, $R^3$, $R^4$ and $R^5$ are as defined in claim 1; or a pharmaceutically acceptable salt thereof.

4. A compound according to claim 3 which is a compound of formula (Ic)

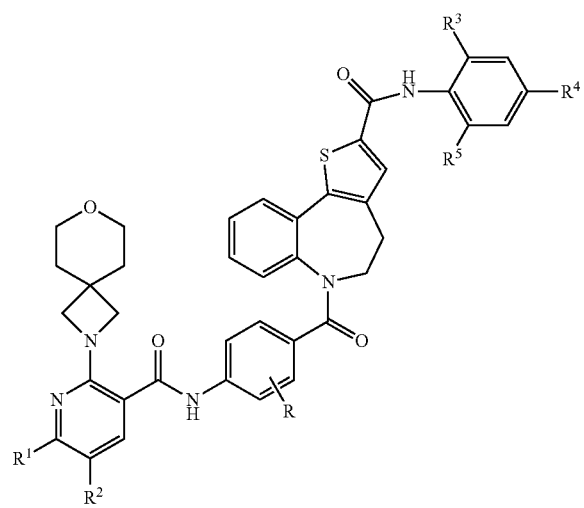

(Ic)

wherein R, $R^1$, $R^2$, $R^3$, $R^4$ and $R^5$ are as defined in claim 1; or a pharmaceutically acceptable salt thereof.

5. A compound according to claim 1 wherein R represents hydrogen or fluoro.

6. A compound according to claim 1 wherein $R^3$ represents hydrogen, hydroxy, halo, cyano, $C_{1-4}$ alkyl, $C_{2-4}$ alkenyl, $C_{2-4}$ alkynyl, $C_{1-4}$ haloalkyl, $C_{3-6}$ cycloalkyl, $C_{1-4}$ alkoxy or $C_{1-4}$ haloalkoxy.

7. A compound according to claim 1 wherein:
   $R^1$ represents hydrogen, $C_{1-4}$ alkyl, $C_{2-4}$ alkenyl, $C_{2-4}$ alkynyl, $C_{1-4}$ haloalkyl, $C_{3-6}$ cycloalkyl, $C_{1-4}$ alkoxy or $C_{1-4}$ haloalkoxy; and
   $R^2$ represents hydrogen, halo, $C_{1-4}$ alkyl, $C_{2-4}$ alkenyl, $C_{2-4}$ alkynyl, $C_{1-4}$ haloalkyl, $C_{3-6}$ cycloalkyl, $C_{1-4}$ alkoxy, $C_{1-4}$ haloalkoxy or cyano.

8. A compound according to claim 7 wherein one of $R^1$ and $R^2$ is $C_{1-4}$ alkyl and the other is hydrogen.

9. A compound according to claim 8 wherein $R^1$ is hydrogen in the 6-position of the pyridine ring and $R^2$ is methyl in the 5-position of the pyridine ring.

10. A compound according to claim 1 wherein:
    $R^1$ and $R^2$ are in positions 6 and 5 respectively of the pyridine ring and are joined to form a bicyclic system comprising either a 5- or 6-membered carbocyclic ring, or a 5- or 6-membered heterocyclic ring, which contains heteroatoms selected from O and S and is fused to said pyridine nucleus, said bicyclic system being selected from the systems listed below:

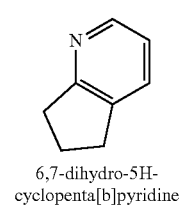
6,7-dihydro-5H-cyclopenta[b]pyridine

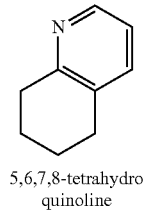
5,6,7,8-tetrahydro quinoline

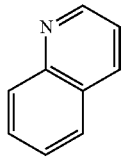
quinoline

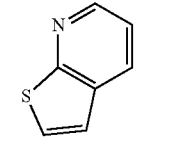
thieno[2,3-b]pyridine

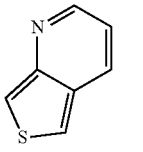
thieno[3,4-b]pyridine

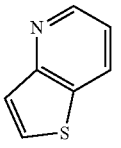
thieno[3,2-b]pyridine

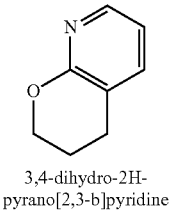
3,4-dihydro-2H-pyrano[2,3-b]pyridine

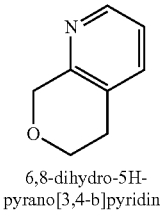
6,8-dihydro-5H-pyrano[3,4-b]pyridine

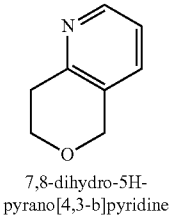
7,8-dihydro-5H-pyrano[4,3-b]pyridine

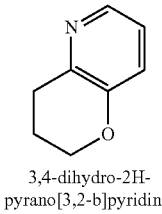
3,4-dihydro-2H-pyrano[3,2-b]pyridine.

11. A compound according to claim 1 wherein $R^3$, $R^4$ and $R^5$ are selected from hydrogen, halo, $C_{1-4}$ alkyl, $C_{2-4}$ alkenyl, $C_{2-4}$ alkynyl, $C_{1-4}$ haloalkyl, $C_{1-4}$ haloalkoxy, $C_{1-4}$ alkoxy and cyano.

12. A compound according to claim 1 wherein one of $R^3$, $R^4$ and $R^5$ is hydrogen and the remainder are substituents other than hydrogen.

13. A compound according to claim 1 wherein two of $R^3$, $R^4$ and $R^5$ are hydrogen and the remainder is a substituent other than hydrogen.

14. A compound according to claim 12 wherein one of $R^3$, $R^4$ and $R^5$ is hydrogen and the remainder occupy positions 2- and 6- of the phenyl ring to which they are attached.

15. A compound according to claim 14 wherein one of $R^3$, $R^4$ and $R^5$ is hydrogen and the remainder are selected from the group consisting of methyl, trifluoromethyl, cyano and halo.

16. A compound according to claim 1 which is selected from the group consisting of:
    6-(4-(2-(7-oxa-2-azaspiro[3.5]nonan-2-yl)nicotinamido)benzoyl)-N-phenyl-5,6-dihydro-4H-benzo[b]thieno[2,3-d]azepine-2-carboxamide;
    6-(4-(2-(7-oxa-2-azaspiro[3.5]nonan-2-yl)nicotinamido)benzoyl)-N-(2-cyanophenyl)-5,6-dihydro-4H-benzo[b]thieno[2,3-d]azepine-2-carboxamide;
    6-(4-(6-methoxy-2-(7-oxa-2-azaspiro[3.5]nonan-2-yl)nicotinamido)benzoyl)-N-(2-fluorophenyl)-5,6-dihydro-4H-benzo[b]thieno[2,3-d]azepine-2-carboxamide;
    6-(4-(5-cyclopropyl-2-(7-oxa-2-azaspiro[3.5]nonan-2-yl)nicotinamido)benzoyl)-N-(2-fluorophenyl)-5,6-dihydro-4H-benzo[b]thieno[2,3-d]azepine-2-carboxamide;
    6-(4-(2-(7-oxa-2-azaspiro[3.5]nonan-2-yl)nicotinamido)benzoyl)-N-(o-tolyl)-5,6-dihydro-4H-benzo[b]thieno[2,3-d]azepine-2-carboxamide;
    6-(4-(2-(7-oxa-2-azaspiro[3.5]nonan-2-yl)nicotinamido)benzoyl)-N-(2-fluorophenyl)-5,6-dihydro-4H-benzo[b]thieno[2,3-d]azepine-2-carboxamide;
    6-(4-(2-(7-oxa-2-azaspiro[3.5]nonan-2-yl)nicotinamido)benzoyl)-N-(2-chlorophenyl)-5,6-dihydro-4H-benzo[b]thieno[2,3-d]azepine-2-carboxamide;
    6-(4-(2-(7-oxa-2-azaspiro[3.5]nonan-2-yl)nicotinamido)benzoyl)-N-(2-ethylphenyl)-5,6-dihydro-4H-benzo[b]thieno[2,3-d]azepine-2-carboxamide;
    6-(4-(2-(7-oxa-2-azaspiro[3.5]nonan-2-yl)nicotinamido)benzoyl)-N-(4-ethynylphenyl)-5,6-dihydro-4H-benzo[b]thieno[2,3-d]azepine-2-carboxamide;
    6-(4-(2-(7-oxa-2-azaspiro[3.5]nonan-2-yl)nicotinamido)benzoyl)-N-(2,6-difluorophenyl)-5,6-dihydro-4H-benzo[b]thieno[2,3-d]azepine-2-carboxamide;
    6-(4-(2-(7-oxa-2-azaspiro[3.5]nonan-2-yl)nicotinamido)benzoyl)-N-(2,4-difluorophenyl)-5,6-dihydro-4H-benzo[b]thieno[2,3-d]azepine-2-carboxamide;
    6-(4-(2-(7-oxa-2-azaspiro[3.5]nonan-2-yl)nicotinamido)benzoyl)-N-(4-chloro-2-fluorophenyl)-5,6-dihydro-4H-benzo[b]thieno[2,3-d]azepine-2-carboxamide;
    6-(4-(2-(7-oxa-2-azaspiro[3.5]nonan-2-yl)nicotinamido)benzoyl)-N-(2-fluoro-4-methylphenyl)-5,6-dihydro-4H-benzo[b]thieno[2,3-d]azepine-2-carboxamide;
    6-(4-(2-(7-oxa-2-azaspiro[3.5]nonan-2-yl)nicotinamido)benzoyl)-N-(2-fluoro-4-methoxyphenyl)-5,6-dihydro-4H-benzo[b]thieno[2,3-d]azepine-2-carboxamide;
    6-(4-(2-(7-oxa-2-azaspiro[3.5]nonan-2-yl)nicotinamido)benzoyl)-N-(2,6-dimethylphenyl)-5,6-dihydro-4H-benzo[b]thieno[2,3-d]azepine-2-carboxamide;
    6-(4-(2-(7-oxa-2-azaspiro[3.5]nonan-2-yl)nicotinamido)benzoyl)-N-(2-fluoro-6-methylphenyl)-5,6-dihydro-4H-benzo[b]thieno[2,3-d]azepine-2-carboxamide;
    6-(4-(2-(7-oxa-2-azaspiro[3.5]nonan-2-yl)nicotinamido)benzoyl)-N-(2-chloro-6-fluorophenyl)-5,6-dihydro-4H-benzo[b]thieno[2,3-d]azepine-2-carboxamide;

6-(4-(2-(7-oxa-2-azaspiro[3.5]nonan-2-yl)nicotinamido) benzoyl)-N-(2-chloro-4-fluorophenyl)-5,6-dihydro-4H-benzo[b]thieno[2,3-d]azepine-2-carboxamide;

6-(4-(2-(7-oxa-2-azaspiro[3.5]nonan-2-yl)nicotinamido) benzoyl)-N-(2,4,6-trifluorophenyl)-5,6-dihydro-4H-benzo[b]thieno[2,3-d]azepine-2-carboxamide;

6-(4-(2-(7-oxa-2-azaspiro[3.5]nonan-2-yl)nicotinamido)-2-fluorobenzoyl)-N-(2-fluorophenyl)-5,6-dihydro-4H-benzo[b]thieno[2,3-d]azepine-2-carboxamide;

6-(4-(2-(7-oxa-2-azaspiro[3.5]nonan-2-yl)nicotinamido)-2-fluorobenzoyl)-N-(2,6-difluorophenyl)-5,6-dihydro-4H-benzo[b]thieno[2,3-d]azepine-2-carboxamide;

6-(4-(2-(7-oxa-2-azaspiro[3.5]nonan-2-yl)nicotinamido)-2-fluorobenzoyl)-N-(2-chloro-6-fluorophenyl)-5,6-dihydro-4H-benzo[b]thieno[2,3-d]azepine-2-carboxamide;

6-(4-(5-methyl-2-(7-oxa-2-azaspiro[3.5]nonan-2-yl)nicotinamido)benzoyl)-N-phenyl-5,6-dihydro-4H-benzo[b]thieno[2,3-d]azepine-2-carboxamide;

N-(2-fluorophenyl)-6-(4-(5-methyl-2-(7-oxa-2-azaspiro[3.5]nonan-2-yl)nicotinamido)benzoyl)-5,6-dihydro-4H-benzo[b]thieno[2,3-d]azepine-2-carboxamide;

N-(2-chlorophenyl)-6-(4-(5-methyl-2-(7-oxa-2-azaspiro[3.5]nonan-2-yl)nicotinamido)benzoyl)-5,6-dihydro-4H-benzo[b]thieno[2,3-d]azepine-2-carboxamide;

6-(4-(5-methyl-2-(7-oxa-2-azaspiro[3.5]nonan-2-yl)nicotinamido)benzoyl)-N-(o-tolyl)-5,6-dihydro-4H-benzo[b]thieno[2,3-d]azepine-2-carboxamide;

N-(2-fluoro-6-methylphenyl)-6-(4-(5-methyl-2-(7-oxa-2-azaspiro[3.5]nonan-2-yl)nicotinamido)benzoyl)-5,6-dihydro-4H-benzo[b]thieno[2,3-d]azepine-2-carboxamide;

N-(2,4-difluorophenyl)-6-(4-(5-methyl-2-(7-oxa-2-azaspiro[3.5]nonan-2-yl)nicotinamido)benzoyl)-5,6-dihydro-4H-benzo[b]thieno[2,3-d]azepine-2-carboxamide;

N-(2-chloro-6-fluorophenyl)-6-(4-(5-methyl-2-(7-oxa-2-azaspiro[3.5]nonan-2-yl)nicotinamido)benzoyl)-5,6-dihydro-4H-benzo[b]thieno[2,3-d]azepine-2-carboxamide;

N-(2-fluoro-6-methylphenyl)-6-(4-(6-methyl-2-(7-oxa-2-azaspiro[3.5]nonan-2-yl)nicotinamido)benzoyl)-5,6-dihydro-4H-benzo[b]thieno[2,3-d]azepine-2-carboxamide;

N-(2-chloro-6-fluorophenyl)-6-(4-(6-methyl-2-(7-oxa-2-azaspiro[3.5]nonan-2-yl)nicotinamido)benzoyl)-5,6-dihydro-4H-benzo[b]thieno[2,3-d]azepine-2-carboxamide;

6-(4-(5,6-dimethyl-2-(7-oxa-2-azaspiro[3.5]nonan-2-yl)nicotinamido)benzoyl)-N-(o-tolyl)-5,6-dihydro-4H-benzo[b]thieno[2,3-d]azepine-2-carboxamide;

6-(4-(5,6-dimethyl-2-(7-oxa-2-azaspiro [3.5]nonan-2-yl)nicotinamido)benzoyl)-N-(2-fluorophenyl)-5,6-dihydro-4H-benzo[b]thieno[2,3-d]azepine-2-carboxamide;

6-(4-(5,6-dimethyl-2-(7-oxa-2-azaspiro[3.5]nonan-2-yl)nicotinamido)benzoyl)-N-(2-fluoro-6-methylphenyl)-5,6-dihydro-4H-benzo[b]thieno[2,3-d]azepine-2-carboxamide;

N-(2,4-difluorophenyl)-6-(4-(5,6-dimethyl-2-(7-oxa-2-azaspiro[3.5]nonan-2-yl)nicotinamido)benzoyl)-5,6-dihydro-4H-benzo[b]thieno[2,3-d]azepine-2-carboxamide;

N-(2-chloro-6-fluorophenyl)-6-(4-(5,6-dimethyl-2-(7-oxa-2-azaspiro[3.5]nonan-2-yl)nicotinamido)benzoyl)-5,6-dihydro-4H-benzo[b]thieno[2,3-d]azepine-2-carboxamide;

and pharmaceutically acceptable salts of any one thereof.

17. A compound according to claim 1 which is selected from the group consisting of:

N-(2-fluoro-6-iodophenyl)-6-(4-(5-methyl-2-(7-oxa-2-azaspiro[3.5]nonan-2-yl)nicotinamido)benzoyl)-5,6-dihydro-4H-benzo[b]thieno[2,3-d]azepine-2-carboxamide;

N-(2-cyclopropyl-6-fluorophenyl)-6-(4-(5-methyl-2-(7-oxa-2-azaspiro[3.5]nonan-2-yl)nicotinamido)benzoyl)-5,6-dihydro-4H-benzo[b]thieno[2,3-d]azepine-2-carboxamide;

6-(4-(2-(7-oxa-2-azaspiro[3.5]nonan-2-yl)-6,7-dihydro-5H-cyclopenta[b]pyridine-3-carboxamido)benzoyl)-N-(2-fluoro-6-methylphenyl)-5,6-dihydro-4H-benzo[b]thieno[2,3-d]azepine-2-carboxamide;

6-(4-(2-(7-oxa-2-azaspiro[3.5]nonan-2-yl)-5,6,7,8-tetrahydroquinoline-3-carboxamido)benzoyl)-N-(2-fluoro-6-methylphenyl)-5,6-dihydro-4H-benzo[b]thieno[2,3-d]azepine-2-carboxamide;

6-(4-(2-(7-oxa-2-azaspiro[3.5]nonan-2-yl)quinoline-3-carboxamido)benzoyl)-N-(2-fluoro-6-methylphenyl)-5,6-dihydro-4H-benzo[b]thieno[2,3-d]azepine-2-carboxamide;

6-(4-(5-cyclopropyl-2-(7-oxa-2-azaspiro[3,5]nonan-2-yl)nicotinamido)benzoyl)-N-(2-fluoro-6-methylphenyl)-5,6-dihydro-4H-benzo[b]thieno[2,3-d]azepine-2-carboxamide;

N-(4-(2-((2-fluoro-6-methylphenyl)carbamoyl)-5,6-dihydro-4H-benzo[b]thieno[2,3-d]azepine-6-carbonyl)phenyl)-2-(7-oxa-2-azaspiro[3.5]nonan-2-yl)-7,8-dihydro-5H-pyrano[4,3-b]pyridine-3-carboxamide;

6-(4-(5-(7-oxa-2-azaspiro[3,5]nonan-2-yl)thieno[3,2-b]pyridine-6-carboxamido)benzoyl)-N-(2,6-difluorophenyl)-5,6-dihydro-4H-benzo[b]thieno[2,3-d]azepine-2-carboxamide;

N-(2-fluoro-6-vinylphenyl)-6-(4-(5-methyl-2-(7-oxa-2-azaspiro[3.5]nonan-2-yl)nicotinamido) benzoyl)-5,6-dihydro-4H-benzo[b]thieno[2,3-d]azepine-2-carboxamide;

N-(2-ethynyl-6-fluorophenyl)-6-(4-(5-methyl-2-(7-oxa-2-azaspiro[3.5]nonan-2-yl)nicotinamido) benzoyl)-5,6-dihydro-4H-benzo[b]thieno[2,3-d]azepine-2-carboxamide;

N-(2,6-difluorophenyl)-6-(4-(5-methyl-2-(7-oxa-2-azaspiro[3.5]nonan-2-yl)nicotinamido)benzoyl)-5,6-dihydro-4H-benzo[b]thieno[2,3-d]azepine-2-carboxamide;

6-(4-(5-methyl-2-(7-oxa-2-azaspiro[3.5]nonan-2-yl)nicotinamido)benzoyl)-N-(2,4,6-trifluorophenyl)-5,6-dihydro-4H-benzo[b]thieno[2,3-d]azepine-2-carboxamide;

N-(2,6-difluorophenyl)-6-(4-(6-methyl-2-(7-oxa-2-azaspiro[3.5]nonan-2-yl)nicotinamido)benzoyl)-5,6-dihydro-4H-benzo[b]thieno[2,3-d]azepine-2-carboxamide;

6-(4-(6-methyl-2-(7-oxa-2-azaspiro[3.5]nonan-2-yl)nicotinamido)benzoyl)-N-(2,4,6-trifluorophenyl)-5,6-dihydro-4H-benzo[b]thieno[2,3-d]azepine-2-carboxamide;

N-(2-cyano-6-fluorophenyl)-6-(4-(5-methyl-2-(7-oxa-2-azaspiro[3.5]nonan-2-yl)nicotinamido)benzoyl)-5,6-dihydro-4H-benzo[b]thieno[2,3-d]azepine-2-carboxamide;

N-(2-fluoro-6-hydroxyphenyl)-6-(4-(5-methyl-2-(7-oxa-2-azaspiro[3.5]nonan-2-yl)nicotinamido)benzoyl)-5,6-dihydro-4H-benzo[b]thieno[2,3-d]azepine-2-carboxamide;

N-(2-fluoro-6-methoxyphenyl)-6-(4-(5-methyl-2-(7-oxa-2-azaspiro[3.5]nonan-2-yl)nicotinamido)benzoyl)-5,6-dihydro-4H-benzo[b]thieno[2,3-d]azepine-2-carboxamide;

N-(2-fluoro-6-(2-hydroxyethoxy)phenyl)-6-(4-(5-methyl-2-(7-oxa-2-azaspiro[3.5]nonan-2-yl)nicotinamido)benzoyl)-5,6-dihydro-4H-benzo[b]thieno[2,3-d]azepine-2-carboxamide;

N-(2-fluoro-6-(2-methoxyethoxy)phenyl)-6-(4-(5-methyl-2-(7-oxa-2-azaspiro[3.5]nonan-2-yl)nicotinamido)benzoyl)-5,6-dihydro-4H-benzo[b]thieno[2,3-d]azepine-2-carboxamide;

N-(2-chloro-6-methylphenyl)-6-(4-(5-methyl-2-(7-oxa-2-azaspiro[3.5]nonan-2-yl)nicotinamido) benzoyl)-5,6-dihydro-4H-benzo[b]thieno[2,3-d]azepine-2-carboxamide;

N-(2,6-dichlorophenyl)-6-(4-(5-methyl-2-(7-oxa-2-azaspiro[3.5]nonan-2-yl)nicotinamido)benzoyl)-5,6-dihydro-4H-benzo[b]thieno[2,3-d]azepine-2-carboxamide;

N-(2-(hydroxymethyl)-6-methylphenyl)-6-(4-(5-methyl-2-(7-oxa-2-azaspiro[3.5]nonan-2-yl)nicotinamido)benzoyl)-5,6-dihydro-4H-benzo[b]thieno[2,3-d]azepine-2-carboxamide;

6-(2-fluoro-4-(5-methyl-2-(7-oxa-2-azaspiro[3.5]nonan-2-yl)nicotinamido)benzoyl)-N-(2,4,6-trifluorophenyl)-5,6-dihydro-4H-benzo[b]thieno[2,3-d]azepine-2-carboxamide;

6-(4-(5-ethyl-2-(7-oxa-2-azaspiro[3.5]nonan-2-yl)nicotinamido)benzoyl)-N-(2-fluoro-6-methylphenyl)-5,6-dihydro-4H-benzo[b]thieno[2,3-d]azepine-2-carboxamide;

N-(2-chloro-6-fluorophenyl)-6-(4-(5-ethyl-2-(7-oxa-2-azaspiro[3.5]nonan-2-yl)nicotinamido)benzoyl)-5,6-dihydro-4H-benzo[b]thieno[2,3-d]azepine-2-carboxamide;

N-(2-cyano-6-methylphenyl)-6-(4-(5-methyl-2-(7-oxa-2-azaspiro[3.5]nonan-2-yl)nicotinamido)benzoyl)-5,6-dihydro-4H-benzo[b]thieno[2,3-d]azepine-2-carboxamide;

N-(2-fluoro-6-(trifluoromethyl)phenyl)-6-(4-(5-methyl-2-(7-oxa-2-azaspiro[3.5]nonan-2-yl)nicotinamido)benzoyl)-5,6-dihydro-4H-benzo[b]thieno[2,3-d]azepine-2-carboxamide;

N-(2,6-dimethylphenyl)-6-(4-(5-methyl-2-(7-oxa-2-azaspiro[3.5]nonan-2-yl)nicotinamido)benzoyl)-5,6-dihydro-4H-benzo[b]thieno[2,3-d]azepine-2-carboxamide;

N-(2-chloro-6-fluorophenyl)-6-(4-(5-cyclopropyl-2-(7-oxa-2-azaspiro[3.5]nonan-2-yl)nicotinamido)benzoyl)-5,6-dihydro-4H-benzo[b]thieno[2,3-d]azepine-2-carboxamide;

N-(2-chloro-6-fluorophenyl)-6-(4-(5-ethynyl-2-(7-oxa-2-azaspiro[3.5]nonan-2-yl)nicotinamido)benzoyl)-5,6-dihydro-4H-benzo[b]thieno[2,3-d]azepine-2-carboxamide;

N-(2-chloro-6-fluorophenyl)-6-(4-(5-(methoxymethyl)-2-(7-oxa-2-azaspiro[3.5]nonan-2-yl)nicotinamido)benzoyl)-5,6-dihydro-4H-benzo[b]thieno[2,3-d]azepine-2-carboxamide;

6-(4-(5-fluoro-2-(7-oxa-2-azaspiro[3.5]nonan-2-yl)nicotinamido)benzoyl)-N-(2-fluoro-6-methylphenyl)-5,6-dihydro-4H-benzo[b]thieno[2,3-d]azepine-2-carboxamide;

6-(4-(5-chloro-2-(7-oxa-2-azaspiro[3.5]nonan-2-yl)nicotinamido)benzoyl)-N-(2-fluoro-6-methylphenyl)-5,6-dihydro-4H-benzo[b]thieno[2,3-d]azepine-2-carboxamide;

N-(2-fluoro-6-methylphenyl)-6-(4-(5-methyl-2-(7-oxa-2-azaspiro[3.5]nonan-2-yl)nicotinamido)benzoyl-2,3,5,6-d4)-5,6-dihydro-4H-benzo[b]thieno[2,3-d]azepine-2-carboxamide;

N-(2-fluoro-6-methylphenyl)-6-(4-(5-methoxy-2-(7-oxa-2-azaspiro[3.5]nonan-2-yl)nicotinamido)benzoyl)-5,6-dihydro-4H-benzo[b]thieno[2,3-d]azepine-2-carboxamide;

6-(4-(5-cyclopropyl-2-(7-oxa-2-azaspiro[3.5]nonan-2-yl)nicotinamido)benzoyl)-N-(2,6-difluorophenyl)-5,6-dihydro-4H-benzo[b]thieno[2,3-d]azepine-2-carboxamide;

N-(2,6-difluorophenyl)-6-(4-(5-(prop-1-en-2-yl)-2-(7-oxa-2-azaspiro[3.5]nonan-2-yl)nicotinamido)benzoyl)-5,6-dihydro-4H-benzo[b]thieno[2,3-d]azepine-2-carboxamide;

6-(4-(2-(7-oxa-2-azaspiro[3.5]nonan-2-yl)-6,7-dihydro-5H-cyclopenta[b]pyridine-3-carboxamido)benzoyl)-N-(2-cyano-6-methylphenyl)-5,6-dihydro-4H-benzo[b]thieno[2,3-d]azepine-2-carboxamide;

6-(4-(2-(7-oxa-2-azaspiro[3.5]nonan-2-yl)-6,7-dihydro-5H-cyclopenta[b]pyridine-3-carboxamido)benzoyl)-N-(2,6-difluorophenyl)-5,6-dihydro-4H-benzo[b]thieno[2,3-d]azepine-2-carboxamide;

6-(4-(2-(7-oxa-2-azaspiro[3.5]nonan-2-yl)-6,7-dihydro-5H-cyclopenta[b]pyridine-3-carboxamido)benzoyl)-N-(2-chloro-6-fluorophenyl)-5,6-dihydro-4H-benzo[b]thieno[2,3-d]azepine-2-carboxamide;

6-(4-(2-(7-oxa-2-azaspiro[3.5]nonan-2-yl)-6,7-dihydro-5H-cyclopenta[b]pyridine-3-carboxamido)-2-fluorobenzoyl)-N-(2-cyano-6-methylphenyl)-5,6-dihydro-4H-benzo[b]thieno[2,3-d]azepine-2-carboxamide;

6-(4-(2-(7-oxa-2-azaspiro[3.5]nonan-2-yl)-6,7-dihydro-5H-cyclopenta[b]pyridine-3-carboxamido)-2-fluorobenzoyl)-N-(2-fluoro-6-methylphenyl)-5,6-dihydro-4H-benzo[b]thieno[2,3-d]azepine-2-carboxamide;

6-(4-(2-(7-oxa-2-azaspiro[3.5]nonan-2-yl)-6,7-dihydro-5H-cyclopenta[b]pyridine-3-carboxamido)-2-fluorobenzoyl)-N-(2,6-difluorophenyl)-5,6-dihydro-4H-benzo[b]thieno[2,3-d]azepine-2-carboxamide;

6-(4-(2-(7-oxa-2-azaspiro[3.5]nonan-2-yl)-6,7-dihydro-5H-cyclopenta[b]pyridine-3-carboxamido)-2-fluorobenzoyl)-N-(2-chloro-6-fluorophenyl)-5,6-dihydro-4H-benzo[b]thieno[2,3-d]azepine-2-carboxamide;

6-(4-(2-(7-oxa-2-azaspiro[3.5]nonan-2-yl)-5,6,7,8-tetrahydroquinoline-3-carboxamido)benzoyl)-N-(2-chloro-6-fluorophenyl)-5,6-dihydro-4H-benzo[b]thieno[2,3-d]azepine-2-carboxamide;

N-(4-(2-((2,6-difluorophenyl)carbamoyl)-5,6-dihydro-4H-benzo[b]thieno[2,3-d]azepine-6-carbonyl)phenyl)-2-(7-oxa-2-azaspiro[3.5]nonan-2-yl)-7,8-dihydro-5H-pyrano[4,3-b]pyridine-3-carboxamide;

N-(4-(2-((2-chloro-6-fluorophenyl)carbamoyl)-5,6-dihydro-4H-benzo[b]thieno[2,3-d]azepine-6-carbonyl)phenyl)-2-(7-oxa-2-azaspiro[3.5]nonan-2-yl)-7,8-dihydro-5H-pyrano[4,3-b]pyridine-3-carboxamide;

6-(4-(2-(7-oxa-2-azaspiro[3.5]nonan-2-yl)quinoline-3-carboxamido)benzoyl)-N-(2-fluorophenyl)-5,6-dihydro-4H-benzo[b]thieno[2,3-d]azepine-2-carboxamide;

6-(4-(2-(7-oxa-2-azaspiro[3.5]nonan-2-yl)quinoline-3-carboxamido)benzoyl)-N-(2,4-difluorophenyl)-5,6-dihydro-4H-benzo[b]thieno[2,3-d]azepine-2-carboxamide;

6-(4-(2-(7-oxa-2-azaspiro[3.5]nonan-2-yl)quinoline-3-carboxamido)benzoyl)-N-(2,6-difluorophenyl)-5,6-dihydro-4H-benzo[b]thieno[2,3-d]azepine-2-carboxamide;

6-(4-(2-(7-oxa-2-azaspiro[3.5]nonan-2-yl)quinoline-3-carboxamido)benzoyl)-N-(2-chloro-6-fluorophenyl)-5,6-dihydro-4H-benzo[b]thieno[2,3-d]azepine-2-carboxamide;

6-(4-(2-(7-oxa-2-azaspiro[3.5]nonan-2-yl)quinoline-3-carboxamido)benzoyl)-N-(2,4,6-trifluorophenyl)-5,6-dihydro-4H-benzo[b]thieno[2,3-d]azepine-2-carboxamide;

N-(2-fluoro-6-methyl-phenyl)-6-(4((5-(7-oxa-2-azaspiro[3.5]nonan-2-yl)thieno[3,2-b]pyridine-6-carbonyl)amino)benzoyl)-4,5-dihydrothieno[3,2-d][1]benzazepine-2-carboxamide;

N-(2-fluoro-6-methylphenyl)-6-(4-(5-methyl-2-(2-oxa-6-azaspiro[3.3]heptan-6-yl)nicotinamido)benzoyl)-5,6-dihydro-4H-benzo[b]thieno[2,3-d]azepine-2-carboxamide;

N-(2-fluoro-6-methylphenyl)-6-(4-(5-methyl-2-(2-oxa-7-azaspiro[3.5]nonan-7-yl)nicotinamido)benzoyl)-5,6-dihydro-4H-benzo[b]thieno[2,3-d]azepine-2-carboxamide;

N-(2,6-difluorophenyl)-6-(4-(5-methyl-2-(2-oxa-7-azaspiro[3.5]nonan-7-yl)nicotinamido)benzoyl)-5,6-dihydro-4H-benzo[b]thieno[2,3-d]azepine-2-carboxamide;

N-(2-chloro-6-fluorophenyl)-6-(4-(5-methyl-2-(2-oxa-7-azaspiro[3.5]nonan-7-yl)nicotinamido)benzoyl)-5,6-dihydro-4H-benzo[b]thieno[2,3-d]azepine-2-carboxamide;

N-(2-fluoro-6-(trifluoromethyl)phenyl)-6-(4-(5-methyl-2-(2-oxa-7-azaspiro[3.5]nonan-7-yl)nicotinamido)benzoyl)-5,6-dihydro-4H-benzo[b]thieno[2,3-d]azepine-2-carboxamide;

N-(2-fluoro-6-methylphenyl)-6-(4-(5-methyl-2-(3-oxa-9-azaspiro[5.5]undecan-9-yl)nicotinamido)benzoyl)-5,6-dihydro-4H-benzo[b]thieno[2,3-d]azepine-2-carboxamide;

and pharmaceutically acceptable salts of any one thereof.

18. A method of treatment of RSV infection or lung disease associated with RSV infection in a subject which comprises administering to said subject an effective amount of a compound according to claim 1.

19. A method of prevention of RSV infection or lung disease associated with RSV infection in a subject which comprises administering to said subject prior to infection an effective amount of a compound according to claim 1.

20. A method according to claim 18 wherein the RSV infection is infection by viruses of the RSV A strain and/or viruses of the RSV B strain.

21. A pharmaceutical composition comprising a compound according to claim 1 optionally in combination with one or more pharmaceutically acceptable diluents or carriers.

22. A pharmaceutical composition according to claim 21 which comprises a second or further active ingredient.

23. A pharmaceutical composition according to claim 22 wherein the second or further active ingredient is selected from anti-viral agents and anti-inflammatory agents.

24. A method according to claim 19 wherein the RSV infection is infection by viruses of the RSV A strain and/or viruses of the RSV B strain.

* * * * *